US009837622B2

United States Patent
Stoessel et al.

(10) Patent No.: US 9,837,622 B2
(45) Date of Patent: Dec. 5, 2017

(54) METAL COMPLEXES

(71) Applicant: Merck Patent GmbH, Darmstadt (DE)

(72) Inventors: Philipp Stoessel, Frankfurt am Main (DE); Dominik Joosten, Frankfurt am Main (DE); Esther Breuning, Ober-Ramstadt (DE); Joachim Kaiser, Darmstadt (DE); Christian Ehrenreich, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 295 days.

(21) Appl. No.: 14/414,298

(22) PCT Filed: Jun. 21, 2013

(86) PCT No.: PCT/EP2013/001844
§ 371 (c)(1),
(2) Date: Apr. 30, 2015

(87) PCT Pub. No.: WO2014/008982
PCT Pub. Date: Jan. 16, 2014

(65) Prior Publication Data
US 2015/0263297 A1   Sep. 17, 2015

(30) Foreign Application Priority Data
Jul. 13, 2012  (EP) .................................... 12005187

(51) Int. Cl.
| | |
|---|---|
| *C07D 471/04* | (2006.01) |
| *H01L 51/00* | (2006.01) |
| *C09K 11/06* | (2006.01) |
| *H05B 33/10* | (2006.01) |
| *C07D 471/14* | (2006.01) |
| *C07D 471/22* | (2006.01) |
| *C07D 491/147* | (2006.01) |
| *C07D 519/00* | (2006.01) |
| *C07F 15/00* | (2006.01) |
| *C07F 5/02* | (2006.01) |
| *C07F 7/08* | (2006.01) |
| *C08G 73/06* | (2006.01) |
| *H01L 51/50* | (2006.01) |
| *H01L 51/52* | (2006.01) |

(52) U.S. Cl.
CPC ........ *H01L 51/0085* (2013.01); *C07D 471/04* (2013.01); *C07D 471/14* (2013.01); *C07D 471/22* (2013.01); *C07D 491/147* (2013.01); *C07D 519/00* (2013.01); *C07F 5/025* (2013.01); *C07F 7/0812* (2013.01); *C07F 7/0818* (2013.01); *C07F 15/0033* (2013.01); *C07F 15/0086* (2013.01); *C08G 73/0688* (2013.01); *C08G 73/0694* (2013.01); *C09K 11/06* (2013.01); *H01L 51/0035* (2013.01); *H01L 51/0043* (2013.01); *H01L 51/0087* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/1466* (2013.01); *C09K 2211/185* (2013.01); *H01L 51/506* (2013.01); *H01L 51/5012* (2013.01); *H01L 51/5016* (2013.01); *H01L 51/5064* (2013.01); *H01L 51/5072* (2013.01); *H01L 51/5092* (2013.01); *H01L 51/5096* (2013.01); *H01L 51/5221* (2013.01); *H01L 2251/301* (2013.01); *H01L 2251/308* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| | | | | |
|---|---|---|---|---|
| 2006/0220004 | A1* | 10/2006 | Stossel | C07D 213/30 257/40 |
| 2007/0166566 | A1* | 7/2007 | Royster, Jr. | C09K 11/06 428/690 |
| 2008/0214818 | A1* | 9/2008 | Chin | C07D 213/72 546/81 |
| 2011/0050092 | A1 | 3/2011 | Takada | |
| 2011/0253988 | A1* | 10/2011 | Molt | C07F 15/0033 257/40 |
| 2011/0284799 | A1 | 11/2011 | Stoessel et al. | |
| 2013/0253617 | A1* | 9/2013 | Anemian | C07F 15/0033 607/88 |
| 2014/0231770 | A1* | 8/2014 | Inoue | H01L 51/0085 257/40 |

FOREIGN PATENT DOCUMENTS

| | | |
|---|---|---|
| CN | 102282150 A | 12/2011 |
| DE | 102010027316 A1 | 1/2012 |
| JP | 2009526071 A | 7/2009 |
| JP | 2011068848 A | 4/2011 |
| JP | 2012092047 A | 5/2012 |
| JP | 2012124360 A | 6/2012 |
| KR | 20120055998 A | 6/2012 |
| WO | 2007095118 A3 | 8/2007 |
| WO | 2010086089 A1 | 8/2010 |
| WO | WO-2011/157339 A1 | 12/2011 |

OTHER PUBLICATIONS

English Translation of the Office Action issued by The State Intellectual Property Office of the Peopel's Republic of China for Chinese Application No. 201380037499.7; Issued Sep. 18, 2015.
International Search Report of PCT/EP2013/001844; International Filing Date Jun. 21, 2013.

* cited by examiner

*Primary Examiner* — Robert S Loewe
(74) *Attorney, Agent, or Firm* — RatnerPrestia

(57) ABSTRACT

The present invention relates to metal complexes and to electronic devices, in particular organic electroluminescent devices, comprising these metal complexes.

23 Claims, No Drawings

METAL COMPLEXES

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold increase in energy and power efficiency is possible using organometallic compounds as phosphorescent emitters. In general, there is still a need for improvement in OLEDs which exhibit triplet emission, in particular with respect to efficiency, operating voltage and lifetime. This applies, in particular, to OLEDs which emit in the relatively short-wave region, i.e. green and in particular blue.

In accordance with the prior art, iridium and platinum complexes, in particular, are employed as triplet emitters in phosphorescent OLEDs. It has been possible to achieve an improvement in these OLEDs by employing metal complexes with polypodal ligands or cryptates, causing the complexes to have higher thermal stability, which results in a longer lifetime of the OLEDs (WO 2004/081017, WO 2005/113563, WO 2006/008069). However, further improvements, in particular with respect to the efficiency and the lifetime of the complexes, are desirable.

The prior art furthermore discloses iridium complexes which contain imidazophenanthridine derivatives or diimidazoquinazoline derivatives as ligands (WO 2007/095118). These complexes may result in blue phosphorescence on use in organic electroluminescent devices, depending on the precise structure of the ligand. Here too, further improvements with respect to efficiency, operating voltage and lifetime are still desirable. Furthermore, there is also still a need for improvement here with respect to the colour coordinates in order to be able to achieve deep-blue emission.

WO 2010/086089 and WO 2011/157339 disclose metal complexes which contain imidazoisoquinoline derivatives as ligands. Good advances in the development of blue triplet emitters have already been achieved using complexes of this type. However, further improvements with respect to efficiency, operating voltage and lifetime are also still desirable here.

The object of the present invention is therefore the provision of novel metal complexes which are suitable as emitters for use in OLEDs. In particular, the object is to provide emitters which are also suitable for blue- or green-phosphorescent OLEDs and which exhibit improved properties with respect to efficiency, operating voltage, lifetime, colour coordinates and/or colour purity, i.e. width of the emission band.

Surprisingly, it has been found that certain metal chelate complexes described in greater detail below achieve this object and are very highly suitable for use in an organic electroluminescent device. The present invention therefore relates to these metal complexes and to organic electroluminescent devices which comprise these complexes.

The invention thus relates to a compound of the formula (1), $$M(L)_n(L')_m \quad \text{formula (1)}$$

which contains a moiety $M(L)_n$ of the formula (2), formula (3) or formula (4):

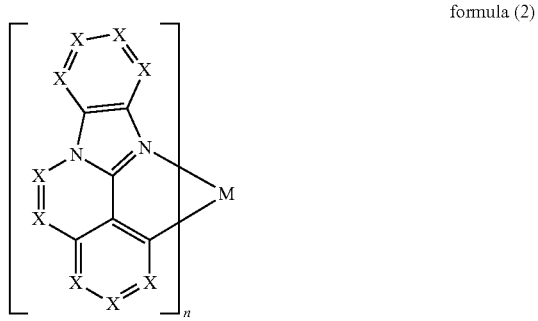

formula (2)

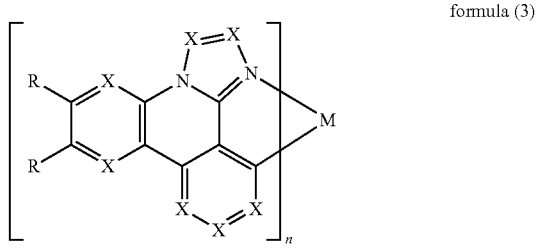

formula (3)

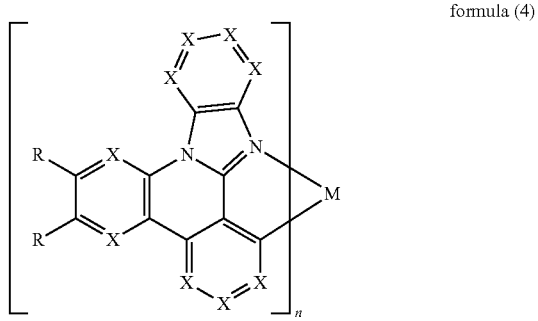

formula (4)

where the following applies to the symbols and indices used:

M is a transition metal;

X is selected on each occurrence, identically or differently, from the group consisting of CR and N;

R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^1$, where one or more non-adjacent $CH_2$ groups may be replaced by $R^1C=CR^1$, $C\equiv C$, $Si(R^1)_2$, $C=O$, $NR^1$, O, S or $CONR^1$ and where one or more H atoms may be replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two adjacent radicals R here may also form a mono- or polycyclic, aliphatic, aromatic or heteroaromatic ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals R$^2$, where one or more non-adjacent CH$_2$ groups may be replaced by R$^2$C=CR$^2$, C≡C, Si(R$^2$)$_2$, C=O, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 40 aromatic ring atoms, which may be substituted by one or more radicals R$^2$, or an aralkyl or heteroaralkyl group having 5 to 40 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$; two or more adjacent radicals R$^1$ with one another or R$^1$ with R here may form a mono- or polycyclic, aliphatic, aromatic or heteroaromatic ring system;

R$^2$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R$^2$ here may also form a mono- or polycyclic, aliphatic ring system with one another;

L' is, identically or differently on each occurrence, any desired co-ligand;

n is 1, 2 or 3;

m is 0, 1, 2, 3 or 4;

a plurality of ligands L may also be linked to one another or L may be linked to L' via a single bond or a divalent or trivalent bridge and thus form a tridentate, tetradentate, pentadentate or hexadentate ligand system;

a substituent R may also additionally coordinate to the metal;

characterised in that two adjacent groups X stand for CR and the respective radicals R, together with the C atoms, form a ring of the following formula (5) or formula (6),

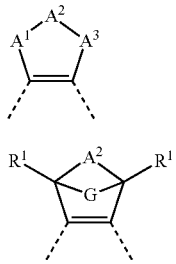

formula (5)

formula (6)

where R$^1$ and R$^2$ have the above-mentioned meanings, the dashed bonds indicate the linking of the two carbon atoms in the ligand, and furthermore:

A$^1$, A$^3$ are, identically or differently on each occurrence, C(R$^3$)$_2$, O, S, NR$^3$ or C(=O);

A$^2$ is C(R$^1$)$_2$, O, S, NR$^3$ or C(=O);

G is an alkylene group having 1, 2 or 3 C atoms, which may be substituted by one or more radicals R$^2$, or is —CR$^2$=CR$^2$— or an ortho-linked arylene or heteroarylene group having 5 to 14 aromatic ring atoms, which may be substituted by one or more radicals R$^2$;

R$^3$ is, identically or differently on each occurrence, F, a straight-chain alkyl or alkoxy group having 1 to 20 C atoms, a branched or cyclic alkyl or alkoxy group having 3 to 20 C atoms, each of which may be substituted by one or more radicals R$^2$, where one or more non-adjacent CH$_2$ groups may be replaced by R$^2$C=CR$^2$, C≡C, Si(R$^2$)$_2$, C=O, NR$^2$, O, S or CONR$^2$ and where one or more H atoms may be replaced by D or F, or an aromatic or heteroaromatic ring system having 5 to 24 aromatic ring atoms, which may in each case be substituted by one or more radicals R$^2$, or an aryloxy or heteroaryloxy group having 5 to 24 aromatic ring atoms, which may be substituted by one or more radicals R$^2$, or an aralkyl or heteroaralkyl group having 5 to 24 aromatic ring atoms, which may be substituted by one or more radicals R$^2$; two radicals R$^3$ here which are bonded to the same carbon atom may form an aliphatic or aromatic ring system with one another and thus form a spiro system; furthermore, R$^3$ may form an aliphatic ring system with an adjacent radical R or R$^1$; with the proviso that two heteroatoms are not bonded directly to one another in A$^1$-A$^2$-A$^3$.

The presence of a moiety of the formula (5) or formula (6), i.e. a condensed-on aliphatic five-membered ring, is essential to the invention. As is evident from the above-mentioned formula (5), the 5-membered ring formed by the two C atoms, A$^1$, A$^2$ and A$^3$ contains no benzylic protons, since R$^3$, if this stands for C(R$^3$)$_2$, is not equal to hydrogen. In the structures of the formulae (5) and (6) depicted above and the further embodiments of these structures indicated as preferred, a double bond is formally depicted between the two carbon atoms. This represents a simplification of the chemical structure, since these two carbon atoms are bonded into an aromatic or heteroaromatic system and the bond between these two carbon atoms is thus formally between the degree of bonding of a single bond and that of a double bond. The drawing-in of the formal double bond should thus not be regarded as limiting for the structure, but instead it is apparent to the person skilled in the art that this is taken to mean an aromatic bond.

"Adjacent groups X" here means that the groups X in the structure are bonded directly to one another.

Furthermore, "adjacent radicals" in the definition of the radicals means that these radicals are bonded to the same C atom or to C atoms which are bonded directly to one another or, if they are not bonded to C atoms which are bonded directly, that this is the next-possible position in which a substituent can be bonded. This is explained again with reference to a specific ligand in the following diagrammatic representation:

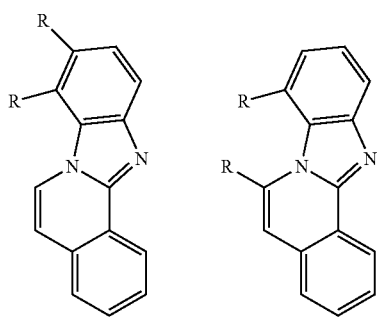

adjacent radicals R on C atoms bonded directly to one another adjacent radicals R with radicals in next-possible position In the complexes of the formula (1), the indices n and m are selected so that the coordination number on the metal M in total, depending on the metal, corresponds to the coordination number which is usual for this metal. For transition metals, this is usually the coordination number 4, 5 or 6, depending on the metal. It is generally known that metal coordination compounds have different coordination numbers, i.e. bind a different number of ligands, depending on the metal and on the oxidation state of the metal. Since the preferred coordination numbers of metals or metal ions in various oxidation states belong to the general expert knowledge of the person skilled in the art in the area of organometallic chemistry or coordination chemistry, it is straightforward for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, cis- or trans-monobenzoindenofluorene, cis- or transdibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charge of the ligands L and L' in such a way that they compensate for the charge of the complexed metal atom M.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal, where lanthanides and actinides are excluded, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here can be in various oxidation states. The above-mentioned metals are preferably in the oxidation states Cr(O), Cr(II), Cr(III), Cr(IV), Cr(VI), Mo(O), Mo(II), Mo(III), Mo(IV), Mo(VI), W(O), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(O), Ni(II), Ni(IV), Pd(II), Pt(II), Pt(IV), Cu(I), Cu(II), Cu(III), Ag(I), Ag(II), Au(I), Au(III) and Au(V). Particular preference is given to Mo(O), W(O), Re(I), Ru(II), Os(II), Rh(III), Cu(I), Ir(III) and Pt(II). Very particular preference is given to Ir(III) and Pt(II), in particular Ir(III).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0. A preferred tetracoordinated metal is Pt(II).

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0. A preferred hexacoordinated metal is Ir(III).

In the ligand L, preferably no, one, two, three or four groups X, particularly preferably no, one, two or three groups X, very particularly preferably no, one or two groups X, stand for N.

Preferred embodiments of the moieties of the formula (2) are the moieties of the following formulae (2-A) to (2-Q), formula (2-A)

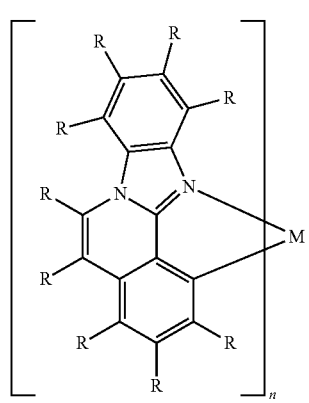

formula (2-B)

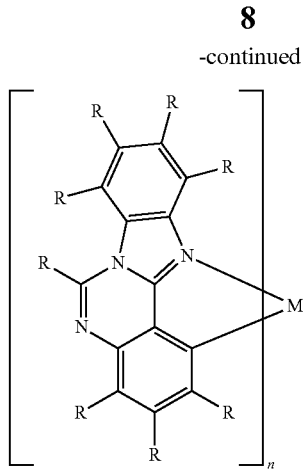

formula (2-C)

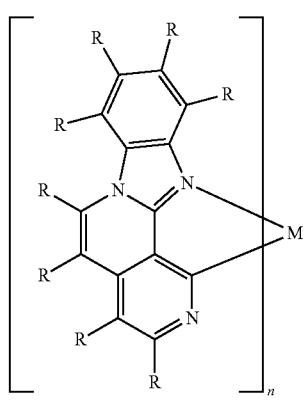

formula (2-D)

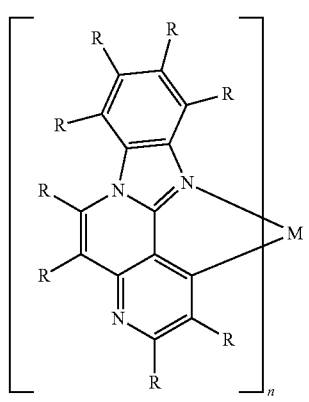

formula (2-E)

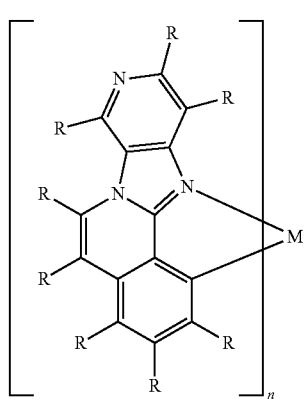

formula (2-F)
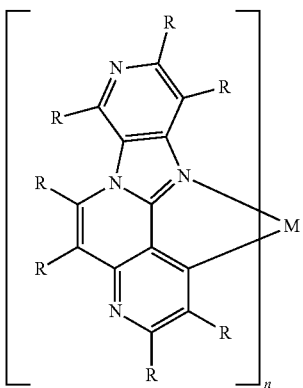
formula (2-G)
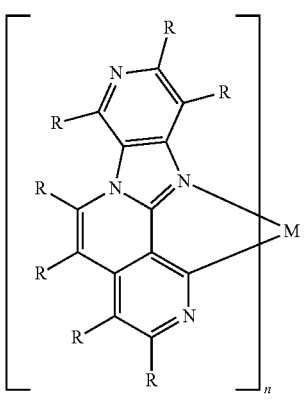
formula (2-H)
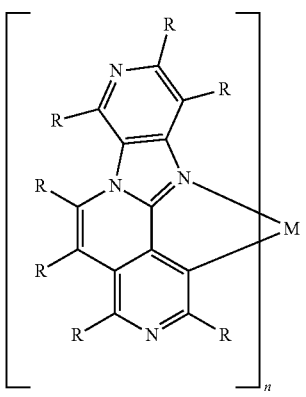
formula (2-I)
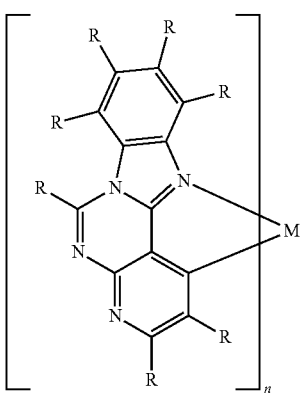
formula (2-J)
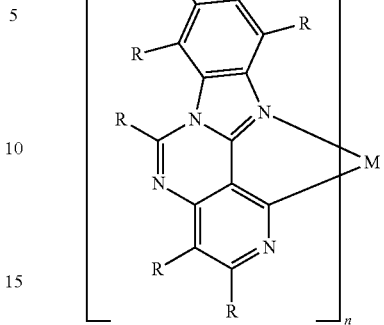
formula (2-Q)
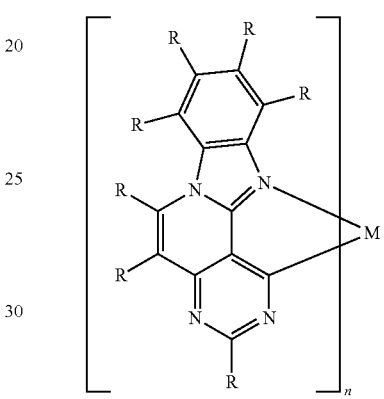
formula (2-L)

formula (2-M)
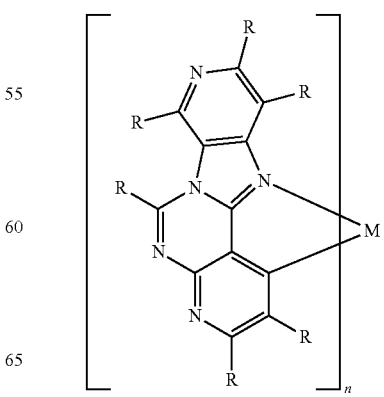

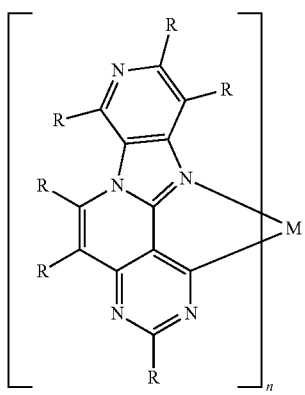
formula (2-N)
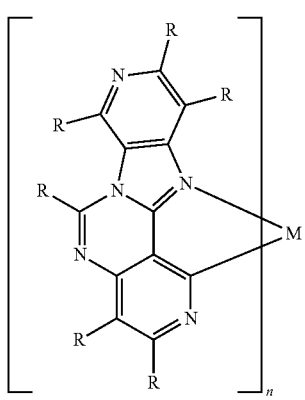
formula (2-O)
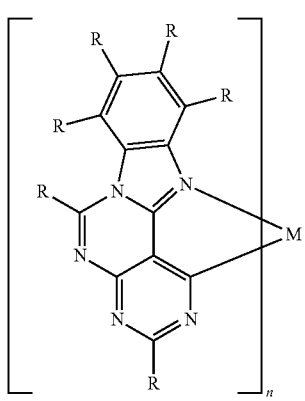
formula (2-P)
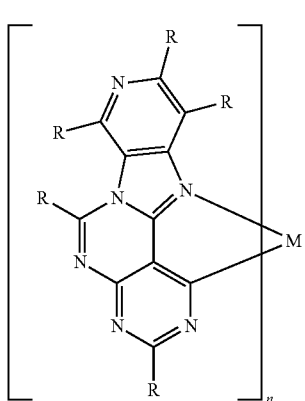
formula (2-Q)
where the symbols and indices used have the above-mentioned meanings.
Preferred embodiments of the moieties of the formula (3) are the moieties of the following formulae (3-A) to (3-F),
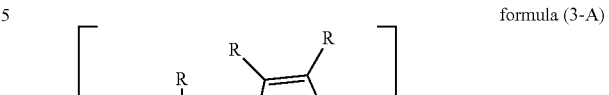
formula (3-A)
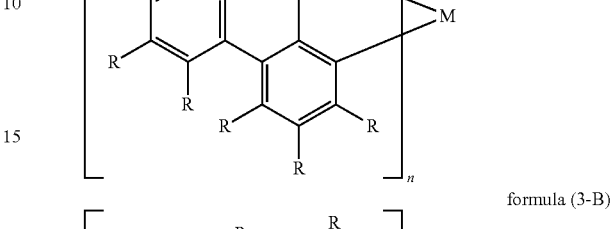
formula (3-B)
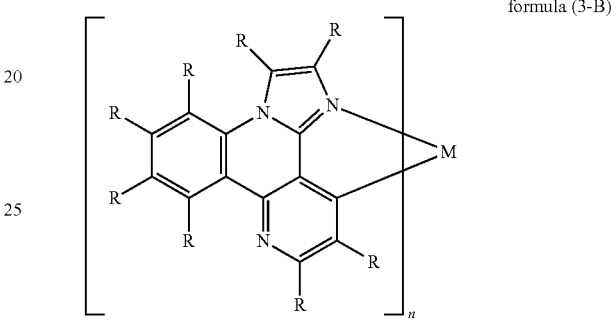
formula (3-C)
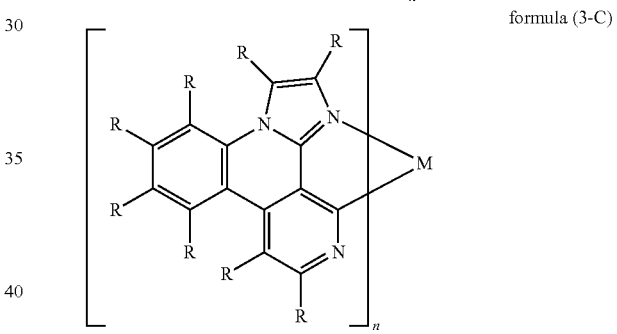
formula (3-D)
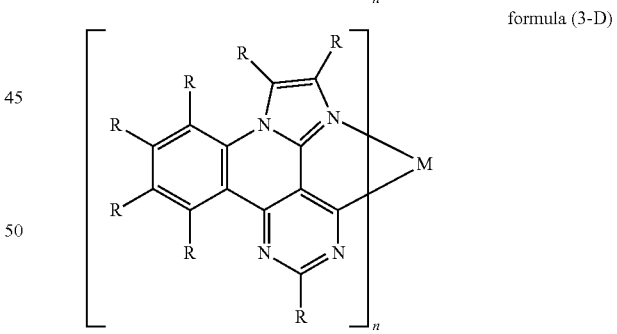
formula (3-E)
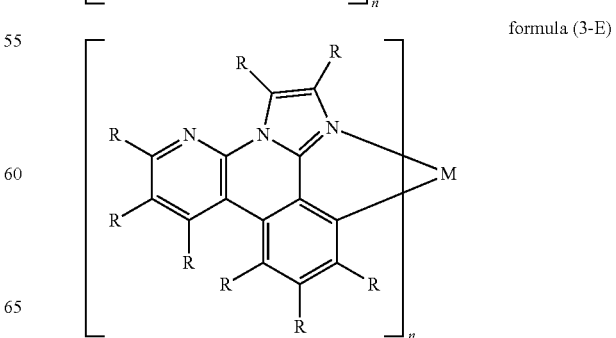

formula (3-F)

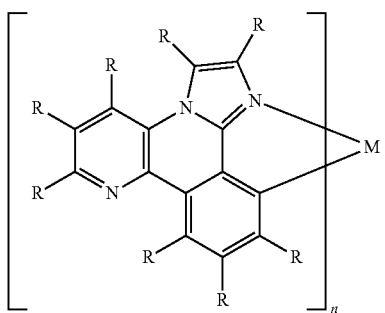

where the symbols and indices used have the above-mentioned meanings.

Preferred embodiments of the moieties of the formula (4) are the moieties of the following formulae (4-A) to (4-F), formula (4-A)

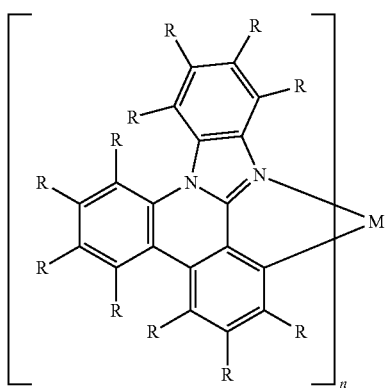

formula (4-B)

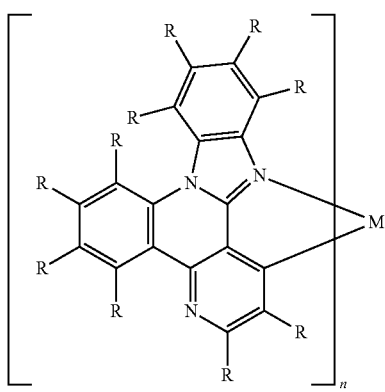

formula (4-C)

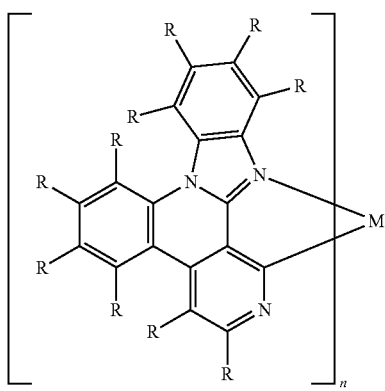

formula (4-D)

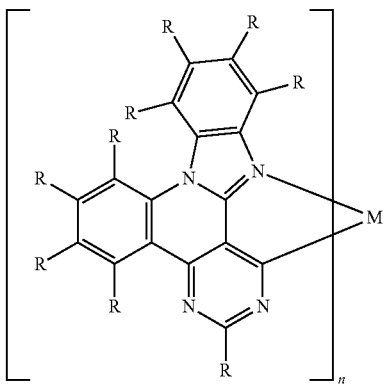

formula (4-E)

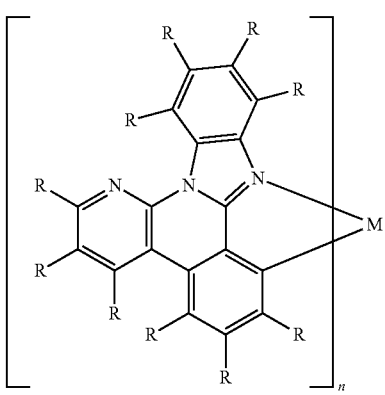

formula (4-F)

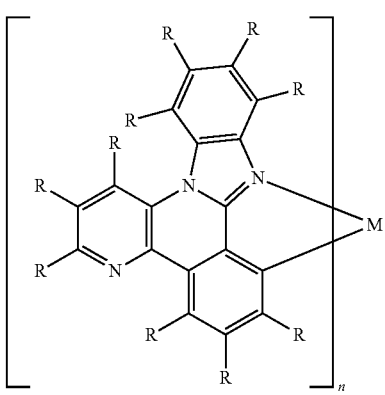

where the symbols and indices used have the above-mentioned meanings.

As described above, it is essential to the invention that two adjacent groups X stand for CR and the respective radicals R, together with the C atoms to which they are bonded, form a ring of the above-mentioned formula (5) or (6).

Preferred positions for adjacent groups X which stand for CR, where the respective radicals R, together with the C atoms to which they are bonded, form a ring of the above-mentioned formula (5) or (6), are depicted in the following formulae (2-1) to (2-5), (3-1) to (3-3) and (4-1) to (4-4):

formula (2-1)
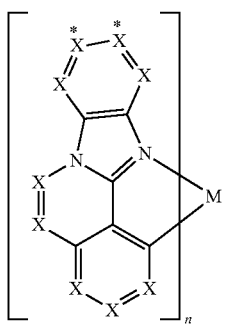
formula (3-1)
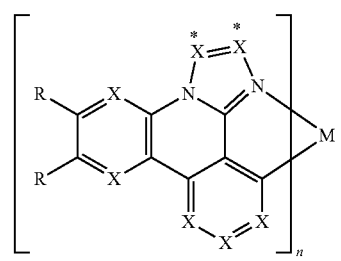
formula (2-2)
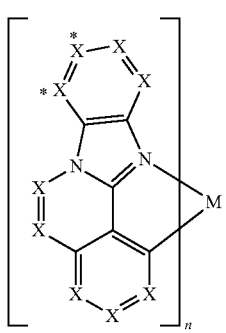
formula (3-2)
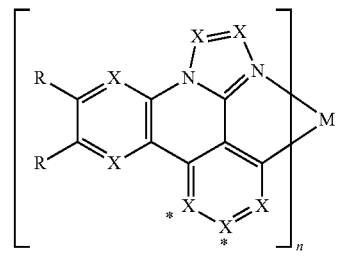
formula (2-3)
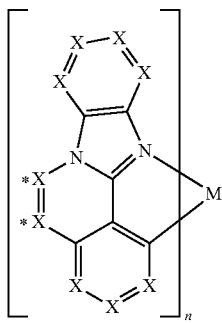
formula (3-3)
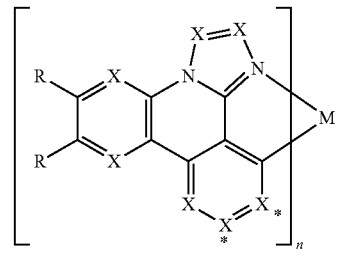
formula (2-4)
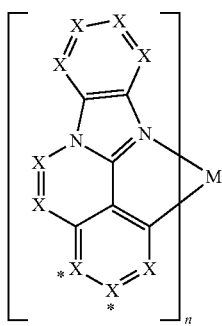
formula (4-1)
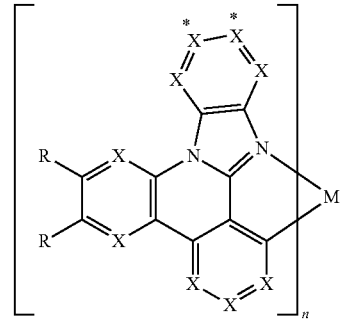
formula (2-5)
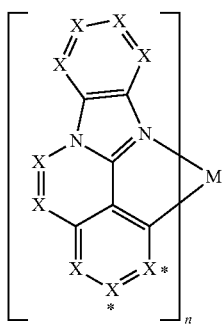
formula (4-2)
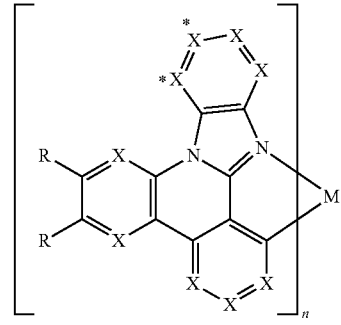

formula (4-3)

formula (4-4)

where the symbols and indices used have the above-mentioned meanings and * in each case denotes the positions which stand for CR, where the respective radicals R, together with the C atoms to which they are bonded, form a ring of the above-mentioned formula (5) or (6).

Preferred embodiments of the groups of the formulae (5) and (6) are described below.

It is essential in the case of the groups of the formulae (5) and (6) that they contain no acidic benzylic protons. Benzylic protons are taken to mean protons which are bonded to a carbon atom which is bonded directly to the heteroaromatic ligand. The absence of acidic benzylic protons is achieved in formula (5) through $A^1$ and $A^3$, if they stand for $C(R^3)_2$, being defined in such a way that $R^3$ is not equal to hydrogen. The absence of acidic benzylic protons is automatically achieved in formula (6) in that it is a bicyclic structure. Owing to the rigid spatial arrangement, $R^1$, if it stands for H, is significantly less acidic than benzylic protons, since the corresponding anion of the bicyclic structure is not mesomerism-stabilised. Even if $R^1$ in formula (6) stands for H, this is a non-acidic proton in the sense of the present application.

In a preferred embodiment of the structure of the formula (5), a maximum of one of the groups $A^1$, $A^2$ and $A^3$ stands for a heteroatom, in particular for O or $NR^3$, and the other two groups stand for $C(R^3)_2$ or $C(R^1)_2$ or $A^1$ and $A^3$ stand, identically or differently on each occurrence, for O or $NR^3$ and $A^2$ stands for $C(R^1)_2$. In a particularly preferred embodiment of the invention, $A^1$ and $A^3$ stand, identically or differently on each occurrence, for $C(R^3)_2$ and $A^2$ stands for $C(R^1)_2$ and particularly preferably for $C(R^3)_2$. Preferred embodiments of the formula (5) are thus the structures of the formulae (5-A), (5-B), (5-C) and (5-D), and a particularly preferred embodiment of the formula (5-A) is the structure of the formula (5-E), formula (5-A)

formula (5-B)

formula (5-C)

formula (5-D)

formula (5-E)

where $R^1$ and $R^3$ have the above-mentioned meanings and $A^1$, $A^2$ and $A^3$ stand, identically or differently on each occurrence, for O or $NR^3$.

In a preferred embodiment of the structure of the formula (6), the radicals $R^1$ which are bonded to the bridgehead stand for H, D, F or $CH_3$. Furthermore, $A^2$ preferably stands for $C(R^1)_2$ or O, and particularly preferably for $C(R^3)_2$. Preferred embodiments of the formula (6) are thus structures of the formulae (6-A) and (6-B), and a particularly preferred embodiment of the formula (6-A) is a structure of the formula (6-C), formula (6-A)

formula (6-B)

-continued formula (6-C)

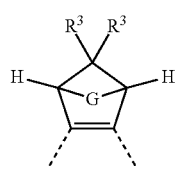

where the symbols used have the above-mentioned meanings.

Furthermore preferably, the group G in the formulae (6), (6-A), (6-B) and (6-C) stands for an ethylene group, which may be substituted by one or more radicals $R^2$, where $R^2$ preferably stands, identically or differently on each occurrence, for H or an alkyl group having 1 to 4 C atoms, or an ortho-arylene group having 6 to 10 C atoms, which may be substituted by one or more radicals $R^2$, but is preferably unsubstituted, in particular an ortho-phenylene group, which may be substituted by one or more radicals $R^2$, but is preferably unsubstituted.

In a further preferred embodiment of the invention, $R^3$ in the groups of the formulae (5) and (6) and in the preferred embodiments stands, identically or differently on each occurrence, for F, a straight-chain alkyl group having 1 to 10 C atoms or a branched or cyclic alkyl group having 3 to 20 C atoms, where in each case one or more non-adjacent $CH_2$ groups may be replaced by $R^2C=CR^2$ and one or more H atoms may be replaced by D or F, or an aromatic or heteroaromatic ring system having 5 to 14 aromatic ring atoms, which may in each case be substituted by one or more radicals $R^2$; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

In a particularly preferred embodiment of the invention, $R^3$ in the groups of the formulae (5) and (6) and in the preferred embodiments stands, identically or differently on each occurrence, for F, a straight-chain alkyl group having 1 to 3 C atoms, in particular methyl, or an aromatic or heteroaromatic ring system having 5 to 12 aromatic ring atoms, which may in each case be substituted by one or more radicals $R^2$, but is preferably unsubstituted; two radicals $R^3$ here which are bonded to the same carbon atom may form an aliphatic or aromatic ring system with one another and thus form a spiro system; furthermore, $R^3$ may form an aliphatic ring system with an adjacent radical R or $R^1$.

Examples of particularly suitable groups of the formula (5) are the groups (5-1) to (5-69) shown below:

(5-1)

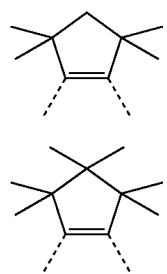

(5-2)

-continued (5-3)

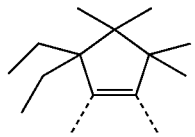

(5-4)

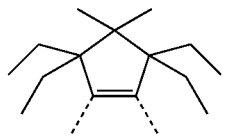

(5-5)

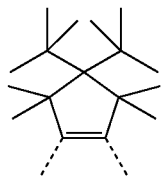

(5-6)

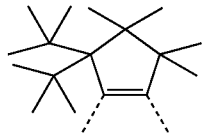

(5-7)

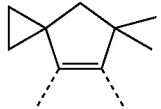

(5-8)

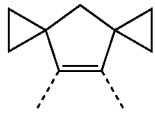

(5-9)

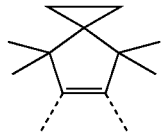

(5-10)

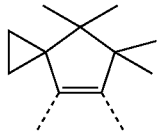

(5-11)

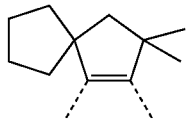

(5-12)

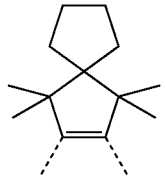

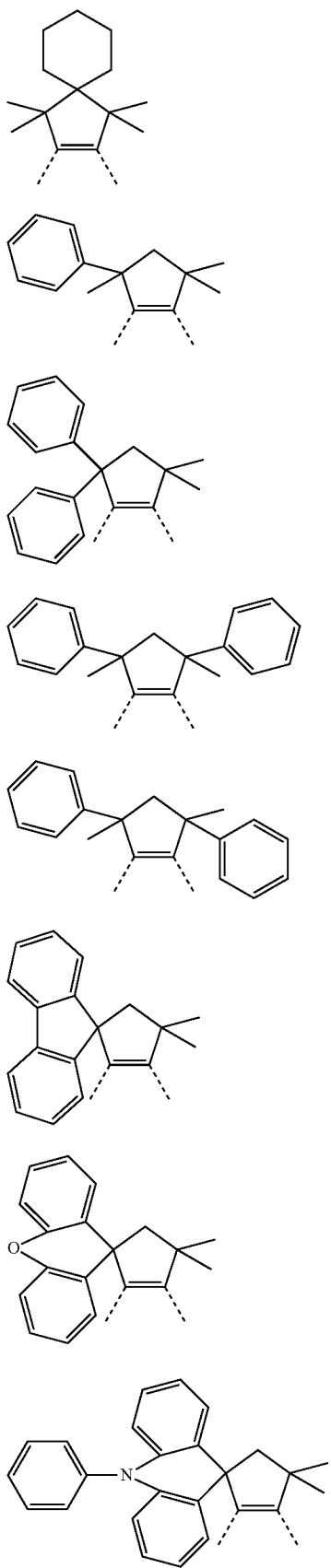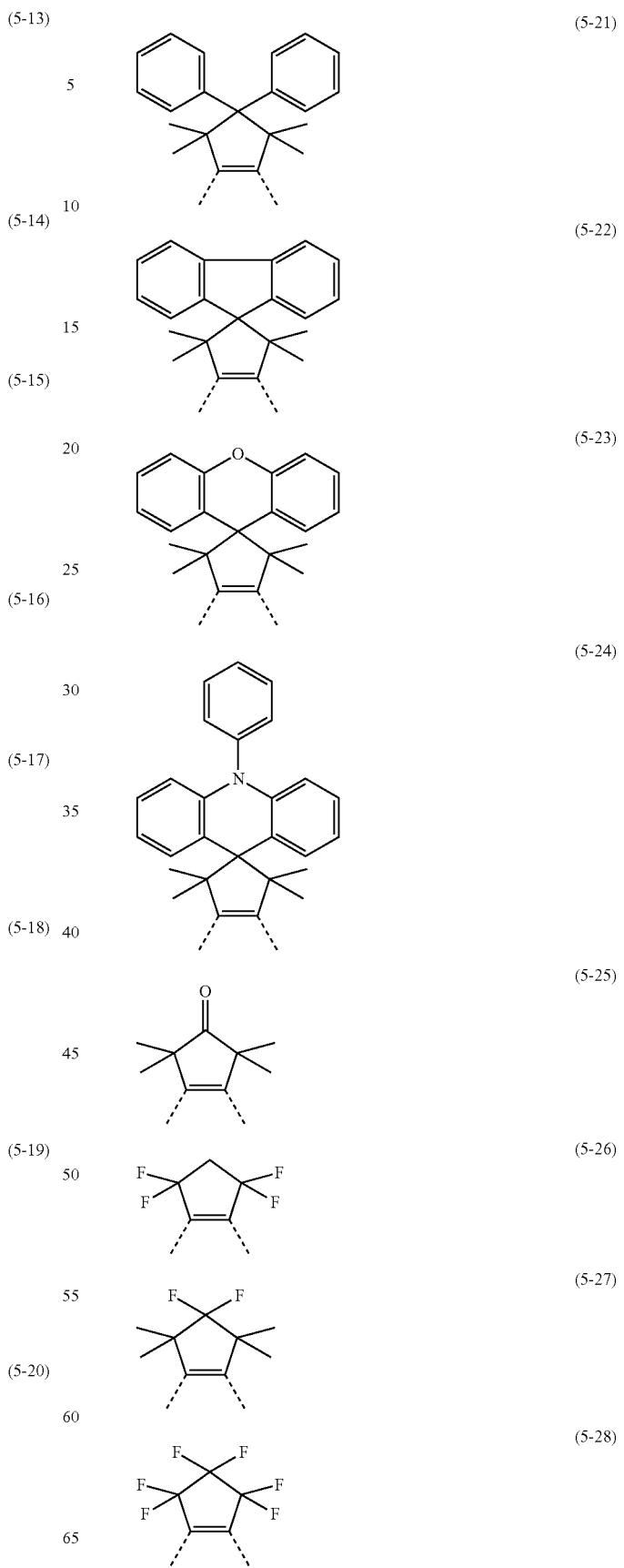

(5-29) 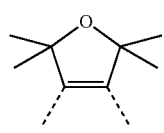
(5-30) 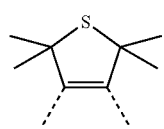
(5-31) 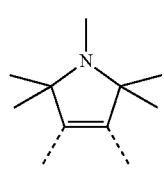
(5-32) 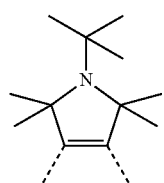
(5-33) 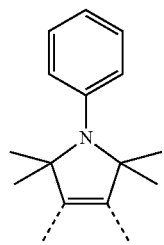
(5-34) 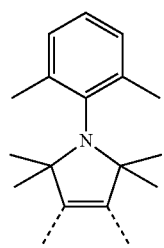
(5-35) 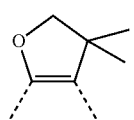
(5-36) 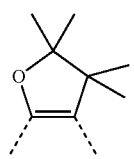
(5-37) 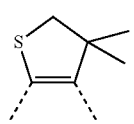
(5-38) 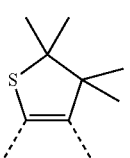
(5-39) 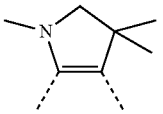
(5-40) 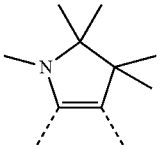
(5-41) 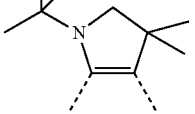
(5-42) 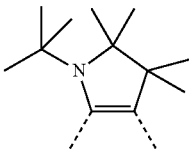
(5-43) 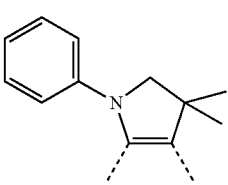
(5-44) 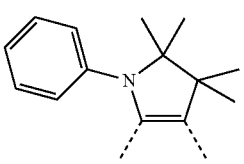
(5-45) 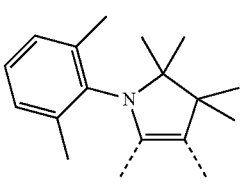
(5-46) 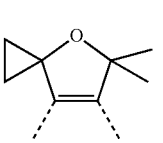
(5-47) 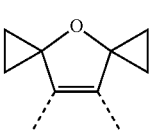

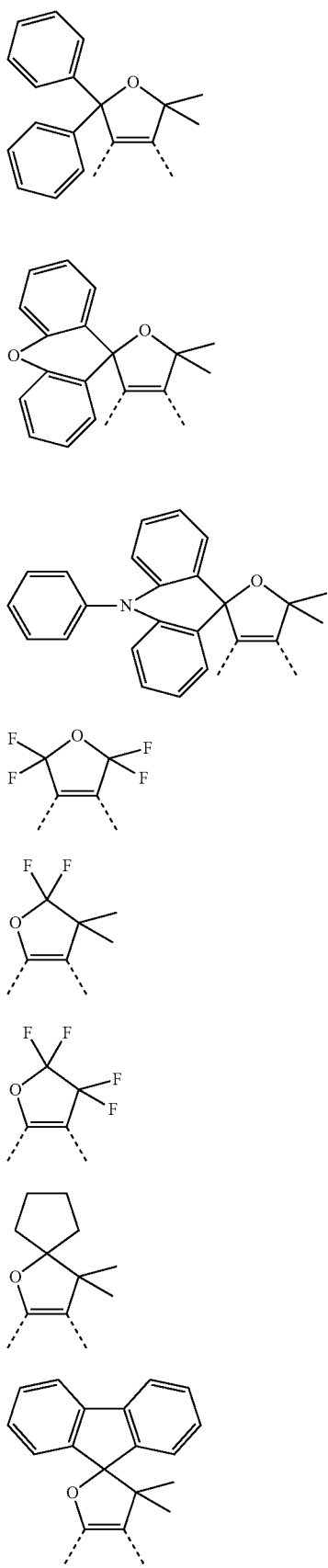
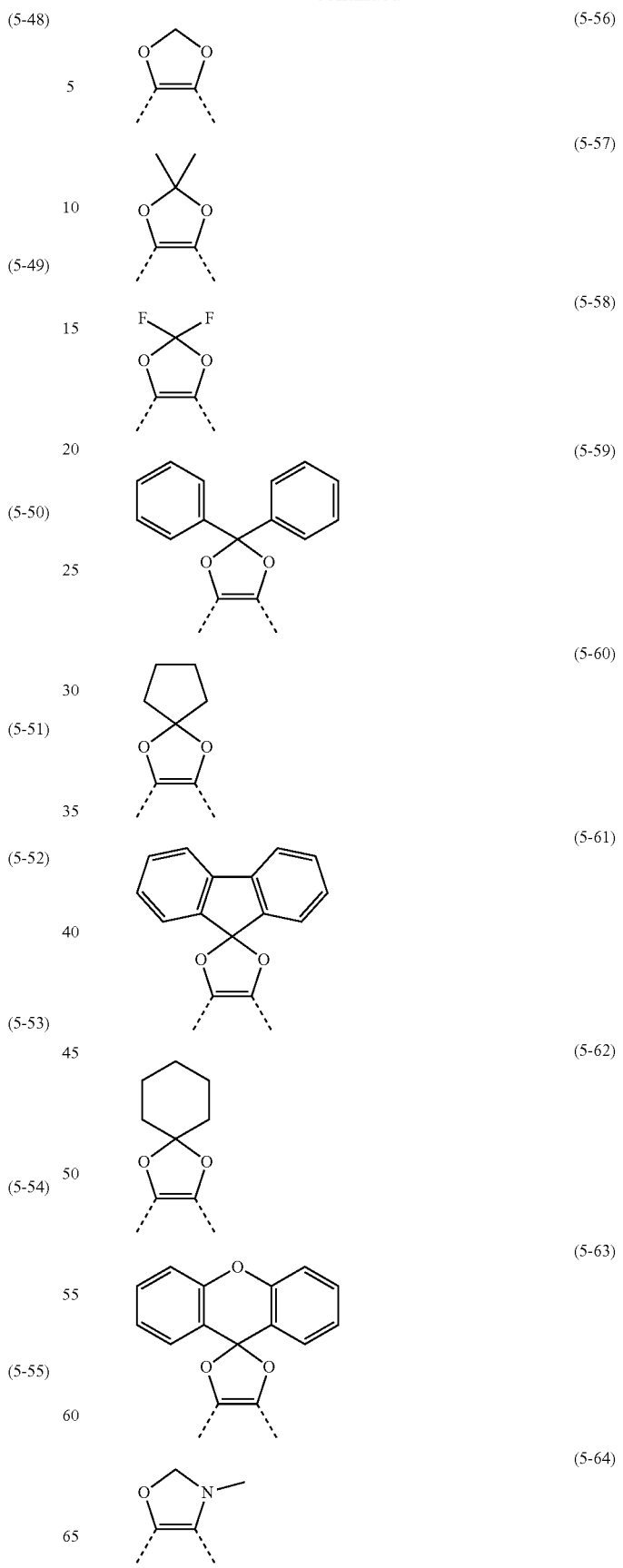

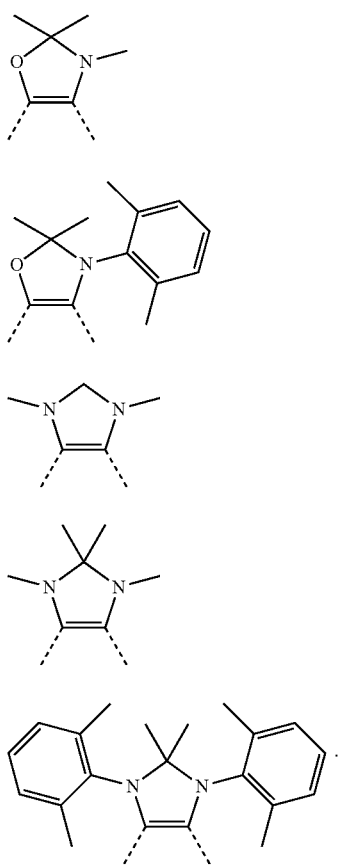
Examples of particularly suitable groups of the formula (6) are groups (6-1) to (6-21) shown below:
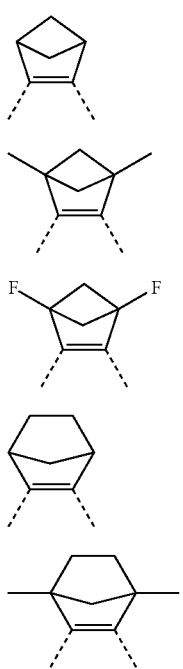
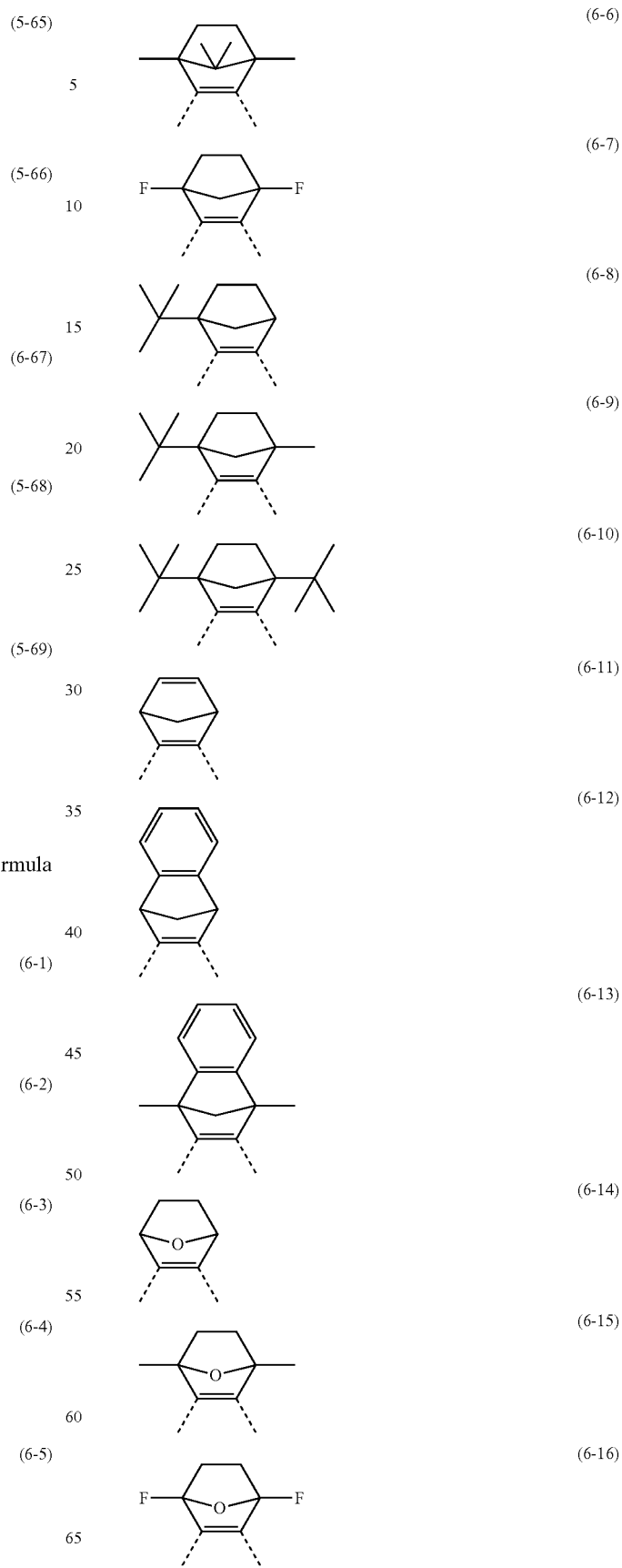

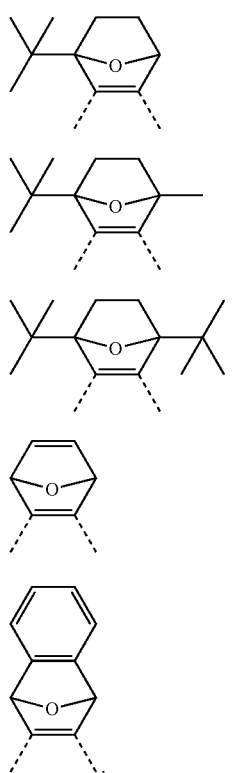

(6-17)

(6-18)

(6-19)

(6-20)

(6-21)

If one or more groups X in the moieties of the formula (2), (3) or (4) stand for nitrogen, it is furthermore preferred in the compounds according to the invention for a group R which is not equal to hydrogen or deuterium to be bonded as substituent adjacent to this nitrogen atom. This R is preferably a group selected from $CF_3$, $OCF_3$, alkyl or alkoxy groups having 1 to 10 C atoms, in particular branched or cyclic alkyl or alkoxy groups having 3 to 10 C atoms, aromatic or heteroaromatic ring systems or aralkyl or heteroaralkyl groups. These groups are bulky groups. Furthermore, this radical R may preferably also form a ring of the formula (5) or (6) with an adjacent radical R.

If the radical R which is adjacent to a nitrogen atom stands for an alkyl group, this alkyl group then preferably has 4 to 10 C atoms. It is furthermore preferably a secondary or tertiary alkyl group in which the secondary or tertiary C atom is either bonded directly to the ligand or is bonded to the ligand via a $CH_2$ group. This alkyl group is particularly preferably selected from the structures of the following formulae (R-1) to (R-33), where the linking of these groups to the ligand is in each case also drawn in:

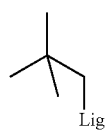

(R-1)

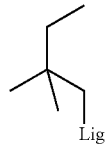

(R-2)

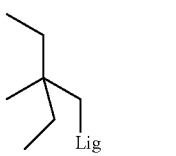

(R-3)

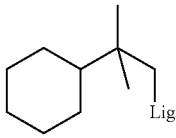

(R-4)

(R-5)

(R-6)

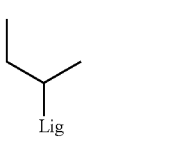

(R-7)

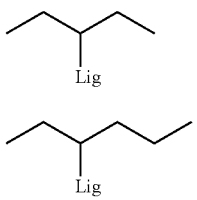

(R-8)

(R-9)

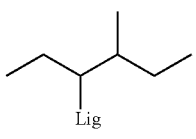

(R-10)

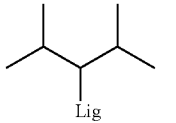

(R-11)

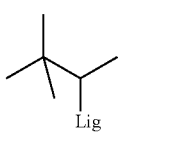

(R-12)

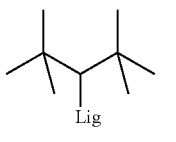

(R-13)

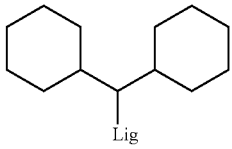

(R-14)

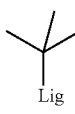
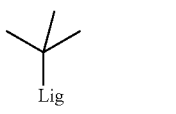

(R-15) 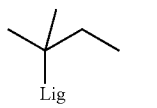
(R-16) 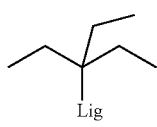
(R-17) 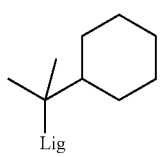
(R-18) 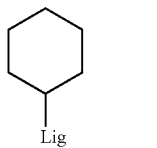
(R-19) 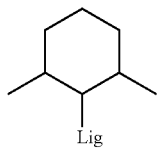
(R-20) 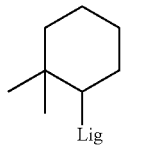
(R-21) 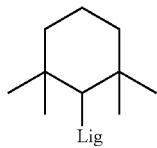
(R-22) 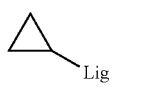
(R-23) 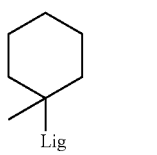
(R-24) 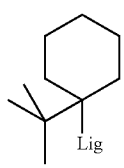

(R-25) 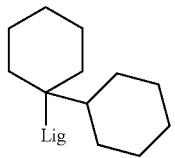
(R-26) 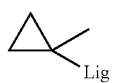
(R-27) 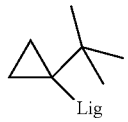
(R-28) 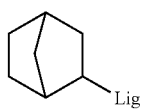
(R-29) 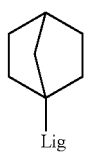
(R-30) 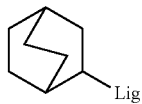
(R-31) 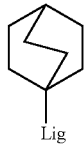
(R-32) 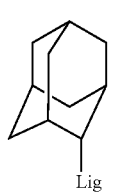
(R-33) 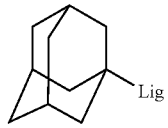

where Lig denotes the link of the alkyl group to the ligand.

If the radical R which is adjacent to a nitrogen atom stands for an alkoxy group, this alkoxy group then preferably has 3 to 10 C atoms. This alkoxy group is preferably selected from the structures of the following formulae (R-34) to (R-47), where the linking of these groups to the ligand is in each case also drawn in:

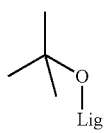 (R-34)

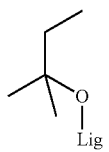 (R-35)

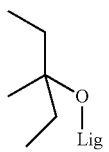 (R-36)

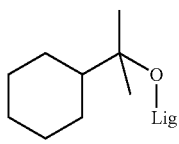 (R-37)

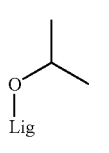 (R-38)

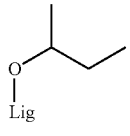 (R-39)

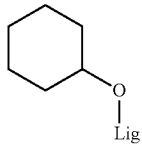 (R-40)

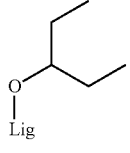 (R-41)

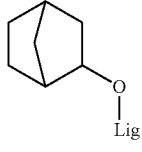 (R-42)

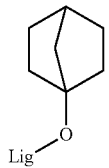 (R-43)

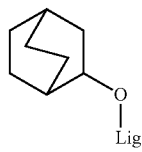 (R-44)

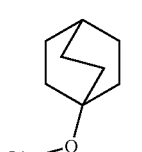 (R-45)

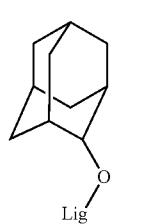 (R-46)

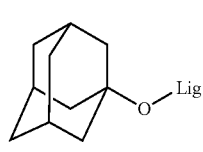 (R-47)

where Lig denotes the link of the alkyl group to the ligand.

If the radical R which is adjacent to a nitrogen atom stands for a dialkylamino group, each of these alkyl groups then preferably has 1 to 8 C atoms, particularly preferably 1 to 6 C atoms. Examples of suitable alkyl groups are methyl, ethyl or the structures shown above as groups (R-1) to (R-33). The dialkylamino group is particularly preferably selected from the structures of the following formulae (R-48) to (R-55), where the linking of these groups to the ligand is in each case also drawn in:

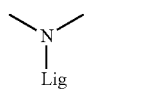 (R-48)

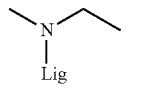 (R-49)

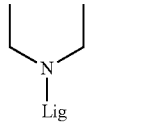 (R-50)

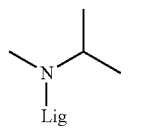 (R-51)

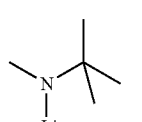 (R-52)

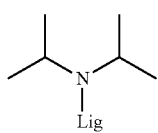 (R-53)
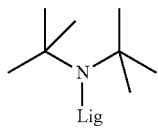 (R-54)
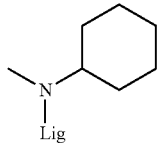 (R-55)
where Lig denotes the link of the alkyl group to the ligand.
If the radical R which is adjacent to a nitrogen atom stands for an aralkyl group, this aralkyl group is then preferably selected from the structures of the following formulae (R-56) to (R-69), where the linking of these groups to the ligand is in each case also drawn in:
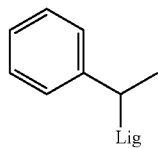 (R-56)
(R-57)
(R-58)
(R-59)
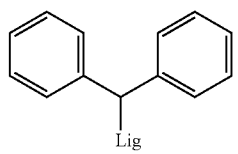 (R-60)
(R-61)
(R-62)
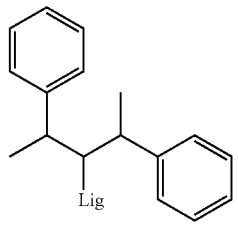 (R-63)
(R-64)
(R-65)
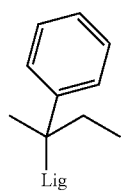 (R-66)
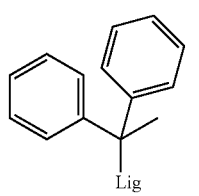 (R-67)
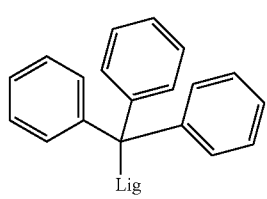

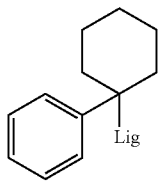 (R-68)

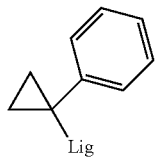 (R-69)

where Lig denotes the link of the aralkyl group to the ligand, and the phenyl groups may each be substituted by one or more radicals $R^1$.

If the radical R which is adjacent to a nitrogen atom stands for an aromatic or heteroaromatic ring system, this aromatic or heteroaromatic ring system then preferably has 5 to 30 aromatic ring atoms, particularly preferably 5 to 24 aromatic ring atoms. This aromatic or heteroaromatic ring system furthermore preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae (R-70) to (R-84), where the linking of these groups to the ligand is in each case also drawn in:

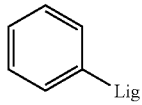 (R-70)

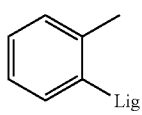 (R-71)

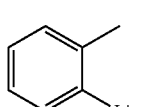 (R-72)

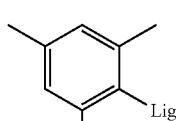 (R-73)

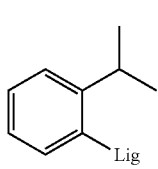 (R-74)

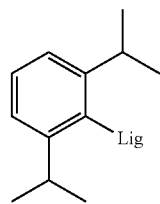 (R-75)

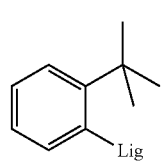 (R-76)

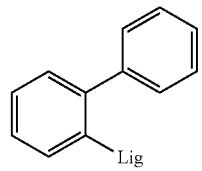 (R-77)

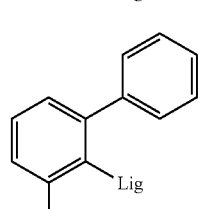 (R-78)

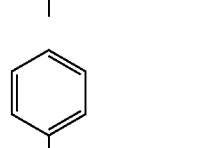 (R-79)

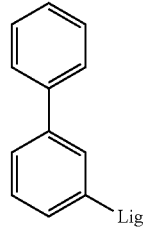 (R-80)

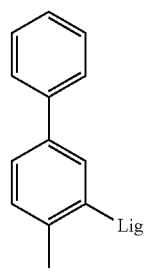 (R-81)

(R-82)
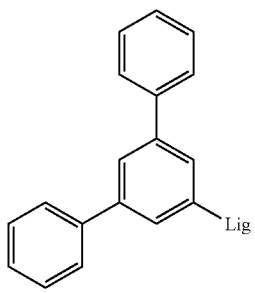

(R-83)
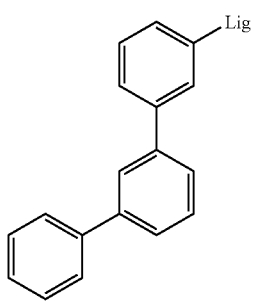

(R-84)
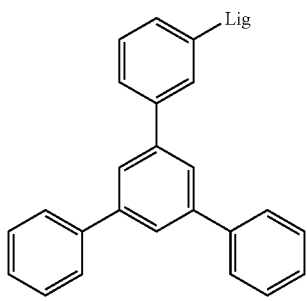

where Lig denotes the link of the aromatic or heteroaromatic ring system to the ligand, and the phenyl groups may each be substituted by one or more radicals $R^1$.

The heteroaromatic ring system is furthermore preferably selected from the structures of the following formulae (R-85) to (R-112), where the linking of these groups to the ligand is in each case also drawn in:

(R-85)
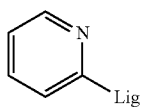

(R-86)
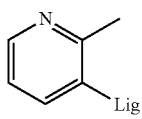

(R-87)
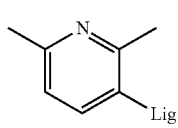

(R-88)
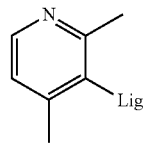

(R-89)
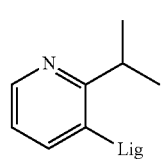

(R-90)
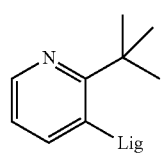

(R-91)

(R-92)

(R-93)
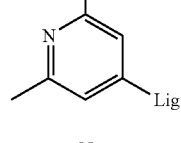

(R-94)

(R-95)
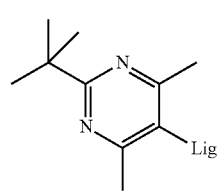

(R-96)
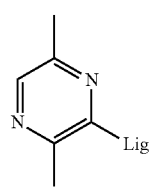

(R-97) 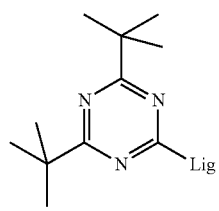
(R-98) 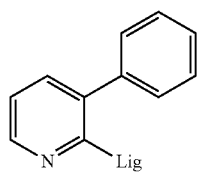
(R-99) 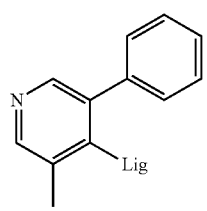
(R-100) 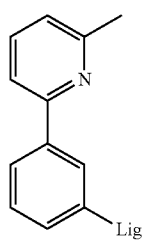
(R-101) 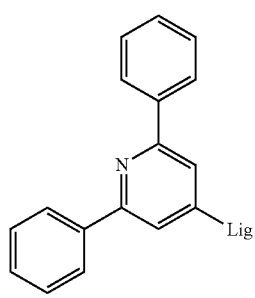
(R-102) 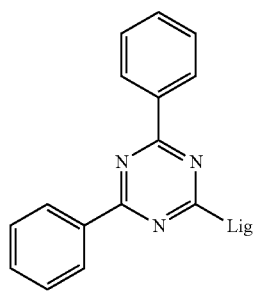
(R-103) 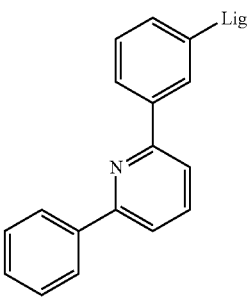
(R-104) 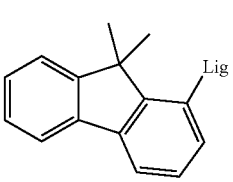
(R-105) 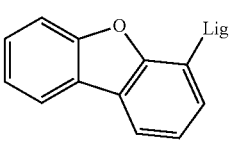
(R-106) 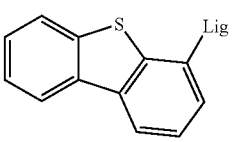
(R-107) 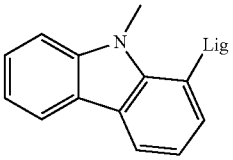
(R-108) 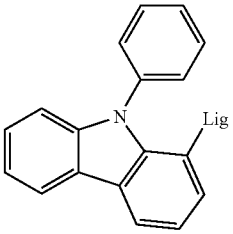
(R-109) 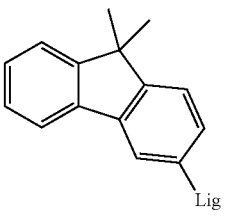
(R-110) 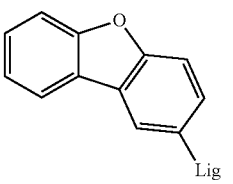

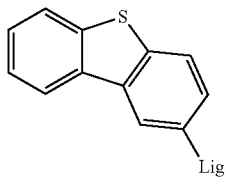

(R-111)

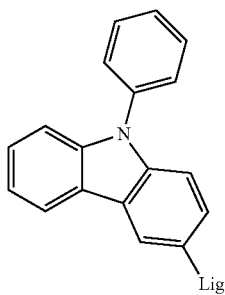

(R-112)

where Lig denotes the link of the aromatic or heteroaromatic ring system to the ligand, and the aromatic and heteroaromatic groups may each be substituted by one or more radicals $R^1$.

If further or other radicals R are bonded in the moiety of the formula (2), (3) or (4), these radicals R are preferably selected on each occurrence, identically or differently, from the group consisting of H, D, F, Br, I, $N(R^1)_2$, CN, $Si(R^1)_3$, $B(OR^1)_2$, $C(=O)R^1$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 30 aromatic ring atoms, which may in each case be substituted by one or more radicals $R^1$; two adjacent radical R or R with $R^1$ here may also form a mono- or polycyclic, aliphatic or aromatic ring system with one another. These radicals R are particularly preferably selected on each occurrence, identically or differently, from the group consisting of H, D, F, $N(R^1)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^1$; two adjacent radicals R or R with $R^1$ here may also form a mono- or polycyclic, aliphatic or aromatic ring system with one another.

It is furthermore possible for the substituent R which is bonded in the ortho-position to the metal coordination to represent a coordinating group which is likewise coordinated or bonded to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. Examples of moieties ML of the formula (2) are the structures of the following formulae (7) to (12):

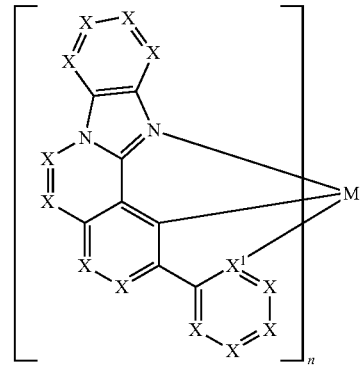

formula (7)

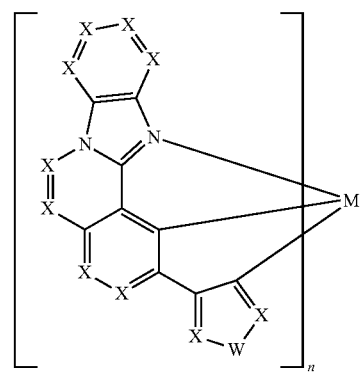

formula (8)

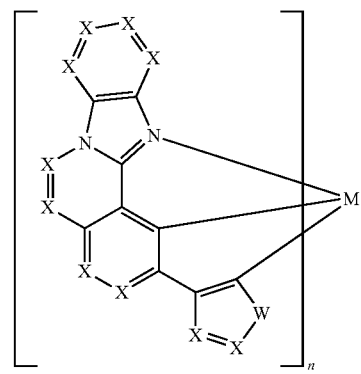

Formel (9)

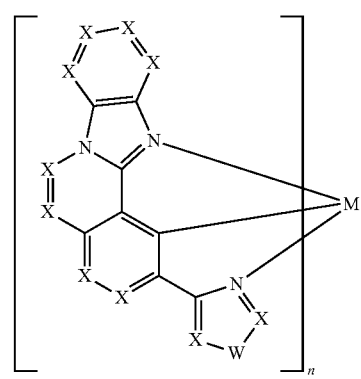

Formel (10)

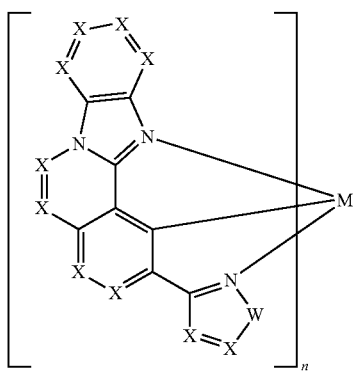

formula (11)

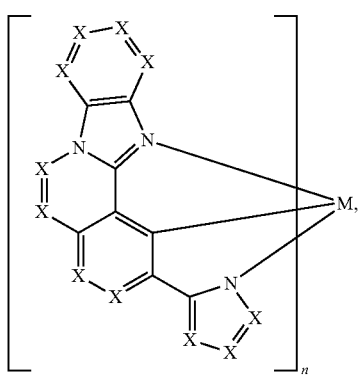

formula (12)

where the symbols and indices have the same meanings as described above, $X^1$ stands, identically or differently on each occurrence, for C or N and W stands, identically or differently on each occurrence, for S, O or $NR^1$.

Formulae (7) to (12) show, merely by way of example, how the substituent R can additionally coordinate to the metal. Other groups R which coordinate to the metal, for example also carbenes, are also accessible entirely analogously without further inventive step. Corresponding moieties ML based on formula (3) or formula (4) are likewise possible entirely analogously.

As described above, a bridging unit which links this ligand L to one or more further ligands L or L' may also be present instead of one of the radicals R. In a preferred embodiment of the invention, a bridging unit is present instead of one of the radicals R, in particular instead of the radicals R which are in the ortho- or meta-position to the coordinating atom, so that the ligands have a tridentate or polydentate or polypodal character. It is also possible for two such bridging units to be present. This results in the formation of macrocyclic ligands or in the formation of cryptates.

Preferred structures containing polydentate ligands are the metal complexes of the following formulae (13) to (18),

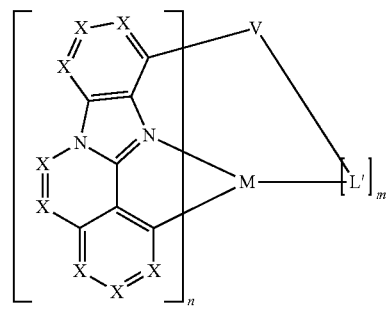

formula (13)

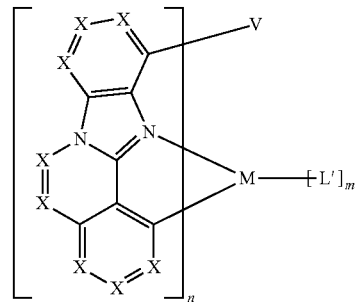

formula (14)

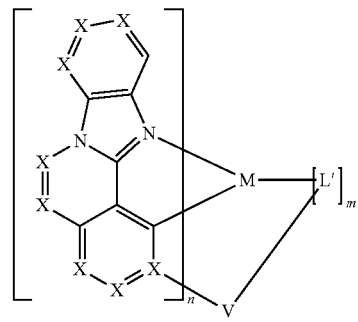

formula (15)

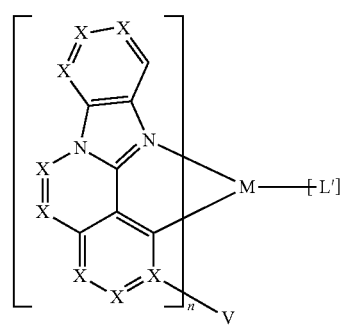

formula (16)

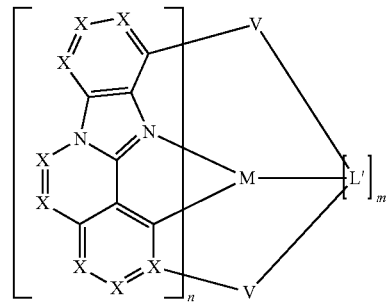

formula (17)

-continued

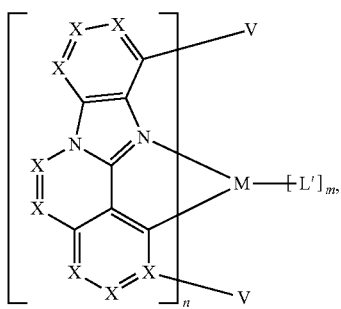

formula (18)

where the symbols and indices used have the above-mentioned meanings.

Structures having moieties of the formula (3) or formula (4) are accessible very analogously.

The ligands can likewise be bridged to one another via the cyclic group of the formula (5) or (6). This is depicted diagrammatically in the following formula (19) for a ligand of the formula (2):

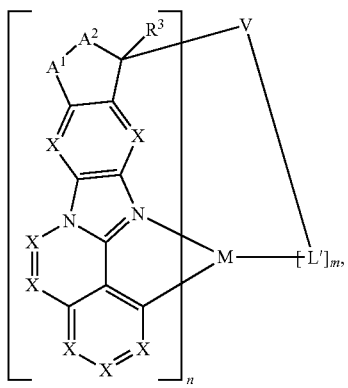

formula (19)

where the symbols and indices used have the above-mentioned meanings and V preferably stands for $CR^1$, a cyclopropyl group, which may be substituted by one or more radicals $R^1$, or a group of the formula $R^1$—$C(CH_2)_2$.

The linking to moieties of the formula (3) or formula (4) can take place analogously to formula (19).

V here preferably represents a single bond or a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged, particularly preferably neutral. The charge of V is preferably selected so that overall a neutral complex forms. The preferences mentioned above for the moiety $ML_n$ apply to the ligands, and n is preferably at least 2.

The precise structure and chemical composition of the group V does not have a significant effect on the electronic properties of the complex since the job of this group is essentially to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^1)^-$, $B(C(R^1)_2)_3$, $(R^1)B(C(R^1)_2)_3^-$, $B(O)_3$, $(R^1)B(O)_3^-$, $B(C(R^1)_2C(R^1)_2)_3$, $(R^1)B(C(R^1)_2C(R^1)_2)_3^-$, $B(C(R^1)_2O)_3$, $(R^1)B(C(R^1)_2O)_3^-$, $B(OC(R^1)_2)_3$, $(R^1)B(OC(R^1)_2)_3^-$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2C(R^1)_2)_3$, $(R^1)Si(C(R^1)_2Si(R^1)_2)_3$, $(R^1)Si(Si(R^1)_2Si(R^1)_2)_3$, N, NO, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)_3^+$, P, $P(R^1)^+$, PO, PS, $P(O)_3$, $PO(O)_3$, $P(OC(R^1)_2)_3$, $PO(OC(R^1)_2)_3$, $P(C(R^1)_2)_3$, $P(R^1)(C(R^1)_2)_3^+$, $PO(C(R^1)_2)_3$, $P(C(R^1)_2C(R^1)_2)_3$, $P(R^1)(C(R^1)_2C(R^1)_2)_3^+$, $PO(C(R^1)_2C(R^1)_2)_3$, $S^+$, $S(C(R^1)_2)_3^+$, $S(C(R^1)_2C(R^1)_2)_3^+$, or a unit of the formula (20), (21), (22), (23) or (24),

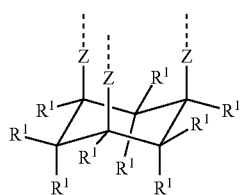

formula (20)

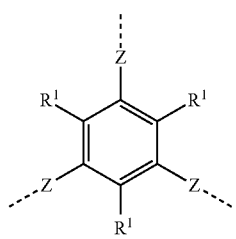

formula (21)

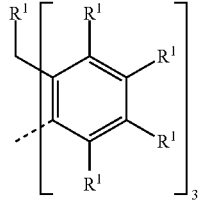

formula (22)

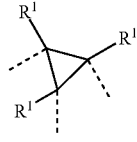

formula (23)

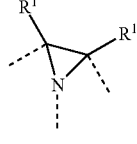

formula (24)

where the dashed bonds in each case indicate the bond to the part-ligands L or L', and Z is selected, identically or differently on each occurrence, from the group consisting of a single bond, O, S, S(=O), $S(=O)_2$, $NR^1$, $PR^1$, $P(=O)R^1$, $C(R^1)_2$, $C(=O)$, $C(=NR^1)$, $C(=C(R^1)_2)$, $Si(R^1)_2$ or $BR^1$. The other symbols used have the meanings given above.

If V stands for a group $CR_2$, the two radicals R may also be linked to one another, and consequently structures such as, for example, 9,9-fluorene, are also suitable groups V.

If V is a divalent group, i.e. bridges two ligands L to one another or one ligand L to L', V is preferably selected, identically or differently on each occurrence, from the group consisting of aus $BR^1$, $B(R^1)_2^-$, $C(R^1)_2$, $C(=O)$, $Si(R^1)_2$, $NR^1$, $PR^1$, $P(R^1)_2^+$, $P(=O)(R^1)$, $P(=S)(R^1)$, O, S, Se, or a unit of the formulae (25) to (34),

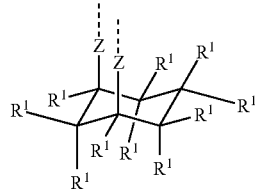

formula (25)

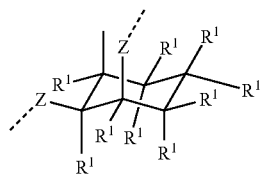

formula (26)

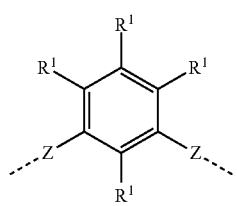

formula (27)

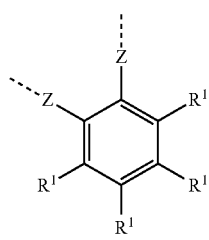

formula (28)

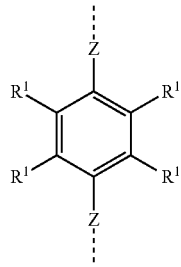

formula (29)

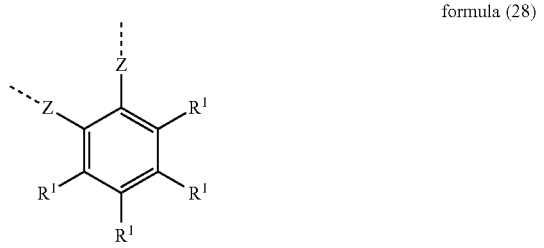

formula (30)

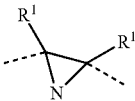

formula (31)

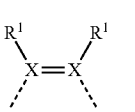

formula (32)

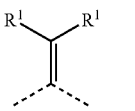

formula (33)

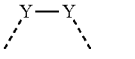

formula (34)

where the dashed bonds in each case indicate the bond to the part-ligands L or L', Y stands on each occurrence, identically or differently, for $C(R^1)_2$, $N(R^1)$, O or S, and the other symbols used each have the meanings indicated above.

Preferred ligands L' as occur in formula (1) are described below. The ligand groups L' can also be selected correspondingly if they are bonded to L via a bridging unit V, as indicated in formulae (13), (15) and (17).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl)phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-C≡$C^-$, tert-butyl-C≡$C^-$, arylacetylides, such as, for example, phenyl-C≡$C^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino)ethyl]-pyridine, 2-[1-(ethylimino)ethyl]pyridine, 2-[1-(isopropylimino)ethyl]pyridine, 2-[1-(tert-butylimino)ethyl]pyridine, diimines, such as, for example, 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino)ethane, 1,2-bis(2,6-diisopropylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(diphenylphosphino)butane, bis(dimethylphosphino)methane, bis(dimethylphosphino)ethane, bis(dimethylphosphino)propane, bis(diethylphosphino)methane, bis(diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol, bis(pyrazolyl) borates, bis(imidazolyl) borates, 3-(2-pyridyl)diazoles or 3-(2-pyridyl)triazoles.

Preferred tridentate ligands are borates of nitrogen-containing heterocycles, such as, for example, tetrakis(1-imidazolyl) borate and tetrakis(1-pyrazolyl) borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (35) to (66) is generally particularly suitable for this purpose, where one group is preferably bonded via a neutral nitrogen atom or a carbene carbon atom and the other group is preferably bonded via a negatively charged carbon atom or a negatively charged nitrogen atom. The ligand L' can then be formed from the groups of the formulae (35) to (66) through these groups bonding to one another in each case at the position denoted by #. The position at which the groups coordinate to the metal is denoted by *. These groups may also be bonded to the ligand L via one or two bridging units V.

formula (35)

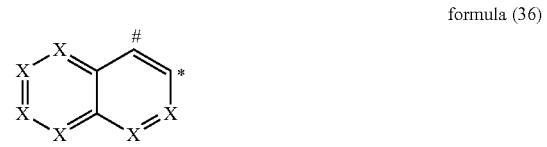

formula (36)

formula (37)

formula (38)


formula (39)

formula (40)

-continued
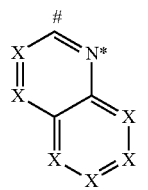
formula (41)
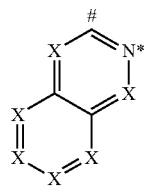
formula (42)
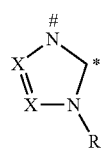
formula (43)
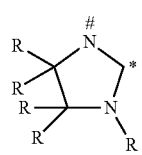
formula (44)
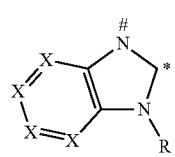
formula (45)
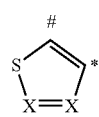
formula (46)
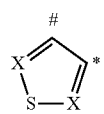
formula (47)
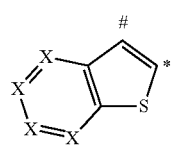
formula (48)
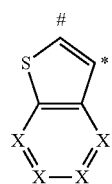
formula (49)
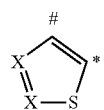
formula (50)
-continued
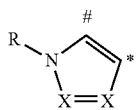
formula (51)
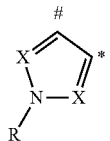
formula (52)
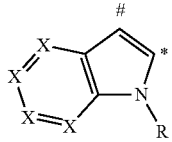
formula (53)
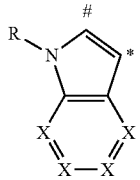
formula (54)
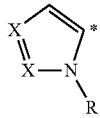
formula (55)
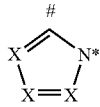
formula (56)
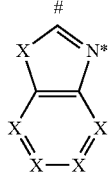
formula (57)
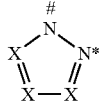
formula (58)
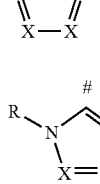
formula (59)
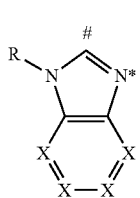
formula (60)

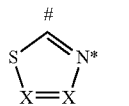 formula (61)

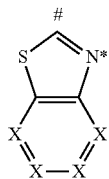 formula (62)

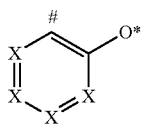 formula (63)

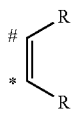 formula (64)

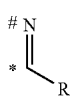 formula (65)

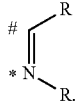 formula (66)

X here stands on each occurrence, identically or differently, for CR or N, where the above-mentioned limitation, that at least two adjacent groups X stand for CR and the radicals R form a ring of the formula (5) or (6), does not apply here; and R has the same meaning as described above. Preferably, a maximum of three symbols X in each group stand for N, particularly preferably a maximum of two symbols X in each group stand for N, very particularly preferably a maximum of one symbol X in each group stands for N. Especially preferably, all symbols X stand for CR.

The formulae (46) to (50), (61) and (62) may furthermore also contain oxygen instead of sulfur.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals R.

Likewise preferred ligands L' are 1,3,5-cis,cis-cyclohexane derivatives, in particular of the formula (67), 1,1,1-tri(methylene)methane derivatives, in particular of the formula (68), and 1,1,1-trisubstituted methanes, in particular of the formula (69) and (70),

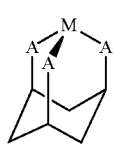 formula (67)

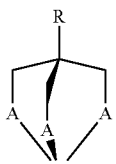 formula (68)

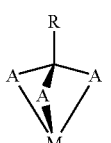 formula (69)

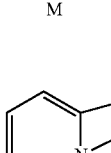 formula (70)

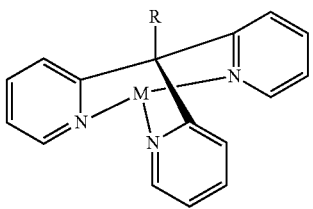

where the coordination to the metal M is shown in each of the formulae, R has the meaning given above, and A stands, identically or differently on each occurrence, for O⁻, S⁻, COO⁻, PR₂ or NR₂.

Preferred radicals R in the structures shown above are selected on each occurrence, identically or differently, from the group consisting of H, D, F, Br, $N(R^1)_2$, CN, $B(OR^1)_2$, $C(=O)R^1$, $P(=O)(R^1)_2$, a straight-chain alkyl group having 1 to 10 C atoms or a straight-chain alkenyl or alkynyl group having 2 to 10 C atoms or a branched or cyclic alkyl group having 3 to 10 C atoms, each of which may be substituted by one or more radicals $R^1$, where one or more H atoms may be replaced by D or F, or an aromatic or heteroaromatic ring system having 5 to 14 aromatic ring atoms, which may in each case be substituted by one or more radicals $R^1$; two or more adjacent radicals R here may also form a mono- or polycyclic, aliphatic, aromatic and/or benzo-fused ring system with one another. Particularly preferred radicals R are selected on each occurrence, identically or differently, from the group consisting of H, D, F, Br, CN, $B(OR^1)_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals $R^1$; two or more radicals R here may also form a mono- or polycyclic, aliphatic, aromatic and/or benzo-fused ring system with one another.

The complexes according to the invention can be facial or pseudofacial or they can be meridional or pseudomeridional.

The ligands L may also be chiral, depending on the structure. This is the case, in particular, if they contain a bicyclic group of the formula (6) or if they contain substituents, for example alkyl, alkoxy, dialkylamino or aralkyl groups, which have one or more stereocentres. Since the basic structure of the complex may also be a chiral structure, the formation of diastereomers and a number of enantiomer pairs is possible. The complexes according to the invention then encompass both the mixtures of the various diastereomers or the corresponding racemates and also the individual isolated diastereomers or enantiomers.

The preferred embodiments indicated above can be combined with one another as desired. In a particularly preferred embodiment of the invention, the preferred embodiments indicated above apply simultaneously.

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (71), with metal ketoketonates of the formula (72), with metal halides of the formula (73) or with dimeric metal complexes of the formula (74) or with metal complexes of the formula (75),

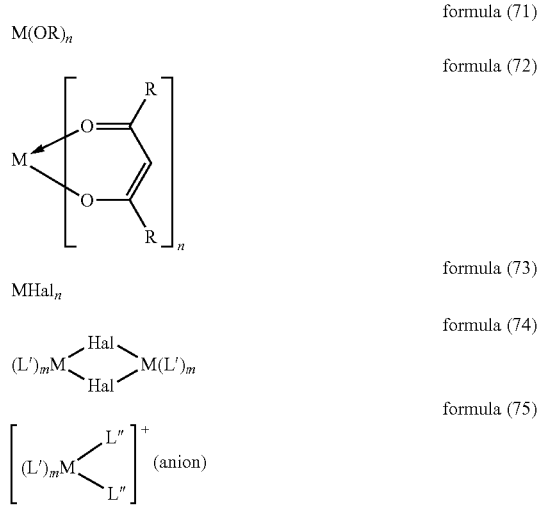

where the symbols M, m, n and R have the meanings indicated above, Hal=F, Cl, Br or I, L" stands for an alcohol, in particular for an alcohol having 1 to 4 C atoms, or a nitrile, in particular acetonitrile or benzonitrile, and (anion) stands for a non-coordinating anion, such as, for example, triflate It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. [IrCl$_2$(acac)$_2$]$^-$, for example Na[IrCl$_2$(acac)$_2$], are particularly suitable. Metal complexes with acetylacetonate derivatives as ligand, for example Ir(acac)$_3$ or tris(2,2,6,6-tetramethylheptane-3,5-dionato)iridium, and IrCl$_3$.xH$_2$O, where x usually stands for a number between 2 and 4.

Suitable platinum starting materials are, for example, PtCl$_2$, K$_2$[PtCl$_4$], PtCl$_2$(DMSO)$_2$, Pt(Me)$_2$(DMSO)$_2$ or PtCl$_2$(benzonitrile)$_2$.

The synthesis of the complexes is preferably carried out as described in WO 2002/060910, WO 2004/085449 and WO 2007/065523. Heteroleptic complexes can also be synthesised, for example, in accordance with WO 2005/042548. The synthesis here can also be activated, for example, thermally, photochemically and/or by microwave radiation. In a preferred embodiment of the invention, the reaction is carried out in the melt without the use of an additional solvent. "Melt" here means that the ligand is in molten form and the metal precursor is dissolved or suspended in this melt. In order to activate the reaction, it is furthermore also possible to add a Lewis acid, for example a silver salt or AlCl$_3$.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The compounds according to the invention can also be mixed with a polymer. It is likewise possible to incorporate these compounds covalently into a polymer. This is possible, in particular, with compounds which are substituted by reactive leaving groups, such as bromine, iodine, chlorine, boronic acid or boronic acid ester, or by reactive, polymerisable groups, such as olefins or oxetanes. These can be used as monomers for the production of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the above-mentioned compounds according to the invention, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to copolymers, where the units of the formula (1) or the preferred embodiments described above are present in amounts of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/022026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also contain further units, for example hole-transport units, in particular those based on triarylamines, and/or electron-transport units.

The present invention again furthermore relates to a formulation comprising a compound according to the invention or an oligomer, polymer or dendrimer according to the invention and at least one further compound. The further compound can be, for example, a solvent. However, the further compound can also be a further organic or inorganic compound which is likewise employed in the electronic device, for example a matrix material. This further compound may also be polymeric.

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention. Furthermore, the compounds according to the invention can be employed for the generation of singlet oxygen or in photocatalysis.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or redemitting triplet emitters.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where suitable p-dopants are metal oxides, for example $MoO_3$ or $WO_3$, or (per)fluorinated electron-deficient aromatic compounds. Further suitable p-dopants are HAT-CN (hexacyanohexaazatriphenylene) or the compound NPD9 from Novaled. A layer of this type simplifies hole injection in materials having a low HOMO, i.e. a large value of the HOMO.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished over the prior art by one or more of the following surprising advantages:

1. The compounds according to the invention are very highly suitable for use in electronic devices, in particular in organic electroluminescent devices, where they result in very good properties.
2. Organic electroluminescent devices comprising compounds of the formula (1) as emitting materials have a very long lifetime.
3. Organic electroluminescent devices comprising compounds of the formula (1) as emitting materials have excellent efficiency. In particular, the efficiency is significantly higher compared with analogous compounds which do not contain a structural unit of the formula (5) or formula (6).
4. Some of the metal complexes according to the invention have a very narrow emission spectrum, which results in high colour purity of the emission, as desired, in particular, for display applications.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are carried out, unless indicated otherwise, in dried solvents under a protective-gas atmosphere. The metal complexes are additionally handled with exclusion of light or under yellow light. The solvents and reagents can be purchased, for example, from Sigma-ALDRICH or ABCR. The respective numbers in square brackets or the numbers indicated for individual compounds relate to the CAS numbers of the compounds known from the literature.

A: Synthesis of the Synthones S:

Example S1: 1,1,2,2,3,3-Hexamethylindane-d18, S1

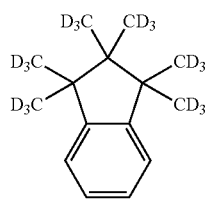 [SMILES: [2H]C([2H])([2H])C1(C([2H])([2H])[2H])c2ccccc2C(C([2H])([2H])[2H])(C([2H])([2H])[2H])C1(C([2H])([2H])[2H])C([2H])([2H])[2H]]

Preparation analogous to J. Baran, et al., J. Org. Chem. 1988, 53, 19, 4626.

18.7 ml (170 mmol) of titanium tetrachloride are added dropwise with vigorous stirring to a mixture, cooled to −78° C., of 160.7 g (1 mol) of 2-chloro-2-phenylpropane-d6 [53102-26-4], 230.8 g (2.4 mol) of 2,3-dimethylbut-2-ene-d12 [69165-86-2] and 2500 ml of anhydrous dichloromethane, and the mixture is stirred for a further 2 h. The cold reaction mixture is poured into 1500 ml of 3 N hydrochloric acid with vigorous stirring, stirred for a further 20 min., the org. phase is separated off, washed twice with 1000 ml of water each time, once with 500 ml of sat. sodium carbonate solution, once with 500 ml of sat. sodium chloride solution, dried over magnesium sulfate, the desiccant is filtered off, the filtrate is freed from dichloromethane in vacuo, and the residue is subjected to fractional distillation (core fraction 60-65° C., about 0.5 mbar). Yield: 163.1 g (740 mmol), 74%; purity: about 95% according to NMR.

The following compounds can be prepared analogously:

| Ex. | Starting materials | Product | Yield |
|---|---|---|---|
| S2 | 1716-38-7/563-79-1 | S2 | 68% |
| S3 | 934-53-2/563-79-1 Use of 4.4 mol of 2,3-dimethylbut-2-ene | S3 | 49% |

Example S4:
6-Bromo-1,1,3,3-tetramethylindan-5-ylamine, S4

6.23 g (10 mmol) of rac-BINAP and then 2.24 g (10 mmol) of palladium(II) acetate are added to a mixture of 166.0 g (500 mmol) of 5,6-dibromo-1,1,3,3-tetramethylindane S16a, 83.9 ml (500 mmol) of benzhydrylidenamine [1013-88-3], 52.9 g (550 mmol) of sodium tert-butoxide and 500 ml of toluene, and the mixture is subsequently heated under reflux for 16 h. After cooling, 500 ml of water are added, the org. phase is separated off, washed twice with 500 ml of sat. sodium chloride solution each time, the toluene is removed in a rotary evaporator, the residue is taken up in 1000 ml of THF, 250 ml of 2 N hydrochloric acid are added, and the reaction mixture is heated under reflux for 16 h. The solvent is removed in vacuo, the residue is taken up in 1000 ml of ethyl acetate, the org. phase is washed with sat. sodium hydrogencarbonate solution until pH=7 has been reached, the org. phase is dried over magnesium sulfate, the desiccant is filtered off, 500 g of silica gel are added to the filtrate, and the solvent is removed in vacuo. The loaded silica gel is placed on a silica-gel column (1500 g, slurried in n-heptane:ethyl acetate, 95:5 vv), firstly the benzophenone is eluted with n-heptane:ethyl acetate (95:5 vv), the eluent is then switched to ethyl acetate, and the product is eluted. Yield: 85.8 g (320 mmol), 64%; purity: about 95% according to $^1$H-NMR.

The following compounds can be prepared analogously:

| Ex. | Starting material | Product | Yield |
|---|---|---|---|
| S5 | 1311465-45-8 | S5 | 58% |

-continued
| Ex. | Starting material | Product | Yield |
|---|---|---|---|
| S6 | 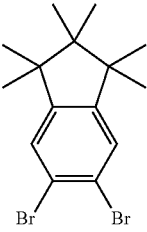 S24 Variant A, step A | 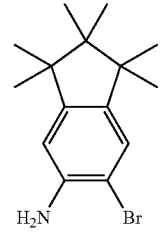 S6 | 67% |
| S7 | 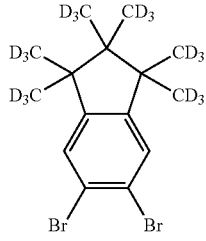 S25 Variant A, step A | 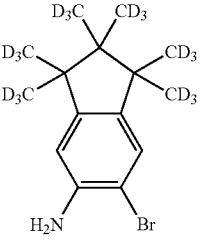 S7 | 66% |
| S8 | 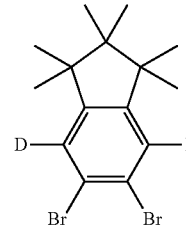 S26 Variant A, step A | 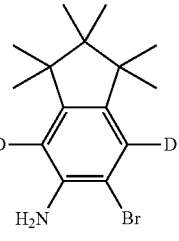 S8 | 65% |
| S9 | 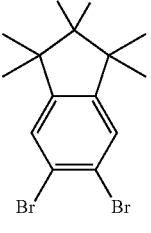 S29 Variant A, step A | 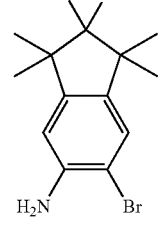 S9 | 59% |
| S10 | 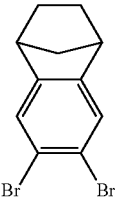 42810-32-2 | 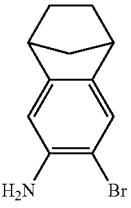 S10 | 61% |
-continued
| Ex. | Starting material | Product | Yield |
|---|---|---|---|
| S11 | 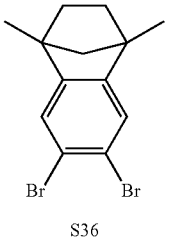 S36 Variant A, step A | 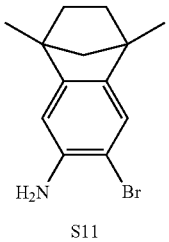 S11 | 63% |
| S12 | 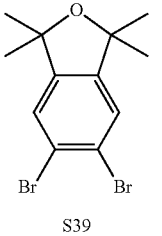 S39 Variant A, step A | 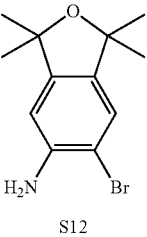 S12 | 58% |
| S13 | 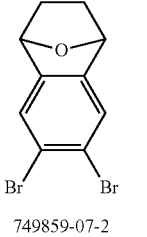 [SMILES: Brc1cc2c(cc1Br)C1CCC2O1] 749859-07-2 | 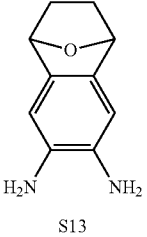 S13 | 55% |
| S14 | 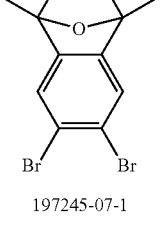 197245-07-1 | 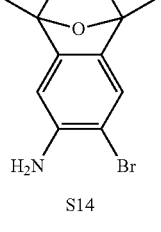 S14 | 36% |
| S15 | 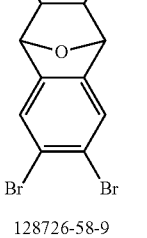 128726-58-9 | 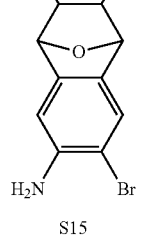 S15 | 71% |

Example S16:
1,1,3,3-Tetramethylindane-5,6-diamine, [83721-95-3], S16

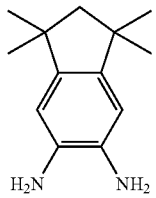

Variant A:
A: 5,6-Dibromo-1,1,3,3-tetramethylindane, S16a

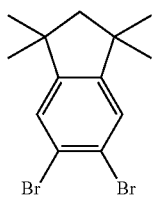

1.3 g of anhydrous iron(III) chloride and then, dropwise with exclusion of light, a mixture of 64.0 ml (1.25 mol) of bromine and 300 ml of dichloromethane are added to a solution of 87.2 g (500 mmol) of 1,1,3,3-tetramethylindane [4834-33-7] in 2000 ml of dichloromethane at such a rate that the temperature does not exceed 25° C., if necessary with countercooling using a cold-water bath. The reaction mixture is stirred at room temperature for a further 16 h, 500 ml of sat. sodium sulfite solution are then added slowly, the aqueous phase is separated off, the organic phase is washed three times with 1000 ml of water each time, dried over sodium sulfate, filtered through a short silica-gel column, and the solvent is then stripped off. Finally, the solid is recrystallised once from a little (about 100 ml) ethanol. Yield: 121.2 g (365 mmol), 73%; purity: about 95% according to $^1$H-NMR.

B: 1,1,3,3-Tetramethylindane-5,6-diamine, S16

9.34 g (15 mmol) of rac-BINAP and then 3.36 g (15 mmol) of palladium(II) acetate are added to a mixture of 121.2 g (365 mmol) of 5,6-dibromo-1,1,3,3-tetramethylindane, 153.2 ml (913 mmol) of benzhydrylidenamine [1013-88-3], 96.1 g (1.0 mol) of sodium tert-butoxide and 1000 ml of toluene, and the mixture is subsequently heated under reflux for 16 h. After cooling, 500 ml of water are added, the org. phase is separated off, washed twice with 500 ml of sat. sodium chloride solution each time, the toluene is removed in a rotary evaporator, the residue is taken up in 500 ml of THF, 200 ml of 2 N hydrochloric acid are added, and the reaction mixture is heated under reflux for 16 h. The solvent is removed in vacuo, the residue is taken up in 1000 ml of ethyl acetate, the org. phase is washed with sodium hydrogencarbonate solution until pH=7 has been reached, the org. phase is dried over magnesium sulfate, the desiccant is filtered off, 500 g of silica gel are added to the filtrate, and the solvent is removed in vacuo. The loaded silica gel is placed on a silica-gel column (1500 g, slurried in n-heptane:ethyl acetate, 95:5 vv), firstly the benzophenone is eluted with n-heptane:ethyl acetate (95:5 vv), the eluent is then switched to ethyl acetate, and the product is eluted. Yield: 56.8 g (278 mmol), 76%; purity: about 95% according to $^1$H-NMR.

Variant B:
A: 5,6-Dinitro-1,1,3,3-tetramethylindane, S16b

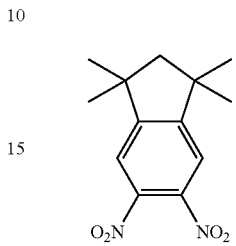

350 ml of 100% by weight nitric acid are slowly added dropwise to a vigorously stirred mixture, cooled to 0° C., of 87.2 g (500 mmol) of 1,1,3,3-tetramethylindane [4834-33-7] and 350 ml of 95% by weight sulfuric acid at such a rate that the temperature does not exceed +5° C. The reaction mixture is subsequently allowed to warm slowly to room temperature over the course of 2-3 h and is then poured into a vigorously stirred mixture of 6 kg of ice and 2 kg of water. The mixture is adjusted to pH=8-9 by addition of 40% by weight NaOH, extracted three times with 1000 ml of ethyl acetate each time, the combined org. phases are washed twice with 1000 ml of water each time, dried over magnesium sulfate, the ethyl acetate is then removed virtually completely in vacuo until crystallisation commences, and the crystallisation is completed by addition of 500 ml of heptane. The beige crystals obtained in this way are filtered off with suction and dried in vacuo. Yield: 121.6 g (460 mmol), 92%; purity: about 94% according to $^1$H-NMR, remainder about 4% of 4,6-dinitro-1,1,3,3-tetramethylindane. About 3% of 4,5-dinitro-1,1,3,3-tetramethylindane can be isolated from the mother liquor.

In some cases—in particular in the case of the bicyclic starting materials—the 4,5-isomer is also formed besides the 4,6-isomer in proportions of up to about 15% (see H. Tanida, J. Am. Chem. Soc. 1965, 87, 21, 4794). This can be separated off by recrystallisation or chromatography, then likewise hydrogenated and used further in the ligand synthesis. The 4,6-isomer likewise formed can be separated off by recrystallisation or chromatography, but proportions of a few % do not adversely affect the further preparation of the ligands, since the m-position of the amino functions does not allow cyclisation to give condensed ligand systems.

B: 1,1,3,3-Tetramethylindane-5,6-diamine, S16

126.9 g (480 mmol) of 5,6-dinitro-1,1,3,3-tetramethylindane, S16b, are hydrogenated in 1200 ml of ethanol on 10 g of palladium/charcoal at room temperature at a hydrogen pressure of 3 bar for 24 h. The reaction mixture is filtered through a Celite bed twice, the brown solid obtained after removal of the ethanol is distilled in a bulb tube (T about 160° C., p about $10^{-4}$ mbar). Yield: 90.3 g (442 mmol), 92%; purity: about 95% according to $^1$H-NMR.

1,1,3,3-Tetramethylindane-5,6-diamine dihydrochloride, S16×2HCl, can be obtained from S16 by dissolution in dichloromethane and introduction of gaseous HCl to saturation and subsequent removal of the dichloromethane.

The following compounds can be prepared analogously:
| Ex. | Starting material | Product | Variant Yield Step A + B |
|---|---|---|---|
| S17 | 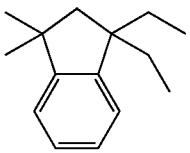 72977-53-8 | 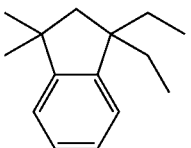 S17 | B 70% |
| S18 | 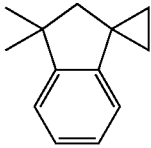 59770-92-2 | 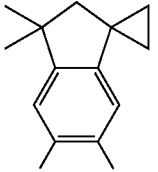 S18 | A 47% |
| S19 | 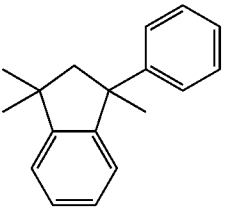 3910-35-8 | 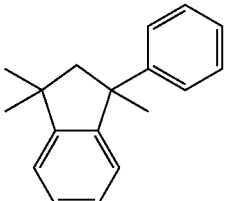 S19 | A 17% |
| S20 | 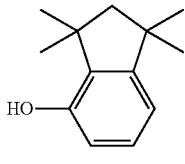 53718-36-8 | 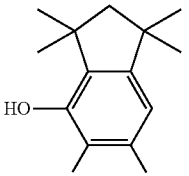 S20 | A 21% |
| S21 | 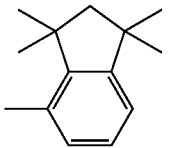 479070-73-0 | 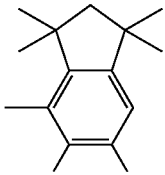 S21 | B 68% |
| S22 | 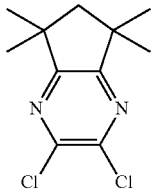 1311465-45-8 | 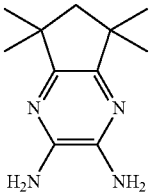 S22 | A only step B 64% |

-continued

| Ex. | Starting material | Product | Variant Yield Step A + B |
|---|---|---|---|
| S23 | 1203-17-4 | S23 | B 76% |
| S24 | 91324-94-6 | S24 | A 63% B 78% |
| S25 | S1 | S25 | B 80% |
| S26 | 142076-41-3 | S26 | B 76% |
| S27 | S2 | S27 | B 60% |

| Ex. | Starting material | Product | Variant Yield Step A + B |
|---|---|---|---|
| S28 | 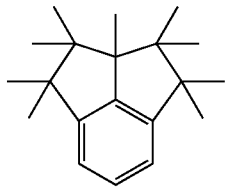<br>S3 | 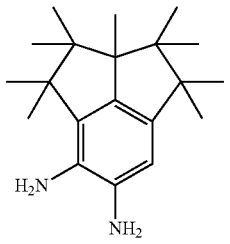<br>S28 | B<br>73% |
| S29 | 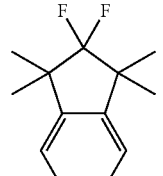<br>59508-28-0 | 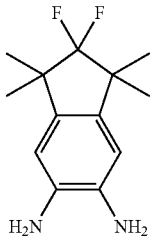<br>S29 | B<br>77% |
| S30 | 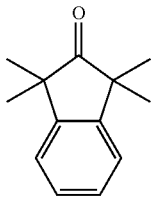<br>5689-12-3 | 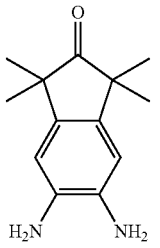<br>81864-09-7<br>S30 | A<br>56% |
| S31 | 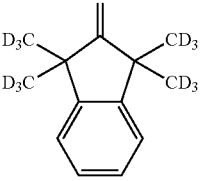<br>153735-62-7 | 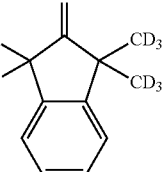<br>S31 | A<br>54% |
| S32 | 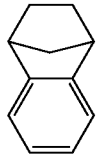<br>4486-29-7 | 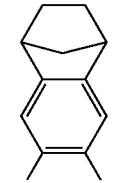<br>124639-03-8<br>S32 | B<br>71% |

-continued
| Ex. | Starting material | Product | Variant Yield Step A + B |
|---|---|---|---|
| S32 | 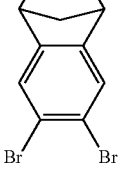<br>42810-32-2 | 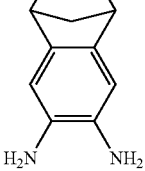<br>124639-03-8<br>S32 | A only step B 70% |
| S33 | 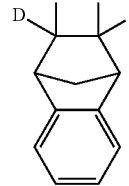<br>15087-73-7 | 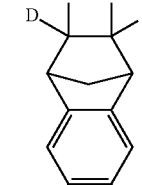<br>S33 | B 75% |
| S34 | 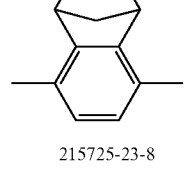<br>215725-23-8 | 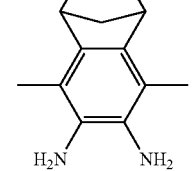<br>S34 | B 83% |
| S35 | 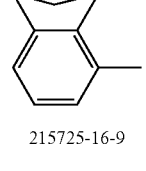<br>215725-16-9 | 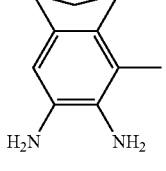<br>S35 | B 58% |
| S36 | 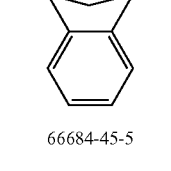<br>66684-45-5 | 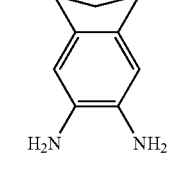<br>S36 | B 70% |

-continued
| Ex. | Starting material | Product | Variant Yield Step A + B |
|---|---|---|---|
| S37 | 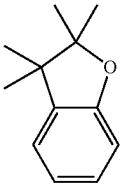<br>124797-68-8 | 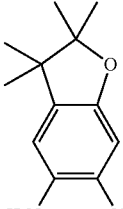<br>S37 | A<br>61% |
| S38 | 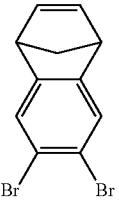<br>137495-57-9 | <br>S38 | A<br>only step B<br>36% |
| S39 | 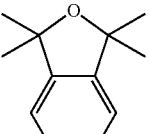<br>113710-83-1 | 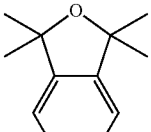<br>S39 | B<br>68% |
| S40 | 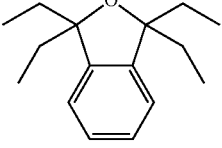<br>65089-09-0 | 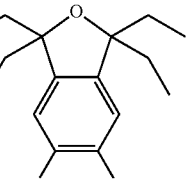<br>S40 | B<br>68% |
| S41 | 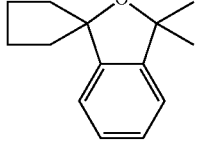<br>1020726-74-2 | 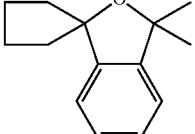<br>S41 | B<br>64% |
| S42 | 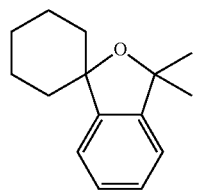<br>59043-55-9 | 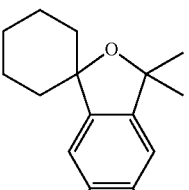<br>S42 | B<br>66% |

-continued
| Ex. | Starting material | Product | Variant Yield Step A + B |
|---|---|---|---|
| S43 | 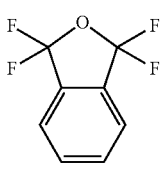 651-39-8 | 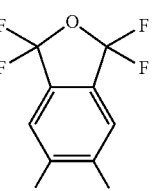 S43 | A 76% |
| S44 | 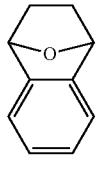 35185-96-7 | 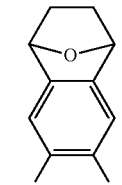 S44 | B 76% |
| S44 | 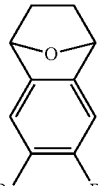 749859-07-2 | 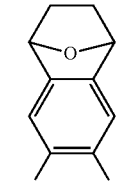 S44 | A only step B 57% |
| S45 | 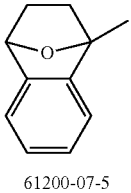 61200-07-5 | 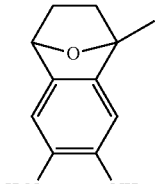 S45 | B 74% |
| S46 | 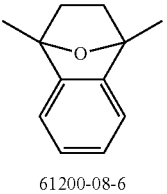 61200-08-6 | 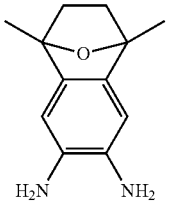 S46 | B 77% |
| S47 | 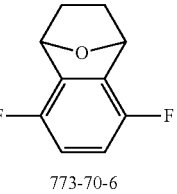 773-70-6 | 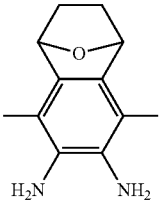 S47 | B 70% |

-continued

| Ex. | Starting material | Product | Variant Yield Step A + B |
|---|---|---|---|
| S48 | 78998-40-0 | S48 | B 59% |
| S49 | 78998-39-7 | S49 | A 62% |
| S50 | 121223-61-8 | S50 | A 60% |
| S51 | 106750-88-3 | S51 | A only step B 69% |
| S52 | 197245-07-1 | S52 | A only step B 74% |

-continued
| Ex. | Starting material | Product | Variant Yield Step A + B |
|---|---|---|---|
| S53 | 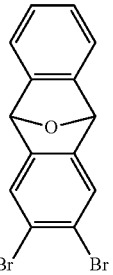<br>128726-58-9 | <br>S53 | A<br>only step B<br>67% |
| S54 | <br>300692-59-5 | <br>S54 | A<br>32% |
| S55 | 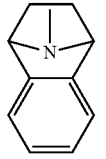<br>55257-99-3 | <br>S55 | A<br>26% |
| S56 | 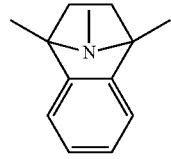<br>169384-31-0 | 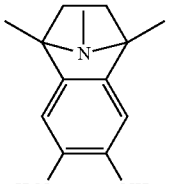<br>S56 | A<br>28% |
| S57 | 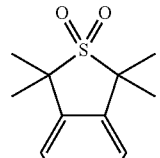<br>135050-18-9 | 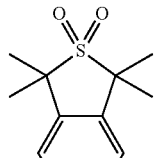<br>S57 | B<br>57% |

-continued
| Ex. | Starting material | Product | Variant Yield Step A + B |
|---|---|---|---|
| S58 | 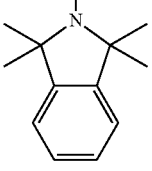 3723-85-1 | 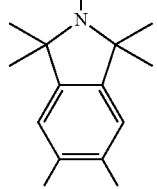 S58 | A 33% |
| S59 | 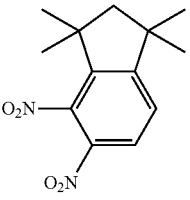 By-product from S16 | 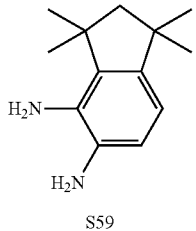 S59 | B Step B 2% |
| S60 | 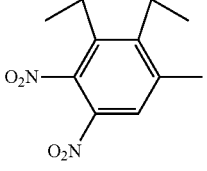 By-product from S21 | 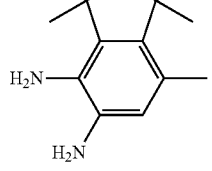 S60 | B Step B 5% |
| S61 | 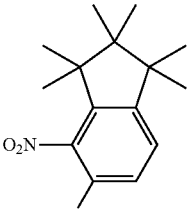 By-product from S24 | 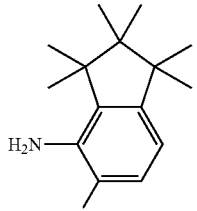 S61 | B Step B 5% |
| S62 | 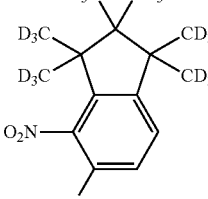 By-product from S25 | 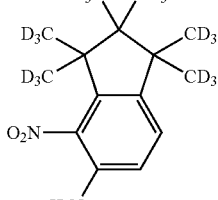 S62 | B Step B 4% |

| Ex. | Starting material | Product | Variant Yield Step A + B |
|---|---|---|---|
| S63 | By-product from S26 | S63 | B Step B 4% |
| S64 | By-product from S27 | S64 | B Step B 7% |
| S65 | 4228-35-7 | S65 | B Step B 91% |
| S66 | By-product from S35 | S66 | B Step B 16% |

Example S67: 7-Bromo-1,2,3,4-tetrahydro-1,4-methanonaphthalene-6-carbaldehyde, S67

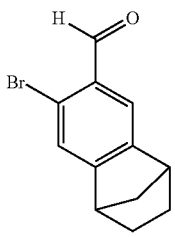 [SMILES: O=Cc1cc2c(cc1Br)C1CCC2C1]

Procedure analogous to J. Organomet. Chem., L. S. Chen et al., 1980, 193, 283-292. 40 ml (100 mmol) of n-BuLi, 2.5 M in hexane, pre-cooled to −110° C., are added to a solution, cooled to −110° C., of 30.2 g (100 mmol) of 6,7-dibromo-1,2,3,4-tetrahydro-1,4-methanonaphthalene [42810-32-2] in a mixture of 1000 ml of THF and 1000 ml of diethyl ether at such a rate that the temperature does not exceed −105° C. The mixture is stirred for a further 30 min., a mixture, pre-cooled to −110° C., of 9.2 ml (120 mmol) of DMF and 100 ml of diethyl ether is then added dropwise, the mixture is then stirred for a further 2 h, allowed to warm to −10° C., 1000 ml of 2 N HCl are added, and the mixture is stirred at room temperature for a further 2 h. The org. phase is separated off, washed once with 500 ml of water, once with 500 ml of sat. sodium chloride solution, dried over magnesium sulfate, the solvent is removed in vacuo, and the residue is subjected to a bulb-tube distillation (T about 90° C., p about $10^{-4}$ mbar). Yield: 15.8 g (63 mmol), 63%; purity: about 95% according to $^1$H-NMR.

6-Bromo-7-formyl-1,2,3,4-tetrahydro-1,4-epoxynaphthalene, S68, can be prepared analogously.

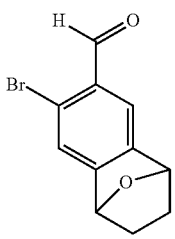 [SMILES: O=Cc1cc2c(cc1Br)C1CCC2O1]

Use of 30.4 g (100 mmol) of 6,7-dibromo-1,2,3,4-tetrahydro-1,4-epoxynaphthalene [749859-07-2]. Yield: 14.4 g (54 mmol), 54%; purity: >95% according to ¹H-NMR.

Example S69: 2-(N-Pivaloylamido)benzaldehyde, S69

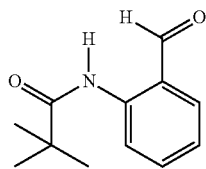

A mixture of 18.5 g (100 mmol) of 2-bromobenzaldehyde [6630-33-7], 14.2 g (140 mmol) of pivalamide [754-10-9], 81.5 g (250 mmol) of caesium carbonate, 1.7 g (3 mmol) of 9,9-dimethyl-4,5-bis(diphenylphosphino)xanthene and 630 mg (2.8 mmol) of palladium(II) acetate in 400 ml of dioxane is stirred at 100° C. for 4 h. After cooling, the solvent is removed in vacuo, the residue is taken up in 1000 ml of ethyl acetate, the org. phase is washed three times with 300 ml of water each time and once with 300 ml of sat. sodium chloride solution and filtered through a short silica-gel column. The solids obtained after the solvent has been stripped off in vacuo are reacted further. Yield: 19.3 g (94 mmol), 94%. Purity: >95% according to ¹H-NMR.

The following derivatives can be prepared analogously:

| Ex. | Bromo-arylaldehyde | Amide | Product | Yield |
|---|---|---|---|---|
| S70 | 6630-33-7 | 20923-67-5 | S70 | 89% |
| S71 | 6630-33-7 | 13146-40-2 | S71 | 87% |
| S72 | 6630-33-7 | 62641-207 | S72 | 92% |
| S73 | 229948-71-4 | 754-10-9 | S73 | 95% |
| S74 | 229948-71-4 | 6045-07-4 | S74 | 94% |

-continued
| Ex. | Bromo-arylaldehyde | Amide | Product | Yield |
|---|---|---|---|---|
| S75 | 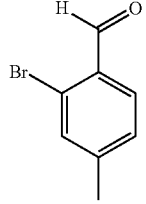<br>824-54-4 | 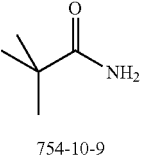<br>754-10-9 | 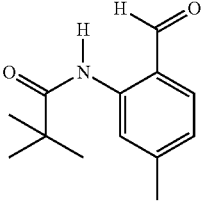<br>S75 | 93% |
| S76 | <br>90221-55-9 | <br>754-10-9 | <br>S76 | 94% |
| S77 | 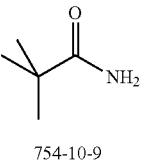<br>90221-55-9 | 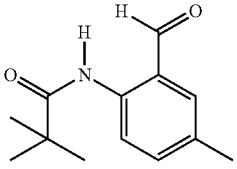<br>4380-68-1 | <br>S77 | 88% |
| S78 | <br>1000990-16-8 | 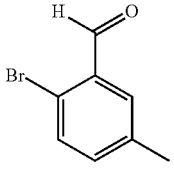<br>754-10-9 | 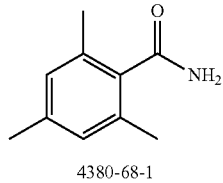<br>S78 | 81% |
| S79 | 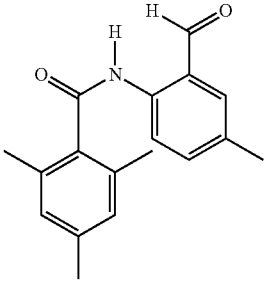<br>246139-77-5 | <br>754-10-9 | <br>S79 | 90% |
| S80 | 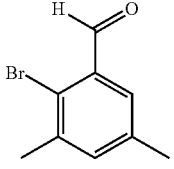<br>246139-77-5 | 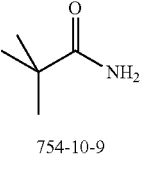<br>1123-24-6 | 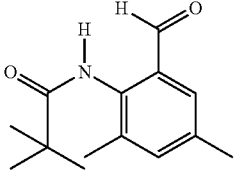<br>S80 | 91% |

| Ex. | Bromo-arylaldehyde | Amide | Product | Yield |
|---|---|---|---|---|
| S81 | 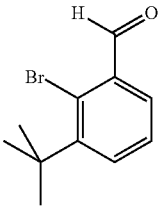<br>1289049-94-0 | 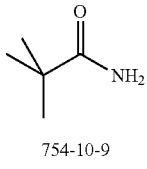<br>754-10-9 | 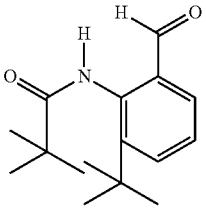<br>S81<br>Chromatographic purification | 21% |
| S82 | 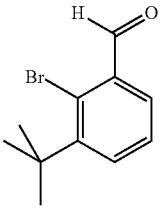<br>1289049-94-0 | 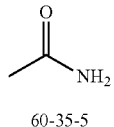<br>60-35-5 | 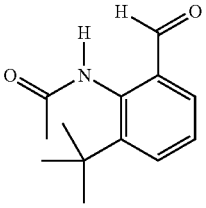<br>S82<br>Chromatographic purification | 27% |
| S83 | 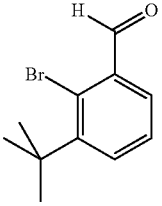<br>1289049-94-0 | 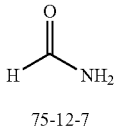<br>75-12-7 | 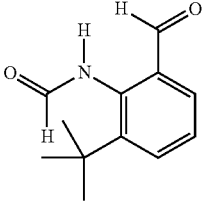<br>S83<br>Chromatographic purification | 33% |
| S84 | 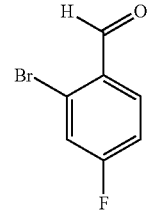<br>59142-68-6 | 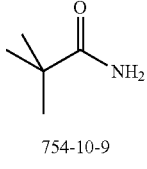<br>754-10-9 | 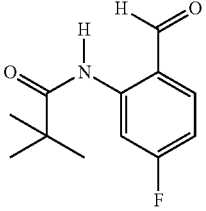<br>S84 | 93% |
| S85 | 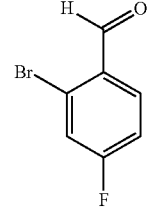<br>59142-68-6 | 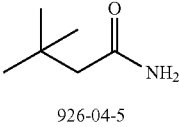<br>926-04-5 | 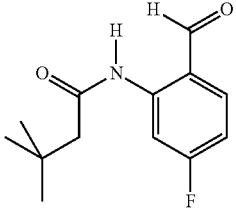<br>S85 | 95% |

| Ex. | Bromo-arylaldehyde | Amide | Product | Yield |
|---|---|---|---|---|
| S86 | 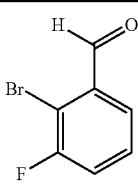<br>891180-59-9 | 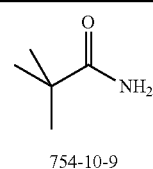<br>754-10-9 | 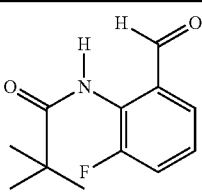<br>S86 | 73% |
| S87 | 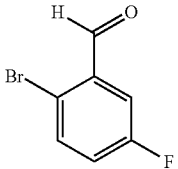<br>94569-84-3 | 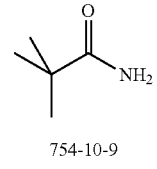<br>754-10-9 | 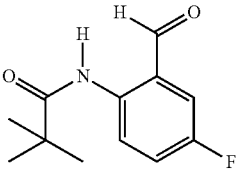<br>S87 | 87% |
| S88 | 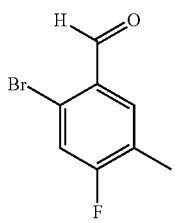<br>916792-17-1 | 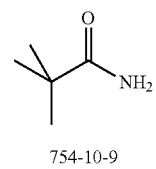<br>754-10-9 | 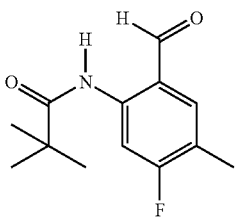<br>S88 | 90% |
| S89 | 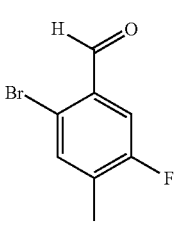<br>916792-21-7 | 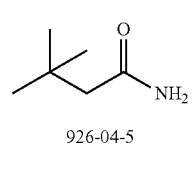<br>926-04-5 | 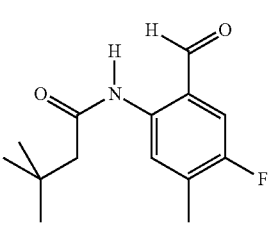<br>S89 | 90% |
| S90 | 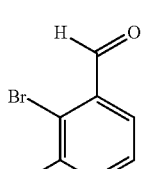<br>446864-55-7 | 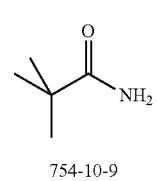<br>754-10-9 | 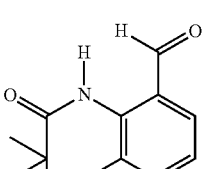<br>S90 | 67% |
| S91 | 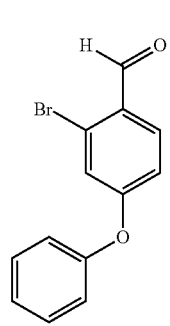<br>69240-52-4 | 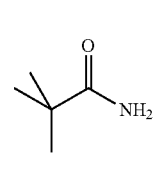<br>754-10-9 | 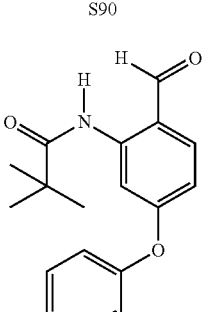<br>S91 | 90% |

-continued
| Ex. | Bromo-arylaldehyde | Amide | Product | Yield |
|---|---|---|---|---|
| S92 | 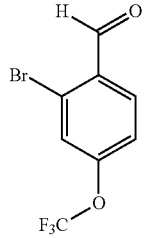 1114808-87-5 | 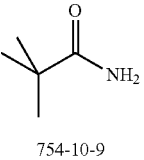 754-10-9 | 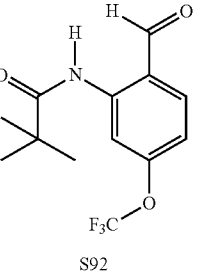 S92 | 92% |
| S93 | 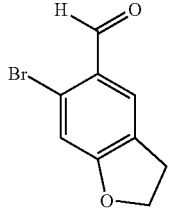 1221160-68-4 | 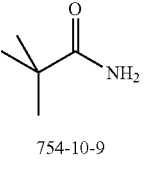 754-10-9 | 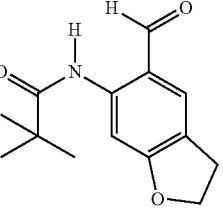 S93 | 88% |
| S94 | 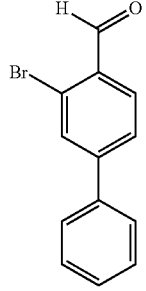 1237125-81-3 | 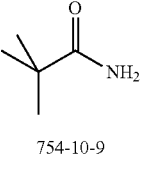 754-10-9 | 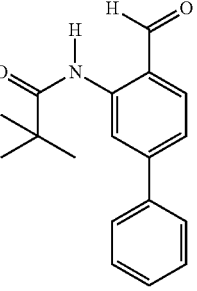 S94 | 94% |
| S95 | 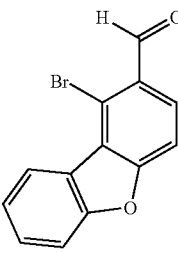 1062569-66-7 | 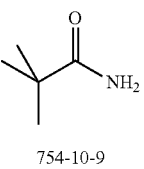 754-10-9 | 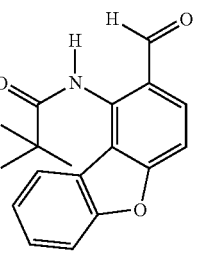 S95 | 93% |
| S96 | 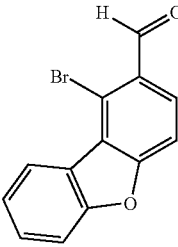 1062569-66-7 | 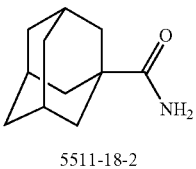 [SMILES: NC(=O)C12CC3CC(CC(C3)C1)C2] 5511-18-2 | 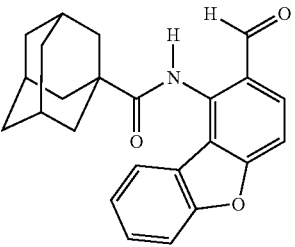 S96 | 96% |

-continued
| Ex. | Bromo-arylaldehyde | Amide | Product | Yield |
|---|---|---|---|---|
| S97 | 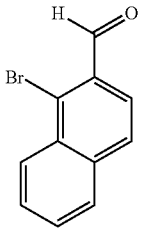<br>3378-82-3 | 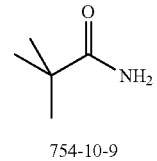<br>754-10-9 | 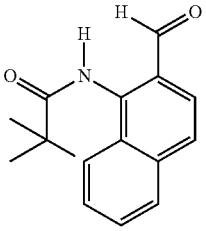<br>S97 | 89% |
| S98 | 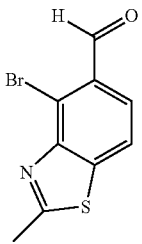<br>1312684-59-5 | 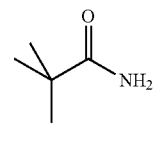<br>754-10-9 | 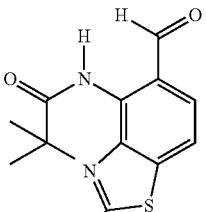<br>S98 | 63% |
| S99 | 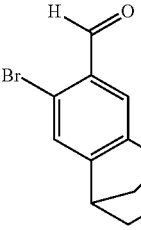<br>S67 | 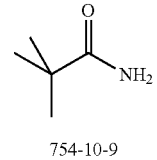<br>754-10-9 | 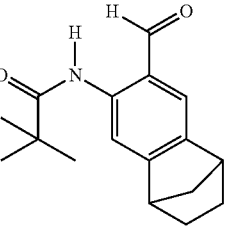<br>S99 | 90% |
| S100 | 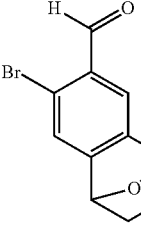<br>S68 | 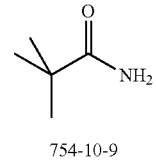<br>754-10-9 | 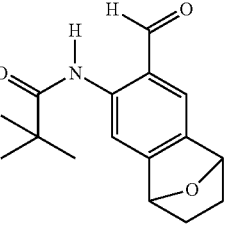<br>S100 | 92% |
| S101 | 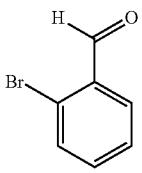<br>6630-33-7 | 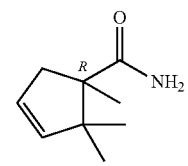<br>173411-22-8 | 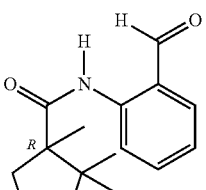<br>S101 | 90% |

| Ex. | Bromo-arylaldehyde | Amide | Product | Yield |
|---|---|---|---|---|
| S102 | S67 | 173411-22-8 | S102 | 83% |

Example S103: 7-(3,3-Dimethylbut-1-ynyl)-1,2,3,4-tetrahydro-1,4-methanonaphthalene-6-carbaldehyde, S103

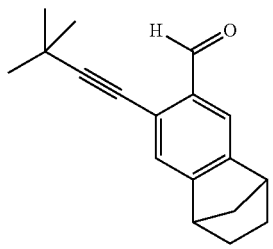 [SMILES: CC(C)(C)C#Cc1cc2c(cc1C=O)C1CCC2C1]

1.6 g (6 mmol) of triphenylphosphine, 674 mg (3 mmol) of palladium(II) acetate, 571 mg (30 mmol) of copper(I) iodide and 15.6 g (190 mmol) of tert-butylacetylene [917-92-0] are added consecutively to a solution of 25.1 g (100 mmol) of 7-bromo-1,2,3,4-tetrahydro-1,4-methanonaphthalene-6-carbaldehyde, S67, in a mixture of 200 ml of DMF and 100 ml of triethylamine, and the mixture is stirred at 65° C. for 4 h. After cooling, the precipitated triethylammonium hydrochloride is filtered off with suction, rinsed with 30 ml of DMF. The filtrate is freed from the solvents in vacuo. The oily residue is taken up in 300 ml of ethyl acetate, the solution is washed five times with 100 ml of water each time and once with 100 ml of saturated sodium chloride solution, and the organic phase is dried over magnesium sulfate. After removal of the ethyl acetate in vacuo, the black oily residue is subjected to a bulb-tube distillation (p about $10^{-4}$ mbar, T=100-120° C.). Yield: 19.2 g (76 mmol), 76%; purity: >96% according to $^1$H-NMR.

The following derivatives can be prepared analogously:

| Ex. | Bromo-aryl-aldehyde | Alkyne | Product | Yield |
|---|---|---|---|---|
| S104 | S67 | 1066-54-2 | S104 | 61% |
| S105 | S68 | 917-92-0 | S105 | 82% |

| Ex. | Bromo-aryl-aldehyde | Alkyne | Product | Yield |
|---|---|---|---|---|
| S106 | 1352329-26-0 | 917-92-0 | S106 | 78% |
| S107 | 1352329-26-0 | 1066-54-2 | S107 | 54% |

Example S108: 2-tert-Butyl-4-(3,3-dimethylbut-1-ynyl)pyridine-5-carboxaldehyde, S108

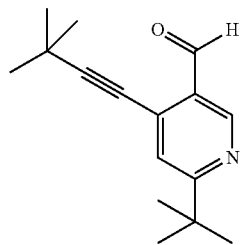 [SMILES: CC(C)(C)C#Cc1cc(C(C)(C)C)ncc1C=O]

315 ml (315 mmol) of diisobutylaluminium hydride, 1 M in toluene, are added dropwise to a solution, cooled to −78° C., of 72.1 g (300 mmol) of 2-tert-butyl-4-(3,3-dimethylbut-1-ynyl)-5-cyanopyridine, S106, in 1500 ml of dichloromethane at such a rate that the temperature does not exceed −65° C. When the addition is complete, the reaction mixture is stirred at −78° C. for a further 2 h, then allowed to warm slowly to room temperature and stirred for a further 12 h. After re-cooling to −10° C., 300 ml of THF and then, with vigorous stirring, 230 ml of 2 N sulfuric acid (exothermic!) are added, and the mixture is stirred at room temperature for a further 12 h.

After re-cooling to −10° C., a solution of 70 g of NaOH in 300 ml of water is added, the aqueous phase is separated off, the organic phase is washed three times with 1000 ml of water each time, once with 500 ml of saturated sodium chloride solution, dried over magnesium sulfate, and the solvent is removed in vacuo. Yield: 69.6 g (286 mmol), 95%. Purity: >95% according to $^1$H-NMR.

S107 is converted analogously into 2-tert-butyl-4-(2-trimethylsilyleth-1-ynyl)-5-cyanopyridine, S109. Yield: 68.7 g (268 mmol), 89%; purity: >95% according to $^1$H-NMR.

Example S110: 2-(2-tert-Butylpyrimidin-5-yl)-5,5,7,7-tetramethyl-1,5,6,7-tetrahydroindeno[5,6-d]imidazole

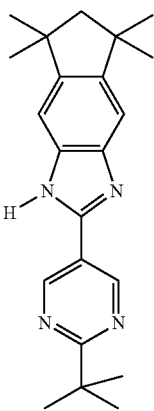

16.9 g (55 mmol) of oxone [70693-62-8] are added in portions with stirring at 10° C. to a solution of 16.4 g (100 mmol) of 2-tert-butylpyrimidine-5-carboxaldehyde [104461-06-5] and 22.5 g (110 mmol) of 1,1,3,3-tetramethylindane-5,6-diamine [83721-95-3], S16, in a mixture of 100 ml of DMF and 3 ml of water, and the mixture is subsequently stirred at room temperature until the aldehyde has reacted completely (about 2 h). The reaction mixture is stirred into a solution of 40 g of potassium carbonate solution in 1000 ml of water, stirred for a further 15 min., the solid formed is filtered off with suction, washed three times with 100 ml of water each time and dried in vacuo. The crude product is recrystallised from ethyl acetate/cyclohexane. Yield: 20.2 g (58 mmol), 58%. Purity: >95% according to $^1$H-NMR.

The following derivatives can be prepared analogously:
| Ex. | Pyrimidine-5 carboxaldehyde | 1,2-Diaminobenzene | Product | Yield |
|---|---|---|---|---|
| S111 | 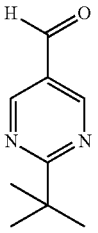 104461-06-5 | 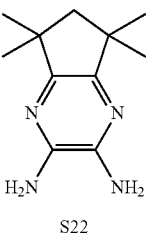 S22 | 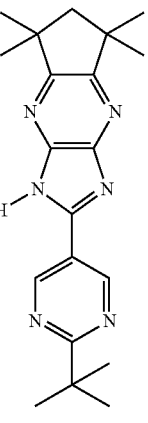 S111 | 31% |
| S112 | 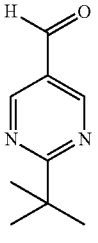 104461-06-5 | 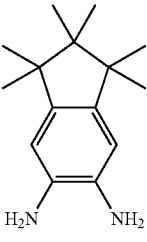 S24 | 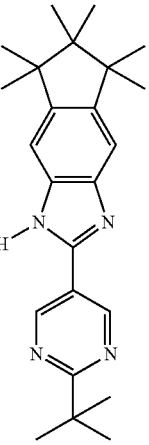 S112 | 48% |
| S113 | 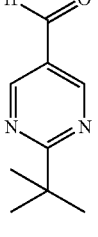 104461-06-5 | 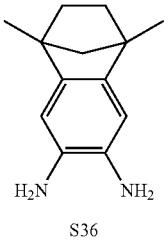 S36 | 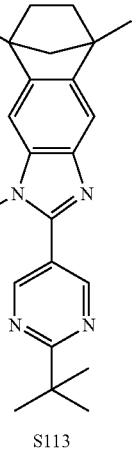 S113 | 45% |

Example S114: 2-tert-Butyl-3-(3,3-dimethylbut-1-ynyl)pyridine-4-carboxaldehyde, S114

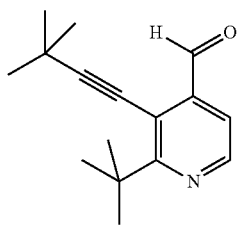 [SMILES: CC(C)(C)C#Cc1c(C=O)ccnc1C(C)(C)C]

Preparation analogous to 7-(3,3-dimethylbut-1-ynyl)-1,2,3,4-tetrahydro-1,4-methanonaphthalene-6-carbaldehyde, S103. Instead of 7-bromo-1,2,3,4-tetrahydro-1,4-methanonaphthalene-6-carbaldehyde, S67, 24.2 g (100 mmol) of 2-tert-butyl-3-bromopyridine-4-carboxaldehyde [1289119-19-2] are employed. Yield: 15.3 g (63 mmol), 63%. Purity: >95% according to $^1$H-NMR.

Analogously, 24.2 g (100 mmol) of 2-tert-butyl-3-bromopyridine-4-carboxaldehyde [1289119-19-2] and 18.7 g (190 mmol) of trimethylsilylacetylene [1066-54-2] are converted into 2-tert-butyl-3-(2-trimethylsilylbut-1-ynyl)pyridine-4-carboxaldehyde, S115. Yield: 14.5 g (56 mmol), 56%; purity: >95% according to $^1$H-NMR.

Example S116: N-(2-tert-Butyl-4-formylpyridin-3-yl)acetamide, S116

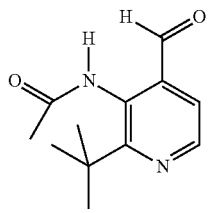

7.5 ml (105 mmol) of acetyl chloride are added dropwise to a solution of 17.8 g (100 mmol) of 2-tert-butyl-3-aminopyridin-4-ylcarbaldehyde [1289036-95-8] in 100 ml of dioxane. The reaction mixture is heated under reflux for 30 min., cooled, added to 500 ml of ice-water and neutralised using sodium hydrogencarbonate. The precipitated solid is filtered off with suction, washed twice with 50 ml of water each time, dried in vacuo and then recrystallised once from DMF/EtOH. Yield: 18.7 g (85 mmol), 85%. Purity: >95% according to $^1$H-NMR.

Example S117: 1,1,3,3-Tetramethyl-2,3-dihydro-1H-cyclopenta[c]isochromen-5-one, S117

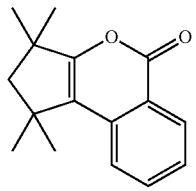 [SMILES: CC1(C)CC(C)(C)c2c1oc(=O)c1ccccc21]

Preparation analogous to A. C. Tadd et al., Chem. Commun. 2009, 6744. A mixture of 14.0 g (100 mmol) of 2,2,4,4-tetramethylcyclopentanone [4694-11-5], 28.3 g (100 mmol) of 1-bromo-2-iodobenzene [583-55-1], 97.7 g (300 mmol) of caesium carbonate, 200 g of glass beads (diameter 3 mm), 2.9 g (5 mmol) of xantphos, 1.1 g (5 mmol) of palladium(II) acetate and 500 ml of toluene is stirred at 80° C. for 24 h. A weak stream of carbon monoxide is then passed through the reaction mixture, and the temperature is increased to 110° C. so that a gentle reflux becomes established. After 16 h, the reaction mixture is allowed to cool, the salts are filtered off with suction through a Celite bed, these salts are rinsed with 1000 ml of toluene, and the filtrate is freed from toluene in vacuo. The residue is recrystallised twice from ethyl acetate/ethanol. Yield: 8.7 g (36 mmol) 36%. Purity: about 95% according to $^1$H-NMR.

Example S118: 1,1,3,3-Tetramethyl-2,3-dihydro-1H-4-oxa-9-azacyclopenta[a]naphthalen-5-one, S118

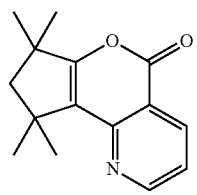 [SMILES: CC1(C)CC(C)(C)c2c1oc(=O)c1cccnc21]

Preparation analogous to S117, using 28.4 g (100 mmol) of 2-iodo-3-bromopyridine [408502-43-2] instead of 1-bromo-2-iodobenzene. Yield: 7.3 g (30 mmol), 30%. Purity: about 95% according to $^1$H-NMR.

B: Synthesis of the ligands L:

1) Ligands of the benzo[4,5]imidazo[2,1-a]isoquinoline Type

General Ligand Synthesis Variant A:

From 1-chloroisoquinolines and 2-haloanilines:

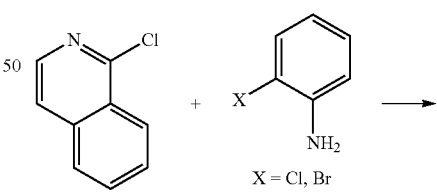

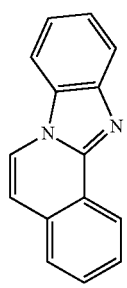

A vigorously stirred mixture of 500 mmol of the 1-chloroisoquinoline derivative, 600 mmol of the 2-haloaniline, 1250 mmol of potassium carbonate, 200 g of glass beads (diameter 3 mm), 10 mmol of triphenylphosphine and 2 mmol of palladium(II) acetate in 1500 ml of o-xylene is heated under reflux for 3-48 h until the 1-chloroisoquinoline derivative has been consumed. After cooling, the solid material is filtered off over a Celite bed, rinsed with 2000 ml of THF, and the filtrate is evaporated to dryness. The residue is dissolved in 100 ml of boiling ethyl acetate, and 800 ml of n-heptane or cyclohexane are slowly added. After cooling, the solid which has crystallised out is filtered off with suction, washed twice with 100 ml of n-heptane each time and dried in vacuo. Non-crystallising oils are chromatographed for purification. The solids or oils obtained in this way are freed from low-boiling components and non-volatile secondary components by fractional bulb-tube distillation or sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L1: L1

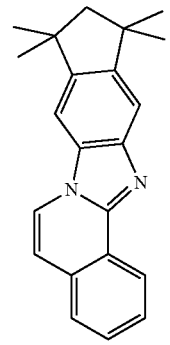

Use of 81.8 g (500 mmol) of 1-chloroisoquinoline [19493-44-8] and 160.9 g (600 mmol) of 6-bromo-1,1,3,3-tetramethylindan-5-ylamine, S4, sublimation of the product at T about 180° C., p about $10^{-4}$ mbar. Yield: 100.6 g (320 mmol), 64%; purity: about 99.5% according to $^1$H-NMR.

The following compounds can be prepared analogously:

| Ex. | 1-Chloroiso-quinoline derivative | 2-Halo-aniline | Product | Yield |
|---|---|---|---|---|
| L2 | 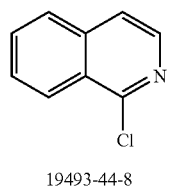<br>19493-44-8 | 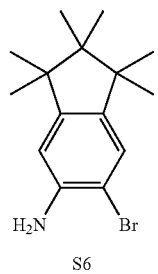<br>S5 | 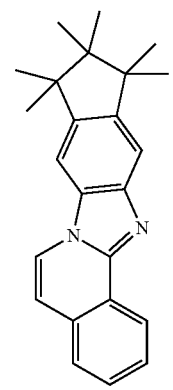 | 58% |
| L3 | 19493-44-8 | S6 | | 68% |

| Ex. | 1-Chloroiso-quinoline derivative | 2-Halo-aniline | Product | Yield |
|---|---|---|---|---|
| L4 | 19493-44-8 | S7 | | 69% |
| L5 | 19493-44-8 | S8 | | 68% |
| L6 | 19493-44-8 | S9 | | 56% |
| L7 | 19493-44-8 | S10 | | 69% |

-continued
| Ex. | 1-Chloroiso-quinoline derivative | 2-Halo-aniline | Product | Yield |
|---|---|---|---|---|
| L8 | 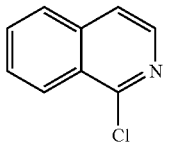<br>19493-44-8 | 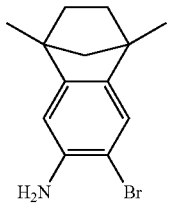<br>S11 | 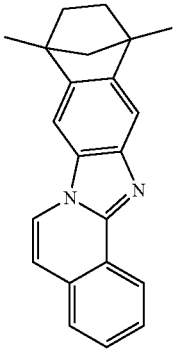 | 64% |
| L9 | 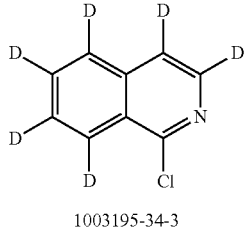 [SMILES: [2H]c1nc(Cl)c2c([2H])c([2H])c([2H])c([2H])c2c1[2H]]<br>1003195-34-3 | 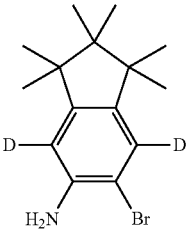<br>S8 | 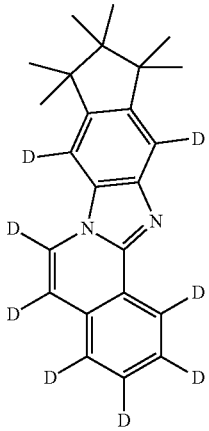 [SMILES: [2H]c1c([2H])c([2H])c2c(c1[2H])c([2H])c([2H])n1c2nc2c([2H])c3c(c([2H])c21)C(C)(C)C(C)(C)C3(C)C] | 64% |
| L10 | 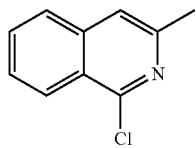<br>7115-16-4 | 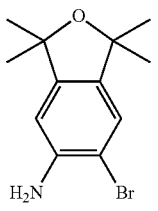<br>S12 | 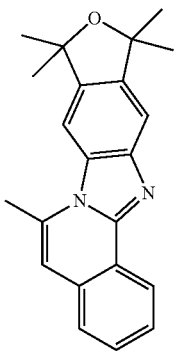 | 59% |
| L11 | 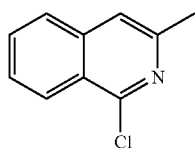<br>7115-16-4 | 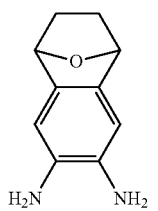<br>S13 | 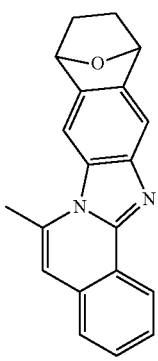 [SMILES: Cc1cc2ccccc2c2nc3cc4c(cc3n12)C1CCC4O1] | 61% |

-continued
| Ex. | 1-Chloroiso-quinoline derivative | 2-Halo-aniline | Product | Yield |
|---|---|---|---|---|
| L12 | 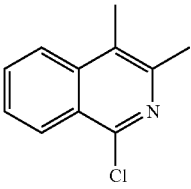<br>15787-20-9 | 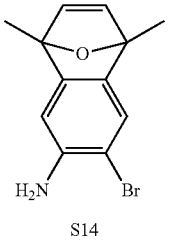<br>S14 | 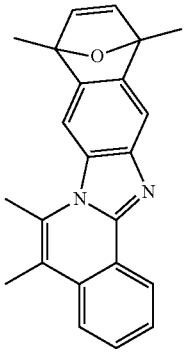 | 34% |
| L13 | 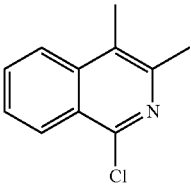<br>15787-20-9 | 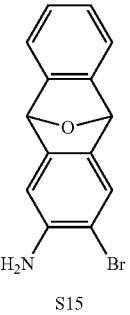 [SMILES: Nc1cc2c(cc1Br)C1OC2c2ccccc21 ; "S15"]<br>S15 | 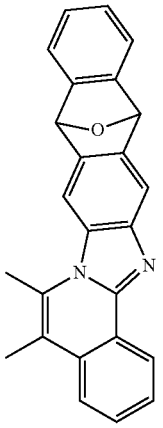 [SMILES: Cc1c(C)n2c3cc4c(cc3nc2c2ccccc12)C1OC4c2ccccc21] | 67% |
| L14 | 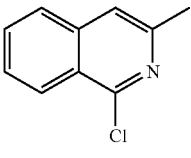<br>7115-16-4 | 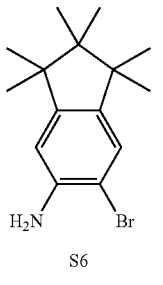<br>S6 | 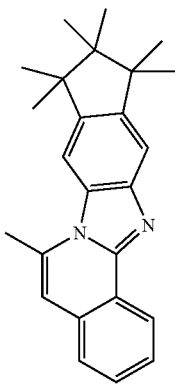 | 65% |

-continued
| Ex. | 1-Chloroiso-quinoline derivative | 2-Halo-aniline | Product | Yield |
|---|---|---|---|---|
| L15 | 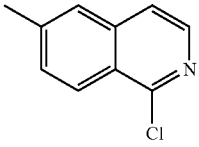<br>209286-73-7 | 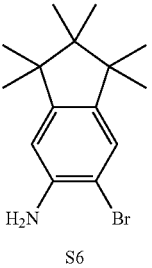<br>S6 | 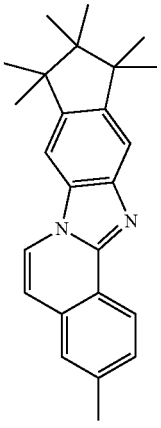 | 60% |
| L16 | 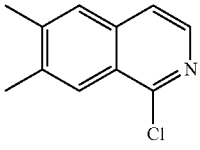<br>1368924-44-0 | 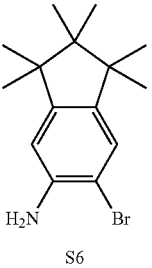<br>S6 | 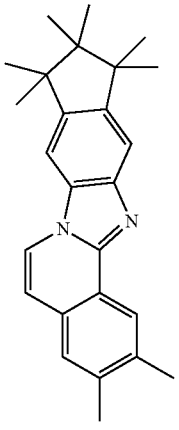 | 61% |
| L17 | 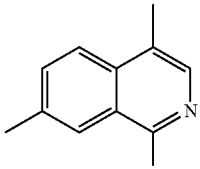<br>1206973-73-0 | 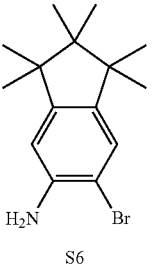<br>S6 | 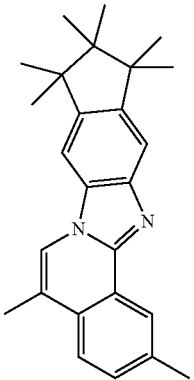 | 65% |

-continued
| Ex. | 1-Chloroiso-quinoline derivative | 2-Halo-aniline | Product | Yield |
|---|---|---|---|---|
| L18 | 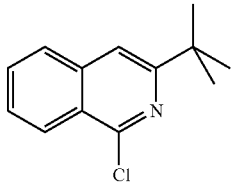 1198271-38-3 | 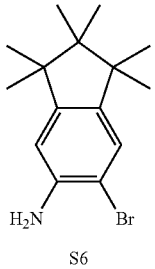 S6 | 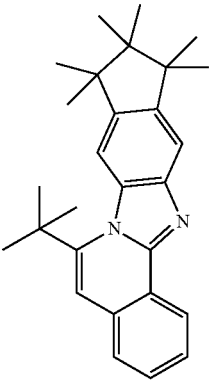 | 67% |
| L19 | 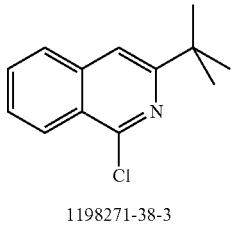 1198271-38-3 | 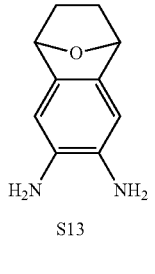 S13 | 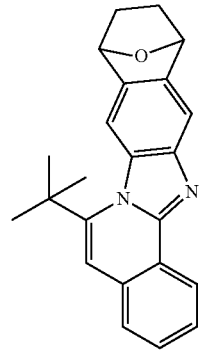 [SMILES: CC(C)(C)c1cc2ccccc2c2nc3cc4c(cc3n12)C1CCC4O1] | 59% |
| L20 | 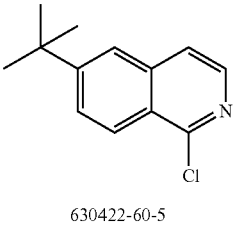 630422-60-5 | 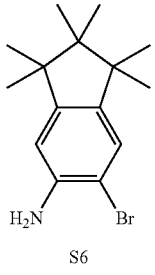 S6 | 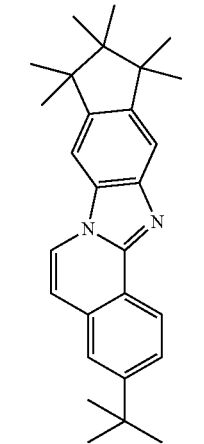 | 60% |

-continued
| Ex. | 1-Chloroiso-quinoline derivative | 2-Halo-aniline | Product | Yield |
|---|---|---|---|---|
| L21 | 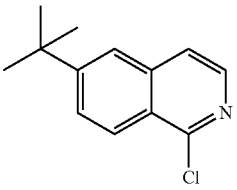<br>630422-60-5 | 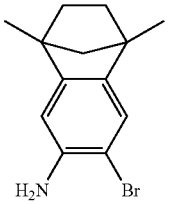<br>S11 | 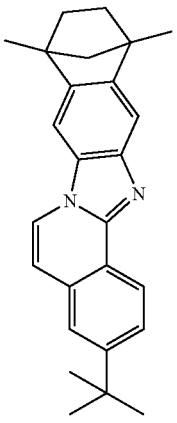 | 63% |
| L22 | 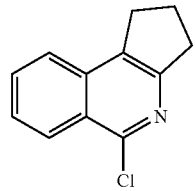<br>630419-61-3 | 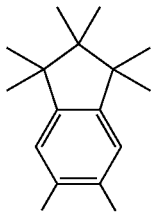<br>S6 | 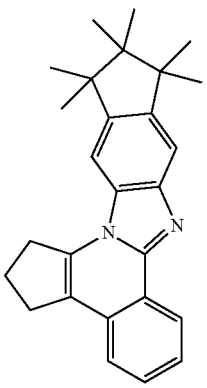 [SMILES: CC1(C)c2cc3nc4c5ccccc5c5c(n4c3cc2C(C)(C)C1(C)C)CCC5] | 43% |
| L23 | 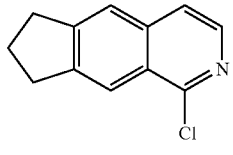<br>1368753-27-8 | 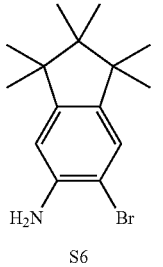<br>S6 |  | 38% |

-continued
| Ex. | 1-Chloroiso-quinoline derivative | 2-Halo-aniline | Product | Yield |
|---|---|---|---|---|
| L24 | 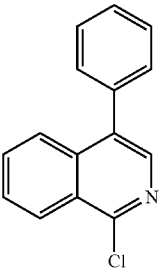<br>65810-96-0 | 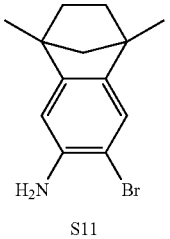<br>S11 | 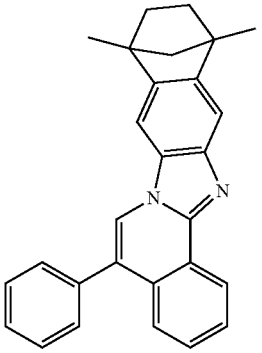 [SMILES: CC12CCC(C)(C1)c1cc3c(cc12)nc1c2ccccc2c(-c2ccccc2)cn31] | 55% |
| L25 | 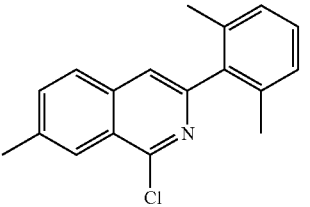<br>1248622-18-5 | 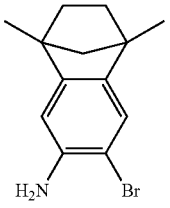<br>S11 | 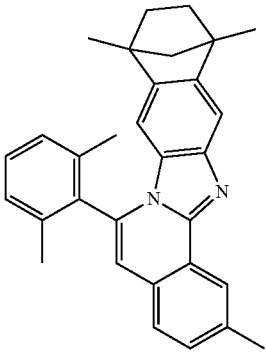 [SMILES: Cc1ccc2cc(-c3c(C)cccc3C)n3c4cc5c(cc4nc3c2c1)C1(C)CCC5(C)C1] | 65% |
| L26 | 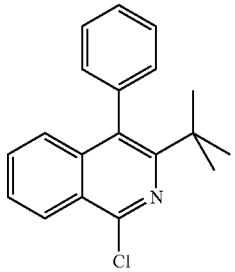<br>55792-01-3 | 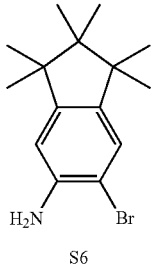<br>S6 | 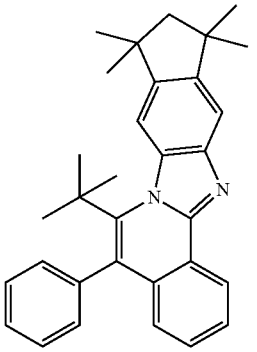 [SMILES: CC(C)(C)c1c(-c2ccccc2)c2ccccc2c2nc3cc4c(cc3n12)C(C)(C)CC4(C)C] | 63% |
| L27 | 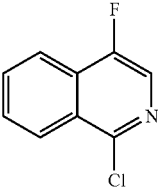<br>435278-06-1 | 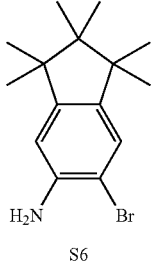<br>S6 | 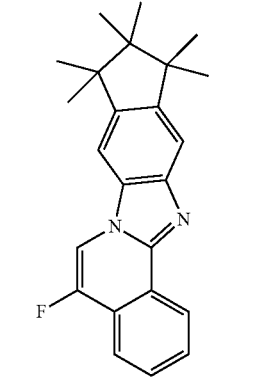 [SMILES: CC1(C)c2cc3nc4c5ccccc5c(F)cn4c3cc2C(C)(C)C1(C)C] | 64% |

-continued

| Ex. | 1-Chloroiso-quinoline derivative | 2-Halo-aniline | Product | Yield |
|---|---|---|---|---|
| L28 | 435278-02-7 | S4 | | 66% |
| L29 | 630422-89-8 | S4 | | 67% |
| L30 | 1369071-11-3 | S4 | | 64% |
| L31 | 59500-31-2 | S11 | | 70% |

-continued

| Ex. | 1-Chloroiso-quinoline derivative | 2-Halo-aniline | Product | Yield |
|---|---|---|---|---|
| L32 | 86761-09-3 | S4 | | 69% |
| L33 | 33279-84-4 | S12 | | 54% |
| L34 | 32081-28-0 | S6 | | 67% |

-continued
| Ex. | 1-Chloroiso-quinoline derivative | 2-Halo-aniline | Product | Yield |
|---|---|---|---|---|
| L35 | 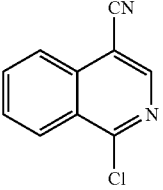 53491-80-8 | 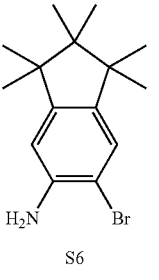 S6 |  | 45% |
| L36 | 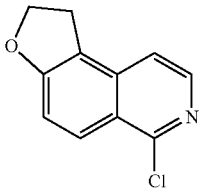 630423-15-3 | 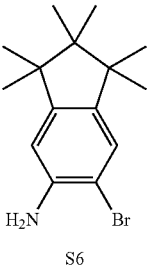 S6 | 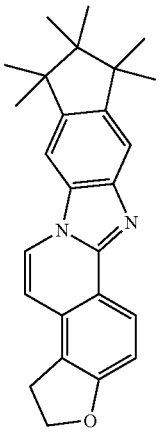 | 31% |
| L37 | 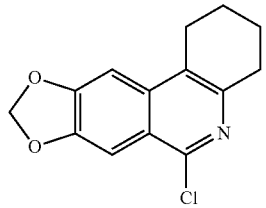 61877-29-0 | 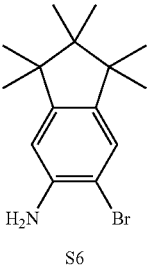 S6 | 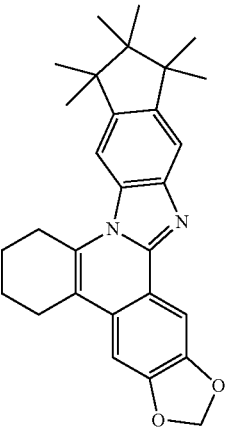 [SMILES: CC1(C)c2cc3nc4c5cc6c(cc5c5c(n4c3cc2C(C)(C)C1(C)C)CCCC5)OCO6] | 27% |

-continued
| Ex. | 1-Chloroiso-quinoline derivative | 2-Halo-aniline | Product | Yield |
|---|---|---|---|---|
| L38 | 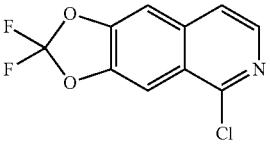<br>630423-54-0 | 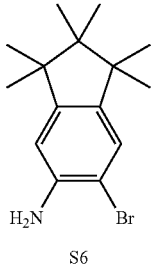<br>S6 | 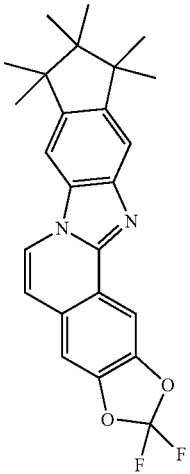 [SMILES: CC1(C)c2cc3nc4c5cc6c(cc5ccn4c3cc2C(C)(C)C1(C)C)OC(F)(F)O6] | 42% |
| L39 | 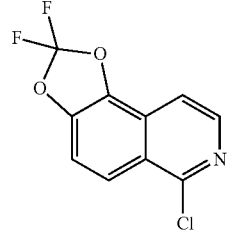<br>630423-52-8 | 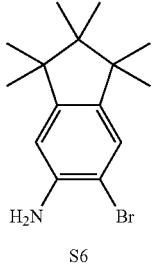<br>S6 | 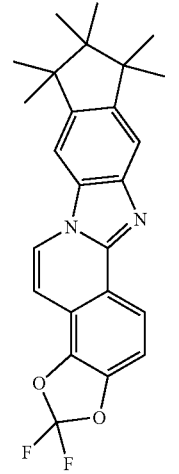 | 37% |
| L40 | 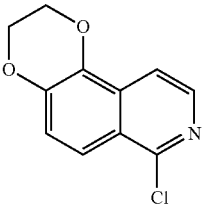<br>630423-50-6 | 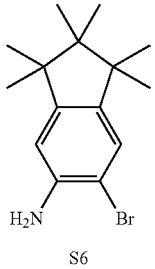<br>S6 | 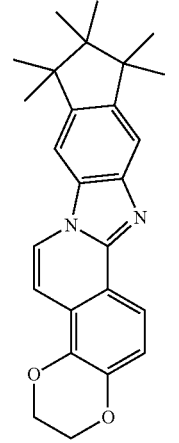 | 57% |

General Ligand Synthesis Variant B:
From 2-alkynylarylaldehydes and 1,2-diaminobenzenes:

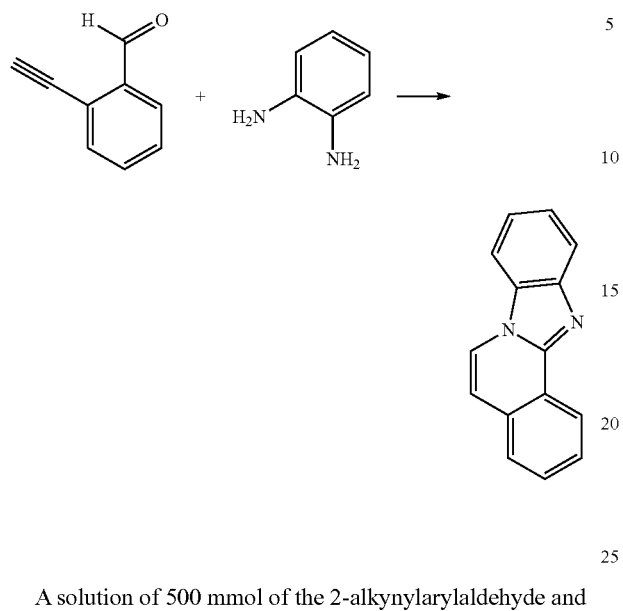

A solution of 500 mmol of the 2-alkynylarylaldehyde and 550 mmol of the 1,2-diaminobenzene in 1000 ml of nitrobenzene is placed in an apparatus consisting of a 2000 ml one-necked flask with stopcock and attached distillation bridge and slowly heated to 200° C. (oil-bath temperature) with stirring, during which the water formed distils off. The mixture is stirred at 200° C. for a further 2 h, the temperature is then increased to about 230° C., and the nitrobenzene is distilled off in a stream of argon. Towards the end of the distillation, a vacuum of about 100 mbar is applied in order to remove final residues of nitrobenzene, the reaction mixture is then allowed to cool. If the crude product is produced in the form of a glass, the glass is mechanically comminuted, oils are mixed directly with 200-400 ml of methanol or acetonitrile, and the mixture is heated under reflux, during which the glass or oil dissolves and the product crystallises out. The crude products obtained in this way already have high purity ($^1$H-NMR typically 97-99%). If desired, they are recrystallised again and then freed from low-boiling components and non-volatile secondary components by fractional bulb-tube distillation or sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L41

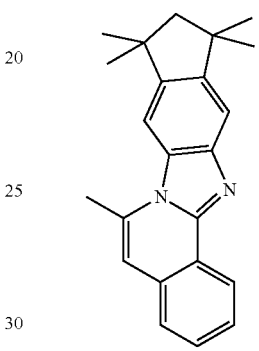

Use of 72.1 g (500 mmol) of 2-(1-propyn-1-yl)benzaldehyde [176910-65-9] and 112.4 g (550 mmol) of 1,1,3,3-tetramethylindane-5,6-diamine [83721-95-3], S16, uptake of the crude product in acetonitrile, recrystallisation from ethyl acetate/methanol, sublimation of the product at T about 210° C., p about $10^{-4}$ mbar. Yield: 99.9 g (304 mmol), 61%; purity: about 99.5% according to $^1$H-NMR.

The following compounds can be prepared analogously:

| Ex. | 2-Alkynylaryl-aldehyde | 1,2-Diamino-benzene | Product | Yield |
|---|---|---|---|---|
| L42 | 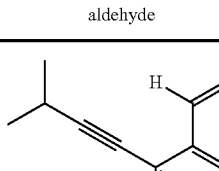 220649-62-7 | 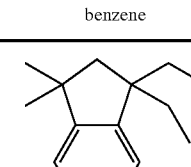 S17 | 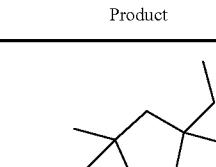 Chromatographic separation of the regioisomer | 54% |

-continued
| Ex. | 2-Alkynylaryl-aldehyde | 1,2-Diamino-benzene | Product | Yield |
|---|---|---|---|---|
| L43 | 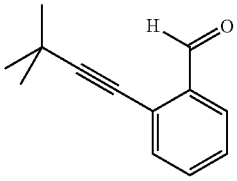 183312-34-7 | 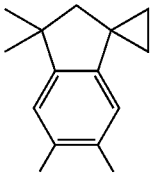 S18 | 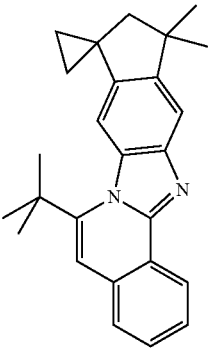 [SMILES: CC(C)(C)c1cc2ccccc2c2nc3nc4c(nc3n12)C(C)(C)CC4(C)C] Chromatographic separation of the regioisomer | 55% |
| L44 | 183312-34-7 | S21 | 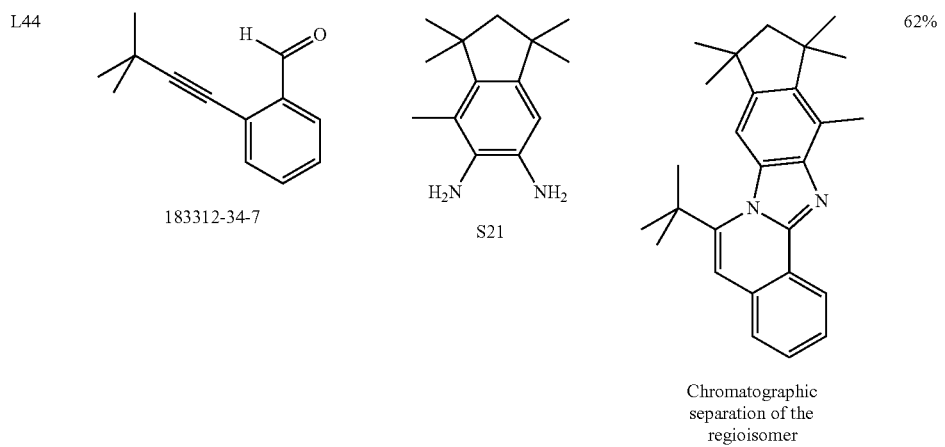 Chromatographic separation of the regioisomer | 62% |
| L45 | 183312-34-7 | S22 | 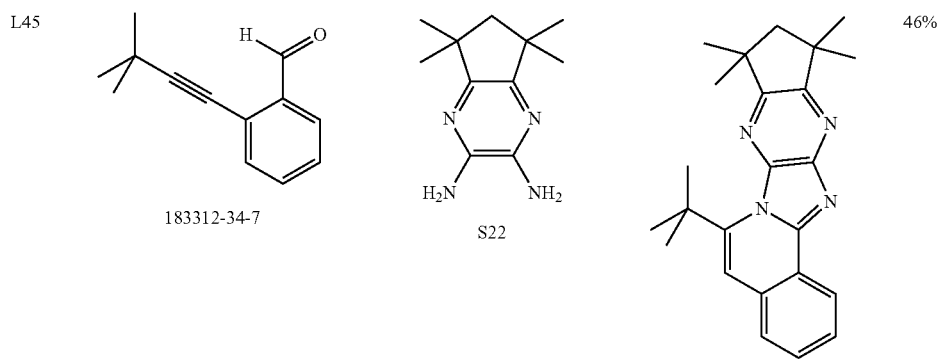 | 46% |

| Ex. | 2-Alkynylaryl-aldehyde | 1,2-Diamino-benzene | Product | Yield |
|---|---|---|---|---|
| L46 | 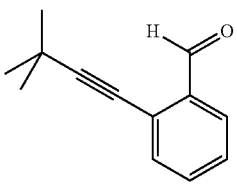<br>183312-34-7 | 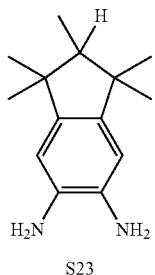<br>S23 | 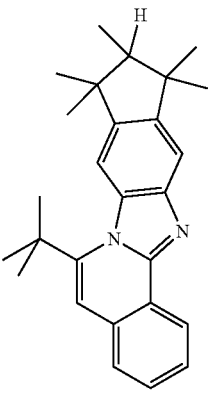 [SMILES: CC1C(C)(C)c2cc3nc4c5ccccc5cc(C(C)(C)C)n4c3cc2C1(C)C] | 48% |
| L47 | 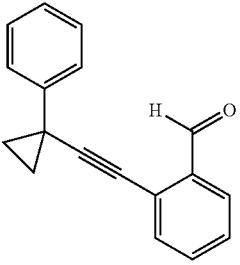<br>1189356-64-6 | 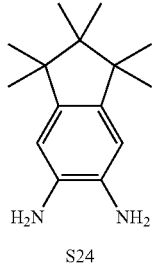<br>S24 | 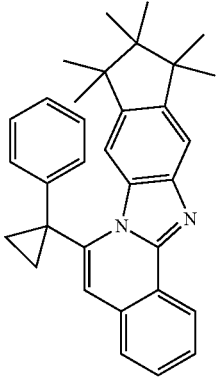 [SMILES: CC1(C)c2cc3nc4c5ccccc5cc(C5(c6ccccc6)CC5)n4c3cc2C(C)(C)C1(C)C] | 40% |
| L48 | 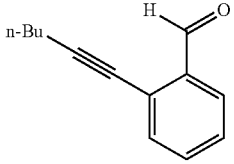<br>872471-05-1 | 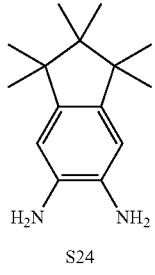<br>S24 | 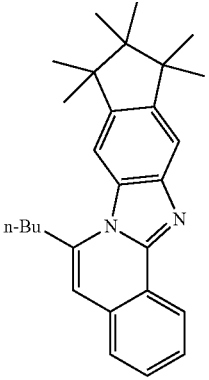 | 51% |
| L49 | 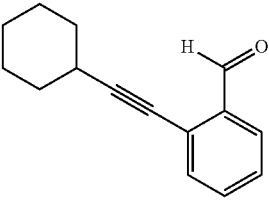<br>396717-17-2 | 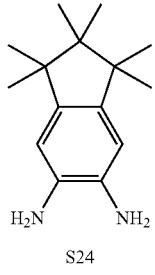<br>S24 | 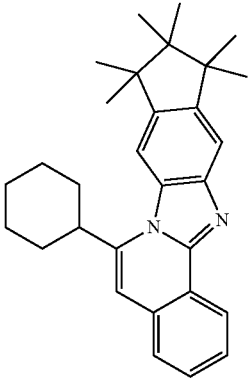 [SMILES: CC1(C)c2cc3nc4c5ccccc5cc(C5CCCCC5)n4c3cc2C(C)(C)C1(C)C] | 43% |

-continued
| Ex. | 2-Alkynylaryl-aldehyde | 1,2-Diamino-benzene | Product | Yield |
|---|---|---|---|---|
| L50 | 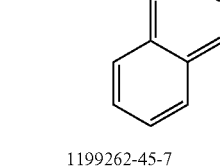 1199262-45-7 | 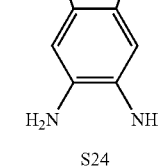 S24 | 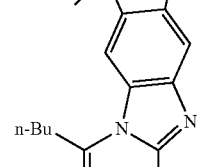 | 52% |
| L51 | 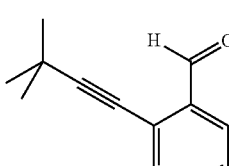 1378013-34-3 | 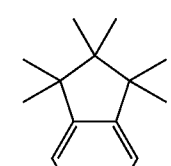 S24 | 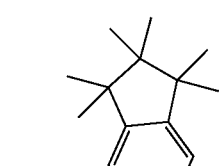 | 59% |
| L52 | 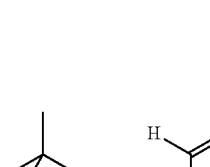 183312-34-7 | 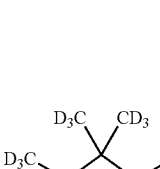 S25 | 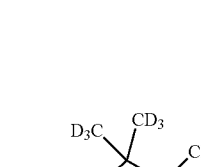 | 60% |

-continued
| Ex. | 2-Alkynylaryl-aldehyde | 1,2-Diamino-benzene | Product | Yield |
|---|---|---|---|---|
| L53 | 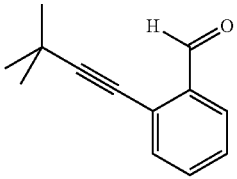<br>183312-34-7 | 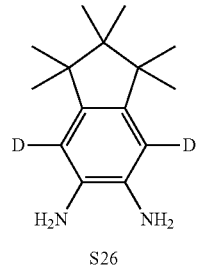 [SMILES: [2H]c1c(N)c(N)c([2H])c2c1C(C)(C)C(C)(C)C2(C)C ; "S26"]<br>S26 | 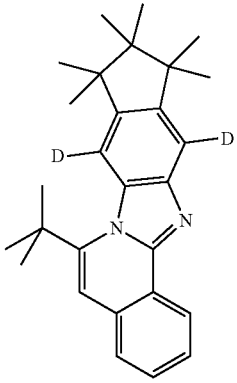 [SMILES: [2H]c1c2c(c([2H])c3c1nc1c4ccccc4cc(C(C)(C)C)n13)C(C)(C)C(C)(C)C2(C)C] | 60% |
| L54 | 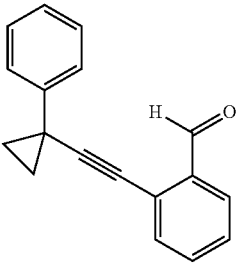<br>1189356-64-6 | 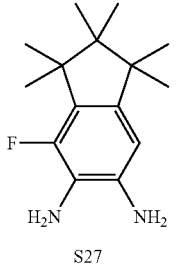 [SMILES: CC1(C)c2cc(N)c(N)c(F)c2C(C)(C)C1(C)C ; "S27"]<br>S27 | 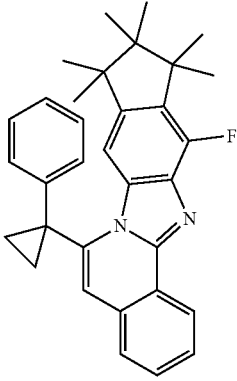<br>Chromatographic separation of the regioisomer | 38% |
| L55 | 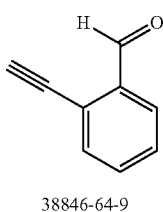<br>38846-64-9 | 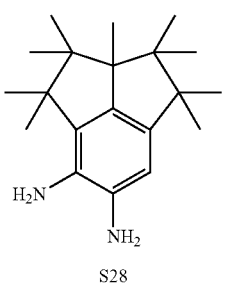<br>S28 | 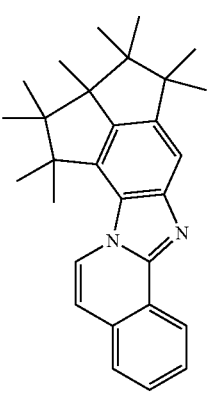<br>Chromatographic separation of the regioisomer | 27% |

-continued
| Ex. | 2-Alkynylaryl-aldehyde | 1,2-Diamino-benzene | Product | Yield |
|---|---|---|---|---|
| L56 | 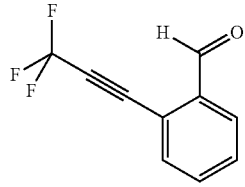 275386-61-3 | 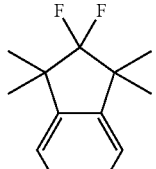 S29 | 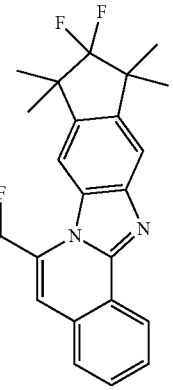 | 58% |
| L57 | 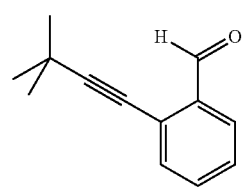 183312-34-7 | 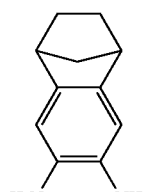 124639-03-8 S32 | 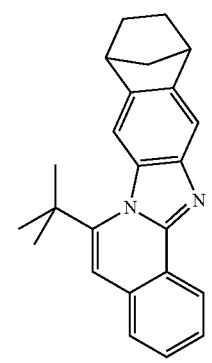 [SMILES: CC(C)(C)c1cc2ccccc2c2nc3cc4c(cc3n12)C1CCC4C1] | 56% |
| L58 | 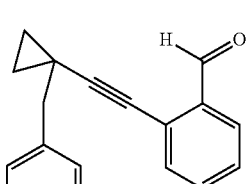 1189356-65-7 | 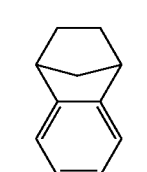 124639-03-8 S32 | 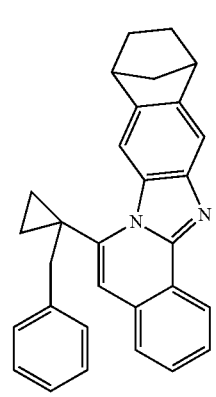 [SMILES: c1ccc(CC2(c3cc4ccccc4c4nc5cc6c(cc5n34)C3CCC6C3)CC2)cc1] | 43% |
| L59 | 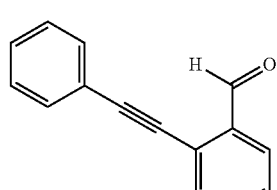 59046-72-9 | 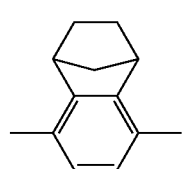 S34 | 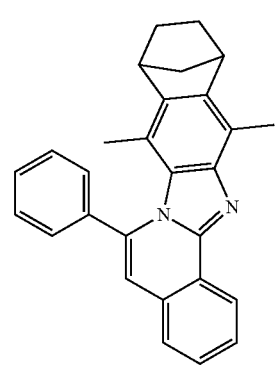 [SMILES: Cc1c2c(c(C)c3c1nc1c4ccccc4cc(-c4ccccc4)n13)C1CCC2C1] | 54% |

-continued
| Ex. | 2-Alkynylaryl-aldehyde | 1,2-Diamino-benzene | Product | Yield |
|---|---|---|---|---|
| L60 | 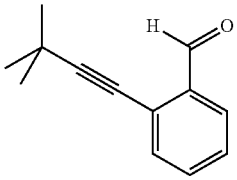<br>183312-34-7 | 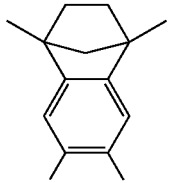<br>S36 | 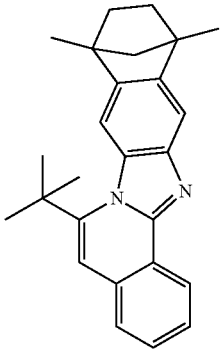 | 55% |
| L61 | 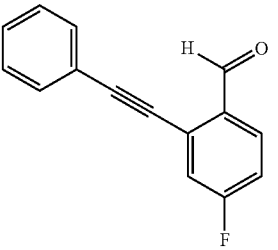<br>1189207-30-4 | 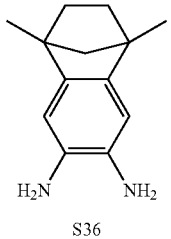<br>S36 | 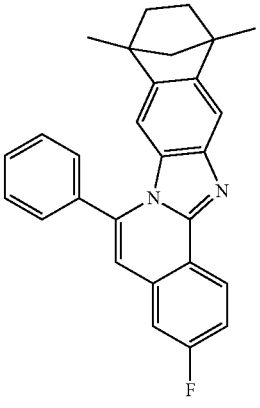 [SMILES: CC12CCC(C)(C1)c1cc3c(cc12)nc1c2ccc(F)cc2cc(-c2ccccc2)n31] | 51% |
| L62 | 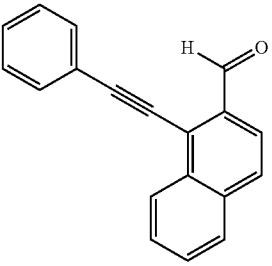<br>712278-61-0 | 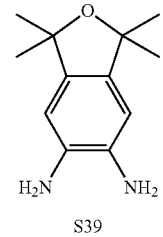<br>S39 | 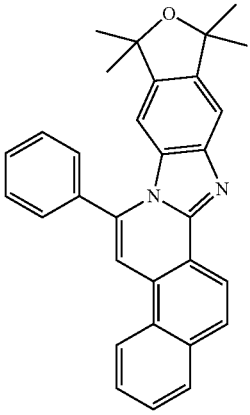 [SMILES: CC1(C)OC(C)(C)c2cc3c(cc21)nc1c2ccc4ccccc4c2cc(-c2ccccc2)n31] | 57% |
| L63 | 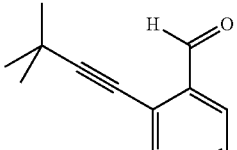<br>183312-34-7 | 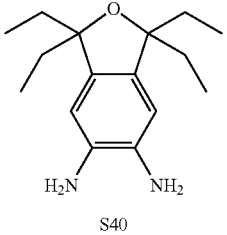 [SMILES: CCC1(CC)OC(CC)(CC)c2cc(N)c(N)cc21 ; "S40"]<br>S40 | 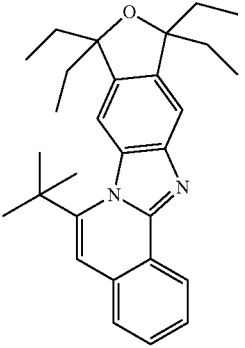 [SMILES: CCC1(CC)OC(CC)(CC)c2cc3c(cc21)nc1c2ccccc2cc(C(C)(C)C)n31] | 49% |

-continued
| Ex. | 2-Alkynylaryl-aldehyde | 1,2-Diamino-benzene | Product | Yield |
|---|---|---|---|---|
| L64 | 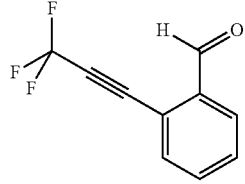 275386-61-3 | 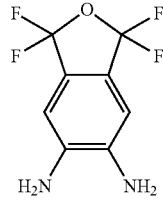 S43 | 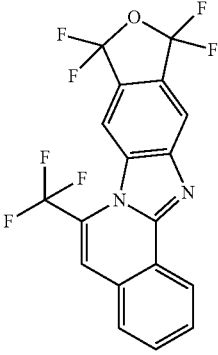 [SMILES: FC(F)(F)c1cc2ccccc2c2nc3cc4c(cc3n12)C(F)(F)OC4(F)F] | 40% |
| L65 | 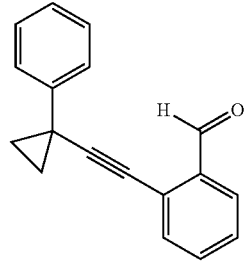 1189356-64-6 | 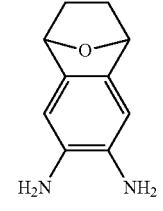 S44 | 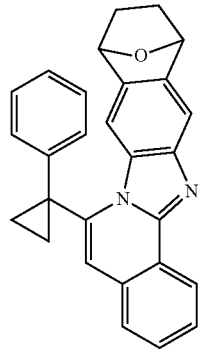 [SMILES: c1ccc(C2(c3cc4ccccc4c4nc5cc6c(cc5n34)C3CCC6O3)CC2)cc1] | 38% |
| L66 | 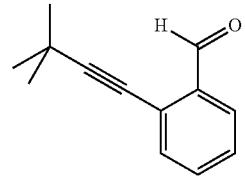 183312-34-7 | 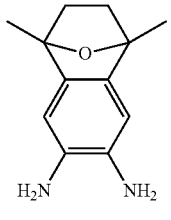 S46 | 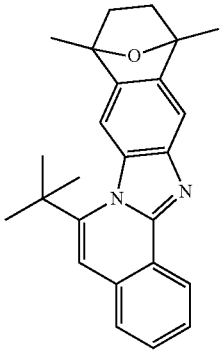 [SMILES: CC(C)(C)c1cc2ccccc2c2nc3cc4c(cc3n12)C1(C)CCC4(C)O1] | 52% |
| L67 | 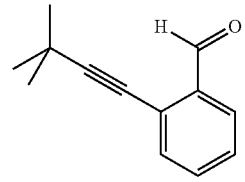 183312-34-7 | 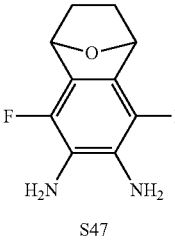 S47 | 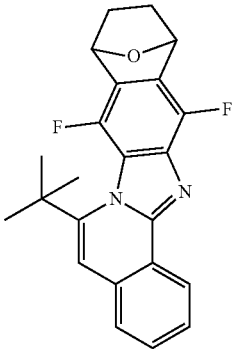 [SMILES: CC(C)(C)c1cc2ccccc2c2nc3c(F)c4c(c(F)c3n12)C1CCC4O1] | 53% |

-continued
| Ex. | 2-Alkynylaryl-aldehyde | 1,2-Diamino-benzene | Product | Yield |
|---|---|---|---|---|
| L68 | <br>183312-34-7 | 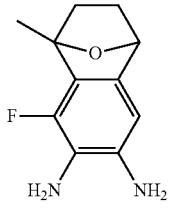<br>S48 | 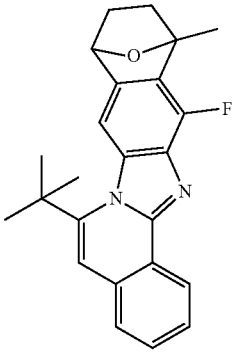<br>Chromatographic separation of the regioisomer | 26% |
| L69 | 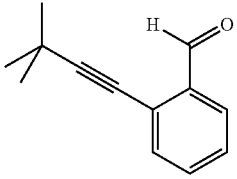<br>183312-34-7 | 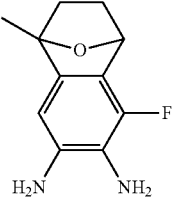<br>S49 | 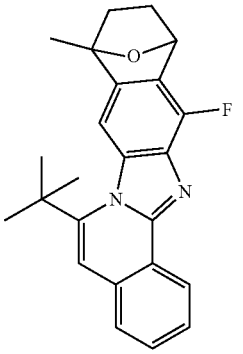<br>Chromatographic separation of the regioisomer | 28% |
| L70 | 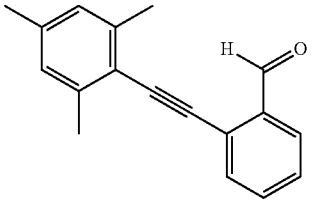<br>1338698-45-5 | 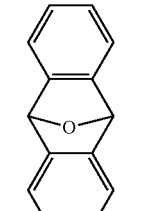<br>S53 | 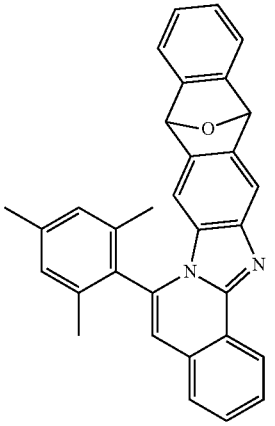 [SMILES: Cc1cc(C)c(-c2cc3ccccc3c3nc4cc5c(cc4n23)C2OC5c3ccccc32)c(C)c1] | 61% |

-continued
| Ex. | 2-Alkynylaryl-aldehyde | 1,2-Diamino-benzene | Product | Yield |
|---|---|---|---|---|
| L71 | 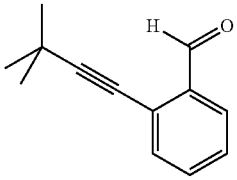<br>183312-34-7 | 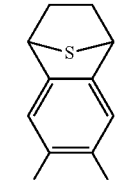<br>S54 | 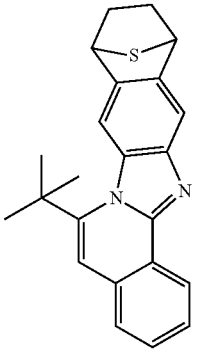 [SMILES: CC(C)(C)c1cc2ccccc2c2nc3cc4c(cc3n12)C1CCC4S1] | 46% |
| L72 | 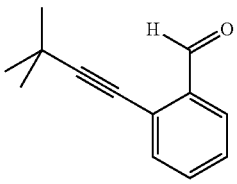<br>183312-34-7 | 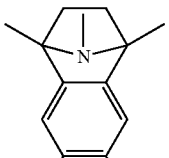<br>S56 | 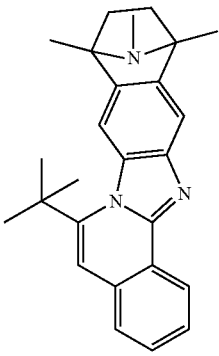 [SMILES: CN1C2(C)CCC1(C)c1cc3c(cc12)nc1c2ccccc2cc(C(C)(C)C)n31] | 20% |
| L73 | 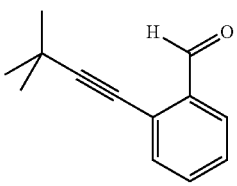<br>183312-34-7 | 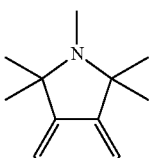<br>S58 | 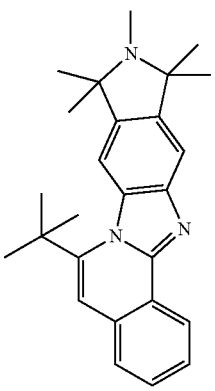 [SMILES: CN1C(C)(C)c2cc3nc4c5ccccc5cc(C(C)(C)C)n4c3cc2C1(C)C] | 23% |
| L74 | 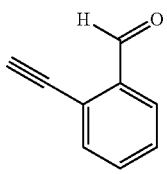<br>38846-64-9 | 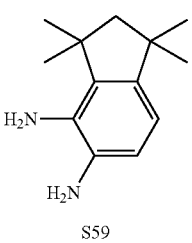<br>S59 | 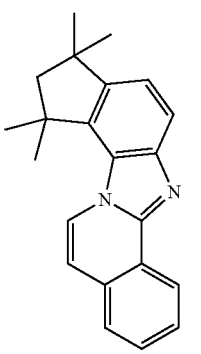<br>Chromatographic separation of the regioisomer | 21% |

-continued
| Ex. | 2-Alkynylaryl-aldehyde | 1,2-Diamino-benzene | Product | Yield |
|---|---|---|---|---|
| L75 | 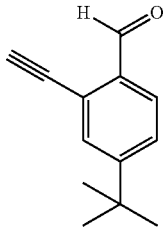 1010447-02-5 | 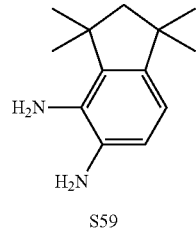 S59 | 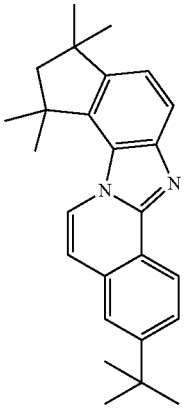 Chromatographic separation of the regioisomer | 23% |
| L76 | 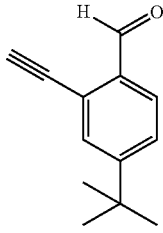 1010447-02-5 | 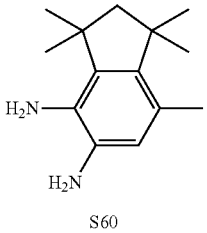 S60 | 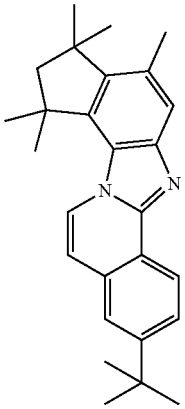 Chromatographic separation of the regioisomer | 26% |
| L77 | 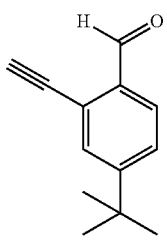 1010447-02-5 | 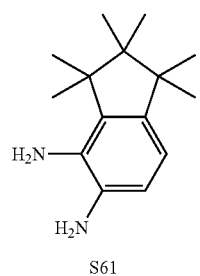 S61 | 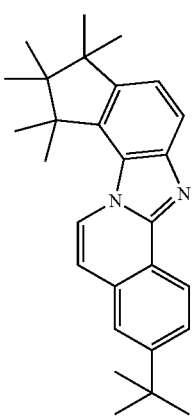 Chromatographic separation of the regioisomer | 20% |

-continued
| Ex. | 2-Alkynylaryl-aldehyde | 1,2-Diamino-benzene | Product | Yield |
|---|---|---|---|---|
| L78 | 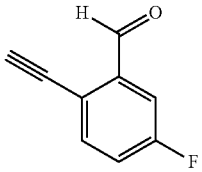 749874-24-6 | 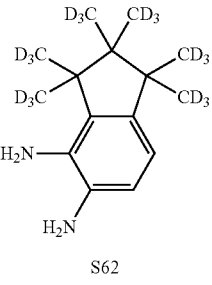 S62 | 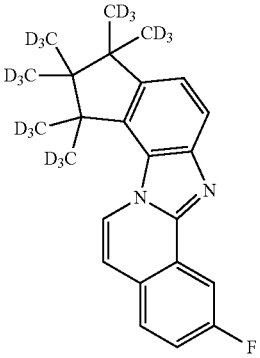 Chromatographic separation of the regioisomer | 18% |
| L79 | 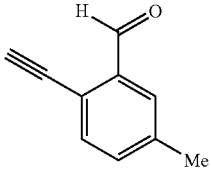 1309565-96-5 | 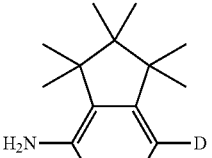 S63 | 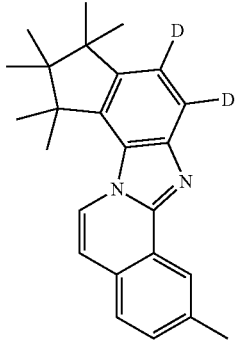 Chromatographic separation of the regioisomer | 20% |
| L80 | 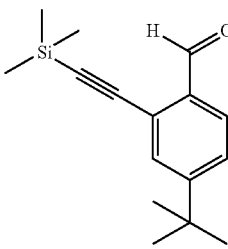 1010446-99-7 | 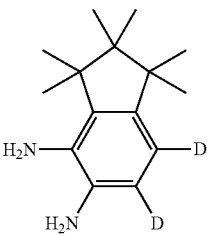 S63 | 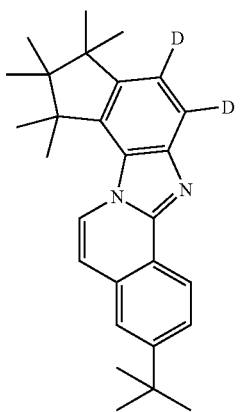 Chromatographic separation of the regioisomer | 22% |

-continued
| Ex. | 2-Alkynylaryl-aldehyde | 1,2-Diamino-benzene | Product | Yield |
|---|---|---|---|---|
| L81 | | | | 24% |
| L82 | | | | 23% |
| L83 | | | | 24% |
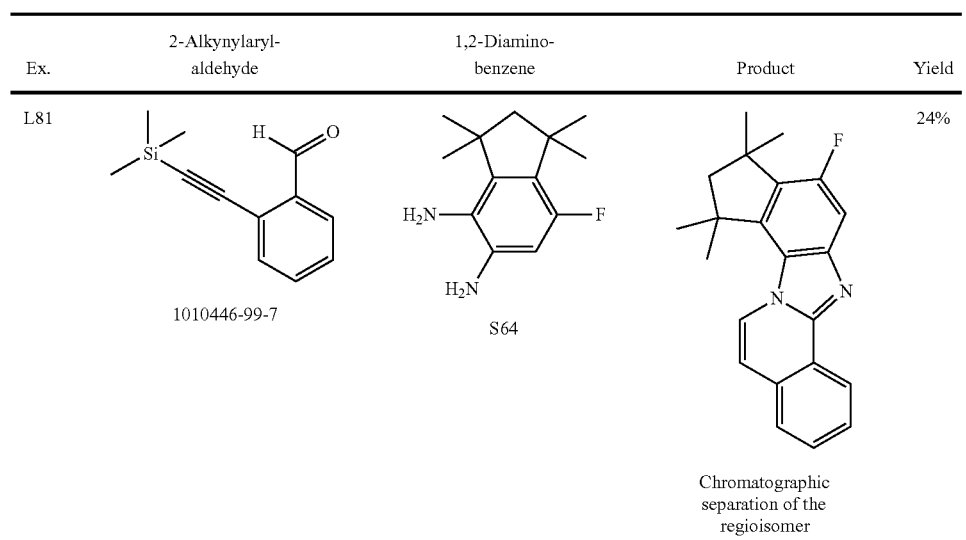
Chromatographic separation of the regioisomer
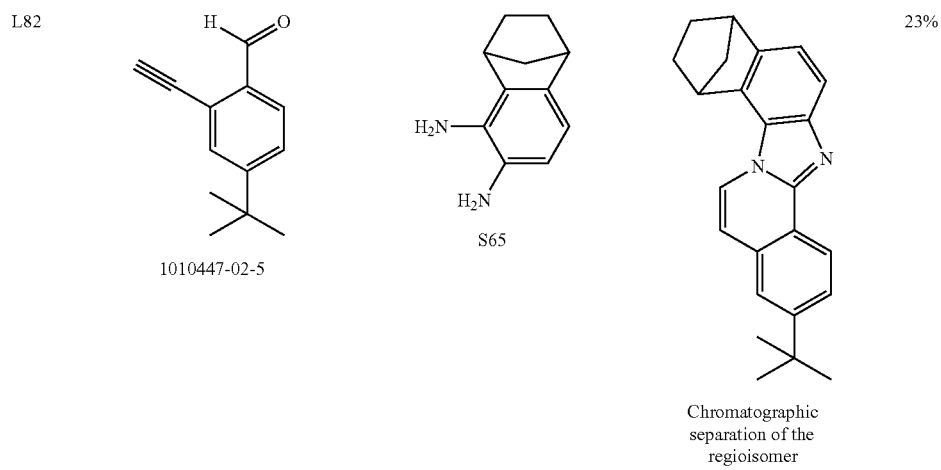
Chromatographic separation of the regioisomer
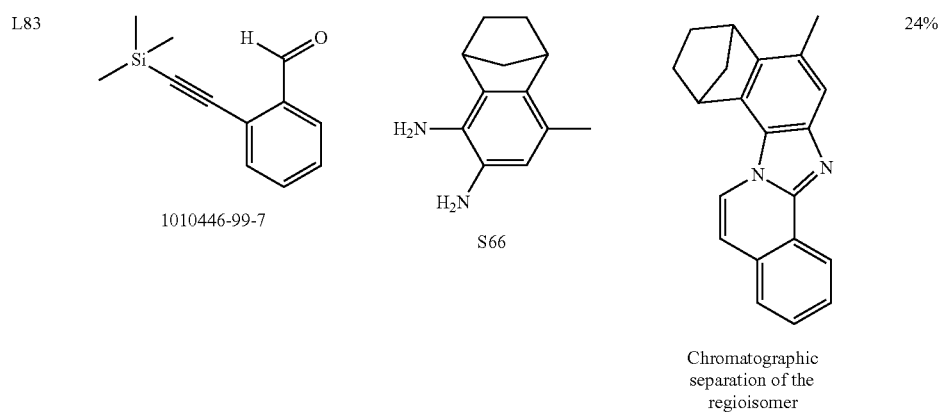
Chromatographic separation of the regioisomer

| Ex. | 2-Alkynylaryl-aldehyde | 1,2-Diamino-benzene | Product | Yield |
|---|---|---|---|---|
| L84 | 1010447-02-5 | S61 | Chromatographic separation of the regioisomer | 26% |
| L85 | S103 | S24 | | 58% |
| L86 | S103 | 81864-05-3 | | 54% |
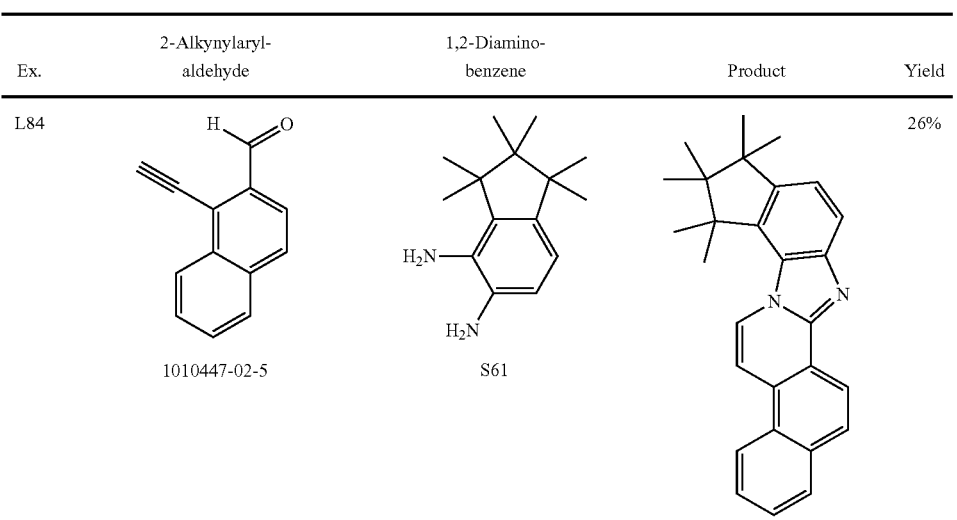
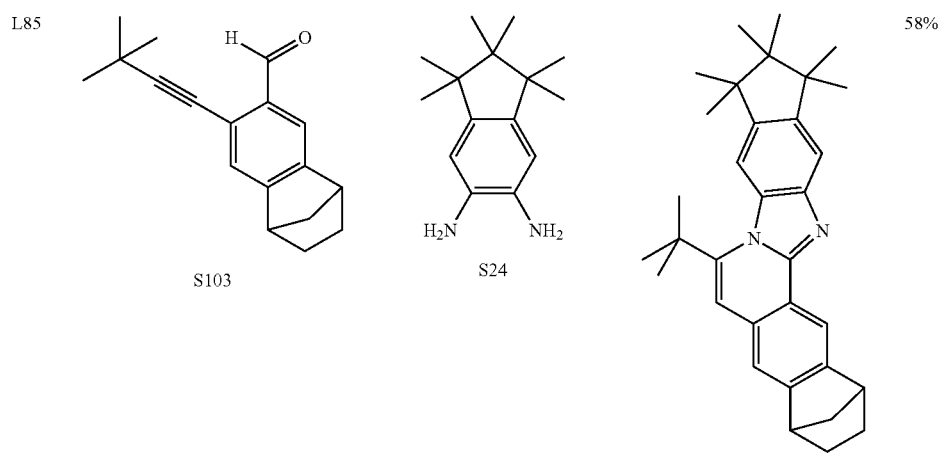
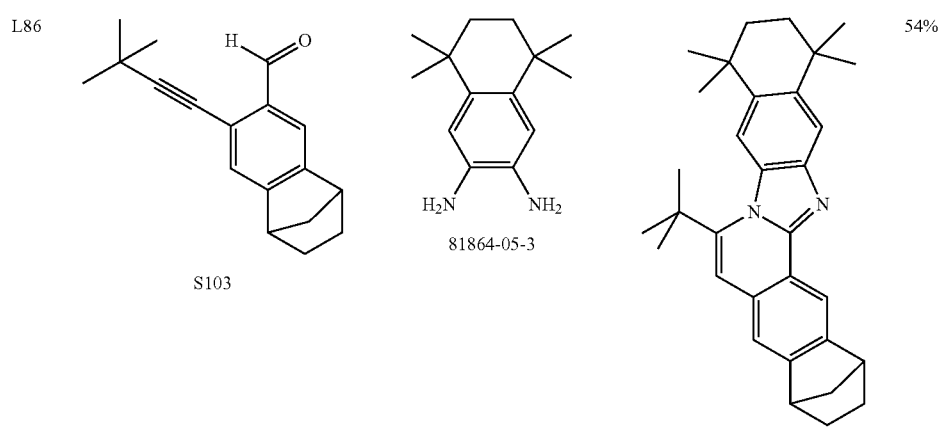

-continued
| Ex. | 2-Alkynylaryl-aldehyde | 1,2-Diamino-benzene | Product | Yield |
|---|---|---|---|---|
| L87 | 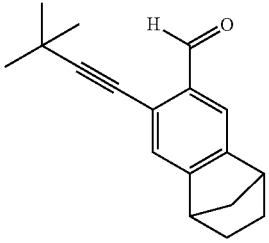<br>S103 | 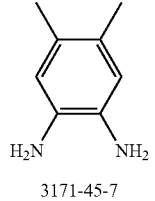<br>3171-45-7 | 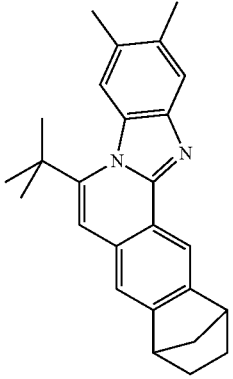 [SMILES: Cc1cc2nc3c4cc5c(cc4cc(C(C)(C)C)n3c2cc1C)C1CCC5C1] | 59% |
| L88 | 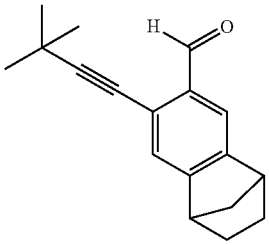<br>S103 | 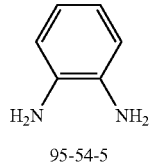<br>95-54-5 | 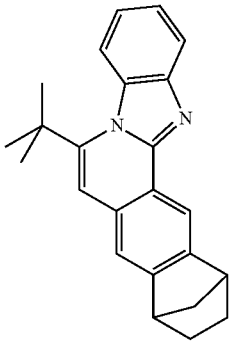 [SMILES: CC(C)(C)c1cc2cc3c(cc2c2nc4ccccc4n12)C1CCC3C1] | 59% |
| L89 | 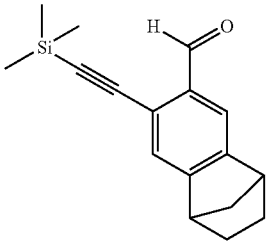<br>S104 | 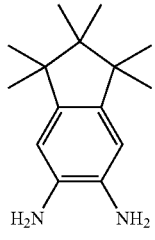<br>S24 | 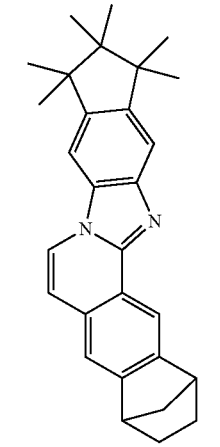 [SMILES: CC1(C)c2cc3nc4c5cc6c(cc5ccn4c3cc2C(C)(C)C1(C)C)C1CCC6C1] | 56% |
| L90 | 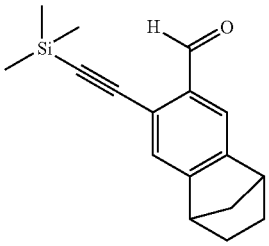<br>S104 | 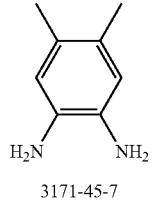<br>3171-45-7 | 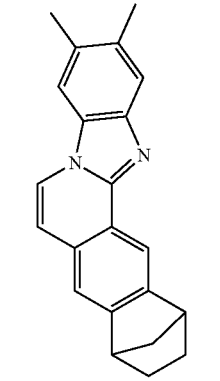 [SMILES: Cc1cc2nc3c4cc5c(cc4ccn3c2cc1C)C1CCC5C1] | 61% |

-continued
| Ex. | 2-Alkynylaryl-aldehyde | 1,2-Diamino-benzene | Product | Yield |
|---|---|---|---|---|
| L91 | 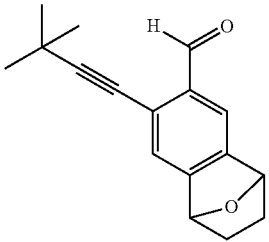 S105 | 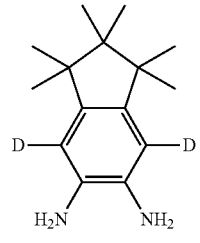 S26 | 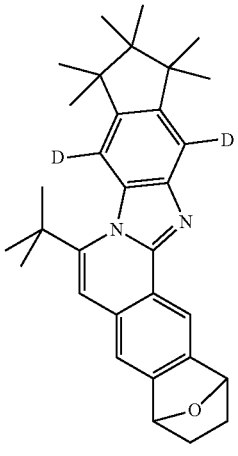 [SMILES: [2H]c1c2c(c([2H])c3c1nc1c4cc5c(cc4cc(C(C)(C)C)n13)C1CCC5O1)C(C)(C)C(C)(C)C2(C)C] | 60% |
| L92 | 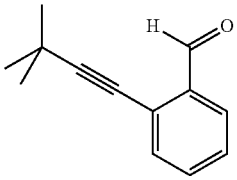 183312-34-7 | 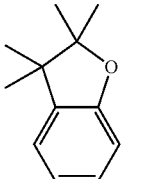 S37 | 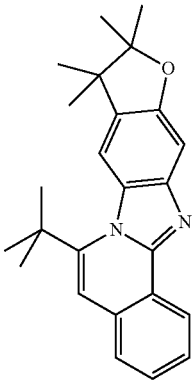<br>Chromatographic separation of the regioisomer | 23% |
| L93 | 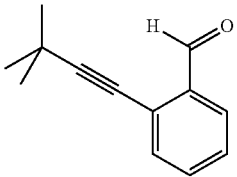 183312-34-7 | 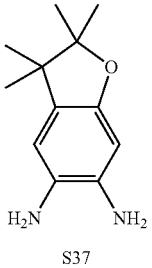 S37 | 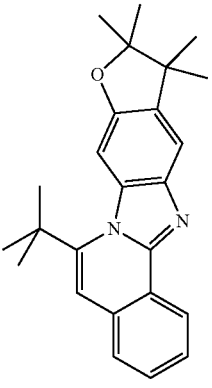<br>Chromatographic separation of the regioisomer | 20% |

-continued
| Ex. | 2-Alkynylaryl-aldehyde | 1,2-Diamino-benzene | Product | Yield |
|---|---|---|---|---|
| L94 | S104 | S37 | Chromatographic separation of the regioisomer | 24% |
| L95 | 183312-34-7 | S37 | Chromatographic separation of the regioisomer | 23% |
General Ligand Synthesis Variant C:
From 1-aminoisoquinolines and 1,2-dihalobenzenes:
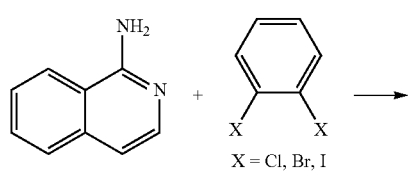
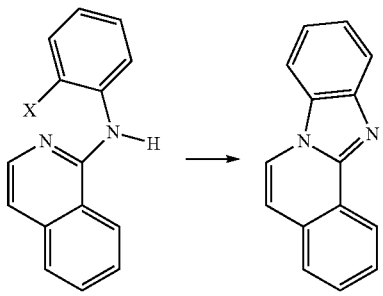

A vigorously stirred mixture of 100 mmol of the 1,2-dihalobenzene, 120 mmol of 1-aminoisoquinoline, 300 mmol of lithium bis(trimethylsilyl)amide, 100 g of glass beads (diameter 3 mm), 5 mmol of xantphos and 5 mmol of palladium(II) acetate in 600 ml of dry 1,4-dioxane is heated under reflux for 72 h until the 1-aminoisoquinoline has been consumed. For cyclisation of the secondary amine, the reaction mixture is cooled, and 10 mmol of copper(I) iodide, 20 mmol of N,N'-ethylenediamine and 230 mmol of potassium carbonate are added. The reaction mixture is refluxed again for 2-4 hours until the secondary amine has been consumed. After cooling, the solid material is filtered off over a Celite bed, rinsed with 1500 ml of dioxane, and the filtrate is evaporated to dryness. The residue is dissolved in 200 ml of dichloromethane and filtered through a silica-gel bed. The bed is rinsed with a mixture of 2000 ml of dichloromethane and 150 ml of ethyl acetate, and the filtrate is evaporated to dryness. The residue is recrystallised and dried in vacuo. The benzo[4,5]-imidazo[2,1-a]isoquinoline obtained in this way is freed from low-boiling components and non-volatile secondary components by bulb-tube distillation or fractional sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L3

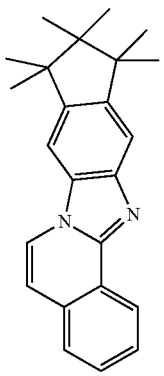

Use of 36.0 g (100 mmol) of 5,6-dibromo-1,1,2,2,3,3-hexamethylindane, S24, variant A, step A, 17.4 g (120 mmol) of 1-aminoisoquinoline [1532-84-9], 50.2 g (300 mmol) of lithium bis(trimethylsilyl)amide, 2.9 g (5 mmol) of xantphos, 1.1 g (5 mmol) of palladium(II) acetate and then 1.9 g (10 mmol) of copper(I) iodide, 1.75 g (20 mmol) of N,N'-ethylenediamine and 31.8 g (230 mmol) of potassium carbonate. The crude product is recrystallised from cyclohexane (about 15 ml/g) and sublimed in vacuo (p=$10^{-5}$ mbar, T=220° C.). Yield: 20.9 g (61 mmol), 61%; purity: about 99.5% according to $^1$H-NMR.

The following compounds are prepared analogously:

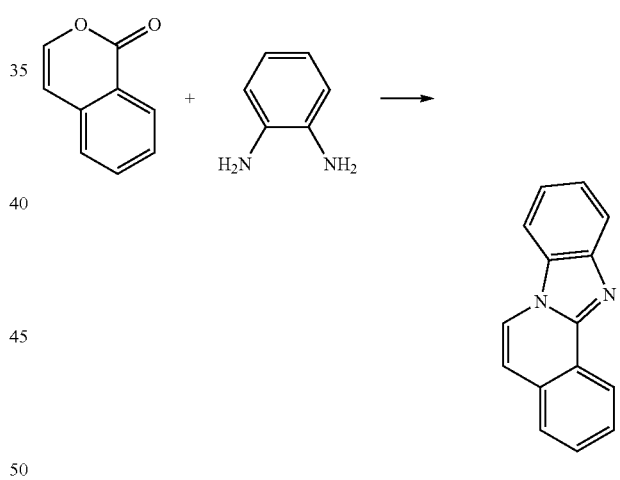

| Ex. | 1-Aminoiso-quinoline derivative | 1,2-Dihalo-benzene | Product | Yield |
|---|---|---|---|---|
| L4 | 1532-84-9 | S25 Variant A, step A | | 63% |
| L7 | 1532-84-9 | 42810-32-2 | | 66% |

General Ligand Synthesis Variant D:
From isocoumarines and 1,2-diaminobenzenes:

Preparation analogous to V. K. Pandey et al., Ind. J. Chem. Section B: 1999, 38B(12), 138.

A mixture of 100 mmol of the isocoumarine derivative, 110 mmol of the 1,2-diaminobenzene, 5 mmol of 4-(N,N-dimethylamino)pyridine and 200 ml of dry pyridine is boiled on a water separator, with pyridine being discharged from time to time until the pyridine has been substantially distilled off. Towards the end, a weak vacuum is applied in order to remove pyridine residues. After cooling, the viscous to glass-like residue is taken up in 200 ml of methanol and dissolved at elevated temperature, during which the product begins to crystallise. After cooling, the product is filtered off with suction and washed with a little methanol. After recrystallisation (methanol, ethanol, acetone, dioxane, DMF, etc.) of the benzo[4,5]imidazo-[2,1-a]isoquinoline obtained in this way, the latter is freed from low-boiling components and non-volatile secondary components by bulb-tube distillation or fractional sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L276

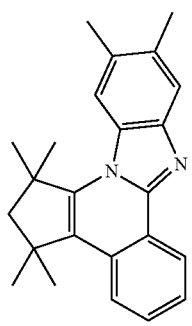 [SMILES: Cc1cc2nc3c4ccccc4c4c(n3c2cc1C)C(C)(C)CC4(C)C]

Use of 24.4 g (100 mmol) of 1,1,3,3-tetramethyl-2,3-dihydro-1H-cyclopenta[c]isochromen-5-one, S117, 15.0 g (110 mmol) of 4,5-dimethyl-1,2-diaminobenzene [3171-45-7], 611 mg (5 mmol) of 4-(N,N-dimethylamino)pyridine. The crude product is recrystallised from cyclohexane (about 15 ml/g) and sublimed in vacuo (p=$10^{-5}$ mbar, T=220° C.). Yield: 16.4 g (48 mmol), 48%; purity: about 99.5% according to $^1$H-NMR.

The following compounds are prepared analogously:

| Ex. | Isocoumarine | 1,2-Diamino-benzene | Product | Yield |
|---|---|---|---|---|
| L277 | S117 | S24 | | 45% |
| L278 | S117 | 124639-03-8 S32 | | 43% |

2) Ligands of the benzo[4,5]imidazo[2,1-c]quinazoline Type
General Ligand Synthesis Variant A:
From 2-amidoarylaldehydes and 1,2-diaminobenzenes

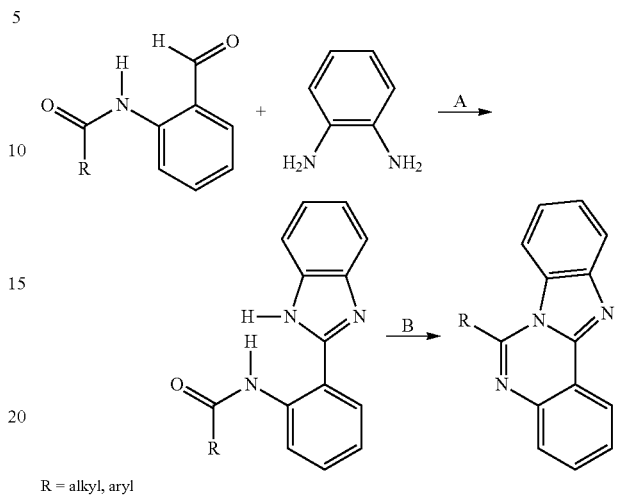

R = alkyl, aryl

Step A:
A solution of 100 mmol of the 2-amidoarylaldehyde and 110 mmol of the 1,2-diaminobenzene in 70 ml of ethanol is placed in a 500 ml round-bottomed flask with water separator and stirred at 50° C. for 30 min. 70 ml of nitrobenzene are then added, and the temperature is increased stepwise to gentle reflux of the nitrobenzene, with the ethanol and water formed being distilled off during the heating. After 4 h under gentle reflux, the mixture is allowed to cool to 50° C., 40 ml of methanol are added, the mixture is then allowed to cool fully with stirring, stirred at room temperature for a further 2 h, the crystals of 2-(2-amidophenyl)benzimidazole formed are then filtered off with suction, washed twice with 20 ml of methanol each time and dried in vacuo. If the 2-(2-amidophenyl)benzimidazole does not crystallise out, the solvent is removed in vacuo, and the residue is employed in step B.
Step B:
Variant A:
350 mmol of the corresponding carbonyl chloride and 50 mmol of the corresponding carboxylic acid are added to a vigorously stirred mixture (precision glass stirrer) of 100 mmol of the 2-(2-amidophenyl)benzimidazole and 150 ml of dioxane or diethylene glycol dimethyl ether, and the mixture is heated under reflux (typically 4-48 h) until the 2-(2-amidophenyl)benzimidazole has reacted. Corresponding carbonyl chlorides and carboxylic acids are those which form the respective amide radical.

After cooling, the reaction mixture is introduced with vigorous stirring into a mixture of 1000 g of ice and 300 ml of aqueous conc. ammonia. If the product is produced in the form of a solid, this is filtered off with suction, washed with water and sucked dry. If the product is produced in the form of an oil, this is extracted with three portions of 300 ml each of ethyl acetate or dichloromethane. The organic phase is separated off, washed with 500 ml of water and evaporated in vacuo. The crude product is taken up in ethyl acetate or dichloromethane, filtered through a short column of aluminium oxide, basic, activity grade 1, or silica gel in order to remove brown impurities. After recrystallisation (methanol, ethanol, acetone, dioxane, DMF, etc.) of the benzo[4,5]imidazo[2,1-c]quinazoline obtained in this way, the latter is freed from low-boiling components and non-volatile secondary components by bulb-tube distillation or fractional sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Variant B:

Analogous procedure to variant A, but 50 mmol of water are added instead of the carboxylic acid.

Variant C:

Analogous procedure to variant A, but no carboxylic acid is added.

Example L96

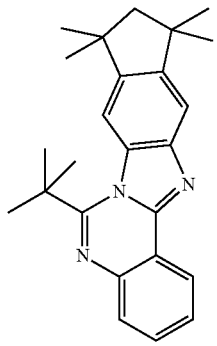 [SMILES: CC(C)(C)c1nc2ccccc2c2nc3cc4c(cc3n12)C(C)(C)CC4(C)C]

Step A:

Use of 20.5 g (100 mmol) of S69 and 22.5 g (110 mmol) of S16.

The 2,2-dimethyl-N-[2-(5,5,7,7-tetramethyl-1,5,6,6-tetrahydroindeno[5,6-d]-imidazol-2-yl)phenyl]propionamide crystallises out, yield 31.6 g (81 mmol) 81%; purity: 97% according to $^1$H-NMR.

Step B, Variant A:

Use of 31.6 g (81 mmol) of 2,2-dimethyl-N-[2-(5,5,7,7-tetramethyl-1,5,6,6-tetrahydroindeno[5,6-d]imidazol-2-yl) phenyl]propionamide (step A), 120 ml of dioxane, 33.8 g (280 mmol) of pivaloyl chloride [3282-30-2] and 4.1 g (40 mmol) of pivalic acid [75-98-9], reaction time 16 h, the crude product is produced in the form of a solid on neutralisation, recrystallisation from DMF/ethanol, fractional sublimation of the product twice at T about 170° C., p about $10^{-4}$ mbar. Yield: 19.3 g (52 mmol), 64%; purity: about 99.5% according to $^1$H-NMR.

General Ligand Synthesis Variant B:

From 2-formamidoarylaldehydes and 1,2-diaminobenzenes

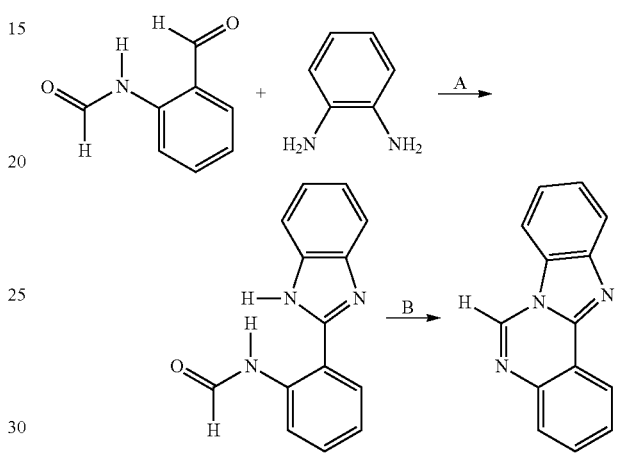

Step A:

Analogous to step A of the reaction of 2-amidoarylaldehydes and 1,2-diaminobenzenes.

Step B:

100 mmol of the 2-(2-formamidophenyl)benzimidazole are suspended in 100 ml of dioxane. After addition of 1 ml of pyridine, 500 mmol of thionyl chloride are added dropwise to the reaction mixture, which is then stirred at room temperature until the reaction is complete (typically 24 h). the further work-up is carried out as described under step B of the reaction of 2-amidoarylaldehydes and 1,2-diaminobenzenes.

The following compounds can be prepared analogously:

| Ex. | 2-Amidoaryl-aldehyde | 1,2-Diamino-benzene | Product | Yield |
|---|---|---|---|---|
| L97 | S70 | S16 | | 55% |

-continued

| Ex. | 2-Amidoaryl-aldehyde | 1,2-Diamino-benzene | Product | Yield |
|---|---|---|---|---|
| L98 | S73 | S16 | | 59% |
| L99 | S76 | S16 | | 61% |
| L100 | S83 | S16 | | 60% |
| L101 | S87 | S16 | | 58% |

| Ex. | 2-Amidoaryl-aldehyde | 1,2-Diamino-benzene | Product | Yield |
|---|---|---|---|---|
| L102 | 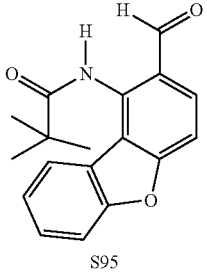 S95 | 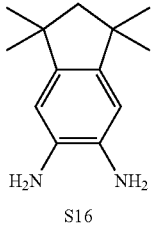 S16 | 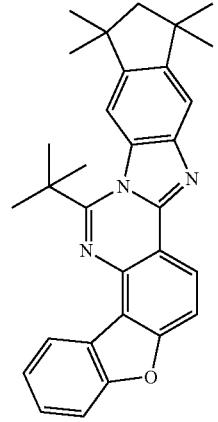 [SMILES: CC(C)(C)c1nc2c(ccc3oc4ccccc4c32)c2nc3cc4c(cc3n12)C(C)(C)CC4(C)C] | 57% |
| L103 | 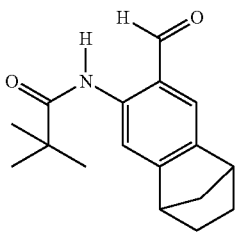 S99 | 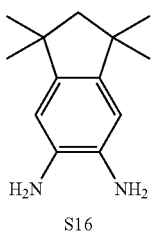 S16 | 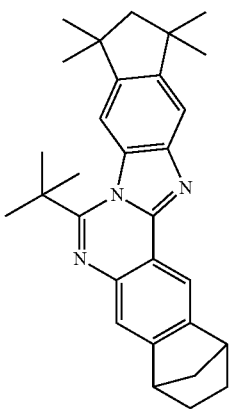 [SMILES: CC(C)(C)c1nc2cc3c(cc2c2nc4cc5c(cc4n12)C(C)(C)CC5(C)C)C1CCC3C1] | 58% |
| L104 | 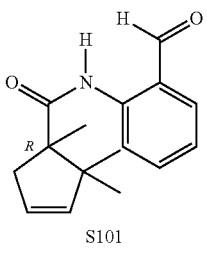 S101 | 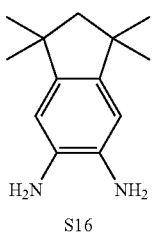 S16 | 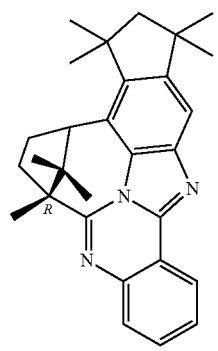 Gen. ligand synthesis variant B | 14% |

-continued
| Ex. | 2-Amidoaryl-aldehyde | 1,2-Diamino-benzene | Product | Yield |
|---|---|---|---|---|
| L105 | 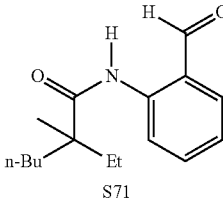 S71 | 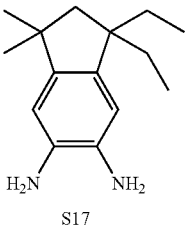 S17 | 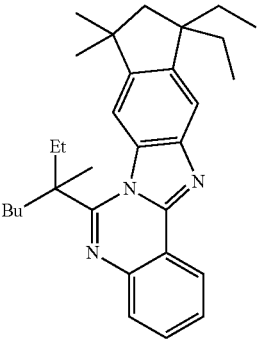<br>Chromatographic separation of the regioisomer | 23% |
| L106 | 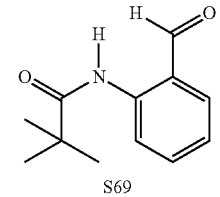 S69 | 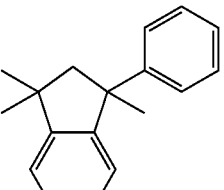 S19 | 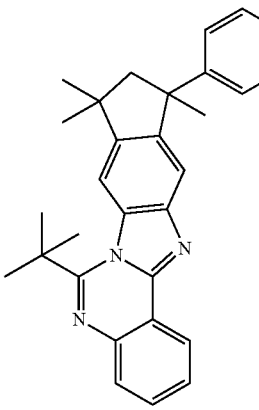<br>Chromatographic separation of the regioisomer | 15% |
| L107 | 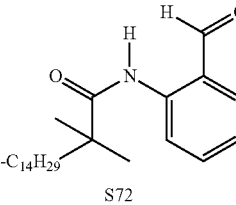 S72 | 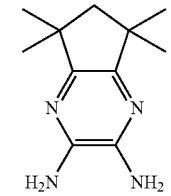 S22 | 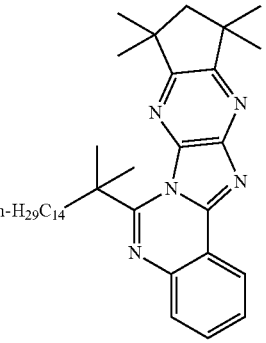 | 43% |

-continued

| Ex. | 2-Amidoaryl-aldehyde | 1,2-Diamino-benzene | Product | Yield |
|---|---|---|---|---|
| L108 | S74 | S23 | | 57% |
| L109 | S69 | S24 | | 55% |
| L110 | S73 | S24 | | 56% |

| Ex. | 2-Amidoaryl-aldehyde | 1,2-Diamino-benzene | Product | Yield |
|---|---|---|---|---|
| L111 | S75 | S24 | | 50% |
| L112 | S77 | S24 | | 58% |
| L113 | S79 | S24 | | 58% |

-continued

| Ex. | 2-Amidoaryl-aldehyde | 1,2-Diamino-benzene | Product | Yield |
|---|---|---|---|---|
| L114 | S80 | S24 | | 47% |
| L115 | S81 | S24 | | 44% |
| L116 | S84 | S24 | | 53% |

| Ex. | 2-Amidoaryl-aldehyde | 1,2-Diamino-benzene | Product | Yield |
|---|---|---|---|---|
| L117 | 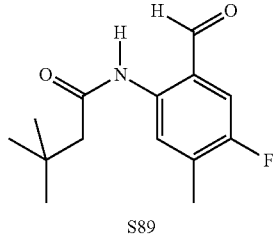 S89 | 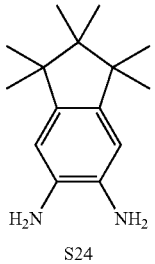 S24 | 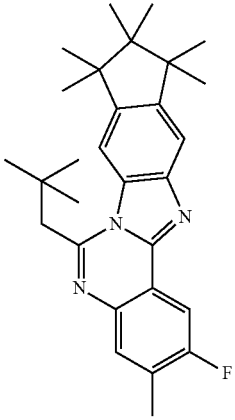 [SMILES: Cc1cc2nc(CC(C)(C)C)n3c4cc5c(cc4nc3c2cc1F)C(C)(C)C(C)(C)C5(C)C] | 49% |
| L118 | 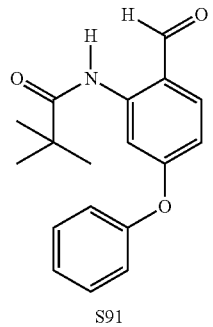 S91 | 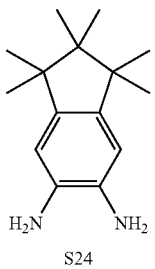 S24 | 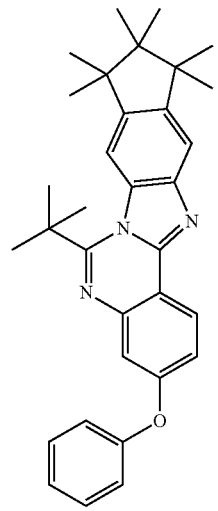 [SMILES: CC(C)(C)c1nc2cc(Oc3ccccc3)ccc2c2nc3cc4c(cc3n12)C(C)(C)C(C)(C)C4(C)C] | 39% |
| L119 | 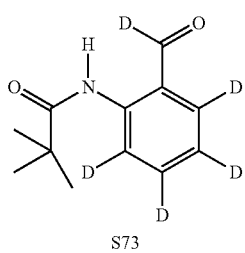 S73 | 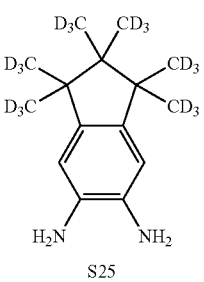 S25 | 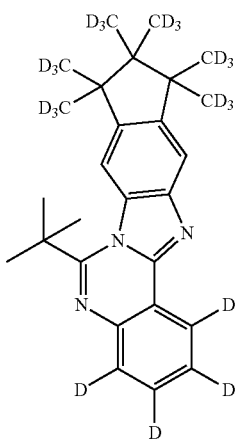 [SMILES: [2H]c1c([2H])c([2H])c2c(nc(C(C)(C)C)n3c4cc5c(cc4nc23)C(C([2H])([2H])[2H])(C([2H])([2H])[2H])C(C([2H])([2H])[2H])(C([2H])([2H])[2H])C5(C([2H])([2H])[2H])C([2H])([2H])[2H])c1[2H]] | 50% |

-continued
| Ex. | 2-Amidoaryl-aldehyde | 1,2-Diamino-benzene | Product | Yield |
|---|---|---|---|---|
| L120 | 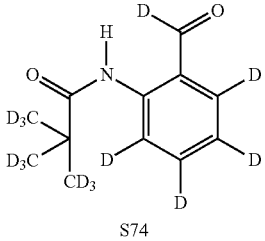 S74 | 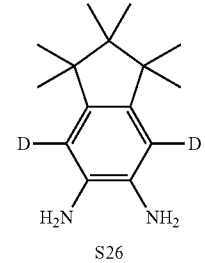 S26 | 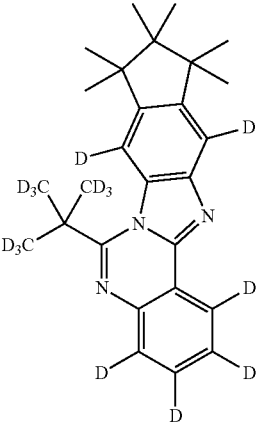 [SMILES: [2H]c1c([2H])c([2H])c2c(nc(C(C([2H])([2H])[2H])(C([2H])([2H])[2H])C([2H])([2H])[2H])n3c2nc2c([2H])c4c(c([2H])c23)C(C)(C)C(C)(C)C4(C)C)c1[2H]] | 54% |
| L121 | 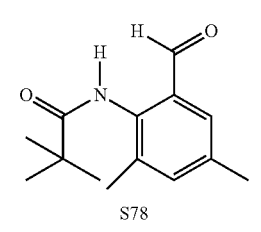 S78 | 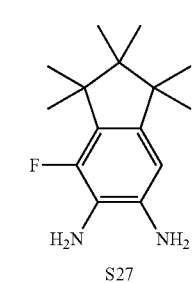 S27 | 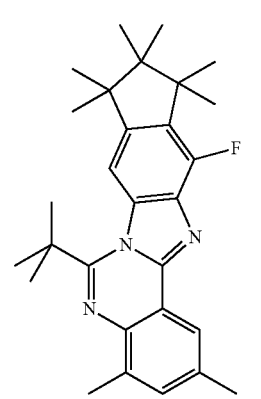 Chromatographic separation of the regioisomer | 26% |
| L122 | 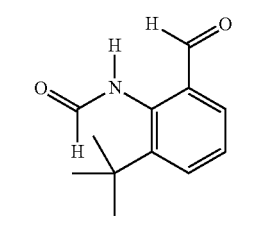 S83 | 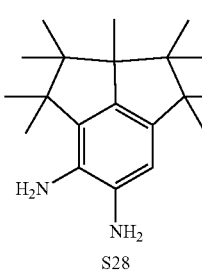 S28 | 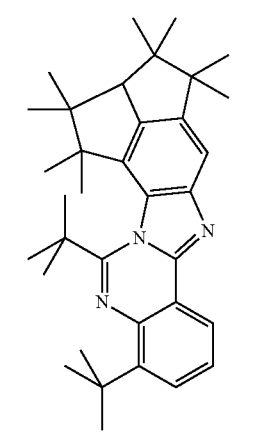 Chromatographic separation of the regioisomer | 20% |

-continued
| Ex. | 2-Amidoaryl-aldehyde | 1,2-Diamino-benzene | Product | Yield |
|---|---|---|---|---|
| L123 | 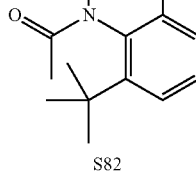<br>S82 | 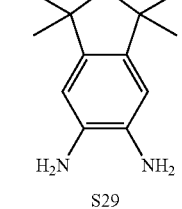<br>S29 | 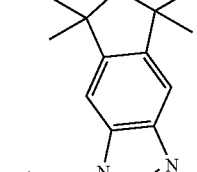 | 51% |
| L124 | 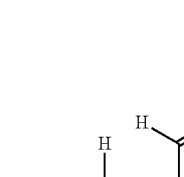<br>S85 | 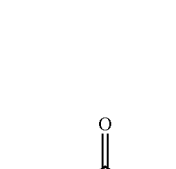<br>S30 | 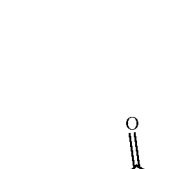 | 33% |
| L125 | <br>S86 | <br>S31 | 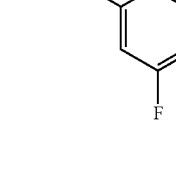 | 30% |

-continued
| Ex. | 2-Amidoaryl-aldehyde | 1,2-Diamino-benzene | Product | Yield |
|---|---|---|---|---|
| L126 | 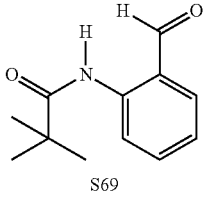 S69 | 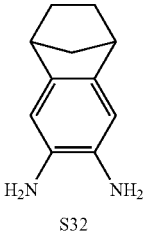 S32 | 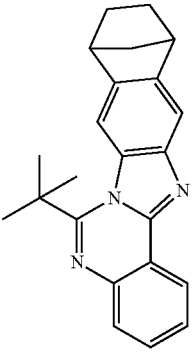 | 56% |
| L127 | 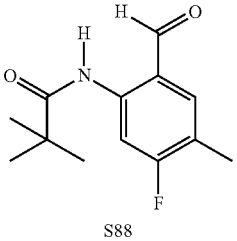 S88 | 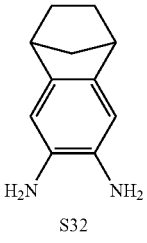 S32 | 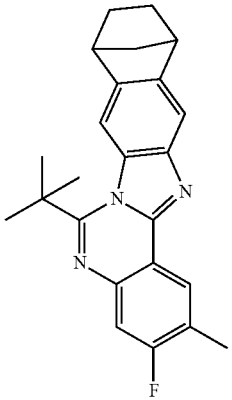 [SMILES: Cc1cc2c(cc1F)nc(C(C)(C)C)n1c3cc4c(cc3nc21)C1CCC4C1] | 53% |
| L128 | 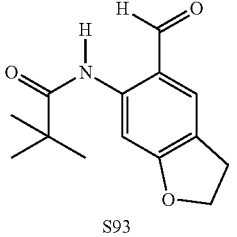 S93 | 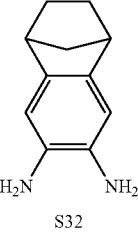 S32 | 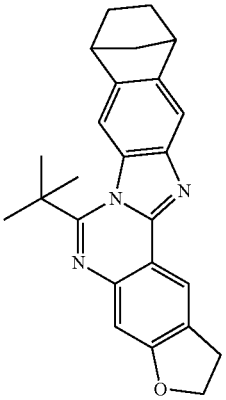 [SMILES: CC(C)(C)c1nc2cc3c(cc2c2nc4cc5c(cc4n12)C1CCC5C1)CCO3] | 41% |

-continued
| Ex. | 2-Amidoaryl-aldehyde | 1,2-Diamino-benzene | Product | Yield |
|---|---|---|---|---|
| L129 | 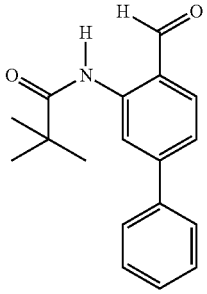<br>S94 | 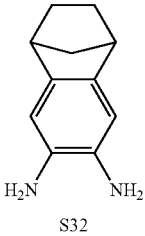<br>S32 | 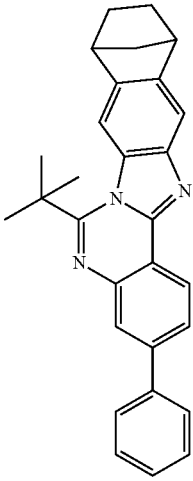 [SMILES: CC(C)(C)c1nc2cc(-c3ccccc3)ccc2c2nc3cc4c(cc3n12)C1CCC4C1] | 53% |
| L130 | 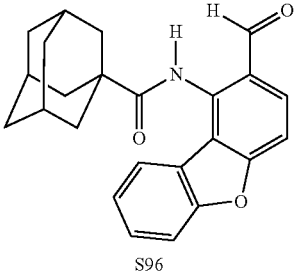 [SMILES: O=Cc1ccc2oc3ccccc3c2c1NC(=O)C12CC3CC(CC(C3)C1)C2 ; "S96"]<br>S96 | 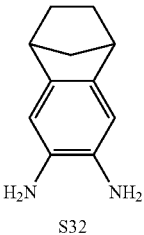<br>S32 | 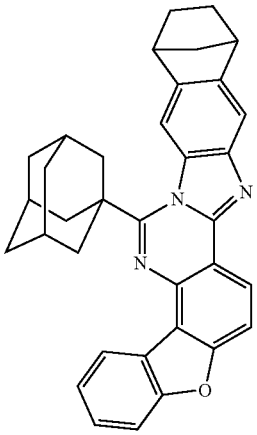 [SMILES: c1ccc2c(c1)oc1ccc3c(nc(C45CC6CC(CC(C6)C4)C5)n4c5cc6c(cc5nc34)C3CCC6C3)c12] | 46% |
| L131 | 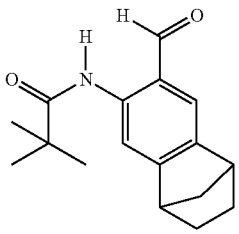<br>S99 | 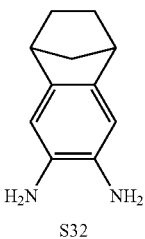 [SMILES: Nc1cc2c(cc1N)C1CCC2C1 ; "S32"]<br>S32 | 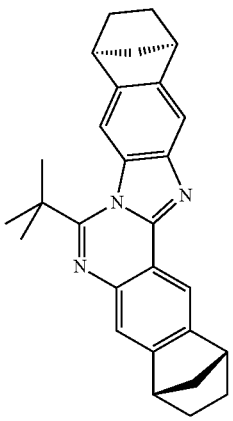<br>Chromatographic separation of the diastereomers | 18% |

| Ex. | 2-Amidoaryl-aldehyde | 1,2-Diamino-benzene | Product | Yield |
|---|---|---|---|---|
| L132 | 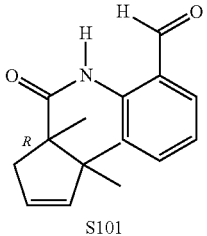 S101 | 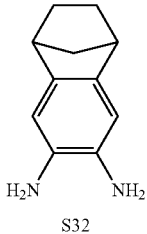 S32 | 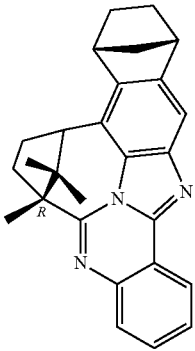 Gen. ligand synthesis variant B, T = 100° C. Chromatographic separation of the diastereomers | 20% |
| L133 | 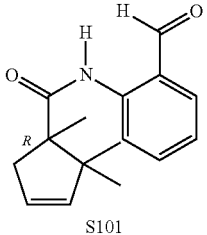 S101 | 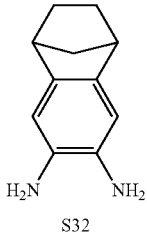 S32 | 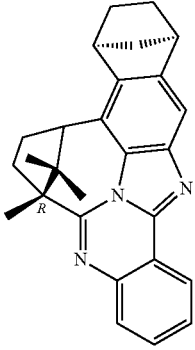 Gen. ligand synthesis variant B, T = 100° C. Chromatographic separation of the diastereomers | 13% |
| L134 | 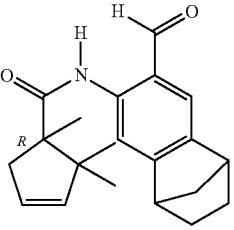 S102 | 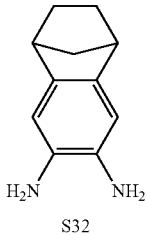 S32 | 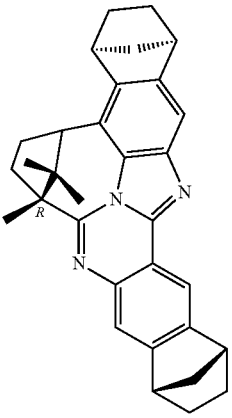 Gen. ligand synthesis variant B, T = 100° C. Chromatographic separation of the diastereomers | 14% |

-continued

| Ex. | 2-Amidoaryl-aldehyde | 1,2-Diamino-benzene | Product | Yield |
|---|---|---|---|---|
| L135 | S97 | S33 | | 56% |
| L136 | S82 | S35 | Chromatographic separation of the regioisomer | 24% |
| L137 | S90 | S36 | | 22% |

| Ex. | 2-Amidoaryl-aldehyde | 1,2-Diamino-benzene | Product | Yield |
|---|---|---|---|---|
| L138 | 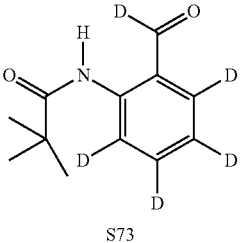 S73 | 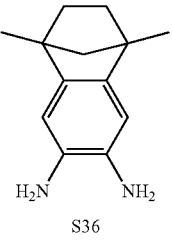 S36 | 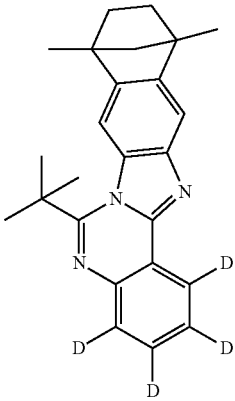 [SMILES: [2H]c1c([2H])c([2H])c2c(nc(C(C)(C)C)n3c4cc5c(cc4nc23)C2(C)CCC5(C)C2)c1[2H]] | 55% |
| L139 | 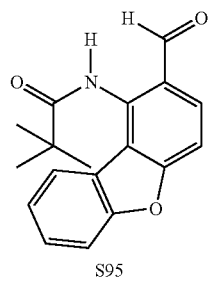 S95 | 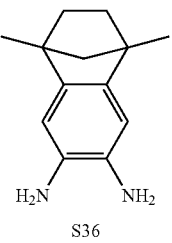 S36 | 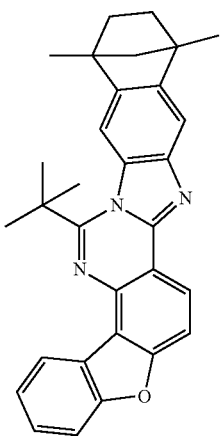 [SMILES: CC(C)(C)c1nc2c(ccc3oc4ccccc4c32)c2nc3cc4c(cc3n12)C1(C)CCC4(C)C1] | 47% |
| L140 | 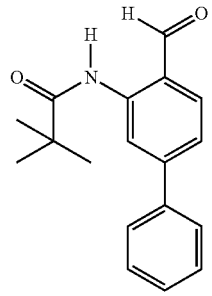 S94 | 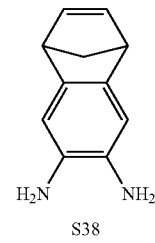 S38 | 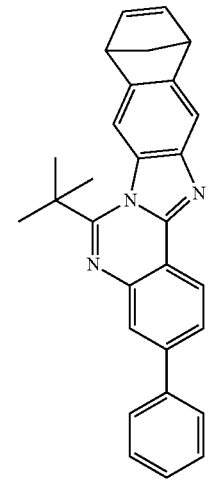 [SMILES: CC(C)(C)c1nc2cc(-c3ccccc3)ccc2c2nc3cc4c(cc3n12)C1C=CC4C1] | 30% |

| Ex. | 2-Amidoaryl-aldehyde | 1,2-Diamino-benzene | Product | Yield |
|---|---|---|---|---|
| L141 | 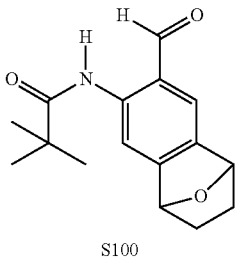 S100 | 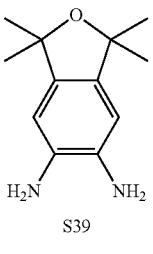 S39 | 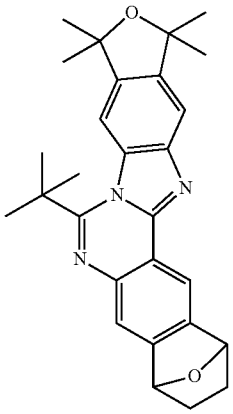 [SMILES: CC(C)(C)c1nc2cc3c(cc2c2nc4cc5c(cc4n12)C(C)(C)OC5(C)C)C1CCC3O1] | 48% |
| L142 | 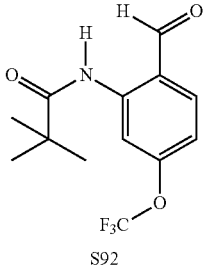 S92 | 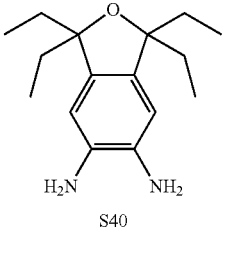 S40 | 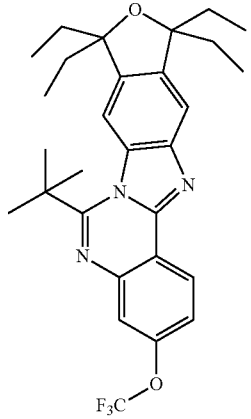 [SMILES: CCC1(CC)OC(CC)(CC)c2cc3c(cc21)nc1c2ccc(OC(F)(F)F)cc2nc(C(C)(C)C)n31] | 44% |
| L143 | 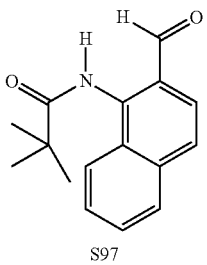 S97 | 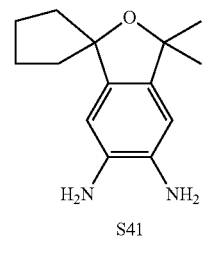 S41 | 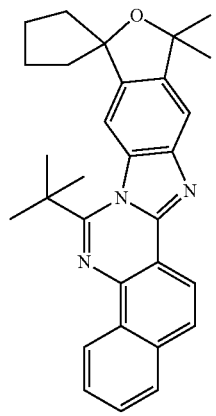 Chromatographic separation of the regioisomer | 25% |

-continued

| Ex. | 2-Amidoaryl-aldehyde | 1,2-Diamino-benzene | Product | Yield |
|---|---|---|---|---|
| L144 | S92 | S43 | | 41% |
| L145 | S79 | S44 | | 54% |
| L146 | S78 | S46 | | 56% |
| L147 | S72 | S47 | | 28% |

-continued
| Ex. | 2-Amidoaryl-aldehyde | 1,2-Diamino-benzene | Product | Yield |
|---|---|---|---|---|
| L148 | 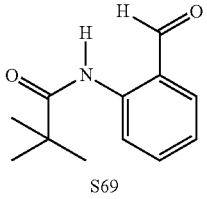 S69 | 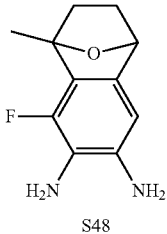 S48 | 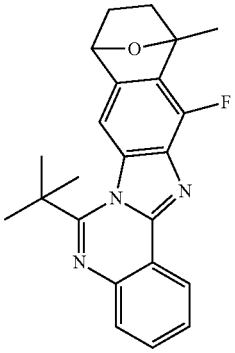 Chromatographic separation of the regioisomer | 17% |
| L149 | 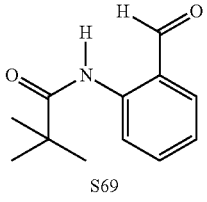 S69 | 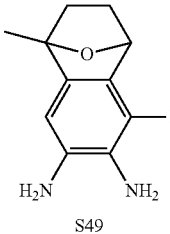 S49 | 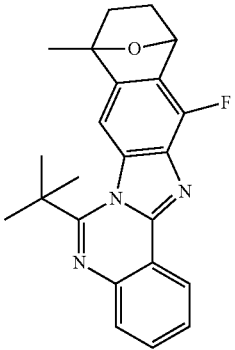 Chromatographic separation of the regioisomer | 22% |
| L150 | 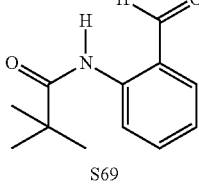 S69 | 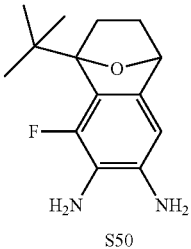 S50 | 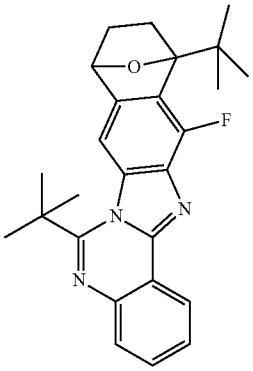 Chromatographic separation of the regioisomer | 18% |

US 9,837,622 B2
207                                                                                                          208
-continued
| Ex. | 2-Amidoaryl-aldehyde | 1,2-Diamino-benzene | Product | Yield |
|---|---|---|---|---|
| L151 | 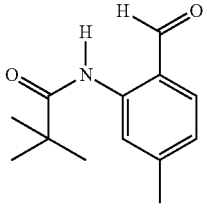<br>S75 | 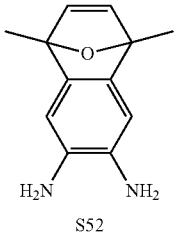<br>S52 | 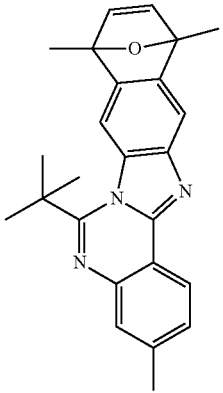 [SMILES: Cc1ccc2c(c1)nc(C(C)(C)C)n1c3cc4c(cc3nc21)C1(C)C=CC4(C)O1] | 32% |
| L152 | 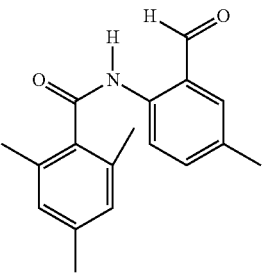<br>S77 | 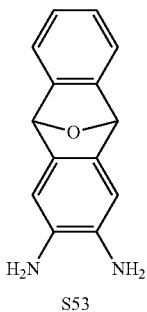 [SMILES: Nc1cc2c(cc1N)C1OC2c2ccccc21 ; "S53"]<br>S53 | 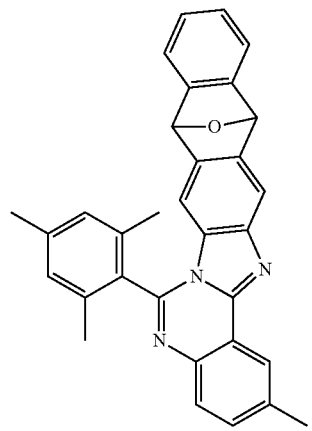 | 51% |
| L153 | 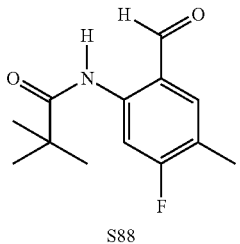 [SMILES: Cc1cc(C=O)c(NC(=O)C(C)(C)C)cc1F ; "S88"]<br>S88 | 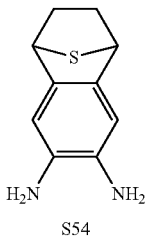<br>S54 | 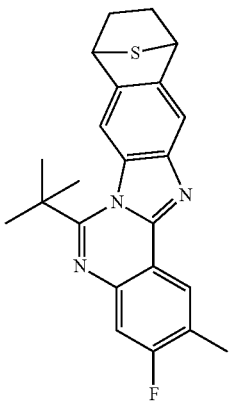 | 46% |

-continued
| Ex. | 2-Amidoaryl-aldehyde | 1,2-Diamino-benzene | Product | Yield |
|---|---|---|---|---|
| L154 | 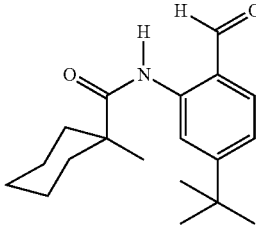<br>S80 | 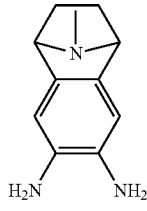<br>S55 | 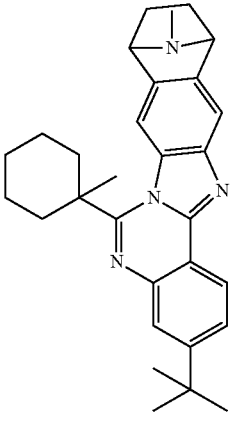 [SMILES: CN1C2CCC1c1cc3c(cc12)nc1c2ccc(C(C)(C)C)cc2nc(C2(C)CCCCC2)n31] | 21% |
| L155 | 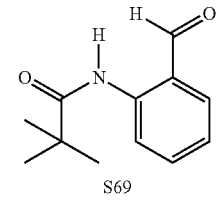<br>S69 | 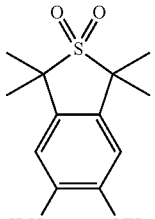<br>S57 | 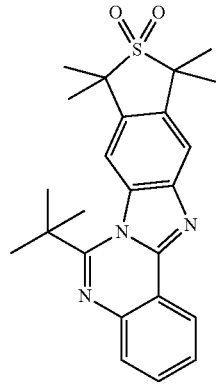 [SMILES: CC(C)(C)c1nc2ccccc2c2nc3cc4c(cc3n12)C(C)(C)S(=O)(=O)C4(C)C] | 26% |
| L156 | 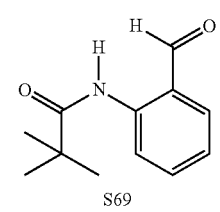<br>S69 | 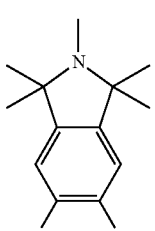<br>S58 | 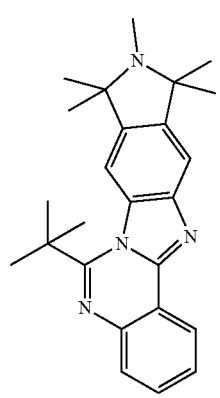 [SMILES: CN1C(C)(C)c2cc3nc4c5ccccc5nc(C(C)(C)C)n4c3cc2C1(C)C] | 20% |

-continued
| Ex. | 2-Amidoaryl-aldehyde | 1,2-Diamino-benzene | Product | Yield |
|---|---|---|---|---|
| L157 | 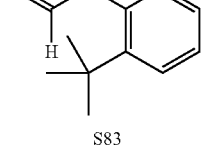 S83 | 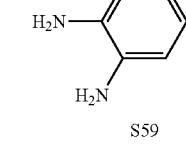 S59 | 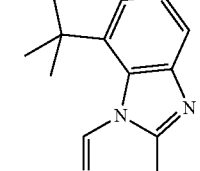 Chromatographic separation of the regioisomer | 16% |
| L158 |  S83 |  S60 | 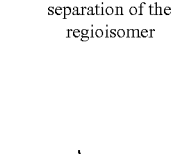 Chromatographic separation of the regioisomer | 18% |
| L159 | 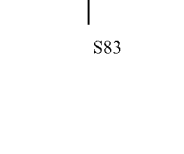 S83 | 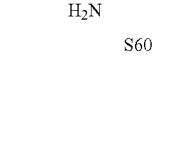 S61 | 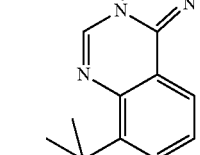 Chromatographic separation of the regioisomer | 23% |

-continued

| Ex. | 2-Amidoaryl-aldehyde | 1,2-Diamino-benzene | Product | Yield |
|---|---|---|---|---|
| L160 | S83 | S62 | Chromatographic separation of the regioisomer | 20% |
| L161 | S83 | S63 | Chromatographic separation of the regioisomer | 21% |
| L162 | S83 | S64 | Chromatographic separation of the regioisomer | 24% |

-continued
| Ex. | 2-Amidoaryl-aldehyde | 1,2-Diamino-benzene | Product | Yield |
|---|---|---|---|---|
| L163 | 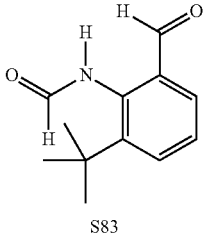 S83 | 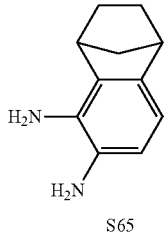 S65 | 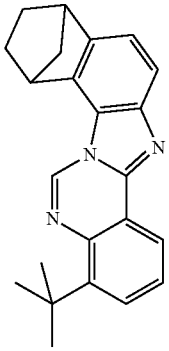 Chromatographic separation of the regioisomer | 25% |
| L164 | 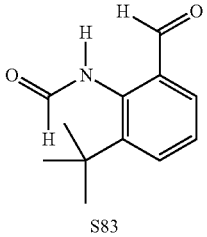 S83 | 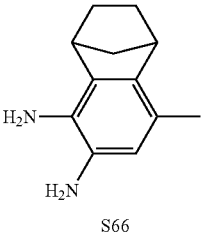 S66 | 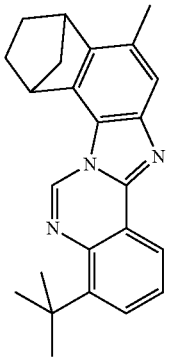 Chromatographic separation of the regioisomer | 24% |
| L165 | 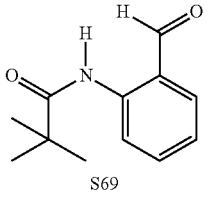 S69 | 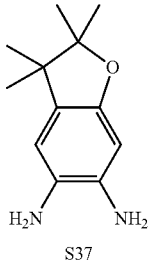 S37 | 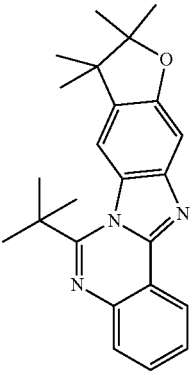 Chromatographic separation of the regioisomer | 19% |

| Ex. | 2-Amidoaryl-aldehyde | 1,2-Diamino-benzene | Product | Yield |
|---|---|---|---|---|
| L166 | 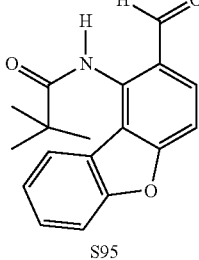 S95 | 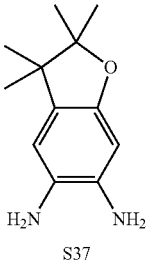 S37 | 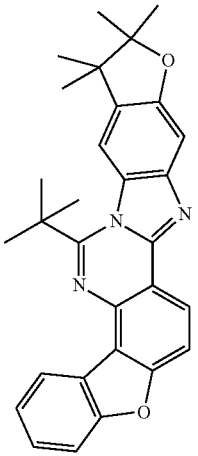 Chromatographic separation of the regioisomer | 22% |

3) Ligands of the 2,6a,11-triazabenzo[a]fluorene Type
General Ligand Synthesis Variant A:
From 4-alkynyl-3-formylpyridines and 1,2-diaminobenzenes:

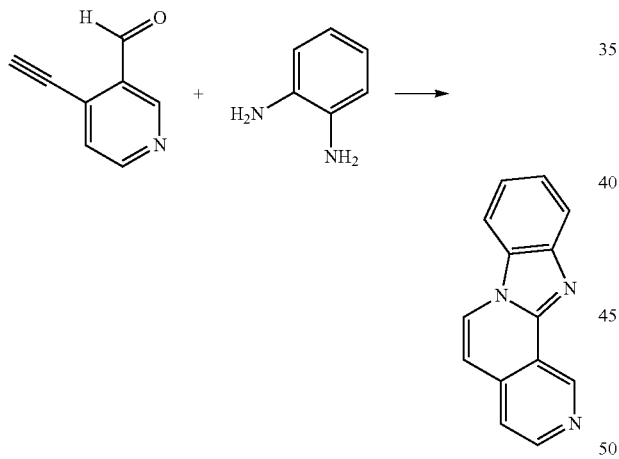

A solution of 500 mmol of the 4-alkynyl-3-formylpyridine and 550 mmol of the 1,2-diaminobenzene in 1000 ml of nitrobenzene is placed in an apparatus consisting of a 2000 ml one-necked flask with stopcock and attached distillation bridge and slowly heated to 200° C. (oil-bath temperature) with stirring, during which the water formed distils off. The mixture is stirred at 200° C. for a further 2 h, the temperature is then increased to about 230° C., and the nitrobenzene is distilled off in a stream of argon. Towards the end of the distillation, a vacuum of about 100 mbar is applied in order to remove final residues of nitrobenzene, the reaction mixture is then allowed to cool. If the crude product is produced in the form of a glass, the glass is mechanically comminuted, oils are mixed directly with 200-400 ml of methanol or acetonitrile, and the mixture is heated under reflux, during which the glass or oil dissolves and the product crystallises out. The crude products obtained in this way frequently already have high purity ($^1$H-NMR typically 97-99%). If desired, they are recrystallised again and then freed from low-boiling components and non-volatile secondary components by fractional bulb-tube distillation or sublimation (p about $10^{-4}$-$10^{-5}$ mbar, T about 160-250° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L167

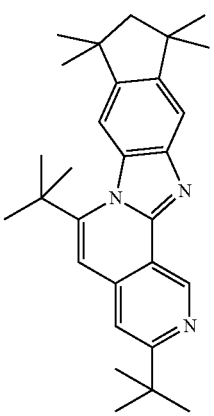

Use of 121.7 g (500 mmol) of S108 and 112.4 g (550 mmol) of S16. Recrystallisation of the crude product from dioxane/EtOH once, fractional sublimation of the product twice at T about 190° C., p about $10^{-4}$ mbar. Yield: 124.0 g (290 mmol), 58%; purity: >99.5% according to $^1$H-NMR.

The following compounds can be prepared analogously:

| Ex. | 4-Alkynyl-3-formyl-pyridine | 1,2-Diamino-benzene | Product | Yield |
|---|---|---|---|---|
| L168 | S108 | S22 | | 55% |
| L169 | S108 | S24 | | 56% |
| L170 | S108 | S25 | | 56% |

-continued

| Ex. | 4-Alkynyl-3-formyl-pyridine | 1,2-Diamino-benzene | Product | Yield |
|---|---|---|---|---|
| L171 | S108 | S26 | | 58% |
| L172 | S108 | S32 | | 54% |
| L173 | S108 | S36 | | 55% |

-continued
| Ex. | 4-Alkynyl-3-formyl-pyridine | 1,2-Diamino-benzene | Product | Yield |
|---|---|---|---|---|
| L174 | 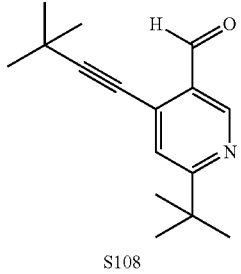 [SMILES: CC(C)(C)C#Cc1cc(C(C)(C)C)ncc1C=O ; "S108"]<br>S108 | 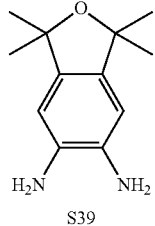<br>S39 | 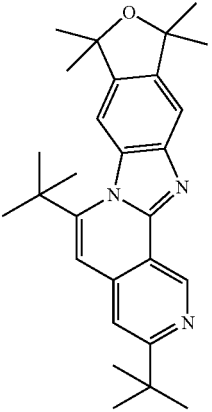 | 55% |
| L175 | 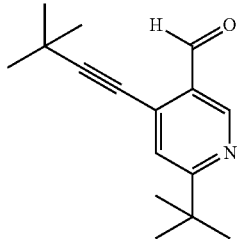<br>S108 | 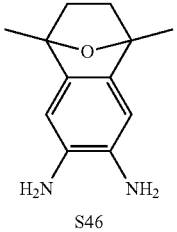<br>S46 | 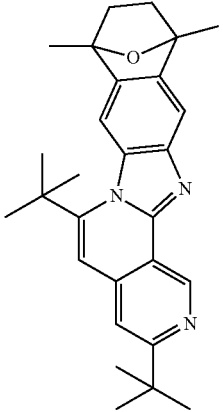 [SMILES: CC(C)(C)c1cc2cc(C(C)(C)C)n3c4cc5c(cc4nc3c2cn1)C1(C)CCC5(C)O1] | 51% |
| L176 | 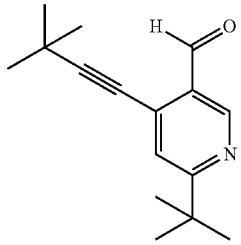<br>S108 | 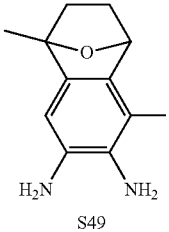<br>S49 | 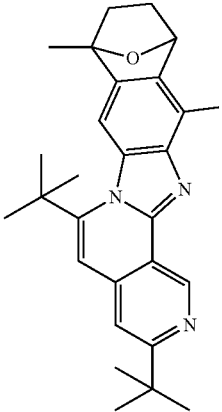<br>Chromatographic separation of the regioisomer | 24% |

-continued

| Ex. | 4-Alkynyl-3-formyl-pyridine | 1,2-Diamino-benzene | Product | Yield |
|---|---|---|---|---|
| L177 | S108 | S57 | | 33% |
| L178 | S109 | S24 | | 59% |
| L179 | S109 | S21 | | 25% Chromatographic separation of the regioisomer |

| Ex. | 4-Alkynyl-3-formyl-pyridine | 1,2-Diamino-benzene | Product | Yield |
|---|---|---|---|---|
| L180 | S109 | S28 | 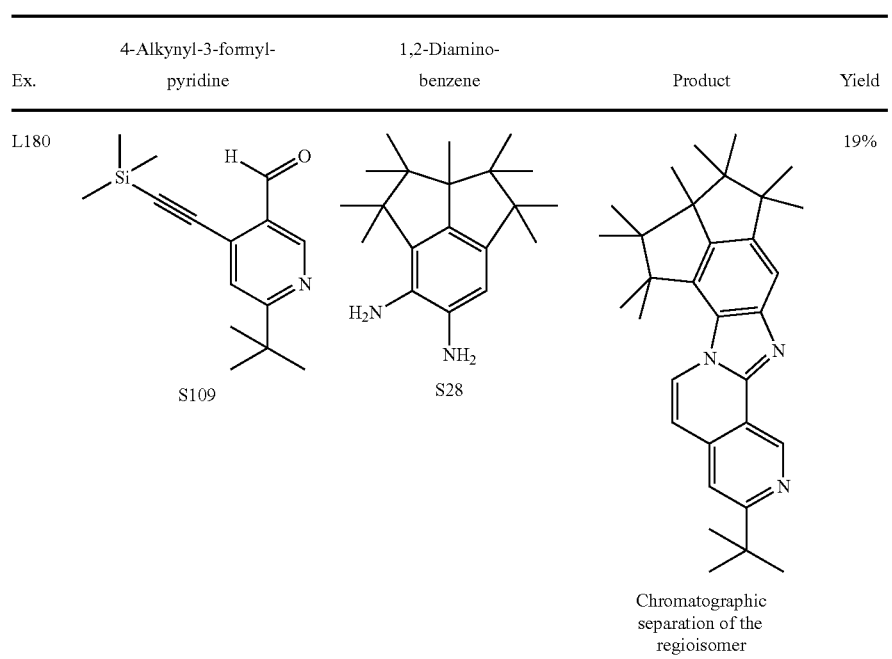 Chromatographic separation of the regioisomer | 19% |
| L181 | S109 | 124639-03-8 S32 | 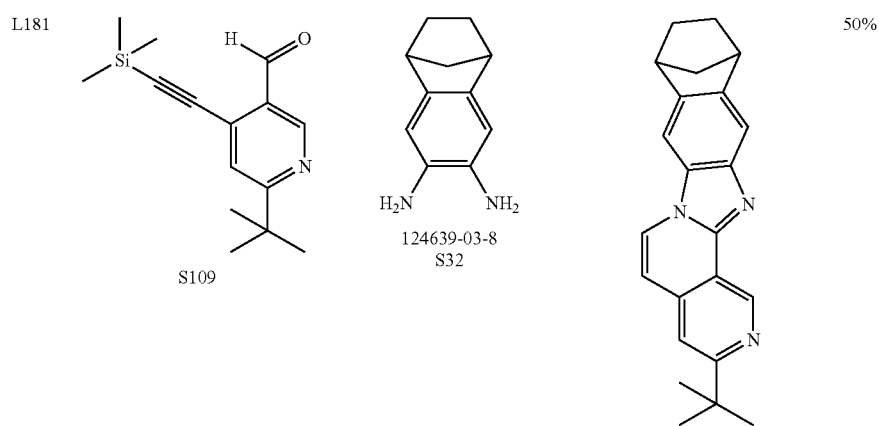 | 50% |
| L182 | S109 | S36 | 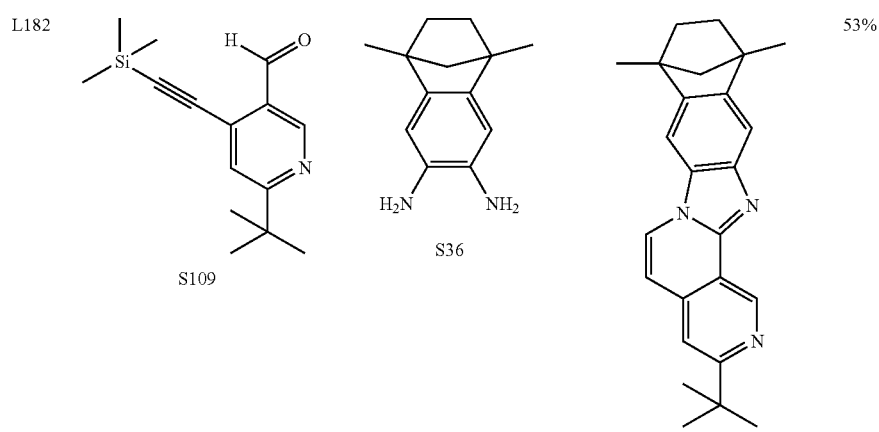 | 53% |

-continued

| Ex. | 4-Alkynyl-3-formyl-pyridine | 1,2-Diamino-benzene | Product | Yield |
|---|---|---|---|---|
| L183 | S109 | S43 | | 55% |
| L184 | S109 | S46 | | 49% |
| L185 | S109 | S58 | | 26% |

-continued

| Ex. | 4-Alkynyl-3-formyl-pyridine | 1,2-Diamino-benzene | Product | Yield |
|---|---|---|---|---|
| L186 | S109 | S59 | Chromatographic separation of the regioisomer | 18% |
| L187 | S109 | S60 | Chromatographic separation of the regioisomer | 20% |
| L188 | S109 | S61 | Chromatographic separation of the regioisomer | 21% |

-continued
| Ex. | 4-Alkynyl-3-formyl-pyridine | 1,2-Diamino-benzene | Product | Yield |
|---|---|---|---|---|
| L189 | 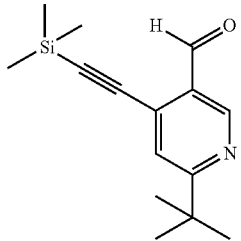 S109 | 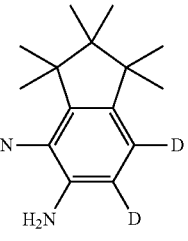 S63 | 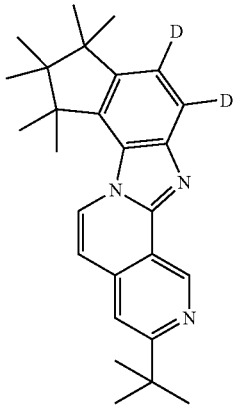 Chromatographic separation of the regioisomer | 18% |
| L190 | 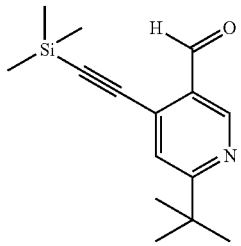 S109 | 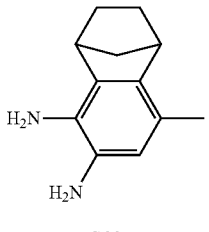 S66 | 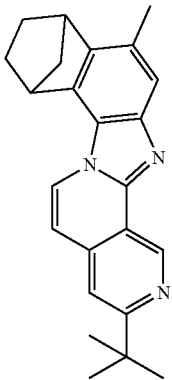 Chromatographic separation of the regioisomer | 19% |
| L191 | 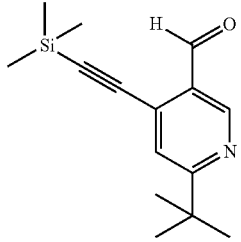 S109 | 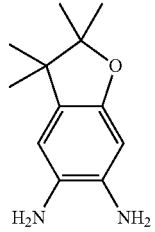 S37 | 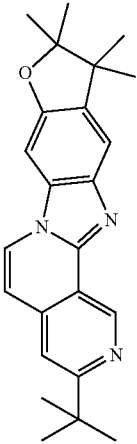 Chromatographic separation of the regioisomer | 17% |

General Ligand Synthesis Variant B:
From 2,7-naphthyridin-1-ylamines and 1,2-dihalobenzenes:

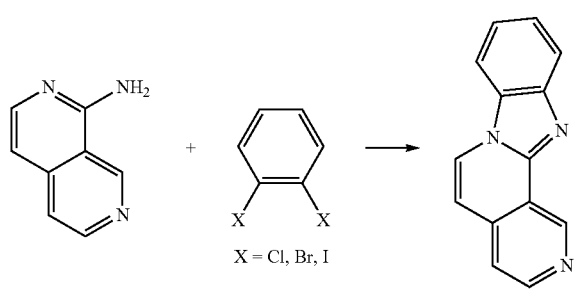

A vigorously stirred mixture of 100 mmol of the 1,2-dihalobenzene, 120 mmol of the 2,7-naphthyridin-1-ylamine, 300 mmol of lithium bis(trimethylsilyl)amide, 100 g of glass beads (diameter 3 mm), 5 mmol of xantphos and 5 mmol of palladium(II) acetate in 600 ml of dry 1,4-dioxane is heated under reflux for 72 h until the 1-aminoisoquinoline has been consumed. After cooling, the solid material is filtered off over a Celite bed, rinsed with 1500 ml of dioxane, and the filtrate is evaporated to dryness. The residue is dissolved in 400 ml of dichloromethane and filtered through a silica-gel bed. The bed is rinsed with a mixture of 2000 ml of dichloro methane and 150 ml of ethyl acetate, and the filtrate is evaporated to dryness. The residue is recrystallised and dried in vacuo. The 2,6a,11-triazabenzo[a]fluorene obtained in this way is freed from low-boiling components and non-volatile secondary components by bulb-tube distillation or fractional sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L178

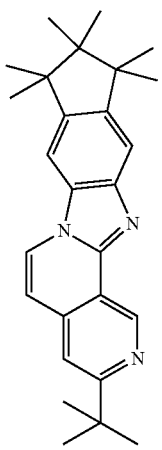

Use of 36.0 g (100 mmol) of 5,6-dibromo-1,1,2,2,3,3-hexamethylindane, S24, variant A, step A, 24.3 g (120 mmol) of 6-tert-butyl-2,7-naphthyridin-1-ylamine [1352329-35-1], 50.2 g (300 mmol) of lithium bis(trimethylsilyl)amide, 2.9 g (5 mmol) of xantphos and 1.1 g (5 mmol) of palladium(II) acetate. The crude product is recrystallised from ethanol (about 7 ml/g) and sublimed in vacuo (p=$10^{-5}$ mbar, T=230° C.). Yield: 27.2 g (68 mmol), 68%; purity: about 99.5% according to $^1$H-NMR.

The following compounds can be prepared analogously:

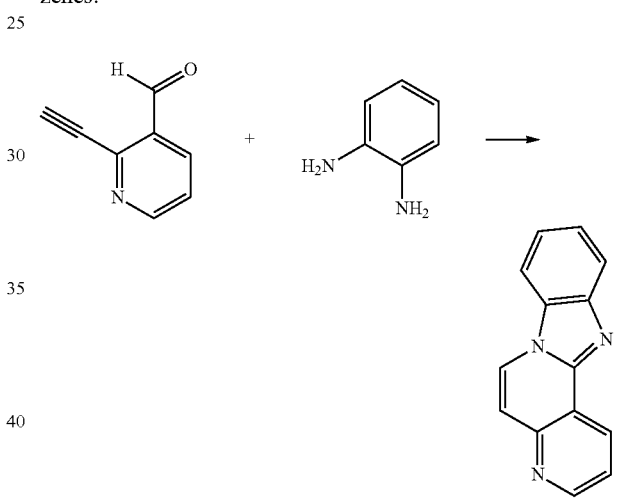

| Ex. | 2,7-Naphthyridin-1-ylamine | 1,2-Dihalobenzene | Product | Yield |
|---|---|---|---|---|
| L192 | 1352329-35-1 | 42810-32-2 | | 66% |

4) Ligands of the 4,6a,11-triazabenzo[a]fluorene Type
General Ligand Synthesis Variant A:
From 2-alkynyl-3-formylpyridines and 1,2-diaminobenzenes:

Preparation analogous to 3) variant A, ligands of the 2,6a,11-triazabenzo[a]fluorene type.

Example L192

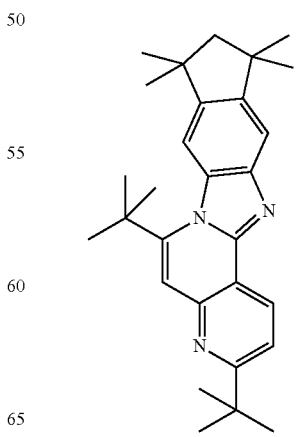

Use of 121.7 g (500 mmol) of 2-(3,3-dimethylbutyn-1-yl)-6-(1,1-dimethyl-ethyl)pyridine-3-carboxaldehyde [1352329-59-9] and 112.4 g (550 mmol) of S16. Recrystallisation of the crude product from dioxane/EtOH once, fractional sublimation of the product twice at T about 190° C., p about $10^{-4}$ mbar. Yield: 121.0 g (283 mmol), 56%; purity: >99.5% according to $^1$H-NMR.

The following derivatives can be prepared analogously:

| Ex. | 2-Alkynyl-3-formyl pyridine | 1,2-Diamino-benzene | Product | Yield |
|---|---|---|---|---|
| L193 | 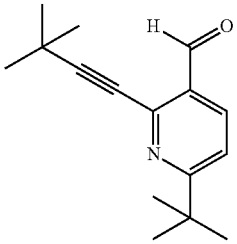 1352329-59-9 | 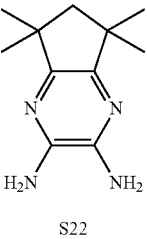 S22 | 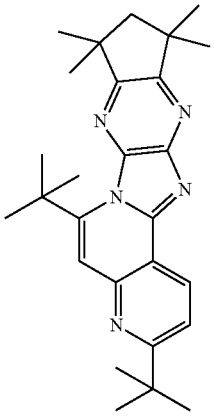 [SMILES: CC(C)(C)c1ccc2c(cc(C(C)(C)C)n3c4nc5c(nc4nc23)C(C)(C)CC5(C)C)n1] | 47% |
| L194 | 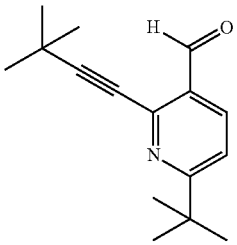 1352329-59-9 | 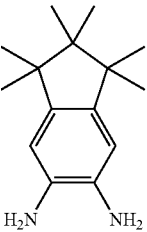 S24 | 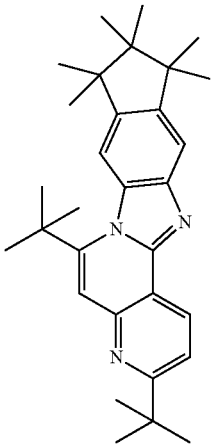 [SMILES: CC(C)(C)c1ccc2c(cc(C(C)(C)C)n3c4cc5c(cc4nc23)C(C)(C)C(C)(C)C5(C)C)n1] | 55% |
| L195 | 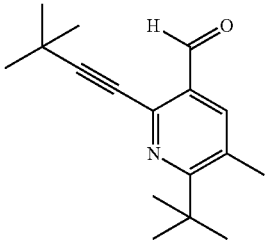 1352331-90-8 | 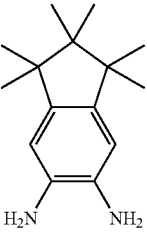 S24 | 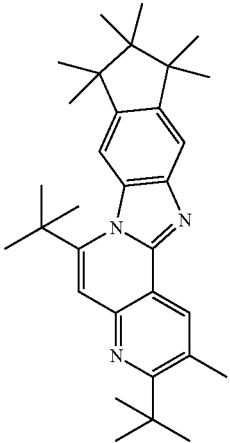 [SMILES: Cc1cc2c(cc(C(C)(C)C)n3c4cc5c(cc4nc23)C(C)(C)C(C)(C)C5(C)C)nc1C(C)(C)C] | 53% |

-continued
| Ex. | 2-Alkynyl-3-formyl pyridine | 1,2-Diamino-benzene | Product | Yield |
|---|---|---|---|---|
| L196 | 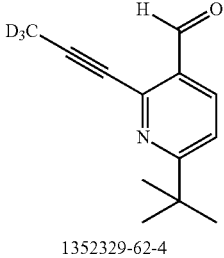 [SMILES: [2H]C([2H])([2H])C#Cc1nc(C(C)(C)C)ccc1C=O ; "1352329-62-4"]<br>1352329-62-4 | 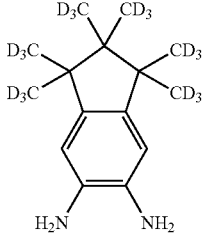<br>S25 | 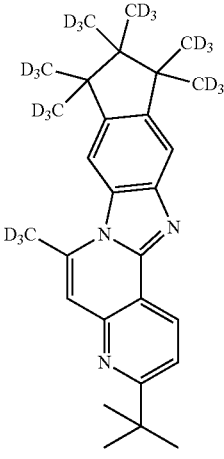 [SMILES: [2H]C([2H])([2H])c1cc2nc(C(C)(C)C)ccc2c2nc3cc4c(cc3n12)C(C([2H])([2H])[2H])(C([2H])([2H])[2H])C(C([2H])([2H])[2H])(C([2H])([2H])[2H])C4(C([2H])([2H])[2H])C([2H])([2H])[2H]] | 53% |
| L197 | 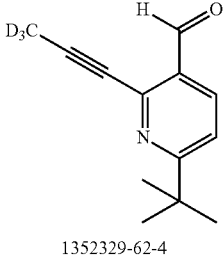 [SMILES: [2H]C([2H])([2H])C#Cc1nc(C(C)(C)C)ccc1C=O ; "1352329-62-4"]<br>1352329-62-4 | 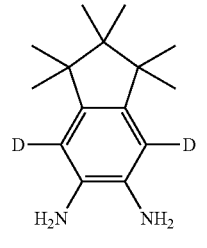<br>S26 | 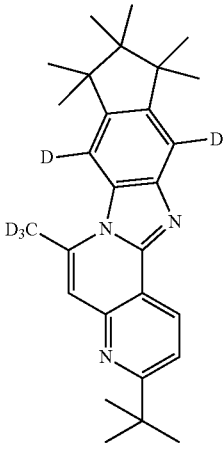 [SMILES: [2H]c1c2c(c([2H])c3c1nc1c4ccc(C(C)(C)C)nc4cc(C([2H])([2H])[2H])n13)C(C)(C)C(C)(C)C2(C)C] | 54% |
| L198 | 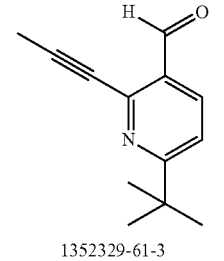<br>1352329-61-3 | 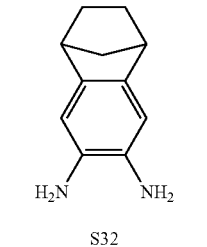 [SMILES: Nc1cc2c(cc1N)C1CCC2C1 ; "S32"]<br>S32 | 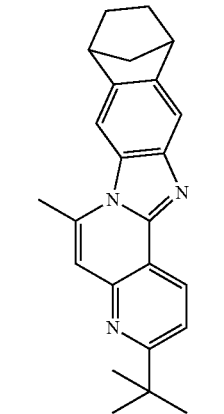 [SMILES: Cc1cc2nc(C(C)(C)C)ccc2c2nc3cc4c(cc3n12)C1CCC4C1] | 51% |

-continued

| Ex. | 2-Alkynyl-3-formyl pyridine | 1,2-Diamino-benzene | Product | Yield |
|---|---|---|---|---|
| L199 | 1352331-90-8 | S32 | | 49% |
| L200 | 1352329-62-4 | S36 | | 52% |
| L201 | 1352329-64-6 | S39 | | 55% |

-continued

| Ex. | 2-Alkynyl-3-formyl pyridine | 1,2-Diamino-benzene | Product | Yield |
|---|---|---|---|---|
| L202 | 1352329-59-9 | S46 | | 54% |
| L203 | 1352329-59-9 | S57 | | 38% |
| L204 | 1352329-60-2 | S24 | | 54% |

-continued
| Ex. | 2-Alkynyl-3-formyl pyridine | 1,2-Diamino-benzene | Product | Yield |
|---|---|---|---|---|
| L205 | 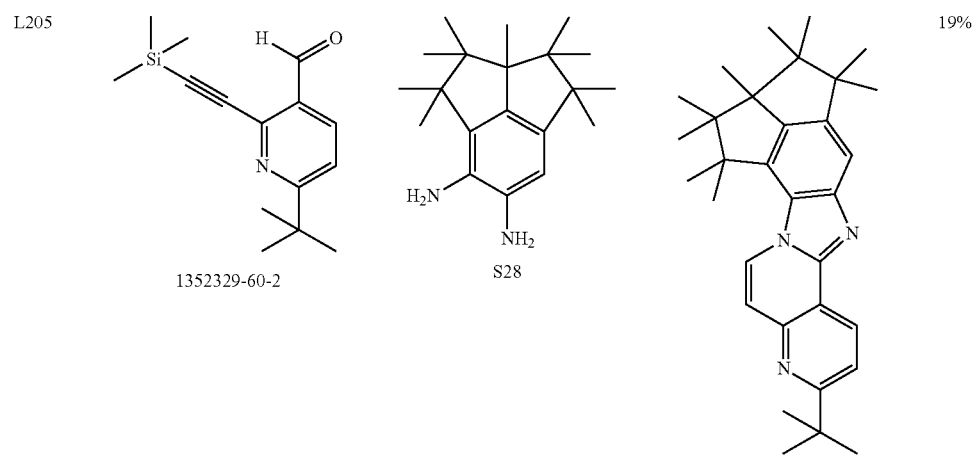 1352329-60-2 | S28 | Chromatographic separation of the regioisomer | 19% |
| L206 | 1352329-60-2 | 124639-03-8 S32 | 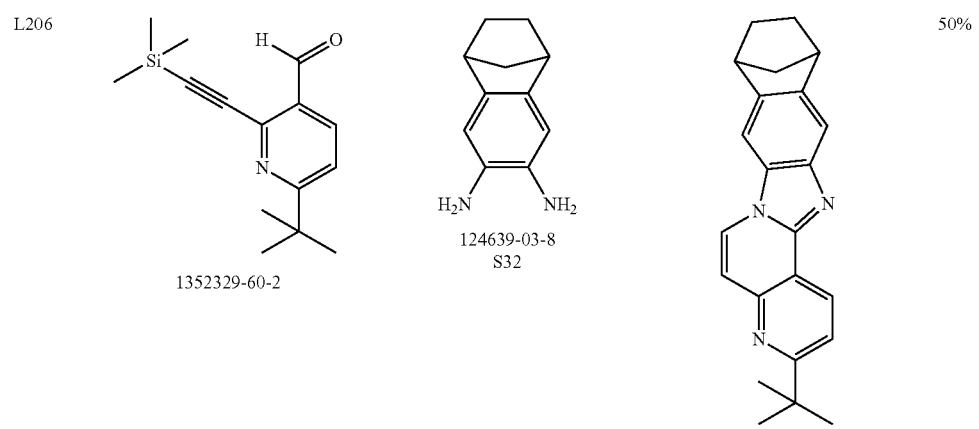 | 50% |
| L207 | 1352329-60-2 | S36 | 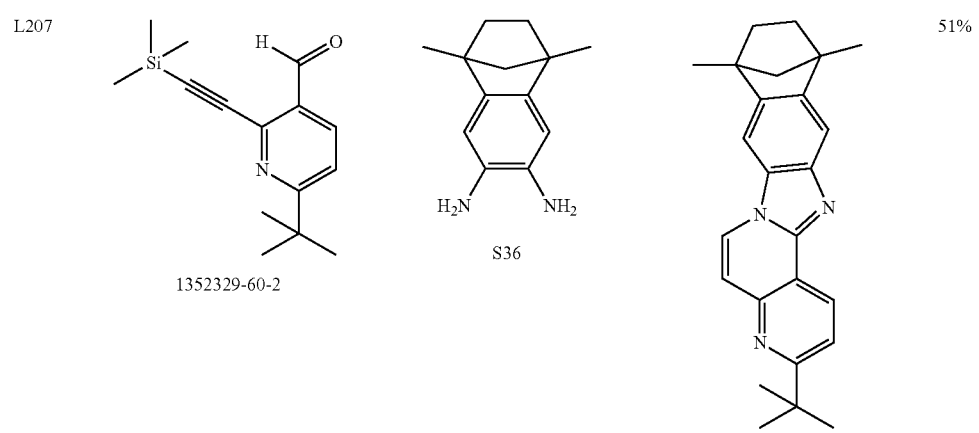 | 51% |

-continued

| Ex. | 2-Alkynyl-3-formyl pyridine | 1,2-Diamino-benzene | Product | Yield |
|---|---|---|---|---|
| L208 | 1352329-60-2 | S46 | | 48% |
| L209 | 1352329-60-2 | S59 | Chromatographic separation of the regioisomer | 20% |
| L210 | 1352329-60-2 | S60 | Chromatographic separation of the regioisomer | 19% |

| Ex. | 2-Alkynyl-3-formyl pyridine | 1,2-Diamino-benzene | Product | Yield |
|---|---|---|---|---|
| L211 | 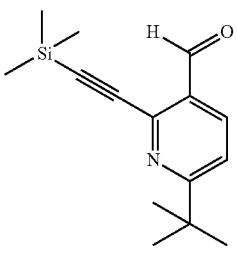<br>1352329-60-2 | 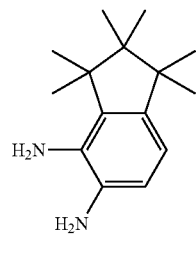<br>S61 | 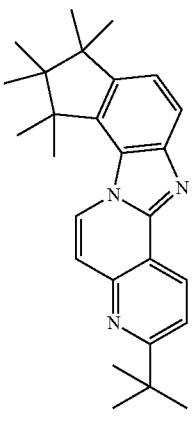<br>Chromatographic separation of the regioisomer | 20% |
| L212 | 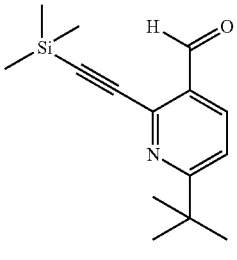<br>1352329-60-2 | 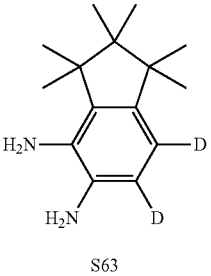 [SMILES: [2H]c1c([2H])c2c(c(N)c1N)C(C)(C)C(C)(C)C2(C)C ; "S63"]<br>S63 | 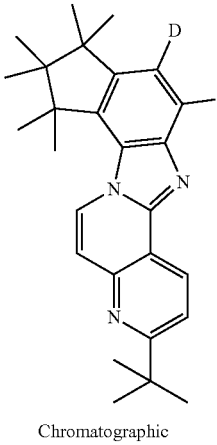<br>Chromatographic separation of the regioisomer | 20% |
| L213 | 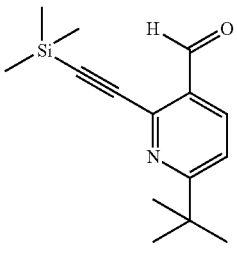<br>1352329-60-2 | 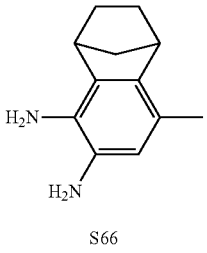<br>S66 | 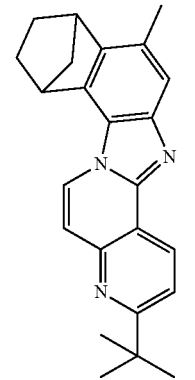<br>Chromatographic separation of the regioisomer | 18% |

| Ex. | 2-Alkynyl-3-formyl pyridine | 1,2-Diamino-benzene | Product | Yield |
|---|---|---|---|---|
| L214 | 1352329-59-9 | S37 | 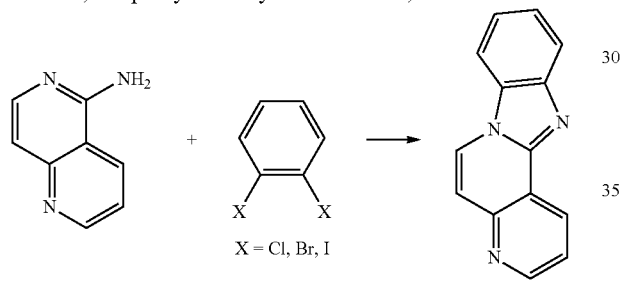 Chromatographic separation of the regioisomer | 17% |

General Ligand Synthesis Variant B:
From 1,6-naphthyridin-5-ylamines and 1,2-dihalobenzenes:

X = Cl, Br, I

Preparation analogous to 3) variant B, ligands of the 2,6a,11-triazabenzo[a]fluorene type.

Example L204

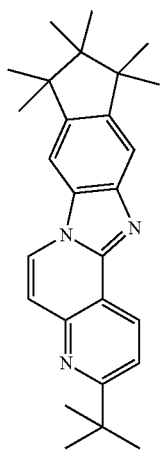

Use of 36.0 g (100 mmol) of 5,6-dibromo-1,1,2,2,3,3-hexamethylindane, S24, variant A, step A, 24.3 g (120 mmol) of 2-tert-butyl-1,6-naphthyridin-5-ylamine [1352329-32-8], 50.2 g (300 mmol) of lithium bis(trimethylsilyl)amide, 2.9 g (5 mmol) of xantphos and 1.1 g (5 mmol) of palladium(II) acetate. The crude product is recrystallised from ethanol (about 7 ml/g) and sublimed in vacuo (p=$10^{-5}$ mbar, T=230° C.). Yield: 26.0 g (65 mmol), 65%; purity: about 99.5% according to $^1$H-NMR.

General Ligand Synthesis Variant C:
From pyrano[4,3-b]pyridin-5-ones and 1,2-aminobenzenes:

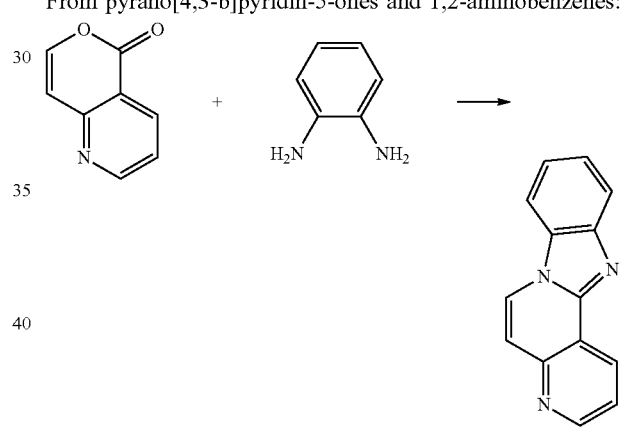

Preparation analogous to V. K. Pandey et al., Ind. J. Chem., Section B: 1999, 38B(12), 138.

A mixture of 100 mmol of the pyrano[3,2-b]pyridin-2-one, 110 mmol of the 1,2-diaminobenzene, 5 mmol of 4-(N,N-dimethylamino)pyridine and 200 ml of dry pyridine is boiled on a water separator, with pyridine being discharged from time to time until the pyridine has been substantially distilled off. Towards the end, a weak vacuum is applied in order to remove pyridine residues. After cooling, the viscous to glass-like residue is taken up in 200 ml of methanol and dissolved at elevated temperature, with the product beginning to crystallise. After cooling, the product is filtered off with suction and washed with a little methanol. After recrystallisation (methanol, ethanol, acetone, dioxane, DMF, etc.) of the resultant 4,6a,11-triazabenzo[a]fluorene, the latter is freed from low-boiling components and non-volatile secondary components by bulb-tube distillation or fractional sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L279

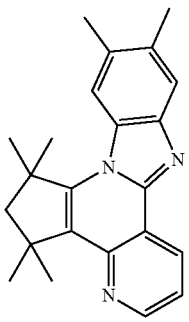 [SMILES: Cc1cc2nc3c4cccnc4c4c(n3c2cc1C)C(C)(C)CC4(C)C]

Use of 24.3 g (100 mmol) of 1,1,3,3-tetramethyl-2,3-dihydro-1H-4-oxa-9-azacyclopenta[a]naphthalen-5-one, S118, 15.0 g (110 mmol) of 4,5-dimethyl-1,2-diaminobenzene [3171-45-7], 611 mg (5 mmol) of 4-(N,N-dimethylamino)pyridine. The crude product is recrystallised from methanol/ethyl acetate and sublimed in vacuo (p=10$^{-5}$ mbar, T=220° C.). Yield: 14.7 g (43 mmol), 43%; purity: about 99.5% according to $^1$H-NMR.

The following compounds can be prepared analogously:

| Ex. | Pyrano[4,3-b]-pyridin-5-one | 1,2-Diamino-benzene | Product | Yield |
|---|---|---|---|---|
| L280 | S118 | S24 | | 40% |
| L281 | S118 | 124639-03-8 S32 | | 39% |
| L282 | S118 | [68176-57-8] | Chromatographic separation of the regioisomer | 19% |

5) Ligands of the 3,6a,11-triazabenzo[a]fluorene Type

General Ligand Synthesis:

From 3-alkynyl-4-formylpyridines and 1,2-diaminobenzenes:

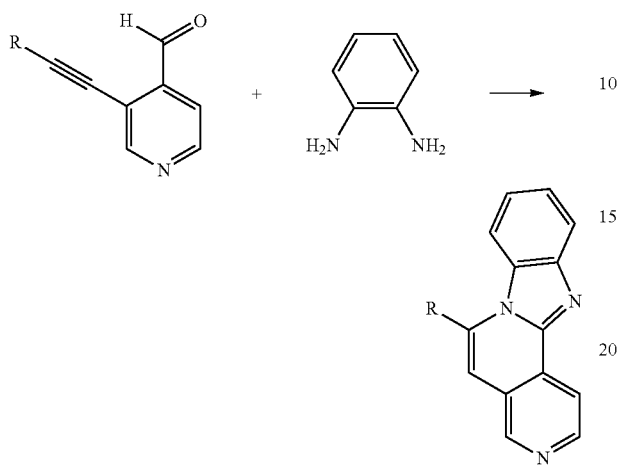

Preparation analogous to 3) variant A, ligands of the 2,6a,11-triazabenzo[a]fluorene type.

Example L215

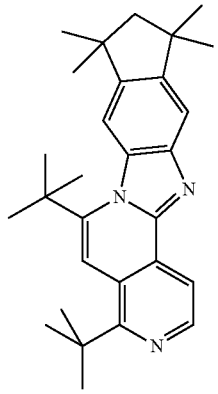 [SMILES: CC(C)(C)c1nccc2c1cc(C(C)(C)C)n1c3cc4c(cc3nc21)C(C)(C)CC4(C)C]

Use of 121.7 g (500 mmol) of 2-tert-butyl-3-(3,3-dimethylbut-1-ynyl)pyridine-4-carboxaldehyde, S114, and 112.4 g (550 mmol) of S16. Recrystallisation of the crude product from dioxane/EtOH once, fractional sublimation of the product twice at T about 190° C., p about $10^{-4}$ mbar. Yield: 113.3 g (265 mmol), 53%; purity: >99.5% according to $^1$H-NMR.

The following derivatives can be prepared analogously:

| Ex. | 3-Alkynyl-4-formyl pyridine | 1,2-Diamino-benzene | Product | Yield |
|---|---|---|---|---|
| L216 | S114 | S22 | | 54% |
| L217 | S114 | S24 | | 49% |

-continued

| Ex. | 3-Alkynyl-4-formyl pyridine | 1,2-Diamino-benzene | Product | Yield |
|---|---|---|---|---|
| L218 | S114 | S26 | | 50% |
| L219 | S114 | S36 | | 52% |
| L220 | S115 | S24 | | 53% |

-continued
| Ex. | 3-Alkynyl-4-formyl pyridine | 1,2-Diamino-benzene | Product | Yield |
|---|---|---|---|---|
| L221 | S115 | S28 | Chromatographic separation of the regioisomer | 19% |
| L222 | S115 | S36 | | 50% |
| L223 | S115 | S61 | Chromatographic separation of the regioisomer | 19% |
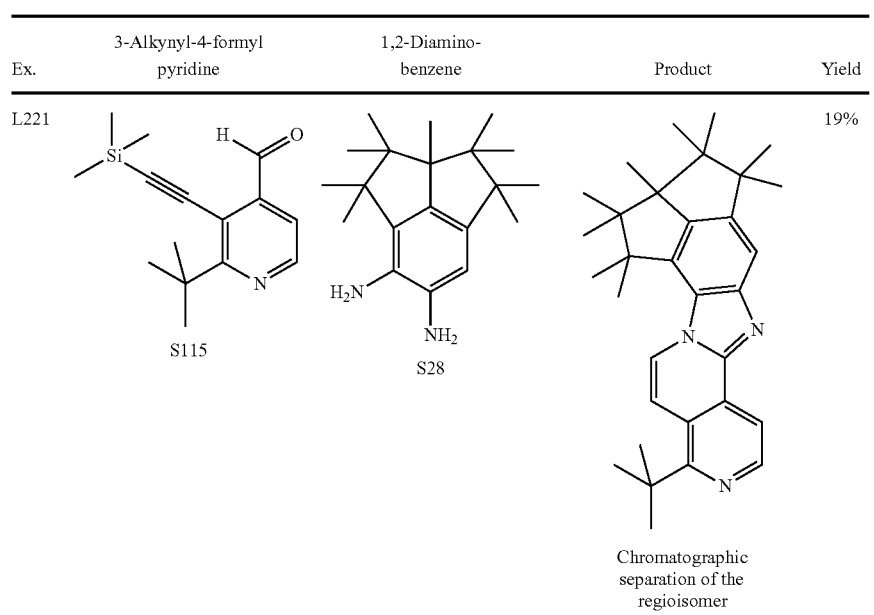
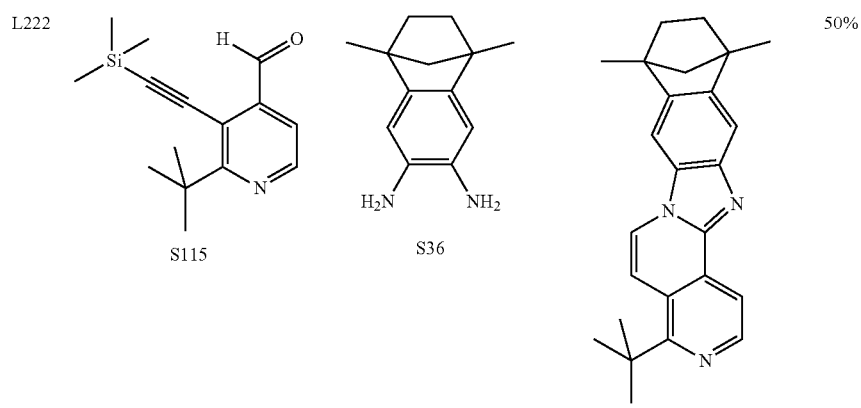
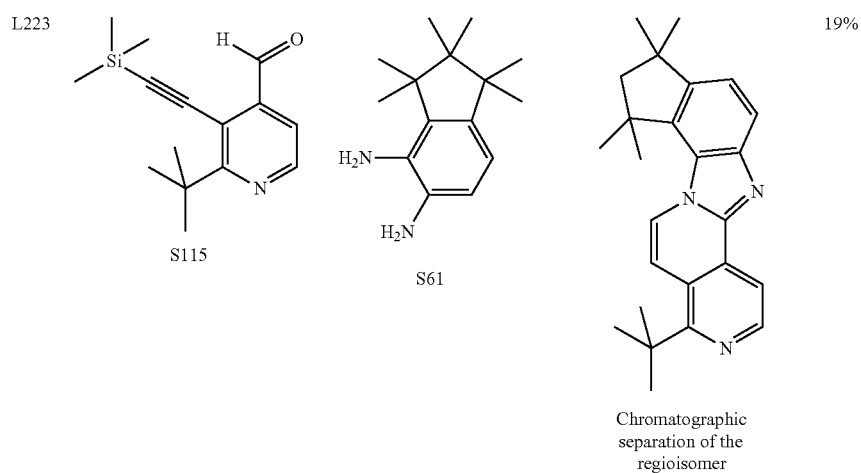

-continued

| Ex. | 3-Alkynyl-4-formyl pyridine | 1,2-Diamino-benzene | Product | Yield |
|---|---|---|---|---|
| L224 | S115 | S66 | Chromatographic separation of the regioisomer | 18% |
| L225 | S115 | S37 | Chromatographic separation of the regioisomer | 20% |

6) Ligands of the 6a,7,11- and of the 6a,10,11-triazabenzo[a]-fluorene Type

General Ligand Synthesis:

From 2-alkynylarylaldehydes and 2,3-diaminopyridines:

Examples L226 and L227

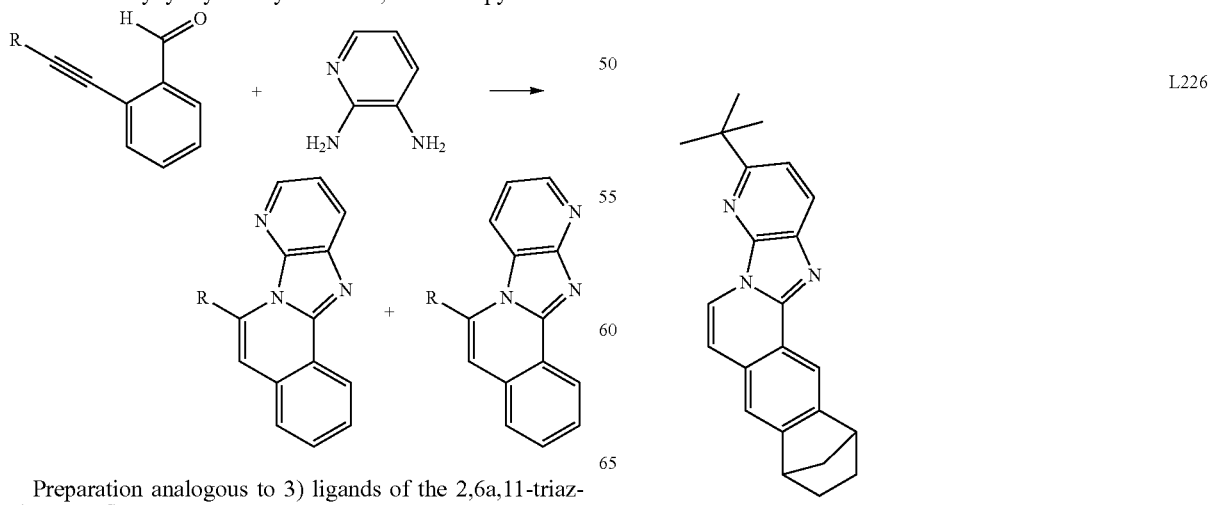

L226

Preparation analogous to 3) ligands of the 2,6a,11-triazabenzo[a]fluorene type.

-continued

L227 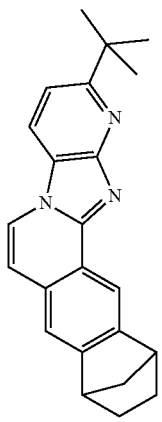

Use of 134.2 g (500 mmol) of S104 and 90.9 g (550 mmol) of 2,3-diamino-6-tert-butylpyridine [893444-20-7]. Chromatographic separation of the regioisomers on silica gel (heptane:ethyl acetate, 10:1 vv), fractional sublimation of the products twice at T about 180° C., p about $10^{-4}$ mbar.

Yield of L226: 41.7 g (112 mmol), 22%; purity: >99.5% according to $^1$H-NMR.

Yield of L227: 44.4 g (130 mmol), 26%; purity: >99.5% according to $^1$H-NMR.

The following derivatives can be prepared analogously:

| Ex. | 2-Alkynylaryl-aldehyde | 2,3-Diamino-pyridine | Product | Yield |
|---|---|---|---|---|
| L228 | S105 | 893444-20-7 | | 18% |
| L229 | S105 | 893444-20-7 | | 21% |

7) Ligands of the 6a,8,11- and of the 6a,9,11-triazabenzo[a]-fluorene Type

General Ligand Synthesis:
From 2-alkynylarylaldehydes and 3,4-diaminopyridines:

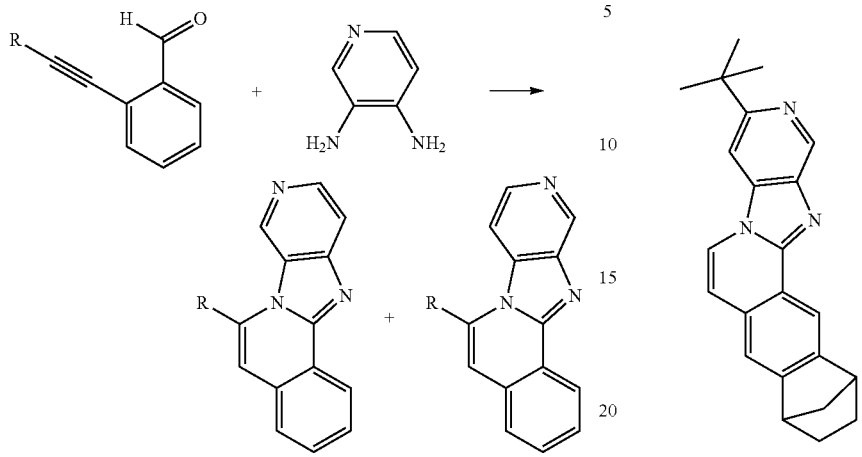

Preparation analogous to 3) ligands of the 2,6a,11-triazabenzo[a]fluorene type.

Examples L230 and L231

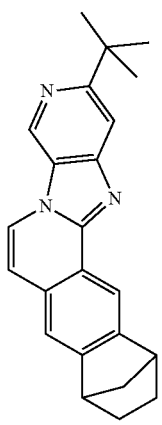

L230

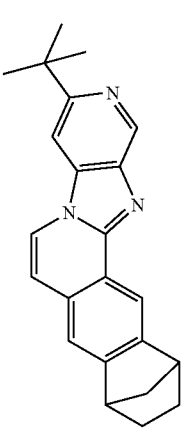

L231

Use of 134.2 g (500 mmol) of S104 and 90.9 g (550 mmol) of 3,4-diamino-6-tert-butylpyridine [1237537-50-6]. Chromatographic separation of the regioisomers on silica gel (heptane:ethyl acetate, 10:1 vv), fractional sublimation of the products twice at T about 180° C., p about $10^{-4}$ mbar.

Yield of L230: 48.8 g (143 mmol), 28%; purity: >99.5% according to $^1$H-NMR.

Yield of L231: 33.5 g (98 mmol), 19%; purity: >99.5% according to $^1$H-NMR.

The following derivatives can be prepared analogously:

| Ex. | 2-Alkynylaryl-aldehyde | 2,3-Diamino-pyridine | Product | Yield |
|---|---|---|---|---|
| L232 | 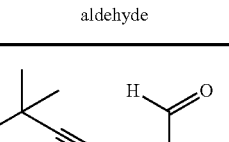 S105 | 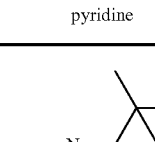 1237537-50-6 | 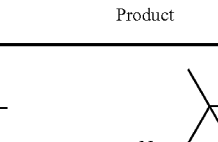 | 22% |

| Ex. | 2-Alkynylaryl-aldehyde | 2,3-Diamino-pyridine | Product | Yield |
|---|---|---|---|---|
| L233 | S105 | 1237537-50-6 | | 19% |

8) Ligands of the 2,5,6a,11-tetraazabenzo[a]fluorene Type

General Ligand Synthesis:

From 4-amido-3-cyanopyridines and 1,2-diaminobenzenes, Variant A:

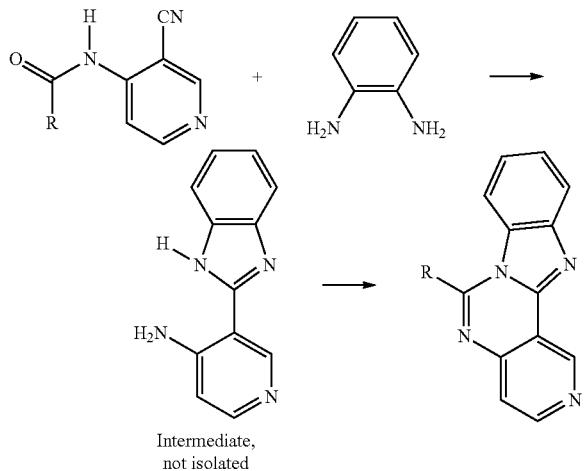

Intermediate, not isolated

A mixture of 100 mmol of the 4-amido-3-cyanopyridine, 210 mmol of the 1,2-diaminobenzene and 100 ml of nitrobenzene is heated stepwise to a gentle reflux and stirred until the 4-amido-3-cyanopyridine has been consumed (typically 6-16 h). The nitrobenzene is then distilled off, firstly in a stream of argon and, towards the end, by application of a vacuum (about 100 mbar). Besides the 3-(1H-benzimidazol-2-yl)pyridin-4-ylamine, the crude product obtained in this way also contains 1 eq. of 2-R-1H-benzimidazole. This mixture is reacted without further purification. After cooling under argon, glass-like residues are comminuted mechanically, oils are taken up, without further treatment, in 250 ml of dioxane or diethylene glycol dimethyl ether, 500 mmol of the corresponding carbonyl chloride and 50 mmol of the corresponding carboxylic acid are added, and the mixture is heated under reflux with vigorous stirring (precision glass stirrer) until the reacxtion is complete (typically 4-48 h). Corresponding carbonyl chlorides and carboxylic acids are those which form the respective amide radical. After cooling, the reaction mixture is introduced with vigorous stirring into a mixture of 1000 g of ice and 300 ml of aqueous conc. ammonia. If the product is produced in the form of a solid, this is filtered off with suction, washed with water and sucked dry. If the product is produced in the form of an oil, this is extracted with three portions of 300 ml each of ethyl acetate or dichloromethane. The organic phase is separated off, washed with 500 ml of water and evaporated in vacuo. The crude product is taken up in ethyl acetate or dichloromethane, filtered through a short column of aluminium oxide, basic, activity grade 1 or silica gel in order to remove brown impurities. After recrystallisation (methanol, ethanol, acetone, dioxane, DMF, etc.) in order to remove the 1 R—C(O)-2-R-benzimidazole, the 2,5,6a,11-tetraazabenzo[a]fluorene obtained in this way is freed from low-boiling components and non-volatile secondary components by bulb-tube distillation or fractional sublimation (p about $1 \times 10^{-5}$ mbar, T about 150-230° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

From 4-amido-3-cyanopyridines and 1,2-diaminobenzene dihydrochlorides, Variant B

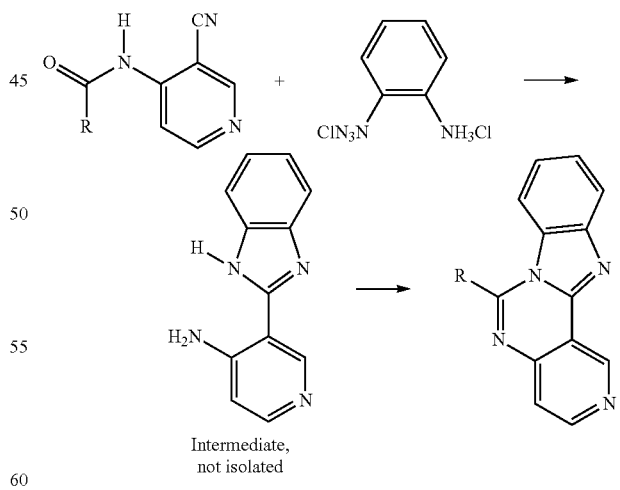

Intermediate, not isolated

A mixture, homogenised in a mortar, of 100 mmol of the 4-amido-3-cyanopyridine and 300 mmol of the 1,2-diaminobenzene dihydrochloride is adjusted in an oil bath preheated to 240° C. and left at this temperature for 3.5 h. After cooling, the deep-blue melt is dissolved in a mixture of 150 ml of ethanol and 300 ml of water at elevated temperature, and a solution of 40 g of sodium carbonate in 200 ml of water is then added dropwise with vigorous stirring (note: foaming, evolution of carbon dioxide). When the addition is complete, the mixture is stirred for a further 30 min., the grey solid is then filtered off with suction, washed three times with 100 ml of water each time and dried in vacuo. A 1:1 mixture of the 3-(1H-benzimidazol-2-yl)pyridin-4-ylamine and the 2-R-1H-benzimidazole is formed, which is cyclised as described under A without further purification and subsequently purified.

Example L234, Variant A

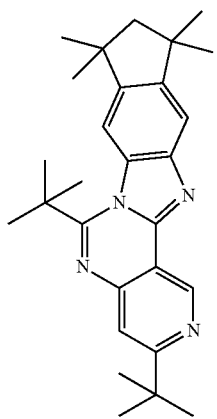

Use of 25.9 g (100 mmol) of N-(2-tert-butyl-5-cyanopyridin-4-yl)-2,2-dimethylpropionamide [1352329-37-3] and 42.9 g (210 mmol) of S16, 60.3 g (500 mmol) of pivaloyl chloride [3282-30-2], 5.1 g (50 mmol) of pivalic acid [75-98-9], 250 ml of diethylene glycol dimethyl ether, reaction time 8 h, the crude product is produced in the form of a solid on neutralisation, recrystallisation from DMF/ethanol, fractional sublimation of the product twice at T about 180° C., p about $10^{-4}$ mbar. Yield: 21.1 g (51 mmol), 51%; purity: about 99.5% according to $^1$H-NMR.

Example L234, Variant B

Use of 25.9 g (100 mmol) of N-(2-tert-butyl-5-cyanopyridin-4-yl)-2,2-dimethylpropionamide [1352329-37-3] and 83.2 g (300 mmol) of S16×2 HCl, 60.3 g (500 mmol) of pivaloyl chloride [3282-30-2], 5.1 g (50 mmol) of pivalic acid [75-98-9], 250 ml of diethylene glycol dimethyl ether, reaction time 8 h, the crude product is produced in the form of a solid on neutralisation, recrystallisation from DMF/ethanol, fractional sublimation of the product twice at T about 180° C., p about $10^{-4}$ mbar. Yield: 32.5 g (76 mmol), 76%; purity: about 99.5% according to $^1$H-NMR.

The following derivatives can be prepared analogously:

| Ex. | 2-Amido-3-cyanopyridine | 2,3-Diaminobenzene | Product Variant | Yield |
|---|---|---|---|---|
| L235 | 1352329-37-3 | S22 | A | 36% |
| L236 | 1352329-37-3 | S24 × 2 HCl | B | 68% |

-continued
| Ex. | 2-Amido-3-cyanopyridine | 2,3-Diamino-benzene | Product Variant | Yield |
|---|---|---|---|---|
| L237 | 1352329-37-3 | S26 × 2 HCl | B | 65% |
| L238 | 1352329-37-3 | S36 × 2 HCl | B | 67% |
| L239 | 1352329-37-3 | S40 | A | 47% |
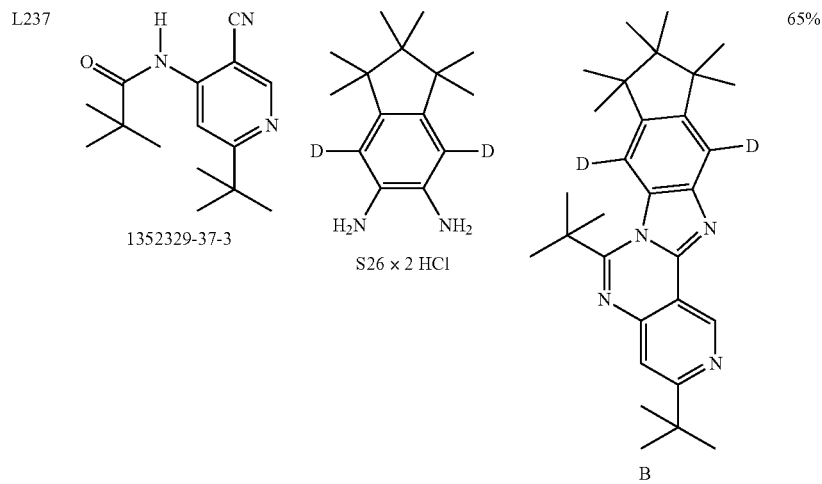
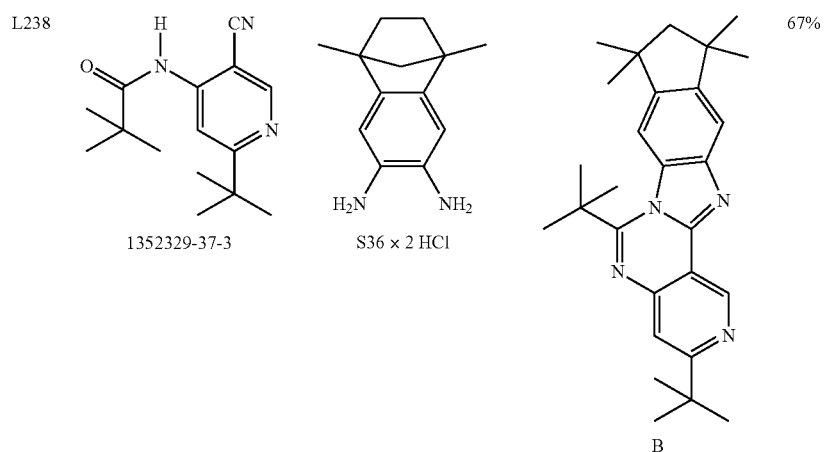
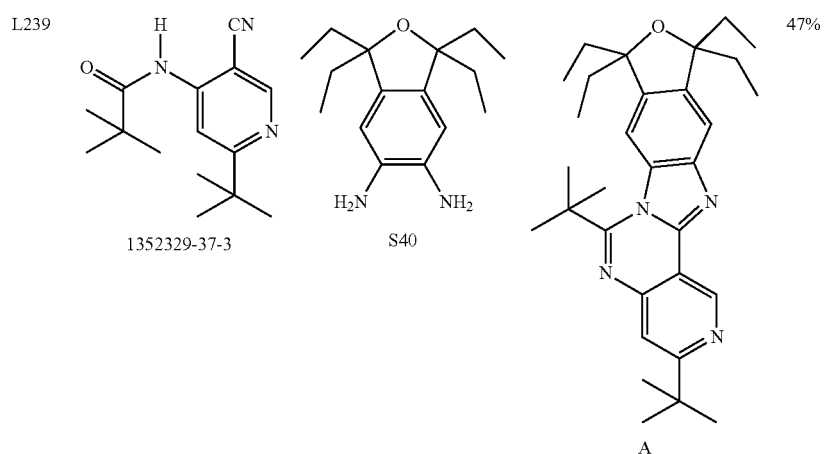

-continued
| Ex. | 2-Amido-3-cyanopyridine | 2,3-Diamino-benzene | Product Variant | Yield |
|---|---|---|---|---|
| L240 | 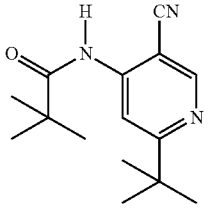<br>1352329-37-3 | 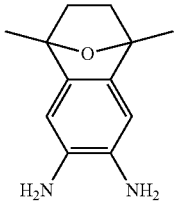<br>S46 × 2 HCl | 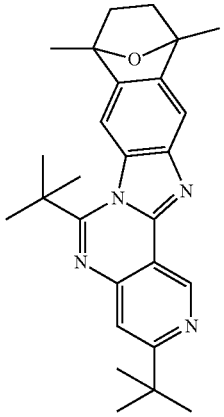<br>A | 45% |
| L241 | 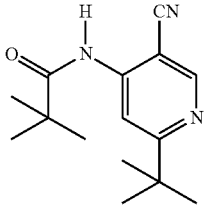<br>1352329-37-3 | 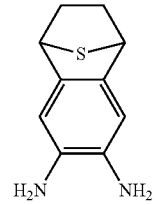<br>S54 × 2 HCl | 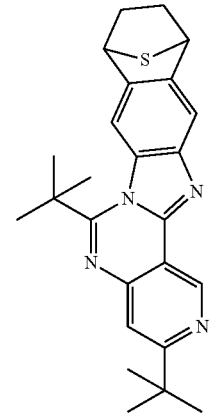<br>B | 27% |
| L242 | 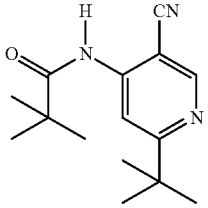<br>1352329-37-3 | 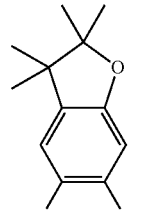<br>S37 × 2 HCl | 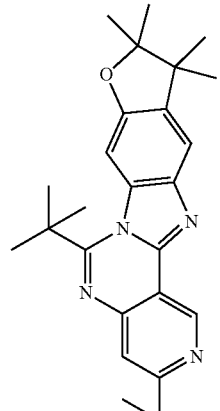<br>B<br>Chromatographic separation of the regioisomer | 20% |

9) Ligands of the 4,5,6a,11-tetraazabenzo[a]fluorene Type
   General Ligand Synthesis:
   From 2-amido-3-cyanopyridines and 1,2-diaminobenzenes:

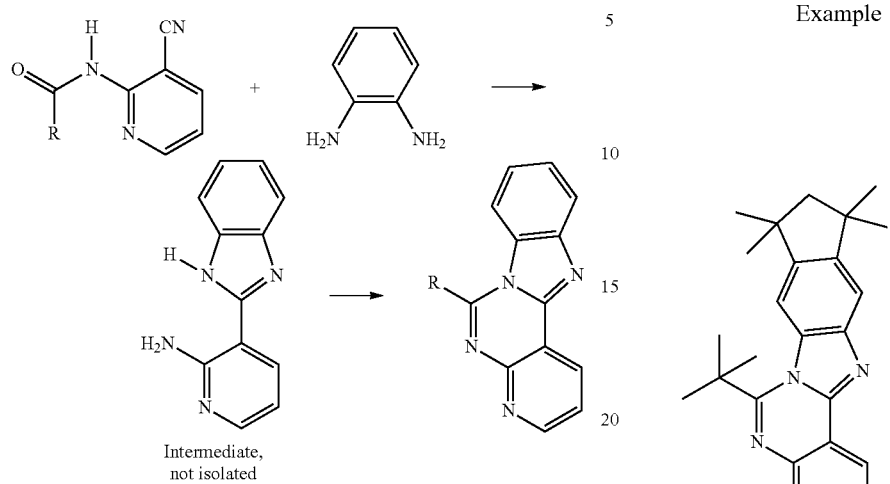

Intermediate,
not isolated

From 2-amido-3-cyanopyridines and 1,2-diaminobenzene dihydrochlorides, Variant B

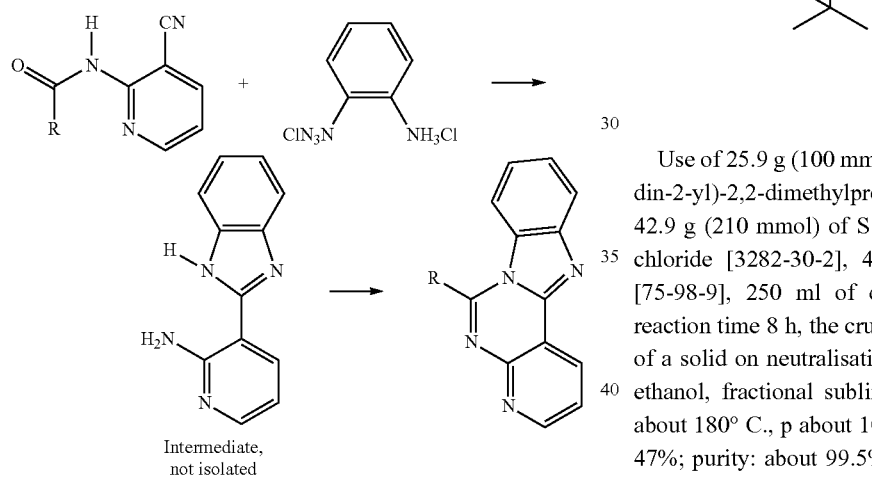

Intermediate,
not isolated

Preparation analogous to 8) ligands of the 2,5,6a,11-tetraazabenzo[a]-fluorene type.

Example L243, Variant A

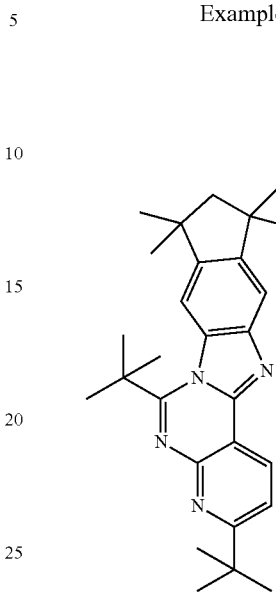

Use of 25.9 g (100 mmol) of N-(6-tert-butyl-3-cyanopyridin-2-yl)-2,2-dimethylpropionamide [1352329-36-2] and 42.9 g (210 mmol) of S16, 60.3 g (500 mmol) of pivaloyl chloride [3282-30-2], 4.1 g (40 mmol) of pivalic acid [75-98-9], 250 ml of diethylene glycol dimethyl ether, reaction time 8 h, the crude product is produced in the form of a solid on neutralisation, recrystallisation from dioxane/ethanol, fractional sublimation of the product twice at T about 180° C., p about $10^{-4}$ mbar. Yield: 20.1 g (47 mmol), 47%; purity: about 99.5% according to $^1$H-NMR.

The following derivatives can be prepared analogously:

| Ex. | 2-Amido-3-cyanopyridine | 1,2-Diaminobenzene | Product | Yield |
|---|---|---|---|---|
| L244 | ![structure] 1352329-36-2 | ![structure] S22 | ![structure] A | 46% |

-continued

| Ex. | 2-Amido-3-cyanopyridine | 1,2-Diamino-benzene | Product | Yield |
|---|---|---|---|---|
| L245 | 111678-77-4 | S24 × 2 HCl | B | 40% |
| L246 | 1352329-36-2 | S36 × 2 HCl | B | 48% |
| L247 | 1352329-36-2 | S37 × 2 HCl | B Chromatographic separation of the regioisomer | 17% |

10) Ligands of the 2,4,6a,11-tetraazabenzo[a]fluorene Type

General Ligand Synthesis:

From pyrimidin-5-ylbenzimidazoles and alkynes:

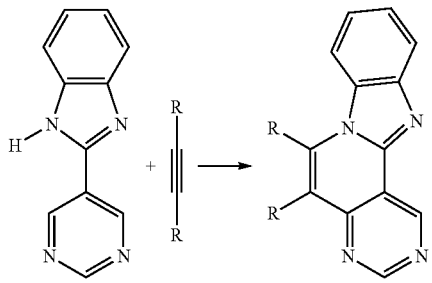

A solution of 100 mmol of the pyrimidin-5-ylbenzimidazole and 110 mmol of the alkyne in 400 ml of DMF is initially introduced in a pressure Schlenk tube, 1.5 g (4 mmol) of tetraphenylcyclopentadiene, 547 mg (1 mmol) of pentamethylcyclopentadienylrhodium chloride dimer and 21.0 g (105 mmol) of copper(II) acetate monohydrate are added, the tube is sealed, and the mixture is stirred at 100° C. for 18 h. After cooling, the DMF is removed in vacuo, the residue is taken up in 1000 ml of THF and filtered through a short silica-gel column. After removal of the THF in vacuo, the oily residue is recrystallised or chromatographed and subsequently freed from low-boiling components and non-volatile secondary components by bulb-tube distillation or fractional sublimation (p about $1 \times 10^{-5}$ mbar, T about 150-230° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

Example L248

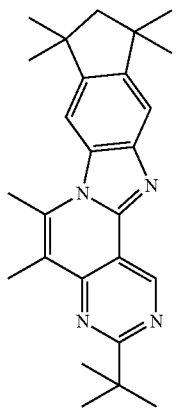

Use of 34.9 g (100 mmol) of 2-(2-tert-butylpyrimidin-5-yl)-5,5,7,7-tetramethyl-1,5,6,7-tetrahydroindeno[5,6-d]imidazole, S110, and 6.0 g (110 mmol) of but-2-yne. Recrystallisation from dioxane/ethanol, fractional sublimation of the product twice at T about 200° C., p about $10^{-4}$ mbar.

Yield: 10.8 g (27 mmol), 27%; purity: about 99.5% according to $^1$H-NMR.

The following derivatives can be prepared analogously:

| Ex. | 2-(2-tert-Butylpyrimidin-5-yl)benzimidazole | Alkyne | Product | Yield |
|---|---|---|---|---|
| L249 | S111 | 503-17-3 | | 31% |
| L250 | S112 | 503-17-3 | | 26% |
| L251 | S113 | 503-17-3 | | 33% |

11) Ligands of the 3,5,6a,11-tetraazabenzo[a]fluorene Type

General Ligand Synthesis:

From 3-amido-4-formylpyridines and 1,2-diaminobenzenes:

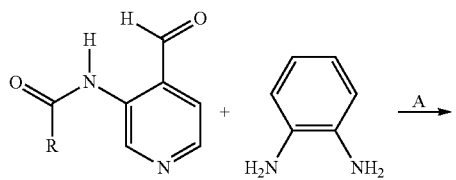

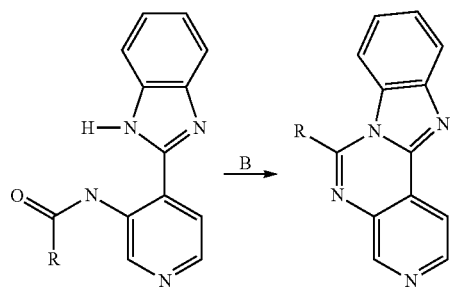

Preparation analogous to 2) ligands of the benzo[4,5]imidazo[2,1-c]quinazoline type.

Example L252, Variant A

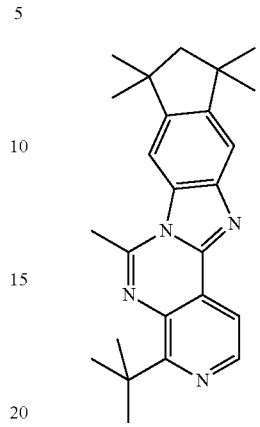

Step A:

Use of 22.0 g (100 mmol) of S116 and 22.5 g (110 mmol) of S16.

The N-[2-tert-butyl-4-(5,5,7,7-tetramethyl-1,5,6,7-tetrahydroindeno[5,6-d]-imidazol-2-yl)pyridin-3-yl]acetamide crystallises out, yield 33.6 g (83 mmol), 83%; purity: 97% according to $^1$H-NMR.

Step B, Variant A:

Use of 33.6 g (83 mmol) of N-[2-tert-butyl-4-(5,5,7,7-tetramethyl-1,5,6,7-tetrahydroindeno[5,6-d]imidazol-2-yl)pyridin-3-yl]acetamide (step A), 100 ml of dioxane, 20.0 ml (280 mmol) of acetyl chloride [75-36-5] and 2.3 ml (40 mmol) of acetic acid [64-19-7], reaction time 16 h, the crude product is produced in the form of a solid on neutralisation, recrystallisation from dioxane/ethanol, fractional sublimation of the product twice at T about 180° C., p about $10^{-4}$ mbar. Yield: 21.6 g (56 mmol), 68%; purity: about 99.5% according to $^1$H-NMR.

The following derivatives can be prepared analogously:

| Ex. | 3-Amido-4-formylpyridine | 1,2-Diaminobenzene | Product Variant | Yield |
|---|---|---|---|---|
| L253 | S116 | S22 | A | 52% |

-continued
| Ex. | 3-Amido-4-formylpyridine | 1,2-Diamino-benzene | Product Variant | Yield |
|---|---|---|---|---|
| L254 | S116 | S24 | A | 55% |
| L255 | S116 | S26 | A | 52% |
| L256 | S116 | S36 | A | 48% |
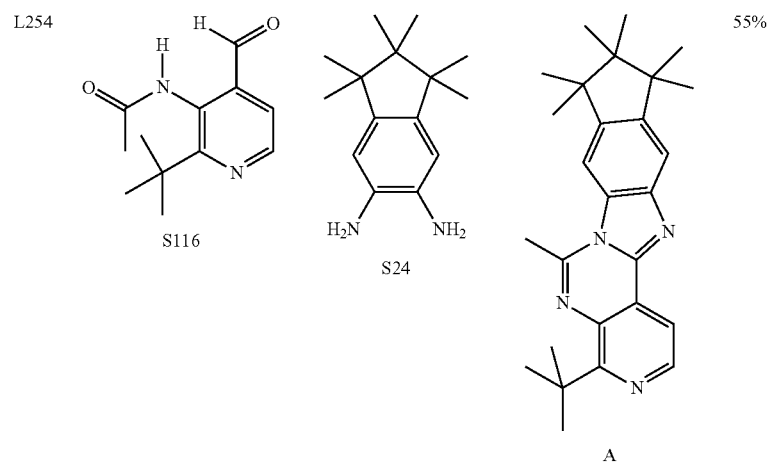
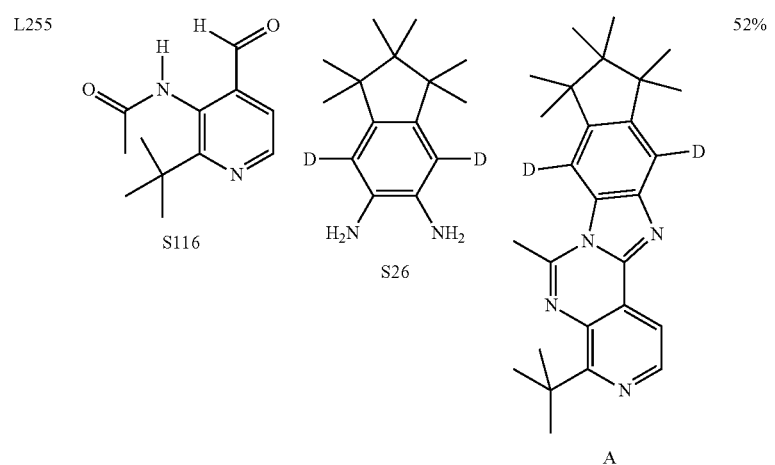
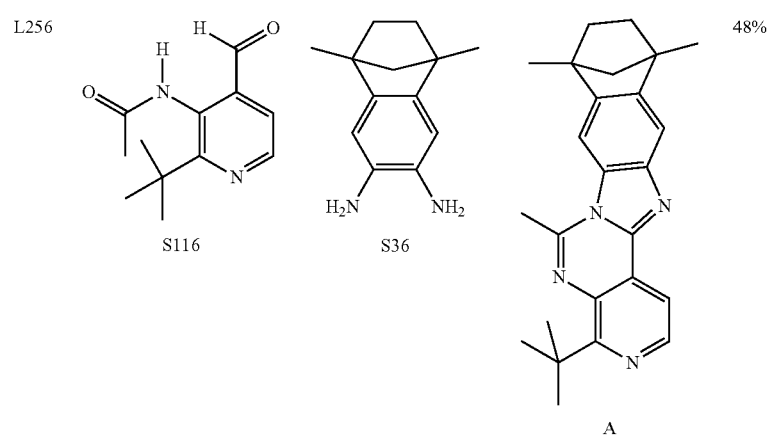

-continued

| Ex. | 3-Amido-4-formylpyridine | 1,2-Diamino-benzene | Product Variant | Yield |
|---|---|---|---|---|
| L257 | S116 | S46 | A | 44% |
| L258 | S116 | S37 | A<br>Chromatographic separation of the regioisomers | 18% |

12) Ligands of the 5,6a,7,11- and 5,6a,10,11-tetraazabenzo[a]fluorene Type

General Ligand Synthesis Variant A:
From 2-amidoarylaldehydes and 2,3-diaminopyridines -continued Preparation analogous to 2) ligands of the benzo[4,5]imidazo[2,1-c]-quinazoline type.

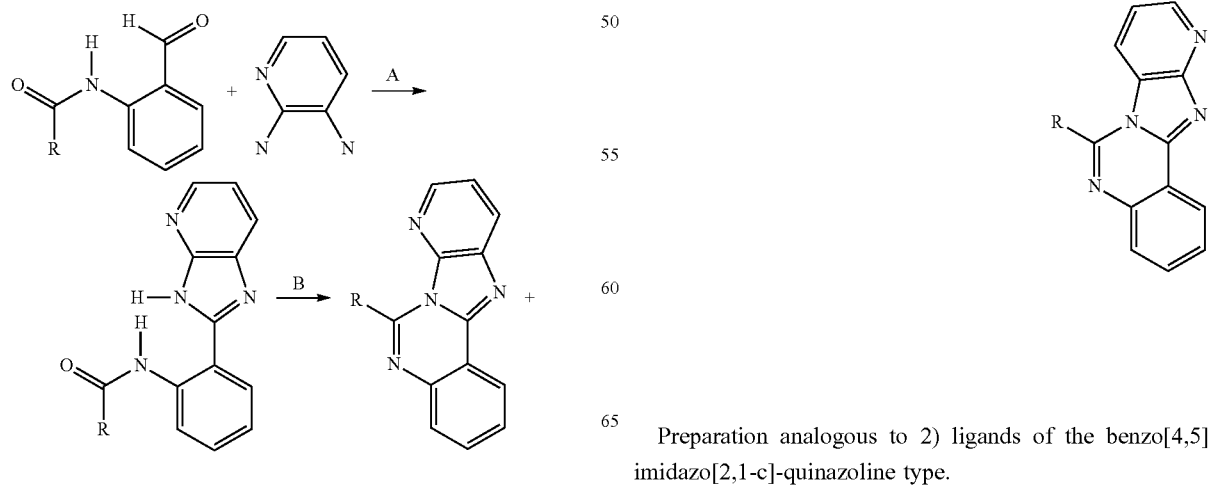

Examples L259 and L260, Variant A

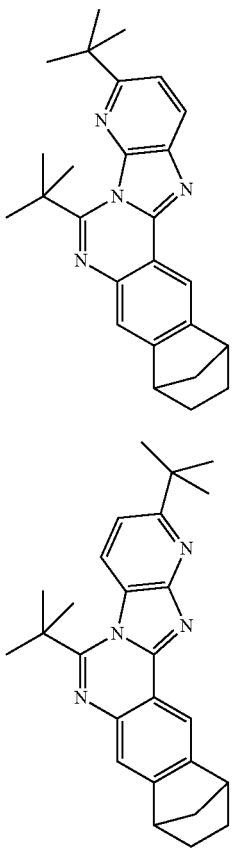

Step A:

L259

Use of 27.1 g (100 mmol) of S99 and 18.2 g (110 mmol) of 2,3-diamino-6-tert-butylpyridine [893444-20-7]. The N-[7-(5-tert-butyl-3H-imidazo[4,5-b]-pyridin-2-yl)-1,2,3,4-tetrahydro-1,4-methanonaphthalen-6-yl]-2,2-dimethylpropanamide crystallises out. Yield: 32.1 g (77 mmol), 77%; purity: 97% according to $^1$H-NMR.

Step B, Variant A:

Use of 32.1 g (77 mmol) of N-[7-(5-tert-butyl-3H-imidazo[4,5-b]pyridin-2-yl)-1,2,3,4-tetrahydro-1,4-methanonaphthalen-6-yl]-2,2-dimethylpropanamide (step A), 100 ml of dioxane, 31.4 g (260 mmol) of pivaloyl chloride [3282-30-2] and 3.8 g (37 mmol) of pivalic acid [75-98-9], reaction time 18 h, the crude product is produced in the form of a solid on neutralisation. Chromatographic separation of the regioisomers on silica gel (heptane:ethyl acetate, 10:1 vv), fractional sublimation of the products twice at T about 180° C., p about $10^{-4}$ mbar.

L260

Yield of L259: 9.1 g (23 mmol), 30%; purity: >99.5% according to $^1$H-NMR.

Yield of L260: 7.2 g (18 mmol), 23%; purity: >99.5% according to $^1$H-NMR.

The following derivatives can be prepared analogously:

| Ex. | 2-Amido-arylaldehyde | 2,3-Diamino-pyridine | Product Variant | Yield |
|---|---|---|---|---|
| L261 | S100 | 893444-20-7 | A | 25% |

-continued

| Ex. | 2-Amido-arylaldehyde | 2,3-Diamino-pyridine | Product Variant | Yield |
|---|---|---|---|---|
| L262 | S100 | 893444-20-7 | A | 21% |

13) Ligands of the 5,6a,8,11- and 5,6a,9,11-tetraazabenzo[a]fluorene Type

General Ligand Synthesis Variant A:

From 2-amidoarylaldehydes and 3,4-diaminopyridines:

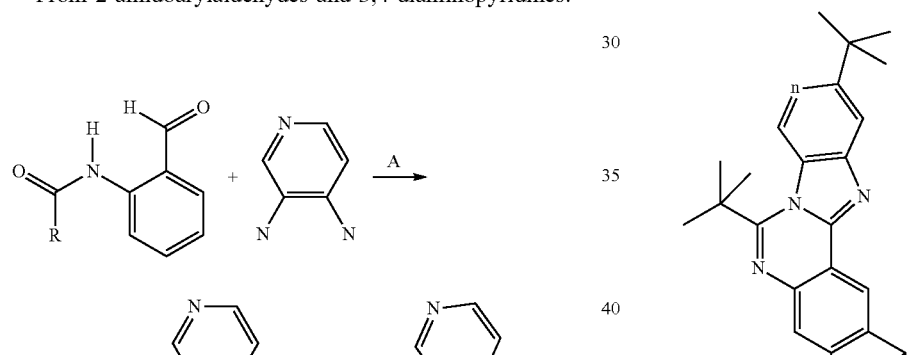

Preparation analogous to 2) ligands of the benzo[4,5]imidazo[2,1-c]-quinazoline type.

Examples L263 and L264, Variant A

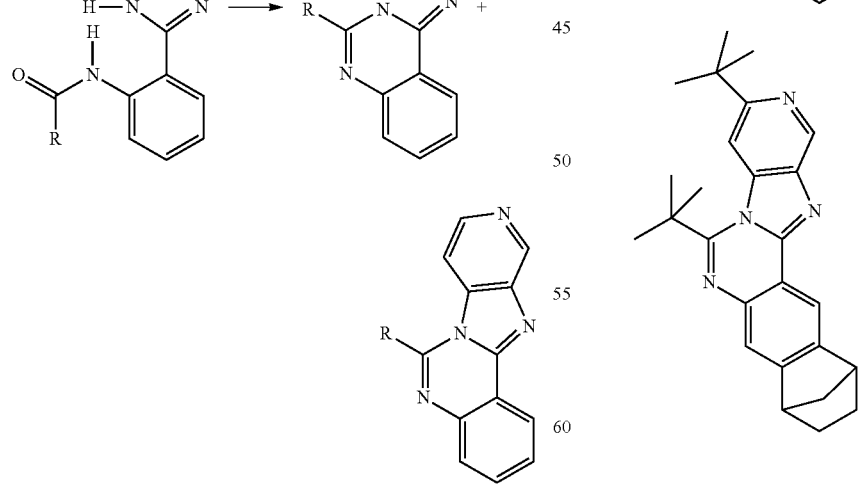

Step A:

Use of 27.1 g (100 mmol) of S99 and 18.2 g (110 mmol) of 3,4-diamino-6-tert-butylpyridine [1237537-50-6]. The N-[7-(6-tert-butyl-3H-imidazo[4,5-c]pyridin-2-yl)-1,2,3,4-tetrahydro-1,4-methanonaphthalen-6-yl]-2,2-dimethylpropanamide crystallises out. Yield: 28.8 g (69 mmol), 77%; purity: 97% according to ¹H-NMR.

Step B, Variant A:

Use of 28.8 g (69 mmol) of N-[7-(6-tert-butyl-3H-imidazo[4,5-c]pyridin-2-yl)-1,2,3,4-tetrahydro-1,4-methanonaphthalen-6-yl]-2,2-dimethylpropanamide (step A), 100 ml of dioxane, 27.9 g (230 mmol) of pivaloyl chloride [3282-30-2] and 3.4 g (33 mmol) of pivalic acid [75-98-9], reaction time 18 h, the crude product is produced in the form of a solid on neutralisation. Chromatographic separation of the regioisomers on silica gel (heptane:ethyl acetate, 10:1 vv), fractional sublimation of the products twice at T about 180° C., p about $10^{-4}$ mbar.

Yield of L263: 7.2 g (18 mmol), 26%; purity: >99.5% according to ¹H-NMR.

Yield of L264: 6.4 g (16 mmol), 23%; purity: >99.5% according to ¹H-NMR.

The following derivatives can be prepared analogously:

| Ex. | 2-Amido-arylaldehyde | 3,4-Diamino-pyridine | Product Variant | Yield |
|---|---|---|---|---|
| L265 | S100 | 1237537-50-6 | A | 25% |
| L266 | S100 | 1237537-50-6 | A | 16% |

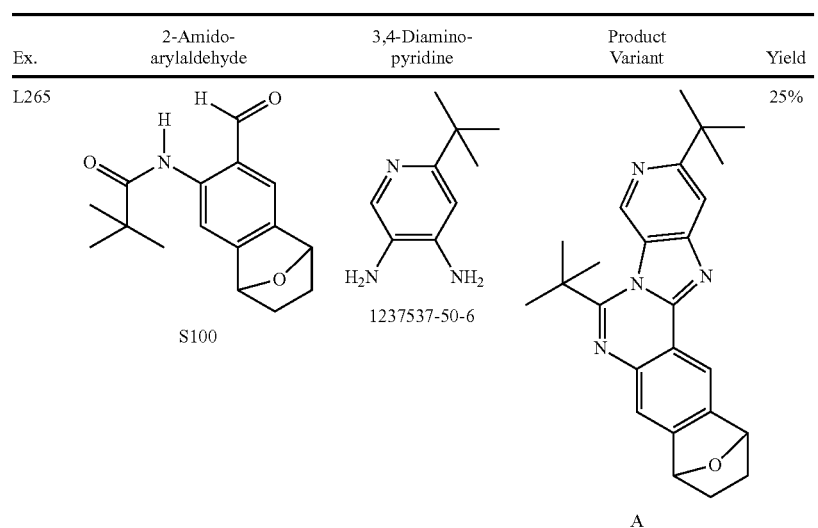

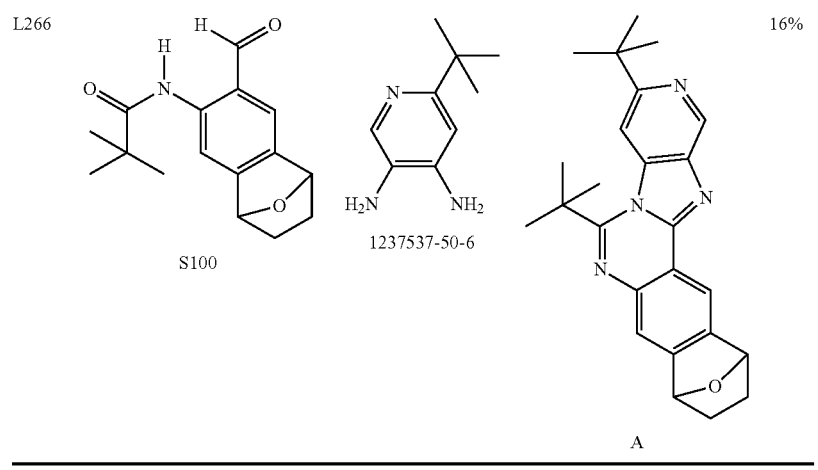

14) Ligands of the 6a,7,9,11- and 6a,8,10,11-tetraazabenzo[a]fluorene Type

General Ligand Synthesis:
From 2-amidoarylaldehydes and 5,6-diaminopyrimidines:

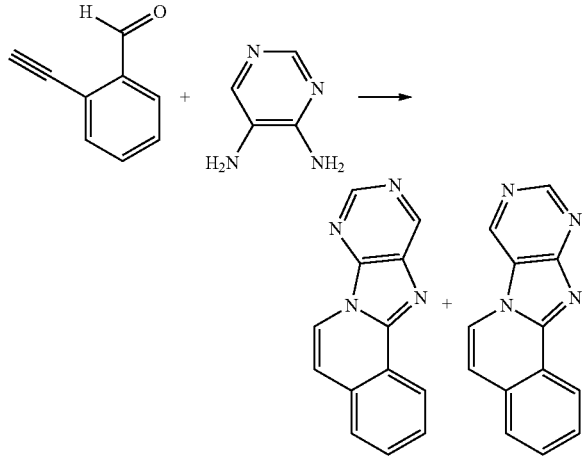

Preparation analogous to 3) ligands of the 2,6a,11-triazabenzo[a]-fluorene type.

Examples L267 and L268

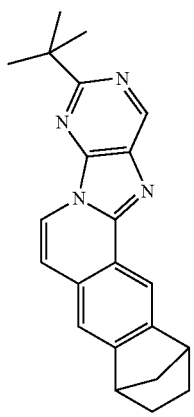

L267

Use of 134.2 g (500 mmol) of S104 and 90.9 g (550 mmol) of 2-tert-butyl-5,6-diaminopyrimidine [18202-78-3]. Chromatographic separation of the regioisomers on silica gel (heptane:ethyl acetate, 10:1 vv), fractional sublimation of the products twice at T about 180° C., p about $10^{-4}$ mbar.

Yield of L267: 53.4 g (156 mmol), 31%; purity: >99.5% according to $^1$H-NMR.

Yield of L268: 34.6 g (101 mmol), 20%; purity: >99.5% according to $^1$H-NMR.

The following derivatives can be prepared analogously:

| Ex. | 2-Alkynylaryl-aldehyde | 5,6-Diamino-pyrimidine | Product | Yield |
|---|---|---|---|---|
| L269 | S105 | 18202-78-3 | | 26% |

| Ex. | 2-Alkynylaryl-aldehyde | 5,6-Diamino-pyrimidine | Product | Yield |
|---|---|---|---|---|
| L270 | S105 | 18202-78-3 | | 23% |

15) Ligands of the 2,4,5,6a,11-pentaazabenzo[a]fluorene Type

General Ligand Synthesis:

From 4-amido-5-methoxycarbonylpyrimidines and 1,2-diaminobenzene dihydrochlorides

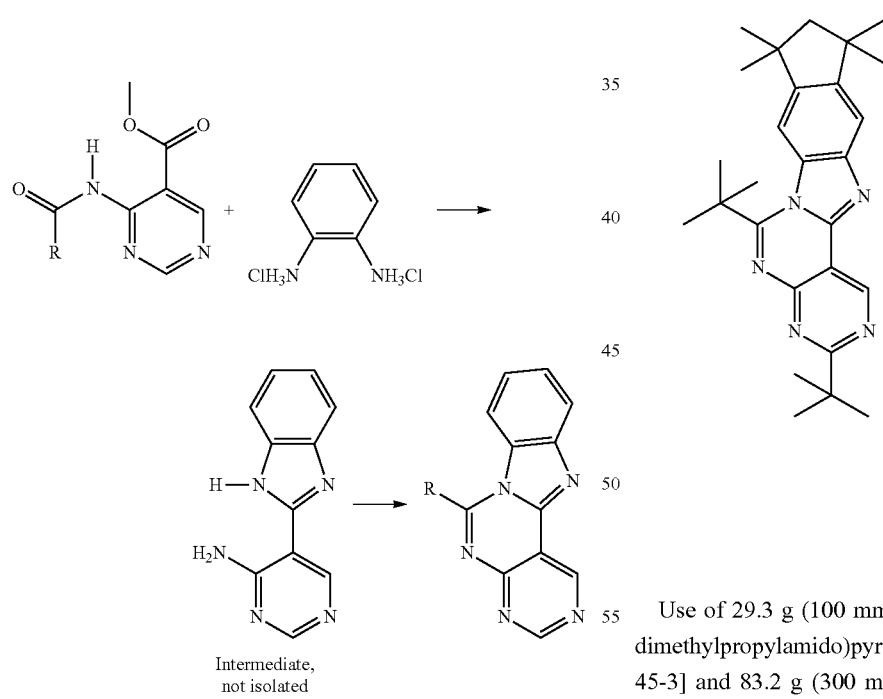

Preparation analogous to 8) variant B ligands of the 2,5,6a,11-tetraazabenzo[a]fluorene type, where the 4-amido-5-methoxycarbonylpyrimidines are employed instead of the 4-amido-3-cyanopyridines.

Example L271

Use of 29.3 g (100 mmol) of methyl 2-tert-butyl-4-(2,2-dimethylpropylamido)pyrimidine-5-carboxylate [1352329-45-3] and 83.2 g (300 mmol) of S16×2 HCl, 60.3 g (500 mmol) of pivaloyl chloride [3282-30-2], 5.1 g (50 mmol) of pivalic acid [75-98-9], 250 ml of diethylene glycol dimethyl ether, reaction time 8 h, the crude product is produced in the form of a solid on neutralisation, recrystallisation from DMF/ethanol, fractional sublimation of the product twice at T about 190° C., p about $10^{-4}$ mbar. Yield: 28.4 g (66 mmol), 66%; purity: about 99.5% according to $^1$H-NMR.

The following derivatives can be prepared analogously:

| Ex. | 4-Amido-5-methoxy-carbonyl-pyrimidine | 1,2-Diamino-benzene dihydrochloride | Product | Yield |
|---|---|---|---|---|
| L272 | 1352329-45-3 | S22 × 2 HCl | | 63% |
| L273 | 1352329-45-3 | S24 × 2 HCl | | 58% |
| L274 | 1352329-45-3 | S36 × 2 HCl | | 55% |

| Ex. | 4-Amido-5-methoxy-carbonyl-pyrimidine | 1,2-Diamino-benzene dihydrochloride | Product | Yield |
|---|---|---|---|---|
| L275 | 1352329-45-3 | S37 × 2 HCl | Chromatographic separation of the regioisomer | 19% |

16) Ligands of the imidazo[1,2-f]phenanthridine Type

General Ligand Synthesis Variant A:

From 6-aminophenanthridines and 2-haloketones:

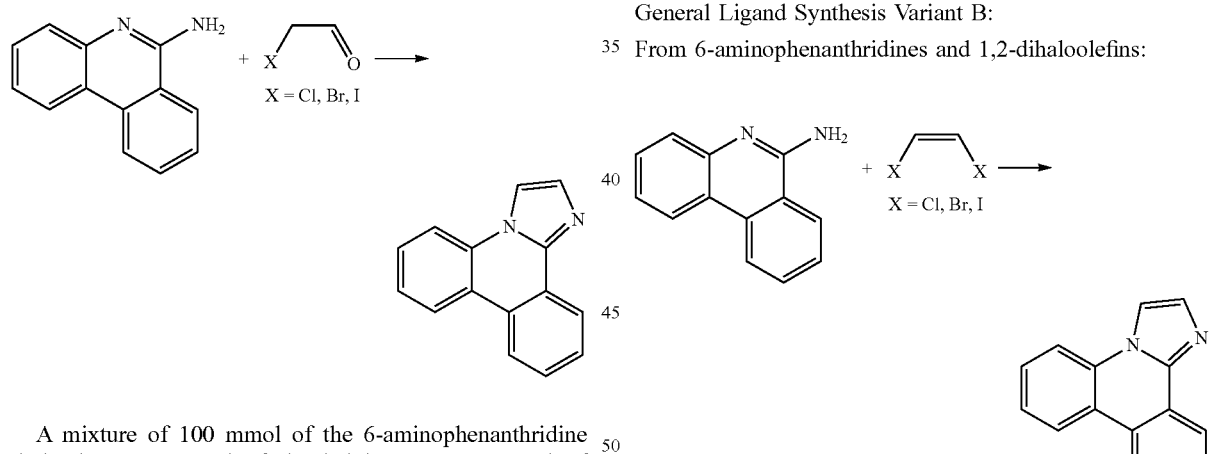

A mixture of 100 mmol of the 6-aminophenanthridine derivative, 300 mmol of the haloketone, 300 mmol of sodium hydrogencarbonate, 300 ml of ethylene glycol and 30 ml of water is stirred at 130° C. for 24 h. A further 300 mmol of the 2-haloketone and 300 mmol of sodium hydrogencarbonate are then added, and the mixture is stirred at 130° C. for a further 24 h. After cooling, the reaction mixture is diluted with 1000 ml of water, extracted three times with 300 ml of ethyl acetate or dichloromethane each time, the combined organic phases are washed with 500 ml of water and with 500 ml of saturated sodium chloride solution, the org. phase is evaporated in vacuo, and the residue is recrystallised or chromatographed on silica gel. The solids or oils obtained in this way are freed from low-boiling components and non-volatile secondary components by fractional bulb-tube distillation or sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

General Ligand Synthesis Variant B:

From 6-aminophenanthridines and 1,2-dihaloolefins:

A mixture of 100 mmol of the 6-aminophenanthridine derivative, 200 mmol of the 1,2-dihaloolefin, 300 mmol of potassium carbonate, 5 mmol of palladium(II) acetate, 30 mmol of triphenylphosphine, 100 g of glass beads (diameter 3 mm) and 200 ml of o-xylene is heated under reflux with vigorous stirring until (typically 6-24 h) the 6-aminophenanthridine has been consumed. After cooling to 80° C., the salts and glass beads are filtered off with suction over a Celite bed, rinsed with 300 ml of hot o-xylene, the filtrate is evaporated to dryness in vacuo, and the residue is recrystallised or chromatographed on silica gel. The solids or oils obtained in this way are freed from low-boiling components and non-volatile secondary components by fractional bulb-tube distillation or sublimation (p about $10^{-4}$-$10^{-5}$ mbar, T about 160-240° C.). Purity according to $^1$H-NMR typically >99.5%.

Example L500

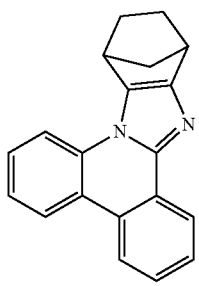 [SMILES: c1ccc2c(c1)c1ccccc1n1c3c(nc21)C1CCC3C1]

Variant A:
Use of 19.4 g (100 mmol) of 6-aminophenanthridine [832-68-8] and 43.4 g (300 mmol) of 3-chloro-(1R,3R,4S)-bicyclo[2.2.1]heptan-2-one [10464-71-8], chromatography on silica gel (ethyl acetate:dichloromethane 80:20 vv), then recrystallisation from DMF/ethanol, fractional sublimation of the product twice at T about 190° C., p about $10^{-4}$ mbar. Yield: 5.4 g (19 mmol), 19%; purity: about 99.5% according to $^1$H-NMR.

Variant B:
Use of 19.4 g (100 mmol) of 6-aminophenanthridine [832-68-8] and 50.4 g (200 mmol) of 2,3-dibromobicyclo[2.2.1]hept-2-ene [75267-72-0], chromatography on silica gel (ethyl acetate:dichloromethane 80:20 vv), then recrystallisation from DMF/ethanol, fractional sublimation of the product twice at T about 190° C., p about $10^{-4}$ mbar. Yield: 10.8 g (38 mmol), 38%; purity: about 99.5% according to $^1$H-NMR.

The following derivatives can be prepared analogously:

| Ex. | 6-Amino-phenanthridine | 2-Haloketone or 1,2-dihalo-olefin | Product | Yield |
|---|---|---|---|---|
| L501 | 832-68-8 | 17215-81-5 | | 13% |
| L502 | 855829-20-8 | 75267-72-0 | | 34% |
| L503 | 946147-22-4 | 75267-72-0 | | 28% |

-continued
| Ex. | 6-Amino-phenanthridine | 2-Haloketone or 1,2-dihalo-olefin | Product | Yield |
|---|---|---|---|---|
| L504 | 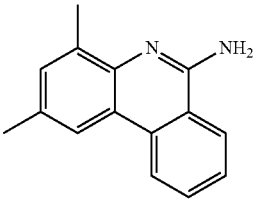 855830-85-2 | 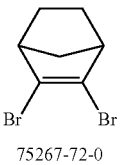 75267-72-0 | 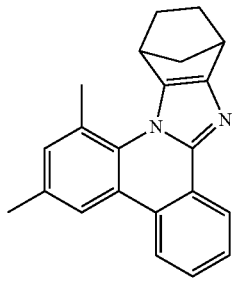 [SMILES: Cc1cc(C)c2c(c1)c1ccccc1c1nc3c(n12)C1CCC3C1] | 29% |
| L505 | 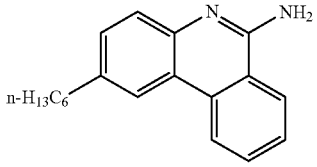 | 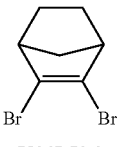 75267-72-0 | 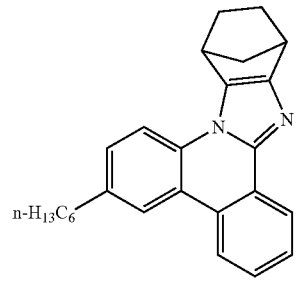 | 35% |
| L506 | 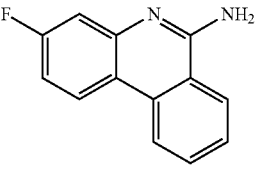 714243-31-9 | 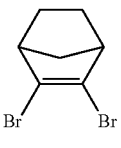 75267-72-0 | 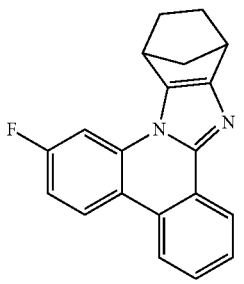 [SMILES: Fc1ccc2c3ccccc3c3nc4c(n3c2c1)C1CCC4C1] | 34% |
| L507 | 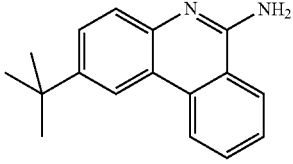 946147-22-4 | 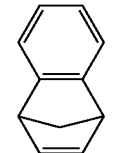 194086-05-0 | 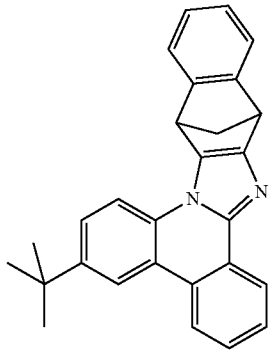 [SMILES: CC(C)(C)c1ccc2c(c1)c1ccccc1c1nc3c(n21)C1CC3c2ccccc21] | 37% |

| Ex. | 6-Amino-phenanthridine | 2-Haloketone or 1,2-dihalo-olefin | Product | Yield |
|---|---|---|---|---|
| L508 | 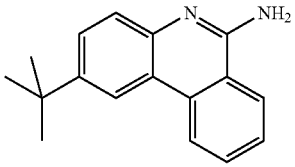 946147-22-4 | 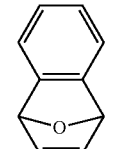 301829-08-3 | 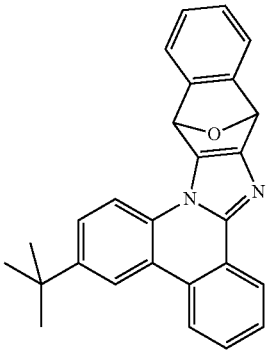 [SMILES: CC(C)(C)c1ccc2c(c1)c1ccccc1c1nc3c(n21)C1OC3c2ccccc21] | 35% |
| L509 | 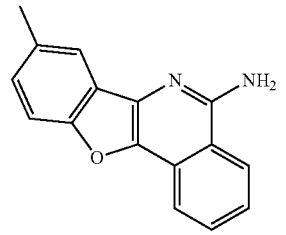 1293961-03-1 | 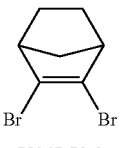 75267-72-0 | 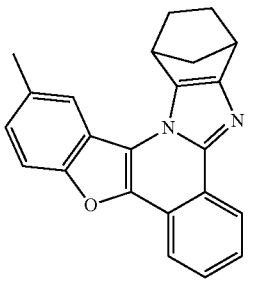 [SMILES: Cc1ccc2oc3c4ccccc4c4nc5c(n4c3c2c1)C1CCC5C1] | 32% |
| L510 | 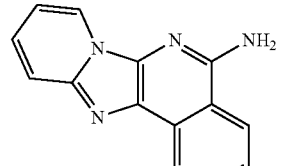 94718-73-7 | 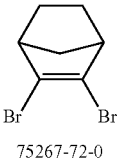 75267-72-0 | 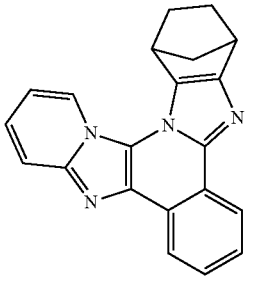 [SMILES: c1ccc2c(c1)c1nc3ccccn3c1n1c3c(nc21)C1CCC3C1] | 27% |

17) Ligands of the 8b,13-diazaindeno[1,2-l]phenanthrene Type

General Ligand Synthesis Variant A:

From 6-aminophenanthridines and 1,2-dihalobenzenes:

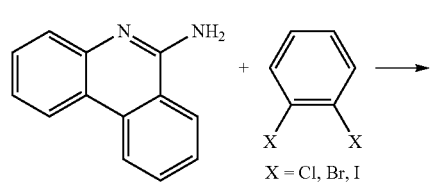

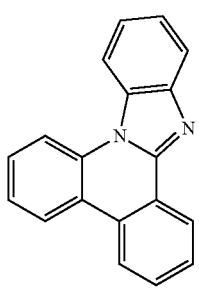

A vigorously stirred mixture of 100 mmol of the 6-aminophenanthridine derivative, 130 mmol of the 1,2-dihalobenzene, 130 mmol of potassium carbonate, 100 g of glass beads (diameter 3 mm), 8 mmol of triphenylphosphine and 2 mmol of palladium(II) acetate in 300 ml of o-xylene is heated under reflux for 3-48 h until the 6-aminophenanthridine derivative has been consumed. After cooling to 80° C., the salts and glass beads are filtered off with suction over a Celite bed, rinsed with 500 ml of hot o-xylene, the filtrate is evaporated to dryness in vacuo, and the residue is recrystallised or chromatographed on silica gel. The solids or oils obtained in this way are freed from low-boiling components and non-volatile secondary components by fractional bulb-tube distillation or sublimation (p about $10^{-4}$-$10^{-5}$ mbar, T about 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

General Ligand Synthesis Variant B:
From 6-halophenanthridines and 1-amino-2-halobenzenes:

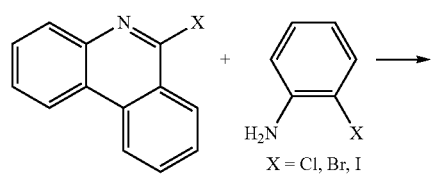

Preparation analogous to 1) ligands of the benzo[4,5]imidazo[2,1-a]-isoquinoline type.

Example L511

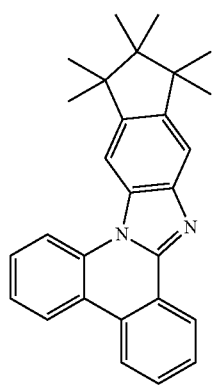 [SMILES: CC1(C)c2cc3nc4c5ccccc5c5ccccc5n4c3cc2C(C)(C)C1(C)C]

Variant B:

Use of 213.67 g (100 mmol) of 6-chlorophenanthridine [15679-03-5] and 35.6 g (120 mmol) of S6, recrystallisation from dioxane/ethanol, fractional sublimation of the product twice at T about 210° C., p about $10^{-4}$ mbar.

Yield: 22.8 g (58 mmol), 58%; purity: about 99.5% according to $^1$H-NMR.

General Ligand Synthesis Variant C:
From 6-aminophenanthridines and 1,2-dihalobenzenes:

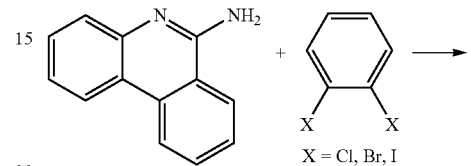

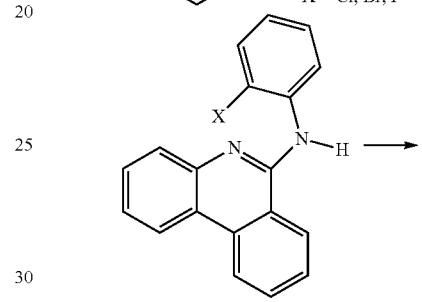

Preparation analogous to 1) variant C, ligands of the benzo[4,5]imidazo[2,1-a]isoquinoline type.

Example L511

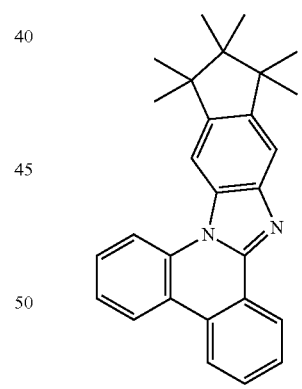

Use of 36.0 g (100 mmol) of 5,6-dibromo-1,1,2,2,3,3-hexamethylindane, S24, variant A, step A, 23.3 g (120 mmol) of 6-aminophenanthridine [832-68-8], 50.2 g (300 mmol) of lithium bis(trimethylsilyl)amide, 2.9 g (5 mmol) of xantphos, 1.1 g (5 mmol) of palladium(II) acetate and then 1.9 g (10 mmol) of copper(I) iodide, 1.75 g (20 mmol) of N,N'-ethylenediamine and 31.8 g (230 mmol) of potassium carbonate. The crude product is recrystallised from dioxane (about 5 ml/g) and sublimed in vacuo (p=$10^{-5}$ mbar, T=240° C.). Yield: 25.5 g (65 mmol), 65%; purity: about 99.5% according to $^1$H-NMR.

The following derivatives can be prepared analogously:
| Ex. | Phenanthridine | 1,2-Dihalo- or 1-amino-2-halobenzene | Product Variant | Yield |
|---|---|---|---|---|
| L512 | 832-68-8 | 1311465-45-8 | A | 53% |
| L513 | 1089735-10-3 | S6 | B | 48% |
| L514 | 946147-22-4 | 42810-32-2 | A | 52% |
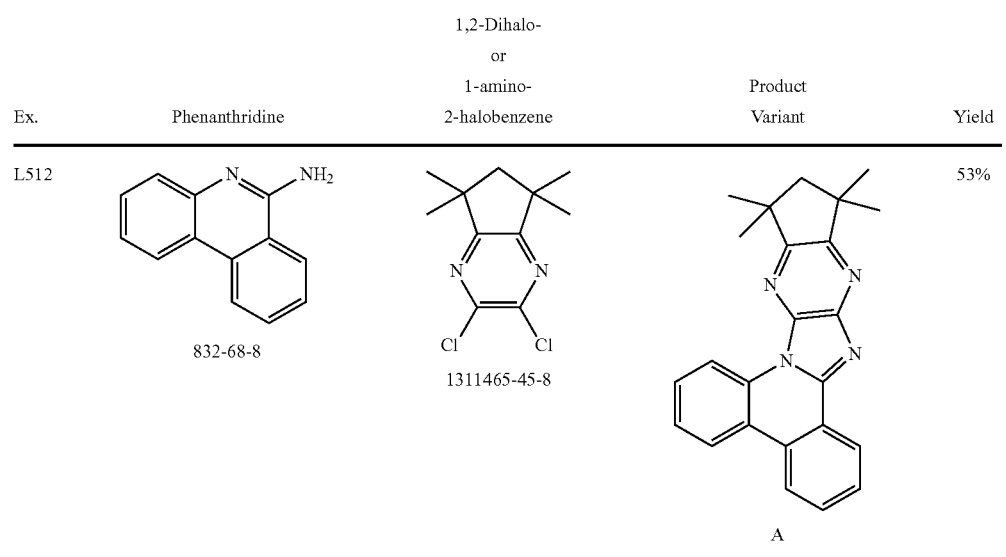
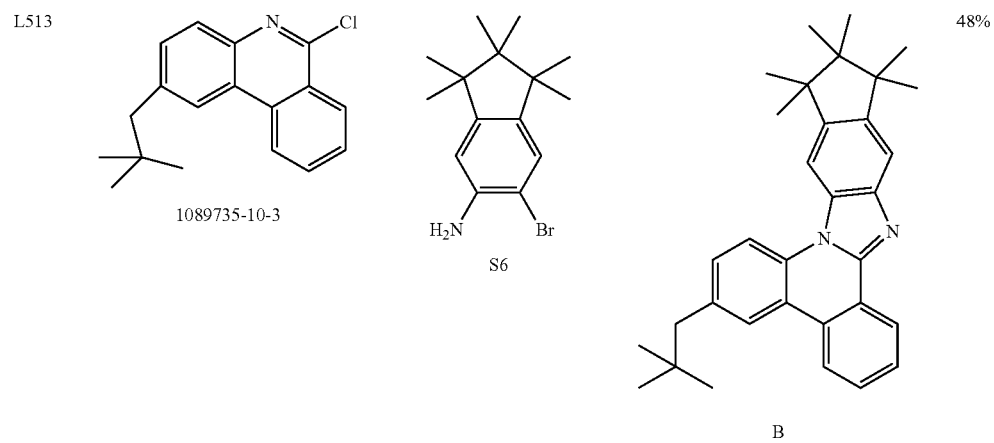
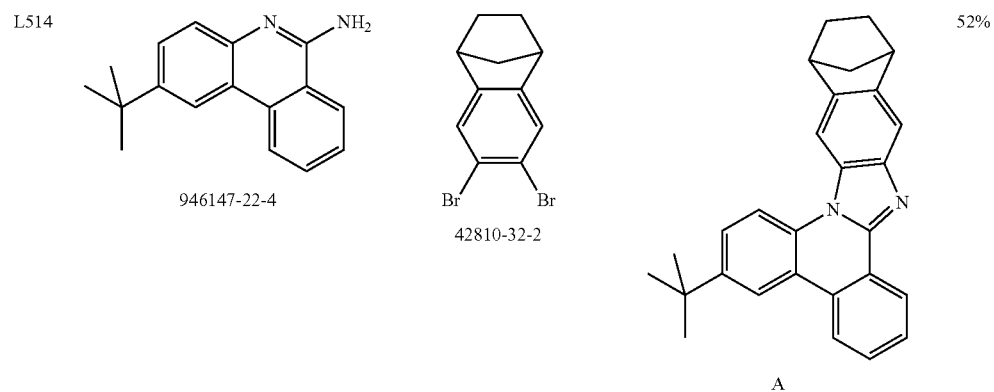

-continued
| Ex. | Phenanthridine | 1,2-Dihalo- or 1-amino- 2-halobenzene | Product Variant | Yield |
|---|---|---|---|---|
| L515 | 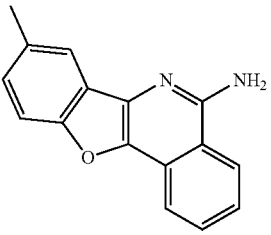<br>1293961-03-1 | 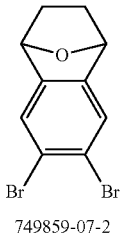<br>749859-07-2 | 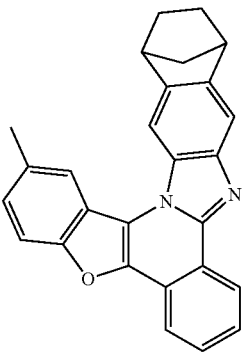<br>A | 40% |
| L516 | 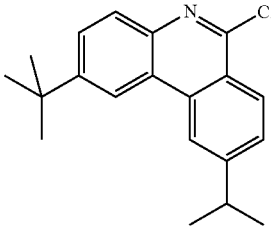<br>946147-36-0 | 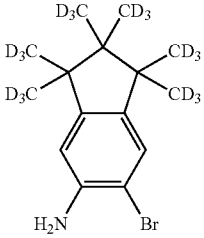<br>S7 | 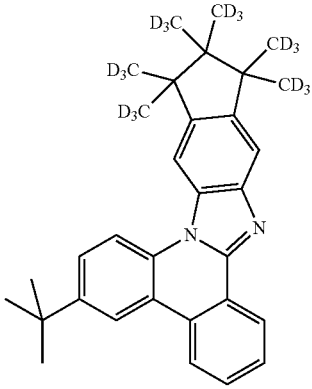<br>B | 55% |
| L517 | 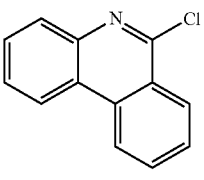<br>15679-03-5 | 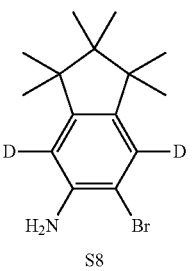 [SMILES: [2H]c1c(N)c(Br)c([2H])c2c1C(C)(C)C(C)(C)C2(C)C ; "S8"]<br>S8 | 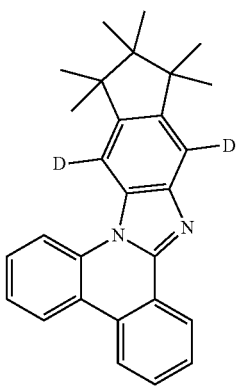<br>B | 58% |

| Ex. | Phenanthridine | 1,2-Dihalo- or 1-amino- 2-halobenzene | Product Variant | Yield |
|---|---|---|---|---|
| L518 | 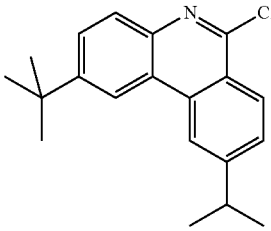<br>946147-36-0 | 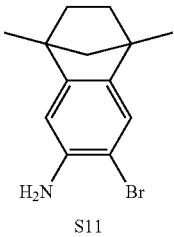<br>S11 | 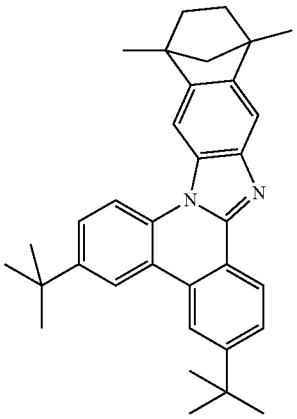B | 50% |

18) Tetradentate Ligands, L283

A) L282-Br

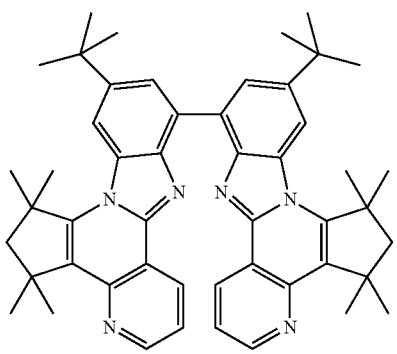 [SMILES: CC(C)(C)c1cc(-c2cc(C(C)(C)C)cc3c2nc2c4cccnc4c4c(n32)C(C)(C)CC4(C)C)c2nc3c4cccnc4c4c(n3c2c1)C(C)(C)CC4(C)C]

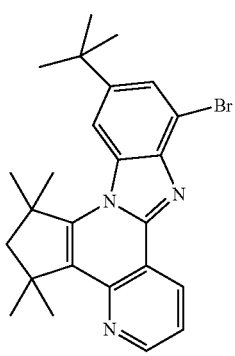 [SMILES: CC(C)(C)c1cc(Br)c2nc3c4cccnc4c4c(n3c2c1)C(C)(C)CC4(C)C]

19.6 g (110 mmol) of NBS are added in portions to a solution, warmed to 100° C., of 37.2 g (100 mmol) of L282 in 300 ml of DMF, and the mixture is subsequently stirred for a further 6 h. The reaction mixture is evaporated to about 150 ml in vacuo, stirred for a further 2 h, the deposited crystals are filtered off with suction and finally washed twice with 50 ml of methanol each time and dried in vacuo. Yield: 35.6 g (79 mmol), 79%. Purity: 97% according to $^1$H-NMR.

B) L282-B

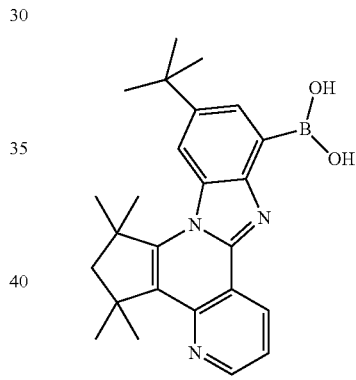

20 ml (50 mmol) of n-butyllithium (2.5 M in hexane) are added dropwise with vigorous stirring to a solution, cooled to −78° C., of 22.5 g (50 mmol) of L282-Br in 500 ml of THF, and the mixture is stirred for a further 30 min. 5.6 ml (50 mmol) of trimethyl borate are added to this solution in one portion, the mixture is stirred for a further 1 h and then allowed to warm to room temperature. The solvent is removed in vacuo, and the residue is employed in the Suzuki coupling C).

C) Suzuki Coupling

A mixture of 22.5 g (50 mmol) of L282-Br and 20.7 g (50 mmol) of L282-B—as obtained under B)—31.8 g (150 mmol) of tripotassium phosphate, 1.8 g (6 mmol) of tri-o-tolylphosphine, 224 mg (1 mmol) of palladium(II) acetate, 300 ml of toluene, 100 ml of dioxane and 300 ml of water is heated under reflux for 12 h. After cooling, the precipitated solid is filtered off with suction, washed twice with 50 ml of toluene each time and three times with 100 ml of ethanol each time. The crude product is recrystallised from sulfolane (about 5 ml/g) and sublimed in vacuo (p=$10^{-5}$ mbar, T=300° C.). Yield: 21.9 g (29 mmol), 58%; purity: about 99.5% according to $^1$H-NMR.

19) Hexadentate Ligands, L284

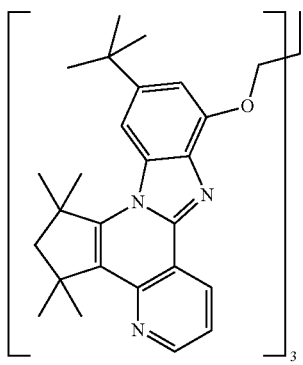

A) L282-OH

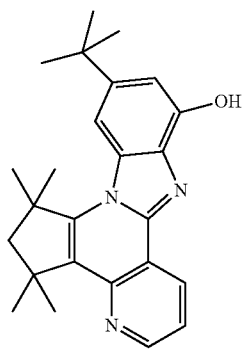 [SMILES: CC(C)(C)c1cc(O)c2nc3c4cccnc4c4c(n3c2c1)C(C)(C)CC4(C)C]

20 ml (50 mmol) of n-butyllithium (2.5 M in hexane) are added dropwise with vigorous stirring to a solution, cooled to −78° C., of 22.5 g (50 mmol) of L282-Br in 500 ml of THF, and the mixture is stirred for a further 30 min. 5.6 ml (50 mmol) of trimethyl borate are added to this solution in one portion, the mixture is stirred for a further 1 h and then allowed to warm to room temperature. The solvent is removed in vacuo, the residue is taken up in 1000 ml of ethyl acetate, the solution is cooled to 5° C., 32 ml of aqueous $H_2O_2$ solution (30% by weight) are added with vigorous stirring, and a solution of 1.4 g of NaOH in 30 ml of water is then added dropwise. After stirring for 3 h, 500 ml of saturated ammonium chloride solution are added, the organic phase is separated off, washed twice with 200 ml of water each time, dried over magnesium sulfate, and the organic phase is then evaporated to a volume of about 50 ml in vacuo. 200 ml of methanol are added to the crystal slurry, the crystals are filtered off with suction, washed once with 50 ml of methanol and dried in vacuo. Yield: 13.5 g (35 mmol), 70%. Purity: 95% according to $^1$H-NMR.

B) L284

1.6 g (40 mmol) of sodium hydride, 60% dispersion in mineral oil, are added in portions to a vigorously stirred solution of 13.5 g (35 mmol) of L282-OH in 100 ml of THF (note: evolution of hydrogen, foaming). When the evolution of hydrogen is complete, 3.1 g (10 mmol) of 1,1,1-tris(bromomethyl)ethane [60111-68-4] are added, and the reaction mixture is heated under reflux for 16 h. After cooling, the THF is removed in vacuo, the residue is taken up in 500 ml of ethyl acetate, washed three times with 200 ml of water each time and once with 100 ml of saturated sodium chloride solution, and the organic phase is dried over sodium sulfate. The residue obtained after removal of the solvent is chromatographed on silica gel (ethyl acetate:n-heptane, 5:1 vv) and then dried in vacuo. Yield: 7.1 g (5.8 mmol), 58%. Purity: 99% according to $^1$H-NMR.

C: Synthesis of the Metal Complexes:
1) Homoleptic Tris-Facial Iridium Complexes:
Variant A: Trisacetylacetonatoiridium(III) as Iridium Starting Material A mixture of 10 mmol of trisacetylacetonatoiridium(III) [15635-87-7] and 60 mmol of the ligand L and a glass-clad magnetic stirrer bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. In order to prevent sublimation of the ligands onto relatively cold parts of the ampoule, the entire ampoule must have the temperature indicated. Alternatively, the synthesis can be carried out in a stirred autoclave with glass insert. After cooling (NOTE: the ampoules are usually under pressure!), the ampoule is opened, the sinter cake is stirred for 3 h with 100 g of glass beads (diameter 3 mm) in 100 ml of a suspension medium (the suspension medium is selected so that the ligand is readily soluble, but the metal complex has low solubility therein, typical suspension media are methanol, ethanol, dichloromethane, acetone, THF, ethyl acetate, toluene, etc.) and mechanically digested in the process. The fine suspension is decanted off from the glass beads, the solid is filtered off with suction, rinsed with 50 ml of the suspension medium and dried in vacuo. The dry solid is placed on a 3-5 cm deep aluminium oxide bed (aluminium oxide, basic, activity grade 1) in a continuous hot extractor and then extracted with an extractant (initially introduced amount about 500 ml, the extractant is selected so that the complex is readily soluble therein at elevated temperature and has low solubility therein when cold, particularly suitable extractants are hydrocarbons, such as toluene, xylenes, mesitylene, naphthalene, o-dichlorobenzene, halogenated aliphatic hydrocarbons are generally unsuitable since they may halogenate or decompose the complexes). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot extraction step is repeated, omitting the aluminium oxide bed from the 2nd extraction. When a purity of 99.5-99.9% has been reached, the metal complex is heated or sublimed. The heating is carried out in a high vacuum (p about $10^{-6}$ mbar) in the temperature range from about 200-300° C. The sublimation is carried out in a high vacuum (p about $10^{-6}$ mbar) in the temperature range from about 300-400° C., with the sublimation preferably being carried out in the form of a fractional sublimation. If ligands in point group C1 are employed in the form of a racemic mixture, the derived fac-metal complexes are produced in the form of a diastereomer mixture. The enantiomer pair Λ,Δ in point group C3 generally has significantly lower solubility in the extractant than that in point group C1, which is consequently enriched in the mother liquor. Separation of the diastereomers by this method is frequently possible. In addition, the diastereomers can also be separated by chromatography. If ligands in point group C1 are employed in enantiomerically pure form, the enantiomer pair Λ,Δ in point group C3 is formed.

Variant B: Tris-(2,2,6,6-tetramethyl-3,5-heptanedionato)iridium(III) as Iridium Starting Material Procedure analogous to variant A, using 10 mmol of tris(2,2,6,6-tetramethyl-3,5-heptanedionato)iridium [99581-86-9] instead of 10 mmol of trisacetylacetonatoiridium(III) [15635-87-7]. The use of this starting material is advantageous since the purity of the crude products obtained is frequently better than in the case of variant A. In addition, the build-up of pressure in the ampoule is frequently not so pronounced.

| Ex. | Ligand L | Ir complex Diastereomer | Variant Reaction temp./reaction time Suspension medium Extractant | Yield |
|---|---|---|---|---|
| Ir(L1)$_3$ | L1 | Ir(L1)$_3$ | A 260° C./100 h DCM Mesitylene | 40% |
| Ir(L1)$_3$ | L1 | Ir(L1)$_3$ | B 280° C./100 h DCM Mesitylene | 48% |
| Ir(L2)$_3$ | L2 | Ir(L2)$_3$ | B 290° C./100 h DCM Mesitylene | 43% |
| Ir(L3)$_3$ | L3 | Ir(L3)$_3$ | as Ex. Ir(L1)$_3$/B | 43% |
| Ir(L4)$_3$ | L4 | Ir(L4)$_3$ | as Ex. Ir(L1)$_3$/B | 45% |
| Ir(L5)$_3$ | L5 | Ir(L5)$_3$ | as Ex. Ir(L1)$_3$/B | 40% |
| Ir(L6)$_3$ | L6 | Ir(L6)$_3$ | as Ex. Ir(L1)$_3$/B | 47% |
| Ir(L7)$_3$ | L7 | Ir(L7)$_3$ Λ,Δ-C3 | as Ex. Ir(L1)$_3$/B | 25% |
| Ir(L8)$_3$ | L8 | Ir(L8)$_3$ Λ,Δ-C3 | as Ex. Ir(L1)$_3$/B | 25% |
| Ir(L9)$_3$ | L9 | Ir(L9)$_3$ | B 280° C./150 h DCM Mesitylene | 41% |
| Ir(L10)$_3$ | L10 | Ir(L10)$_3$ | as Ex. Ir(L1)$_3$/B | 43% |
| Ir(L11)$_3$ | L11 | Ir(L11)$_3$ Λ,Δ-C3 | as Ex. Ir(L1)$_3$/B | 24% |
| Ir(L12)$_3$ | L12 | Ir(L12)$_3$ Λ,Δ-C3 | as Ex. Ir(L1)$_3$/B | 7% |
| Ir(L13)$_3$ | L13 | Ir(L13)$_3$ Λ,Δ-C3 | as Ex. Ir(L1)$_3$/B | 26% |
| Ir(L14)$_3$ | L14 | Ir(L14)$_3$ | as Ex. Ir(L1)$_3$/B | 45% |
| Ir(L15)$_3$ | L15 | Ir(L15)$_3$ | as Ex. Ir(L1)$_3$/B | 47% |

-continued

| Ex. | Ligand L | Ir complex Diastereomer | Variant Reaction temp./ reaction time Suspension medium Extractant | Yield |
|---|---|---|---|---|
| Ir(L16)$_3$ | L16 | Ir(L16)$_3$ | B 280° C./180 h DCM Mesitylene | 43% |
| Ir(L17)$_3$ | L17 | Ir(L17)$_3$ | as Ex. Ir(L16)$_3$ | 38% |
| Ir(L18)$_3$ | L18 | Ir(L18)$_3$ | as Ex. Ir(L1)$_3$/B | 45% |
| Ir(L19)$_3$ | L19 | Ir(L19)$_3$ Λ,Δ-C3 | as Ex. Ir(L1)$_3$/B | 21% |
| Ir(L20)$_3$ | L20 | Ir(L20)$_3$ | as Ex. Ir(L1)$_3$/B | 45% |
| Ir(L21)$_3$ | L21 | Ir(L21)$_3$ Λ,Δ-C3 | as Ex. Ir(L1)$_3$/B | 23% |
| Ir(L22)$_3$ | L22 | Ir(L22)$_3$ | as Ex. Ir(L1)$_3$/B | 23% |
| Ir(L23)$_3$ | L23 | Ir(L23)$_3$ | as Ex. Ir(L16)$_3$ | 21% |
| Ir(L24)$_3$ | L24 | Ir(L24)$_3$ Λ,Δ-C3 | as Ex. Ir(L1)$_3$/B | 26% |
| Ir(L25)$_3$ | L25 | Ir(L25)$_3$ Λ,Δ-C3 | as Ex. Ir(L16)$_3$ | 27% |
| Ir(L26)$_3$ | L26 | Ir(L26)$_3$ | as Ex. Ir(L1)$_3$/B | 44% |
| Ir(L27)$_3$ | L27 | Ir(L27)$_3$ | as Ex. Ir(L1)$_3$/B | 48% |
| Ir(L28)$_3$ | L28 | Ir(L28)$_3$ | as Ex. Ir(L1)$_3$/B | 47% |
| Ir(L29)$_3$ | L29 | Ir(L29)$_3$ | as Ex. Ir(L16)$_3$ | 37% |
| Ir(L30)$_3$ | L30 | Ir(L30)$_3$ | as Ex. Ir(L16)$_3$ | 35% |
| Ir(L31)$_3$ | L31 | Ir(L31)$_3$ Λ,Δ-C3 | as Ex. Ir(L2)$_3$ | 26% |
| Ir(L32)$_3$ | L32 | Ir(L32)$_3$ | as Ex. Ir(L2)$_3$ | 50% |
| Ir(L33)$_3$ | L33 | Ir(L33)$_3$ | as Ex. Ir(L2)$_3$ | 43% |
| Ir(L34)$_3$ | L34 | Ir(L34)$_3$ | as Ex. Ir(L2)$_3$ | 51% |
| Ir(L35)$_3$ | L35 | Ir(L35)$_3$ | as Ex. Ir(L1)$_3$/B | 21% |
| Ir(L36)$_3$ | L36 | Ir(L36)$_3$ | as Ex. Ir(L1)$_3$/B | 19% |
| Ir(L37)$_3$ | L37 | Ir(L37)$_3$ | as Ex. Ir(L16)$_3$ | 30% |
| Ir(L38)$_3$ | L38 | Ir(L38)$_3$ | as Ex. Ir(L16)$_3$ | 17% |
| Ir(L39)$_3$ | L39 | Ir(L39)$_3$ | as Ex. Ir(L1)$_3$/B | 39% |
| Ir(L40)$_3$ | L40 | Ir(L40)$_3$ | as Ex. Ir(L1)$_3$/B | 37% |
| Ir(L41)$_3$ | L41 | Ir(L41)$_3$ | as Ex. Ir(L1)$_3$/B | 46% |
| Ir(L42)$_3$ | L42 | Ir(L42)$_3$ | as Ex. Ir(L1)$_3$/B | 36% |
| Ir(L43)$_3$ | L43 | Ir(L43)$_3$ | as Ex. Ir(L1)$_3$/B | 33% |
| Ir(L44)$_3$ | L44 | Ir(L44)$_3$ | as Ex. Ir(L16)$_3$ | 4% |
| Ir(L45)$_3$ | L45 | Ir(L45)$_3$ | as Ex. Ir(L2)$_3$ | 43% |
| Ir(L46)$_3$ | L46 | Ir(L46)$_3$ Λ,Δ-C3 + C1 | as Ex. Ir(L1)$_3$/B | 45% |
| Ir(L47)$_3$ | L47 | Ir(L47)$_3$ | as Ex. Ir(L1)$_3$/B | 23% |
| Ir(L48)$_3$ | L48 | Ir(L48)$_3$ | as Ex. Ir(L1)$_3$/B | 36% |
| Ir(L49)$_3$ | L49 | Ir(L49)$_3$ | as Ex. Ir(L1)$_3$/B | 39% |
| Ir(L50)$_3$ | L50 | Ir(L50)$_3$ | as Ex. Ir(L1)$_3$/B | 38% |
| Ir(L51)$_3$ | L51 | Ir(L51)$_3$ | as Ex. Ir(L1)$_3$/B | 50% |
| Ir(L52)$_3$ | L52 | Ir(L52)$_3$ | as Ex. Ir(L1)$_3$/B | 48% |
| Ir(L53)$_3$ | L53 | Ir(L53)$_3$ | as Ex. Ir(L1)$_3$/B | 48% |
| Ir(L54)$_3$ | L54 | Ir(L54)$_3$ | as Ex. Ir(L1)$_3$/B | 34% |
| Ir(L55)$_3$ | L55 | Ir(L55)$_3$ Λ,Δ-C3 + C1 | as Ex. Ir(L1)$_3$/B | 41% |
| Ir(L56)$_3$ | L56 | Ir(L56)$_3$ | as Ex. Ir(L1)$_3$/B | 40% |
| Ir(L57)$_3$ | L57 | Ir(L57)$_3$ Λ,Δ-C3 | as Ex. Ir(L1)$_3$/B | 24% |
| Ir(L58)$_3$ | L58 | Ir(L58)$_3$ Λ,Δ-C3 | as Ex. Ir(L1)$_3$/B | 17% |
| Ir(L59)$_3$ | L59 | Ir(L59)$_3$ Λ,Δ-C3 | as Ex. Ir(L16)$_3$ | 2% |
| Ir(L60)$_3$ | L60 | Ir(L60)$_3$ Λ,Δ-C3 | as Ex. Ir(L1)$_3$/B | 23% |
| Ir(L61)$_3$ | L61 | Ir(L61)$_3$ Λ,Δ-C3 | as Ex. Ir(L1)$_3$/B | 18% |
| Ir(L62)$_3$ | L62 | Ir(L62)$_3$ | as Ex. Ir(L2)$_3$ | 40% |
| Ir(L63)$_3$ | L63 | Ir(L63)$_3$ | as Ex. Ir(L1)$_3$/B | 41% |
| Ir(L64)$_3$ | L64 | Ir(L64)$_3$ | as Ex. Ir(L1)$_3$/B | 34% |
| Ir(L65)$_3$ | L65 | Ir(L65)$_3$ Λ,Δ-C3 | as Ex. Ir(L1)$_3$/B | 17% |
| Ir(L66)$_3$ | L66 | Ir(L66)$_3$ Λ,Δ-C3 | as Ex. Ir(L1)$_3$/B | 23% |
| Ir(L67)$_3$ | L67 | Ir(L67)$_3$ Λ,Δ-C3 | as Ex. Ir(L1)$_3$/B | 19% |
| Ir(L68)$_3$ | L68 | Ir(L68)$_3$ Λ,Δ-C3 | as Ex. Ir(L16)$_3$ | 12% |

-continued

| Ex. | Ligand L | Ir complex Diastereomer | Variant Reaction temp./ reaction time Suspension medium Extractant | Yield |
|---|---|---|---|---|
| Ir(L69)$_3$ | L69 | Ir(L69)$_3$ Λ,Δ-C3 | as Ex. Ir(L16)$_3$ | 16% |
| Ir(L70)$_3$ | L70 | Ir(L70)$_3$ Λ,Δ-C3 | as Ex. Ir(L1)$_3$/B | 21% |
| Ir(L71)$_3$ | L71 | Ir(L71)$_3$ Λ,Δ-C3 | as Ex. Ir(L1)$_3$/B | 18% |
| Ir(L72)$_3$ | L72 | Ir(L72)$_3$ Λ,Δ-C3 | as Ex. Ir(L1)$_3$/B | 9% |
| Ir(L73)$_3$ | L73 | Ir(L73)$_3$ | as Ex. Ir(L1)$_3$/B | 17% |
| Ir(L74)$_3$ | L74 | Ir(L74)$_3$ | as Ex. Ir(L1)$_3$/B | 46% |
| Ir(L75)$_3$ | L75 | Ir(L75)$_3$ | as Ex. Ir(L1)$_3$/B | 46% |
| Ir(L76)$_3$ | L76 | Ir(L76)$_3$ | as Ex. Ir(L1)$_3$/B | 48% |
| Ir(L77)$_3$ | L77 | Ir(L77)$_3$ | as Ex. Ir(L1)$_3$/B | 45% |
| Ir(L78)$_3$ | L78 | Ir(L78)$_3$ | as Ex. Ir(L16)$_3$ | 33% |
| Ir(L79)$_3$ | L79 | Ir(L79)$_3$ | as Ex. Ir(L16)$_3$ | 30% |
| Ir(L80)$_3$ | L80 | Ir(L80)$_3$ | as Ex. Ir(L1)$_3$/B | 44% |
| Ir(L81)$_3$ | L81 | Ir(L81)$_3$ | as Ex. Ir(L1)$_3$/B | 45% |
| Ir(L82)$_3$ | L82 | Ir(L82)$_3$ Λ,Δ-C3 | as Ex. Ir(L1)$_3$/B | 22% |
| Ir(L83)$_3$ | L83 | Ir(L83)$_3$ Λ,Δ-C3 | as Ex. Ir(L1)$_3$/B | 26% |
| Ir(L84)$_3$ | L84 | Ir(L84)$_3$ | as Ex. Ir(L2)$_3$ | 51% |
| Ir(L85)$_3$ | L85 | Ir(L85)$_3$ Λ,Δ-C3 | as Ex. Ir(L16)$_3$ | 23% |
| Ir(L85)$_3$ | L85 | Ir(L85)$_3$ C1 | as Ex. Ir(L16)$_3$ | 9% |
| Ir(L86)$_3$ | L86 | Ir(L86)$_3$ Λ,Δ-C3 | as Ex. Ir(L16)$_3$ | 28% |
| Ir(L87)$_3$ | L87 | Ir(L87)$_3$ Λ,Δ-C3 | as Ex. Ir(L16)$_3$ | 25% |
| Ir(L88)$_3$ | L88 | Ir(L88)$_3$ Λ,Δ-C3 | as Ex. Ir(L16)$_3$ | 27% |
| Ir(L89)$_3$ | L89 | Ir(L89)$_3$ Λ,Δ-C3 | as Ex. Ir(L16)$_3$ | 24% |
| Ir(L90)$_3$ | L90 | Ir(L90)$_3$ Λ,Δ-C3 | as Ex. Ir(L16)$_3$ | 26% |
| Ir(L91)$_3$ | L91 | Ir(L91)$_3$ Λ,Δ-C3 | as Ex. Ir(L16)$_3$ | 28% |
| Ir(L92)$_3$ | L92 | Ir(L92)$_3$ | as Ex. Ir(L1)$_3$/B | 42% |
| Ir(L93)$_3$ | L93 | Ir(L93)$_3$ | as Ex. Ir(L1)$_3$/B | 45% |
| Ir(L94)$_3$ | L94 | Ir(L94)$_3$ | as Ex. Ir(L16)$_3$ | 29% |
| Ir(L95)$_3$ | L95 | Ir(L95)$_3$ Λ,Δ-C3 | as Ex. Ir(L16)$_3$ | 22% |
| Ir(L276)$_3$ | L276 | Ir(L276)$_3$ | as Ex. Ir(L1)$_3$/B | 40% |
| Ir(L277) | L277 | Ir(L277)$_3$ | as Ex. Ir(L1)$_3$/B | 38% |
| Ir(L278)$_3$ | L278 | Ir(L278)$_3$ Λ,Δ-C3 | as Ex. Ir(L1)$_3$/B | 22% |
| Ir(L96)$_3$ | L96 | Ir(L96)$_3$ | B 300° C./100 h DCM Mesitylene | 46% |
| Ir(L97)$_3$ | L97 | Ir(L97)$_3$ | as Ex. Ir(L96)$_3$ | 40% |
| Ir(L98)$_3$ | L98 | Ir(L98)$_3$ | B 300° C./180 h DCM Mesitylene | 38% |

-continued

| Ex. | Ligand L | Ir complex Diastereomer | Variant Reaction temp./ reaction time Suspension medium Extractant | Yield |
|---|---|---|---|---|
| Ir(L99)$_3$ | L99 | Ir(L99)$_3$ | as Ex. Ir(L98)$_3$ | 31% |
| Ir(L100)$_3$ | L100 | Ir(L100)$_3$ | as Ex. Ir(L96)$_3$ | 48% |
| Ir(L101)$_3$ | L101 | Ir(L101)$_3$ | as Ex. Ir(L98)$_3$ | 32% |
| Ir(L102)$_3$ | L102 | Ir(L102)$_3$ | as Ex. Ir(L96)$_3$ | 50% |
| Ir(L103)$_3$ | L103 | Ir(L103)$_3$ Λ,Δ-C3 | as Ex. Ir(L98)$_3$ | 19% |
| Ir(L104)$_3$ | L104 | Ir(L104)$_3$ Λ,Δ-C3 | as Ex. Ir(L96)$_3$ | 22% |
| Ir(L105)$_3$ | L105 | Ir(L105)$_3$ Λ,Δ-C3 + C1 | as Ex. Ir(L96)$_3$ | 36% |
| Ir(L106)$_3$ | L106 | Ir(L106)$_3$ Λ,Δ-C3 | as Ex. Ir(L98)$_3$ | 28% |
| Ir(L107)$_3$ | L107 | Ir(L107)$_3$ | as Ex. Ir(L98)$_3$ | 31% |
| Ir(L108)$_3$ | L108 | Ir(L108)$_3$ Λ,Δ-C3 + C1 | as Ex. Ir(L96)$_3$ | 33% |
| Ir(L109)$_3$ | L109 | Ir(L109)$_3$ | as Ex. Ir(L96)$_3$ | 49% |
| Ir(L110)$_3$ | L110 | Ir(L110)$_3$ | as Ex. Ir(L98)$_3$ | 35% |
| Ir(L111)$_3$ | L111 | Ir(L111)$_3$ | as Ex. Ir(L96)$_3$ | 44% |
| Ir(L112)$_3$ | L112 | Ir(L112)$_3$ | as Ex. Ir(L96)$_3$ | 43% |
| Ir(L113)$_3$ | L113 | Ir(L113)$_3$ | as Ex. Ir(L96)$_3$ | 44% |
| Ir(L114)$_3$ | L113 | Ir(L114)$_3$ | as Ex. Ir(L96)$_3$ | 39% |
| Ir(L115)$_3$ | L113 | Ir(L115)$_3$ | as Ex. Ir(L96)$_3$ | 40% |
| Ir(L116)$_3$ | L116 | Ir(L116)$_3$ | as Ex. Ir(L96)$_3$ | 37% |
| Ir(L117)$_3$ | L117 | Ir(L117)$_3$ | as Ex. Ir(L98)$_3$ | 28% |
| Ir(L118)$_3$ | L118 | Ir(L118)$_3$ | as Ex. Ir(L96)$_3$ | 40% |
| Ir(L119)$_3$ | L119 | Ir(L119)$_3$ | as Ex. Ir(L98)$_3$ | 44% |
| Ir(L120)$_3$ | L120 | Ir(L120)$_3$ | as Ex. Ir(L98)$_3$ | 45% |
| Ir(L121)$_3$ | L121 | Ir(L121)$_3$ | as Ex. Ir(L98)$_3$ | 18% |
| Ir(L122)$_3$ | L122 | Ir(L122)$_3$ Λ,Δ-C3 | as Ex. Ir(L96)$_3$ | 19% |
| Ir(L123)$_3$ | L123 | Ir(L123)$_3$ | as Ex. Ir(L96)$_3$ | 36% |
| Ir(L124)$_3$ | L124 | Ir(L124)$_3$ | as Ex. Ir(L96)$_3$ | 37% |
| Ir(L125)$_3$ | L125 | Ir(L125)$_3$ | as Ex. Ir(L96)$_3$ | 41% |
| Ir(L126)$_3$ | L126 | Ir(L126)$_3$ Λ,Δ-C3 | as Ex. Ir(L96)$_3$ | 24% |
| Ir(L127)$_3$ | L127 | Ir(L127)$_3$ Λ,Δ-C3 | as Ex. Ir(L98)$_3$ | 19% |
| Ir(L128)$_3$ | L128 | Ir(L128)$_3$ Λ,Δ-C3 | as Ex. Ir(L98)$_3$ | 17% |
| Ir(L129)$_3$ | L129 | Ir(L129)$_3$ Λ,Δ-C3 | as Ex. Ir(L96)$_3$ | 23% |
| Ir(L130)$_3$ | L130 | Ir(L130)$_3$ Λ,Δ-C3 | as Ex. Ir(L96)$_3$ | 22% |
| Ir(L131)$_3$ | L131 | Ir(L131)$_3$ Λ,Δ-C3 | as Ex. Ir(L98)$_3$ | 22% |
| Ir(L132)$_3$ | L132 | Ir(L132)$_3$ Λ,Δ-C3 | as Ex. Ir(L96)$_3$ | 24% |
| Ir(L133)$_3$ | L133 | Ir(L133)$_3$ Λ,Δ-C3 | as Ex. Ir(L96)$_3$ | 25% |
| Ir(L134)$_3$ | L134 | Ir(L134)$_3$ Λ,Δ-C3 | as Ex. Ir(L98)$_3$ | 21% |
| Ir(L135)$_3$ | L135 | Ir(L135)$_3$ Λ,Δ-C3 | as Ex. Ir(L96)$_3$ | 21% |
| Ir(L136)$_3$ | L136 | Ir(L136)$_3$ Λ,Δ-C3 | as Ex. Ir(L96)$_3$ | 24% |
| Ir(L137)$_3$ | L137 | Ir(L137)$_3$ Λ,Δ-C3 | as Ex. Ir(L96)$_3$ | 17% |
| Ir(L138)$_3$ | L138 | Ir(L138)$_3$ Λ,Δ-C3 | as Ex. Ir(L98)$_3$ | 22% |
| Ir(L139)$_3$ | L139 | Ir(L139)$_3$ Λ,Δ-C3 | as Ex. Ir(L96)$_3$ | 21% |
| Ir(L140)$_3$ | L140 | Ir(L140)$_3$ Λ,Δ-C3 | as Ex. Ir(L96)$_3$ | 14% |
| Ir(L141)$_3$ | L141 | Ir(L141)$_3$ Λ,Δ-C3 | as Ex. Ir(L98)$_3$ | 23% |
| Ir(L142)$_3$ | L142 | Ir(L142)$_3$ | as Ex. Ir(L98)$_3$ | 39% |
| Ir(L143)$_3$ | L143 | Ir(L143)$_3$ | as Ex. Ir(L96)$_3$ | 45% |
| Ir(L144)$_3$ | L144 | Ir(L144)$_3$ | as Ex. Ir(L96)$_3$ | 36% |
| Ir(L145)$_3$ | L145 | Ir(L145)$_3$ Λ,Δ-C3 | as Ex. Ir(L96)$_3$ | 18% |
| Ir(L146)$_3$ | L146 | Ir(L146)$_3$ Λ,Δ-C3 | as Ex. Ir(L98)$_3$ | 24% |

-continued

| Ex. | Ligand L | Ir complex Diastereomer | Variant Reaction temp./ reaction time Suspension medium Extractant | Yield |
|---|---|---|---|---|
| Ir(L147)$_3$ | L147 | Ir(L147)$_3$ Λ,Δ-C3 | as Ex. Ir(L96)$_3$ | 18% |
| Ir(L148)$_3$ | L148 | Ir(L148)$_3$ Λ,Δ-C3 | as Ex. Ir(L96)$_3$ | 19% |
| Ir(L149)$_3$ | L149 | Ir(L149)$_3$ Λ,Δ-C3 | as Ex. Ir(L98)$_3$ | 15% |
| Ir(L150)$_3$ | L150 | Ir(L150)$_3$ Λ,Δ-C3 | as Ex. Ir(L98)$_3$ | 6% |
| Ir(L151)$_3$ | L151 | Ir(L151)$_3$ Λ,Δ-C3 | as Ex. Ir(L96)$_3$ | 16% |
| Ir(L152)$_3$ | L152 | Ir(L152)$_3$ Λ,Δ-C3 | as Ex. Ir(L96)$_3$ | 46% |
| Ir(L153)$_3$ | L153 | Ir(L153)$_3$ Λ,Δ-C3 | as Ex. Ir(L98)$_3$ | 10% |
| Ir(L154)$_3$ | L154 | Ir(L154)$_3$ Λ,Δ-C3 | as Ex. Ir(L96)$_3$ | 8% |
| Ir(L155)$_3$ | L155 | Ir(L155)$_3$ | as Ex. Ir(L96)$_3$ | 23% |
| Ir(L156)$_3$ | L156 | Ir(L156)$_3$ | as Ex. Ir(L96)$_3$ | 14% |
| Ir(L157)$_3$ | L157 | Ir(L157)$_3$ | as Ex. Ir(L96)$_3$ | 48% |
| Ir(L158)$_3$ | L158 | Ir(L158)$_3$ | as Ex. Ir(L96)$_3$ | 46% |
| Ir(L159)$_3$ | L159 | Ir(L159)$_3$ | as Ex. Ir(L96)$_3$ | 47% |
| Ir(L160)$_3$ | L160 | Ir(L160)$_3$ | as Ex. Ir(L96)$_3$ | 47% |
| Ir(L161)$_3$ | L161 | Ir(L161)$_3$ | as Ex. Ir(L96)$_3$ | 44% |
| Ir(L162)$_3$ | L162 | Ir(L162)$_3$ | as Ex. Ir(L96)$_3$ | 40% |
| Ir(L163)$_3$ | L163 | Ir(L163)$_3$ Λ,Δ-C3 | as Ex. Ir(L96)$_3$ | 26% |
| Ir(L164)$_3$ | L164 | Ir(L164)$_3$ Λ,Δ-C3 | as Ex. Ir(L96)$_3$ | 25% |
| Ir(L165)$_3$ | L165 | Ir(L165)$_3$ | as Ex. Ir(L96)$_3$ | 43% |
| Ir(L166)$_3$ | L166 | Ir(L166)$_3$ | as Ex. Ir(L96)$_3$ | 48% |
| Ir(L167)$_3$ | L167 | 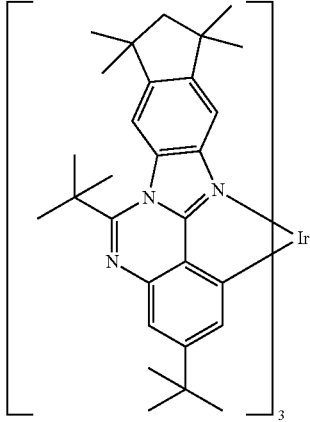 Ir(L167)$_3$ | B 310° C./180 h DCM Mesitylene | 44% |
| Ir(L168)$_3$ | L168 | Ir(L168)$_3$ | B 310° C./200 h DCM Mesitylene | 38% |
| Ir(L169)$_3$ | L169 | Ir(L169)$_3$ | as Ex. Ir(L167)$_3$ | 46% |
| Ir(L170)$_3$ | L170 | Ir(L170)$_3$ | as Ex. Ir(L167)$_3$ | 44% |
| Ir(L171)$_3$ | L171 | Ir(L171)$_3$ | as Ex. Ir(L167)$_3$ | 43% |
| Ir(L172)$_3$ | L172 | Ir(L172)$_3$ Λ,Δ-C3 | as Ex. Ir(L167)$_3$ | 20% |
| Ir(L173)$_3$ | L173 | Ir(L173)$_3$ Λ,Δ-C3 | as Ex. Ir(L167)$_3$ | 25% |
| Ir(L174)$_3$ | L174 | Ir(L174)$_3$ | as Ex. Ir(L167)$_3$ | 45% |
| Ir(L175)$_3$ | L175 | Ir(L175)$_3$ Λ,Δ-C3 | as Ex. Ir(L167)$_3$ | 23% |
| Ir(L176)$_3$ | L176 | Ir(L176$_3$ Λ,Δ-C3 | as Ex. Ir(168)$_3$ | 18% |
| Ir(L177)$_3$ | L177 | Ir(L177)$_3$ | as Ex. Ir(L167)$_3$ | 21% |
| Ir(L178)$_3$ | L178 | Ir(L178)$_3$ | as Ex. Ir(L167)$_3$ | 42% |
| Ir(L179)$_3$ | L179 | Ir(L179)$_3$ | as Ex. Ir(L167)$_3$ | 43% |

-continued

| Ex. | Ligand L | Ir complex Diastereomer | Variant Reaction temp./reaction time Suspension medium Extractant | Yield |
|---|---|---|---|---|
| Ir(L180)₃ | L180 | Ir(L180)₃ Λ,Δ-C3 + 1 | as Ex. Ir(L167)₃ | 45% |
| Ir(L181)₃ | L181 | Ir(L181)₃ Λ,Δ-C3 | as Ex. Ir(L167)₃ | 26% |
| Ir(L182)₃ | L182 | Ir(L182)₃ Λ,Δ-C3 | as Ex. Ir(167)₃ | 20% |
| Ir(L183)₃ | L183 | Ir(L183)₃ | as Ex. Ir(L167)₃ | 36% |
| Ir(L184)₃ | L184 | Ir(L184)₃ Λ,Δ-C3 | as Ex. Ir(L167)₃ | 18% |
| Ir(L185)₃ | L185 | Ir(L185)₃ | as Ex. Ir(L167)₃ | 12% |
| Ir(L186)₃ | L186 | Ir(L186)₃ | as Ex. Ir(L167)₃ | 45% |
| Ir(L187)₃ | L187 | Ir(L187)₃ | as Ex. Ir(L167)₃ | 45% |
| Ir(L188)₃ | L188 | Ir(L188)₃ | as Ex. Ir(L167)₃ | 47% |
| Ir(L189)₃ | L189 | Ir(L189)₃ | as Ex. Ir(L167)₃ | 41% |
| Ir(L190)₃ | L190 | Ir(L190)₃ Λ,Δ-C3 | as Ex. Ir(L167)₃ | 23% |
| Ir(L191)₃ | L191 | Ir(L191)₃ | as Ex. Ir(L167)₃ | 44% |
| Ir(L192)₃ | L192 | 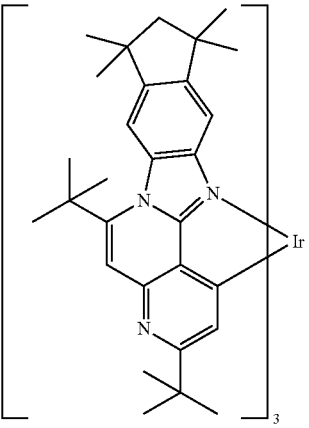 Ir(L192)₃ | B 305° C./180 h Acetone Mesitylene | 46% |
| Ir(L193)₃ | L193 | Ir(L193)₃ | B 310° C./210 h Acetone Mesitylene | 36% |
| Ir(L194)₃ | L194 | Ir(L194)₃ | as Ex. Ir(L192)₃ | 46% |
| Ir(L195)₃ | L195 | Ir(L195)₃ | as Ex. Ir(L193)₃ | 3.5% |
| Ir(L196)₃ | L196 | Ir(L196)₃ | as Ex. Ir(L192)₃ | 44% |
| Ir(L197)₃ | L197 | Ir(L197)₃ | as Ex. Ir(L192)₃ | 45% |
| Ir(L198)₃ | L198 | Ir(L198)₃ Λ,Δ-C3 | as Ex. Ir(L192)₃ | 27% |
| Ir(L199)₃ | L199 | Ir(L199)₃ Λ,Δ-C3 | as Ex. IrL(193)₃ | 26% |
| Ir(L200)₃ | L200 | Ir(L200)₃ Λ,Δ-C3 | as Ex. Ir(L192)₃ | 21% |
| Ir(L201)₃ | L201 | Ir(L201)₃ | as Ex. Ir(L192)₃ | 42% |
| Ir(L202)₃ | L202 | Ir(L202)₃ Λ,Δ-C3 | as Ex. Ir(L192)₃ | 26% |
| Ir(L203)₃ | L203 | Ir(L203)₃ | as Ex. Ir(L192)₃ | 28% |
| Ir(L204)₃ | L204 | Ir(L204)₃ | as Ex. Ir(L192)₃ | 45% |
| Ir(L205)₃ | L205 | Ir(L205)₃ Λ,Δ-C3 + C1 | as Ex. Ir(L192)₃ | 45% |
| Ir(L206)₃ | L206 | Ir(L206)₃ Λ,Δ-C3 | as Ex. Ir(L192)₃ | 20% |
| Ir(L207)₃ | L207 | Ir(L207)₃ Λ,Δ-C3 | as Ex. Ir(L192)₃ | 23% |
| Ir(L208)₃ | L208 | Ir(L208)₃ Λ,Δ-C3 | as Ex. Ir(L192)₃ | 25% |
| Ir(L209)₃ | L209 | Ir(L209)₃ | as Ex. Ir(L192)₃ | 44% |
| Ir(L210)₃ | L210 | Ir(L210)₃ | as Ex. Ir(L192)₃ | 43% |
| Ir(L211)₃ | L211 | Ir(L211)₃ | as Ex. Ir(L192)₃ | 46% |
| Ir(L212)₃ | L212 | Ir(L212)₃ | as Ex. Ir(L192)₃ | 46% |
| Ir(L213)₃ | L213 | Ir(L213)₃ Λ,Δ-C3 | as Ex. Ir(L192)₃ | 21% |

| Ex. | Ligand L | Ir complex Diastereomer | Variant Reaction temp./ reaction time Suspension medium Extractant | Yield |
|---|---|---|---|---|
| Ir(L214)₃ | L214 | Ir(L214)₃ | as Ex. Ir(L192)₃ | 37% |
| Ir(L279)₃ | L279 | Ir(L279)₃ | as Ex. Ir(L192)₃ | 40% |
| Ir(L280)₃ | L280 | Ir(L280)₃ | as Ex. Ir(L192)₃ | 37% |
| Ir(L281)₃ | L281 | Ir(L281)₃ Λ,Δ-C3 | as Ex. Ir(L192)₃ | 19% |
| Ir(L282)₃ | L282 | Ir(L282)₃ | as Ex. Ir(L192)₃ | 33% |
| Ir(L284) | L284 10 mmol | Ir(L284) | as Ex. Ir(192)₃ Addition of 1 ml of tridecane | 16% |
| Ir(L215)₃ | L215 | 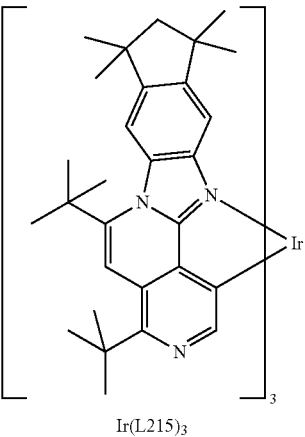 Ir(L215)₃ | B 305° C./180 h Acetone Mesitylene | 45% |
| Ir(L216)₃ | L216 | Ir(L216)₃ | B 310° C./210 h Acetone Mesitylene | 34% |
| Ir(L217)₃ | L217 | Ir(L217)₃ | as Ex. Ir(L215)₃ | 44% |
| Ir(L218)₃ | L218 | Ir(L218)₃ | as Ex. Ir(L215)₃ | 46% |
| Ir(L219)₃ | L219 | Ir(L219)₃ Λ,Δ-C3 | as Ex. Ir(L215)₃ | 22% |
| Ir(L220)₃ | L220 | Ir(L220)₃ | as Ex. Ir(L215)₃ | 45% |
| Ir(L221)₃ | L221 | Ir(L221)₃ Λ,Δ-C3 + C1 | as Ex. Ir(L215)₃ | 44% |
| Ir(L222)₃ | L222 | Ir(L222)₃ Λ,Δ-C3 | as Ex. Ir(L215)₃ | 21% |
| Ir(L223)₃ | L223 | Ir(L223)₃ | as Ex. Ir(L215)₃ | 41% |
| Ir(L224)₃ | L224 | Ir(L224)₃ Λ,Δ-C3 | as Ex. Ir(L215)₃ | 20% |
| Ir(L225)₃ | L225 | Ir(L225)₃ | as Ex. Ir(L215)₃ | 35% |
| Ir(L226)₃ | L226 |  Ir(L226)₃ Λ,Δ-C3 | B 300° C./200 h Acetone Mesitylene | 22% |

-continued

| Ex. | Ligand L | Ir complex Diastereomer | Variant Reaction temp./ reaction time Suspension medium Extractant | Yield |
|---|---|---|---|---|
| Ir(L227)$_3$ | L227 | Ir(L227)$_3$ Λ,Δ-C3 | as Ex. Ir(L226)$_3$ | 24% |
| Ir(L228)$_3$ | L228 | Ir(L228)$_3$ Λ,Δ-C3 | as Ex. Ir(L226)$_3$ | 19% |
| Ir(L229)$_3$ | L229 | Ir(L229)$_3$ Λ,Δ-C3 | as Ex. Ir(L226)$_3$ | 17% |
| Ir(L230)$_3$ | L230 | Ir(L230)$_3$ Λ,Δ-C3 | B 300° C./200 h Acetone Mesitylene | 23% |
| Ir(L231)$_3$ | L231 | Ir(L231)$_3$ Λ,Δ-C3 | as Ex. Ir(L230)$_3$ | 21% |

-continued

| Ex. | Ligand L | Ir complex Diastereomer | Variant Reaction temp./ reaction time Suspension medium Extractant | Yield |
|---|---|---|---|---|
| Ir(L232)₃ | L232 | Ir(L232)₃ Λ,Δ-C3 | as Ex. Ir(L230)₃ | 22% |
| Ir(L233)₃ | L233 | Ir(L233)₃ Λ,Δ-C3 | as Ex. Ir(L230)₃ | 24% |
| Ir(L234)₃ | L234 | 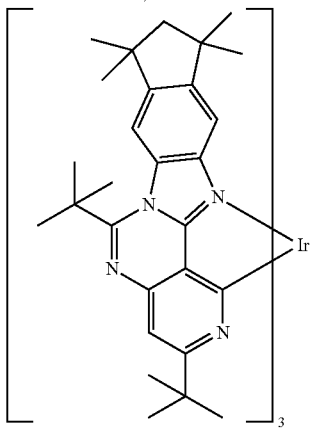 Ir(L234)₃ | B 310° C./180 h Acetone Mesitylene | 40% |
| Ir(L235)₃ | L235 | Ir(L235)₃ | B 310° C./210 h Acetone Mesitylene | 30% |
| Ir(L236)₃ | L236 | Ir(L236)₃ | as Ex. Ir(L234)₃ | 38% |
| Ir(L237)₃ | L237 | Ir(L237)₃ | as Ex. Ir(L234)₃ | 37% |
| Ir(L238)₃ | L238 | Ir(L238)₃ Λ,Δ-C3 | as Ex. Ir(L234)₃ | 18% |
| Ir(L239)₃ | L230 | Ir(L239)₃ | as Ex. Ir(L234)₃ | 33% |
| Ir(L240)₃ | L240 | Ir(L240)₃ Λ,Δ-C3 | as Ex. Ir(L234)₃ | 21% |
| Ir(L241)₃ | L241 | Ir(L241)₃ Λ,Δ-C3 | as Ex. Ir(L234)₃ | 16% |
| Ir(L242)₃ | L242 | Ir(L242)₃ | as Ex. Ir(L234)₃ | 31% |
| Ir(L243)₃ | L243 | 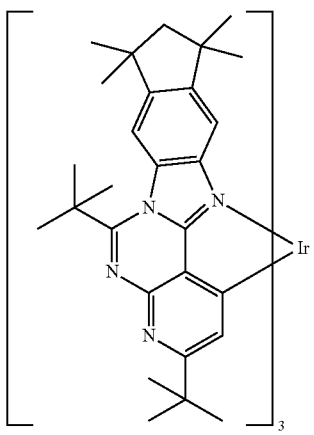 Ir(L243)₃ | B 310° C./210 h THF Mesitylene | 16% |
| Ir(L244)₃ | L244 | Ir(L244)₃ | B 315° C./210 h Acetone Mesitylene | 14% |
| Ir(L245)₃ | L245 | Ir(L245)₃ | as Ex. Ir(L243)₃ | 18% |
| Ir(L246)₃ | L246 | Ir(L246)₃ Λ,Δ-C3 | as Ex. Ir(L243)₃ | 9% |
| Ir(L247)₃ | L247 | Ir(L247)₃ | as Ex. Ir(L243)₃ | 7% |

-continued

| Ex. | Ligand L | Ir complex Diastereomer | Variant Reaction temp./reaction time Suspension medium Extractant | Yield |
|---|---|---|---|---|
| Ir(L248)₃ | L248 | Ir(L248)₃ | B 310° C./210 h Acetone Mesitylene | 16% |
| Ir(L249)₃ | L249 | Ir(L249)₃ | B 315° C./240 h Acetone Mesitylene | 8% |
| Ir(L250)₃ | L250 | Ir(L250)₃ | as Ex. Ir(L248)₃ | 17% |
| Ir(L251)₃ | L251 | Ir(L251)₃ Λ,Δ-C3 | as Ex. Ir(L248)₃ | 6% |
| Ir(L252)₃ | L252 | Ir(L252)₃ | B 310° C./210 h Acetone Mesitylene | 35% |
| Ir(L253)₃ | L253 | Ir(L253)₃ | as Ex. Ir(L252)₃ | 20% |
| Ir(L254)₃ | L254 | Ir(L254)₃ | as Ex. Ir(L252)₃ | 36% |
| Ir(L255)₃ | L255 | Ir(L255)₃ | as Ex. Ir(L252)₃ | 34% |
| Ir(L256)₃ | L256 | Ir(L256)₃ Λ,Δ-C3 | as Ex. Ir(L252)₃ | 17% |
| Ir(L257)₃ | L257 | Ir(L257)₃ Λ,Δ-C3 | as Ex. Ir(L252)₃ | 18% |
| Ir(L258)₃ | L258 | Ir(L258)₃ | as Ex. Ir(L252)₃ | 24% |

-continued

| Ex. | Ligand L | Ir complex Diastereomer | Variant Reaction temp./reaction time Suspension medium Extractant | Yield |
|---|---|---|---|---|
| Ir(L259)₃ | L259 | Ir(L259)₃ Λ,Δ-C3 | B 310° C./200 h Acetone Mesitylene | 21% |
| Ir(L260)₃ | L260 | Ir(L260)₃ Λ,Δ-C3 | as Ex. Ir(L259)₃ | 19% |
| Ir(L261)₃ | L261 | Ir(L261)₃ Λ,Δ-C3 | as Ex. Ir(L259)₃ | 18% |
| Ir(L262)₃ | L262 | Ir(L262)₃ Λ,Δ-C3 | as Ex. Ir(L259)₃ | 16% |
| Ir(L263)₃ | L263 | Ir(L263)₃ Λ,Δ-C3 | B 310° C./200 h Acetone Mesitylene | 20% |

-continued

| Ex. | Ligand L | Ir complex Diastereomer | Variant Reaction temp./ reaction time Suspension medium Extractant | Yield |
|---|---|---|---|---|
| Ir(L264)$_3$ | L264 | Ir(L264)$_3$ Λ,Δ-C3 | as Ex. Ir(L263)$_3$ | 18% |
| Ir(L265)$_3$ | L265 | Ir(L265)$_3$ Λ,Δ-C3 | as Ex. Ir(L263)$_3$ | 16% |
| Ir(L266)$_3$ | L266 | Ir(L266)$_3$ Λ,Δ-C3 | as Ex. Ir(L263)$_3$ | 15% |
| Ir(L267)$_3$ | L267 | Ir(L267)$_3$ Λ,Δ-C3 | B 310° C./220 h Acetone Mesitylene | 15% |
| Ir(L268)$_3$ | L268 | Ir(L268)$_3$ Λ,Δ-C3 | B 310° C./220 h Acetone Mesitylene | 13% |

-continued

| Ex. | Ligand L | Ir complex Diastereomer | Variant Reaction temp./ reaction time Suspension medium Extractant | Yield |
|---|---|---|---|---|
| Ir(L269)₃ | L269 | Ir(L269)₃ Λ,Δ-C3 | as Ex. Ir(L267)₃ | 16% |
| Ir(L270)₃ | L270 | Ir(L270)₃ Λ,Δ-C3 | as Ex. Ir(L267)₃ | 16% |
| Ir(L271)₃ | L271 | 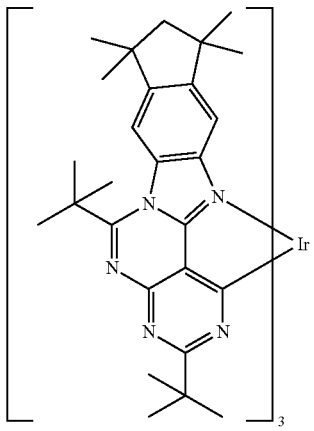<br>Ir(L271)₃ | B 320° C./200 h Acetone Mesitylene | 8% |
| Ir(L272)₃ | L272 | Ir(L272)₃ | as Ex. Ir(L271)₃ | 2% |
| Ir(L273)₃ | L273 | Ir(L273)₃ | as Ex. Ir(L271)₃ | 6% |
| Ir(L274)₃ | L274 | Ir(L274)₃ Λ,Δ-C3 + C1 | as Ex. Ir(L271)₃ | 6% |
| Ir(L275)₃ | L275 | Ir(L275)₃ | as Ex. Ir(L271)₃ | 4% |
| Ir(L500)₃ | L500 | 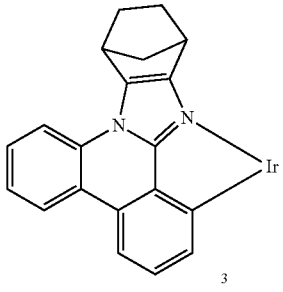<br>Ir(L500)₃ Λ,Δ-C3 | B 270° C./100 h THF Mesitylene | 44% |
| Ir(L501)₃ | L502 | Ir(L501)₃ Λ,Δ-C3 | as Ex. Ir(L500)₃ | 21% |
| Ir(L502)₃ | L503 | Ir(L502)₃ Λ,Δ-C3 | as Ex. Ir(L500)₃ | 20% |
| Ir(L503)₃ | L504 | Ir(L503)₃ Λ,Δ-C3 | as Ex. Ir(L500)₃ | 23% |
| Ir(L504)₃ | L505 | Ir(L504)₃ Λ,Δ-C3 | as Ex. Ir(L500)₃ | 25% |
| Ir(L505)₃ | L506 | Ir(L505)₃ Λ,Δ-C3 | as Ex. Ir(L500)₃ | 19% |
| Ir(L506)₃ | L507 | Ir(L506)₃ Λ,Δ-C3 | as Ex. Ir(L500)₃ | 20% |
| Ir(L507)₃ | L508 | Ir(L507)₃ Λ,Δ-C3 | as Ex. Ir(L500)₃ | 22% |
| Ir(L508)₃ | L509 | Ir(L508)₃ Λ,Δ-C3 | as Ex. Ir(L500)₃ | 22% |
| Ir(L509)₃ | L509 | Ir(L509)₃ Λ,Δ-C3 | as Ex. Ir(L500)₃ | 26% |
| Ir(L510)₃ | L510 | Ir(L510)₃ Λ,Δ-C3 | as Ex. Ir(L500)₃ | 11% |

| Ex. | Ligand L | Ir complex Diastereomer | Variant Reaction temp./reaction time Suspension medium Extractant | Yield |
|---|---|---|---|---|
| Ir(L511)$_3$ | L511 | Ir(L511)$_3$ | B 280° C./150 h Acetone Mesitylene | 56% |
| Ir(L512)$_3$ | L512 | Ir(L512)$_3$ | B 300° C./150 h DCM Mesitylene | 45% |
| Ir(L513)$_3$ | L513 | Ir(L513)$_3$ | as Ex. Ir(L511)$_3$ | 49% |
| Ir(L514)$_3$ | L514 | Ir(L514)$_3$ Λ,Δ-C3 | as Ex. Ir(L511)$_3$ | 23% |
| Ir(L515)$_3$ | L515 | Ir(L515)$_3$ Λ,Δ-C3 | as Ex. Ir(L511)$_3$ | 19% |
| Ir(L516)$_3$ | L516 | Ir(L516)$_3$ | as Ex. Ir(L511)$_3$ | 51% |
| Ir(L517)$_3$ | L517 | Ir(L517)$_3$ | as Ex. Ir(L511)$_3$ | 50% |
| Ir(L518)$_3$ | L518 | Ir(L518)$_3$ Λ,Δ-C3 | as Ex. Ir(L511)$_3$ | 21% |

2) Heteroleptic Iridium Complexes:
Variant A:
Step 1:

A mixture of 10 mmol of sodium bisacetylacetonatodichloroiridate(III) [770720-50-8] and 24 mmol of ligand L and a glass-clad magnetic stirrer bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated (the suspension medium is selected so that the ligand is readily soluble, but the chloro dimer of the formula [Ir(L)$_2$Cl]$_2$ has low solubility therein, typical suspension media are DCM, acetone, ethyl acetate, toluene, etc.) and mechanically digested at the same time. The fine suspension is decanted off from the glass beads, the solid (Ir(L)$_2$Cl]$_2$ which still contains about 2 eq. of NaCl, referred to below as the crude chloro dimer) is filtered off with suction and dried in vacuo.

Step 2:

The crude chloro dimer of the formula [Ir(L)$_2$Cl]$_2$ obtained in this way is suspended in a mixture of 75 ml of 2-ethoxyethanol and 25 ml of water, 13 mmol of the co-ligand CL or the co-ligand compound CL and 15 mmol of sodium carbonate are added. After 20 h under reflux, a further 75 ml of water are added dropwise, after cooling the solid is filtered off with suction, washed three times with 50 ml of water each time and three times with 50 ml of methanol each time and dried in vacuo. The dry solid is placed on an aluminium oxide bed (aluminium oxide, basic activity grade 1) with a depth of 3-5 cm in a continuous hot extractor and then extracted with the extraction medium indicated (initially introduced amount about 500 ml, the extractant is selected so that the complex is readily soluble therein at elevated temperature and has low solubility therein when cold, particularly suitable extractants are hydrocarbons, such as toluene, xylenes, mesitylene, naphthalene, o-dichlorobenzene, halogenated aliphatic hydrocarbons are generally unsuitable since they may halogenate or decompose the complexes). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. Besides the hot extraction method for purification, the purification can also be carried out by chromatography on silica gel or aluminium oxide. The heating is carried out in the temperature range from about 200-300° C. in a high vacuum (p about $10^{-6}$ mbar). The sublimation is carried out in the temperature range from about 300-400° C. in a high vacuum (p about $10^{-6}$ mbar), where the sublimation is preferably carried out in the form of a fractional sublimation.

| Ex. | Ligand L | Co-ligand CL | Ir complex<br>Step 1: reaction temp./reaction time/suspension medium<br>Step 2: extractant | Yield |
|---|---|---|---|---|
| Ir(L3)₂(CL1) | L3 | 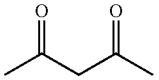<br>123-54-6<br>CL1 | 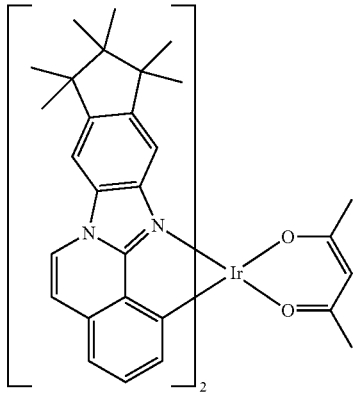<br>260° C./60 h/acetone<br>Xylene | 48% |
| Ir(L16)₂(CL1) | L16 | CL1 | 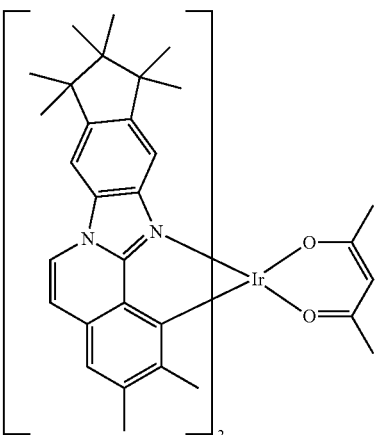<br>270° C./80 h/acetone<br>Xylene | 45% |
| Ir(L32)₂(CL1) | L32 | CL1 | 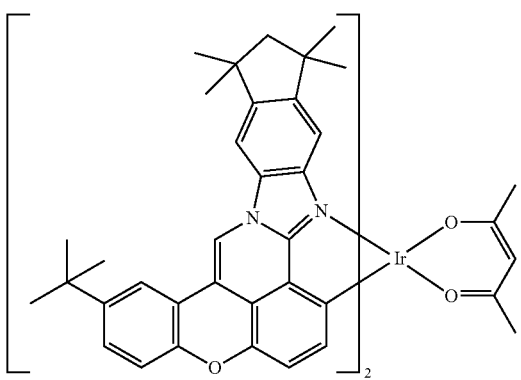<br>as Ex. Ir(L16)₂(CL1) | 56% |

-continued
| Ex. | Ligand L | Co-ligand CL | Ir complex Step 1: reaction temp./reaction time/suspension medium Step 2: extractant | | Yield |
|---|---|---|---|---|---|
| Ir(L79)$_2$(CL2) | L79 | 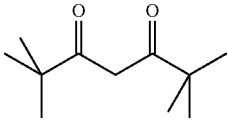<br>1118-71-4<br>CL2 | 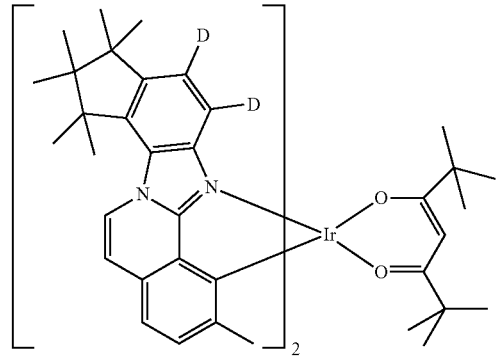<br>280° C./80 h/ethyl acetate<br>Xylene | | 39% |
| Ir(L98)$_2$(CL2) | L98 | CL2 | 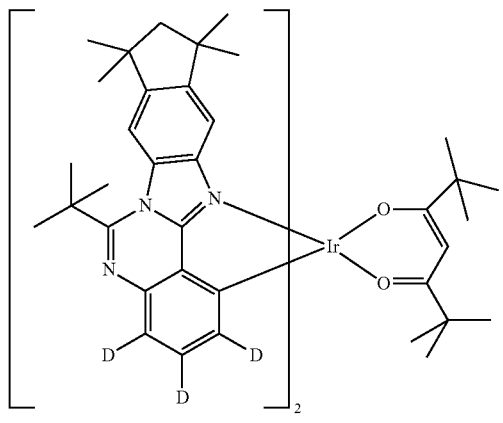<br>290° C./60 h/ethyl acetate<br>Xylene | | 54% |
| Ir(L113)$_2$(CL2) | L113 | CL2 | 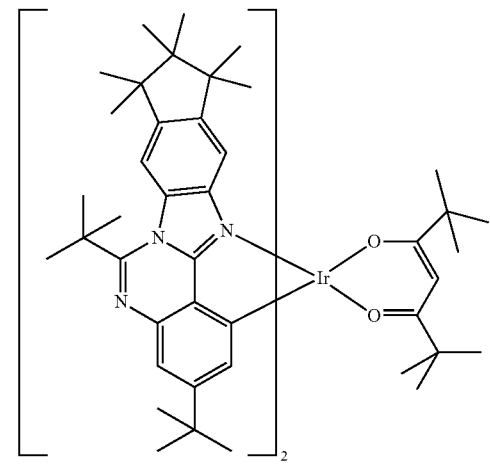<br>as Ex. Ir(L98)$_2$(CL2) | | 60% |

-continued
| Ex. | Ligand L | Co-ligand CL | Ir complex Step 1: reaction temp./reaction time/suspension medium Step 2: extractant | Yield |
|---|---|---|---|---|
| Ir(L127)₂(CL3) | L127 | <br>98-98-6<br>CL3 | 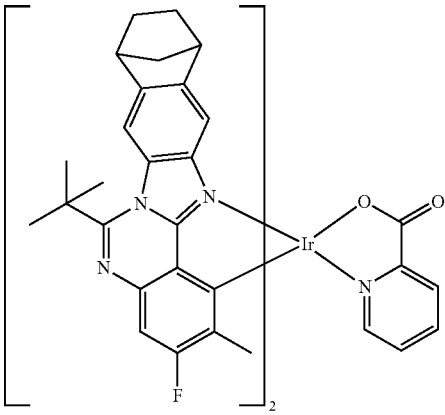<br>as Ex. Ir(L98)₂(CL2)<br>diastereomer mixture | 47% |
| Ir(L158)₂(CL4) | L158 | 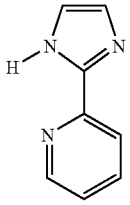<br>18653-75-3<br>CL4 | 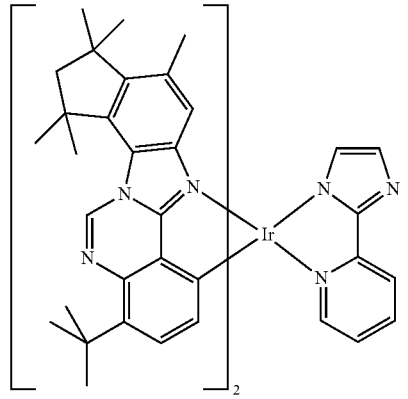<br>as Ex. Ir(L98)₂(CL2) | 44% |
| Ir(L169)₂(CL5) | L169 | 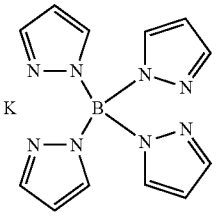<br>14782-58-2<br>CL5 | 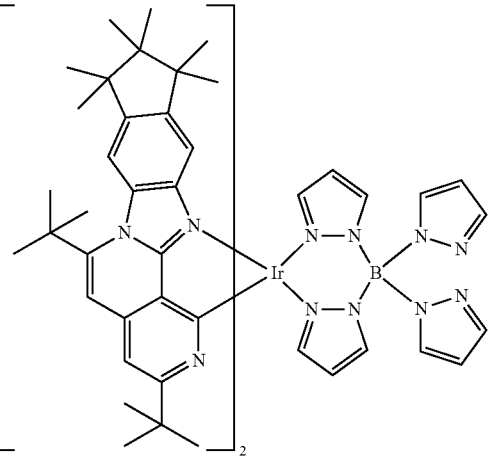<br>295° C./100 h/acetone<br>Mesitylene | 50% |

| Ex. | Ligand L | Co-ligand CL | Ir complex Step 1: reaction temp./reaction time/suspension medium Step 2: extractant | Yield |
|---|---|---|---|---|
| Ir(L195)₂(CL7) | L195 | 219508-27-7 CL6 | 300° C./120 h/acetone Mesitylene | 47% |

Variant B:

Step 1:

See variant A, step 1.

Step 2:

The crude chloro dimer of the formula $[Ir(L)_2Cl]_2$ obtained in this way is suspended in 200 ml of THF, 20 mmol of co-ligand CL, 20 mmol of silver(I) trifluoroacetate and 30 mmol of potassium carbonate are added to the suspension, and the mixture is heated under reflux for 24 h. After cooling, the THF is removed in vacuo. The residue is taken up in 200 ml of a mixture of ethanol and conc. ammonia solution (1:1, vv). The suspension is stirred at room temperature for 1 h, the solid is filtered off with suction, washed twice with 50 ml of a mixture of ethanol and conc. ammonia solution (1:1, vv) each time and twice with 50 ml of ethanol each time and then dried in vacuo. Hot extraction and sublimation as in variant A.

| Ex. | Ligand L | Co-ligand CL | Ir complex Step 1: reaction temp./reaction time/suspension medium Step 2: extractant | Yield |
|---|---|---|---|---|
| Ir(L99)₂(CL7) | L99 | 391604-55-0 CL7 | as Ex. Ir(L98)₂(CL2) | 39% |

-continued
| Ex. | Ligand L | Co-ligand CL | Ir complex Step 1: reaction temp./reaction time/suspension medium Step 2: extractant | Yield |
|---|---|---|---|---|
| Ir(L110)₂(CL8) | L110 | 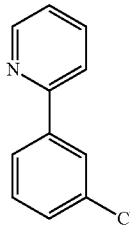<br>4350-51-0<br>CL8 | 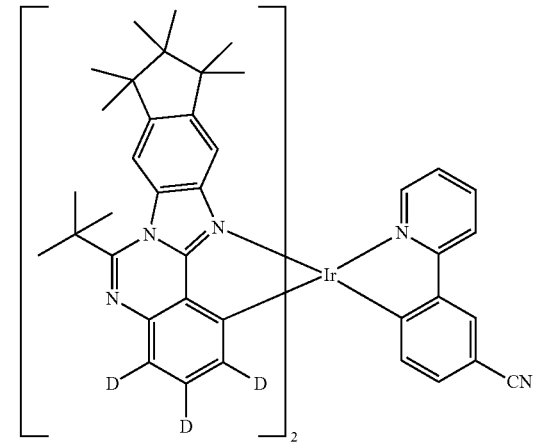<br>as Ex. Ir(L98)₂(CL2) | 31% |
| Ir(L158)₂(CL8) | L158 | 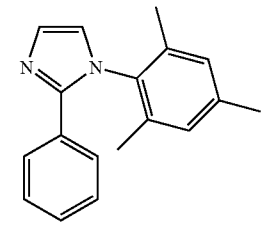<br>1093072-00-4<br>CL9 | 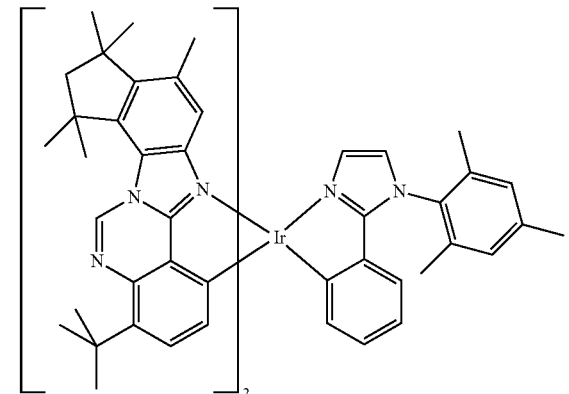<br>290° C./70 h/acetone<br>Xylene | 39% |
| Ir(L195)₂(CL10) | L195 | 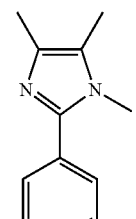<br>152536-39-5<br>CL10 | 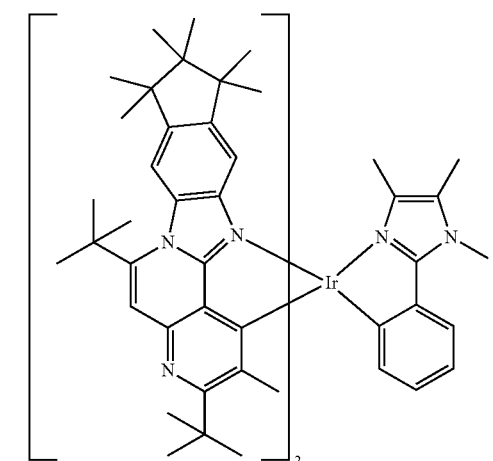<br>300° C./80 h/acetone<br>Xylene | 38% |

Variant C:
Step 1:
 See variant A, step 1.
Step 2:
 The crude chloro dimer of the formula [Ir(L)$_2$Cl]$_2$ obtained in this way is suspended in 1000 ml of dichloromethane and 150 ml of ethanol, 20 mmol of silver(I) trifluoromethanesulfonate are added to the suspension, and the mixture is stirred at room temperature for 24 h. The precipitated solid (AgCl) is filtered off with suction via a short Celite bed, and the filtrate is evaporated to dryness in vacuo. The solid obtained in this way is taken up in 100 ml of ethylene glycol, 20 mmol of co-ligand CL are added, and the mixture is then stirred at 130° C. for 30 h. After cooling, the solid is filtered off with suction, washed twice with 50 ml of ethanol each time and dried in vacuo. Hot extraction and sublimation as in variant A.

| Ex. | Ligand L | Co-ligand CL | Ir complex Step 1: reaction temp./reaction time/suspension medium Step 2: extractant | Yield |
|---|---|---|---|---|
| Ir(L191)$_2$(CL11) | L191 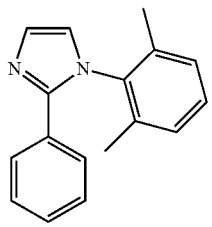 | 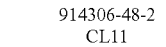 914306-48-2 CL11 | 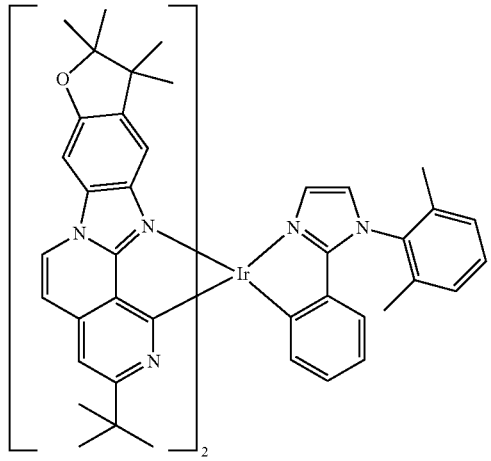 290° C./80 h/acetone Xylene | 46% |
| Ir(L201)$_2$(CL11) | L201 | CL11 | 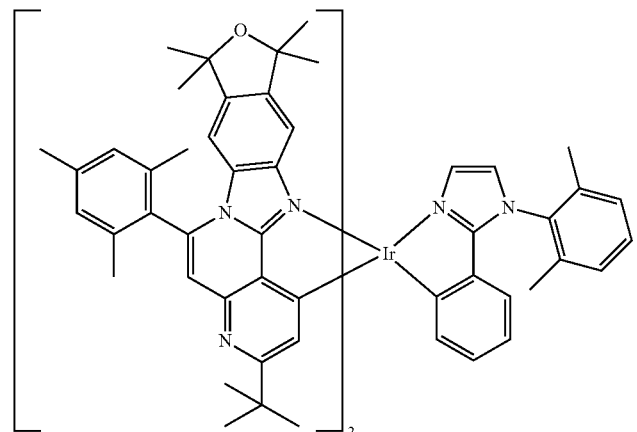 290° C./80 h/acetone Xylene | 39% |

-continued

| Ex. | Ligand L | Co-ligand CL | Ir complex<br>Step 1: reaction temp./reaction time/suspension medium<br>Step 2: extractant | Yield |
|---|---|---|---|---|
| Ir(L220)$_2$(CL12) | L220 | 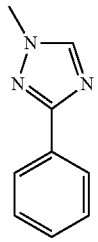<br>39696-58-7<br>CL12 | 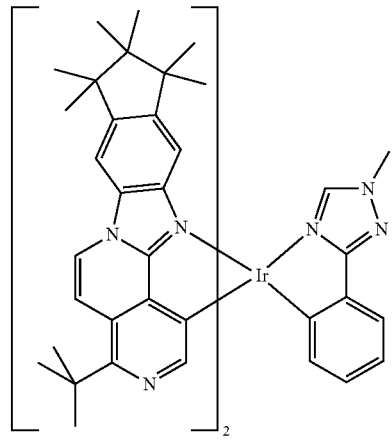<br>300° C./80 h/acetone<br>Xylene | 44% |

Variant E:

A mixture of 10 mmol of the Ir complex Ir(L)$_2$(CL1 or CL2) and 20 mmol of ligand L and a glass-clad magnetic stirrer bar is melted into a 50 ml glass ampoule in vacuo ($10^{-5}$ mbar). The ampoule is heated at the temperature indicated for the time indicated, during which the molten mixture is stirred with the aid of a magnetic stirrer. Further work-up, purification and sublimation as described under 1) Homoleptic tris-facial iridium complexes.

| Ex. | Ir complex Ir(L)$_2$(CL) | Ligand L' | Ir complex<br>Step 1: reaction temp./reaction time/suspension medium<br>Step 2: extractant | Yield |
|---|---|---|---|---|
| Ir(L3)$_2$(L9) | Ir(L3)$_2$(CL1) | L9 | 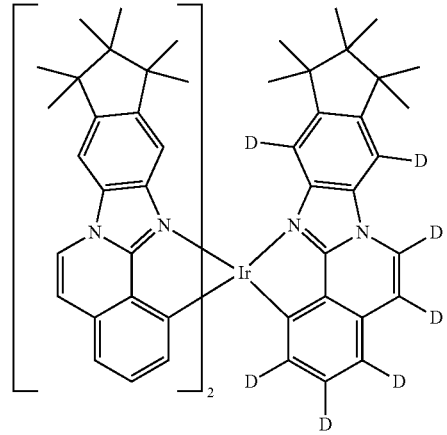<br>280° C./80 h/DCM<br>Mesitylene | 39% |

-continued

| Ex. | Ir complex Ir(L)₂(CL) | Ligand L' | Ir complex Step 1: reaction temp./reaction time/suspension medium Step 2: extractant | Yield |
|---|---|---|---|---|
| Ir(L98)₂(L53) | Ir(L98)₂(CL2) | L53 | 300° C./70 h/DCM Mesitylene | 43% |
| Ir(L113)₂(L109) | Ir(L113)₂(CL2) | L109 | 300° C./70 h/DCM Mesitylene | 44% |
| Ir(L113)₂(L204) | Ir(L113)₂(CL2) | L204 | 305° C./70 h/DCM Mesitylene | 36% |

3) Heteroleptic Platinum Complexes:

A mixture of 10 mmol of platinum(II) chloride and 12 mmol of ligand L and a glass-clad magnetic stirrer bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated (the suspension medium is selected so that the ligand is readily soluble, but the chloro dimer of the formula $[Ir(L)_2Cl]_2$ has low solubility therein, typical suspension media are DCM, acetone, ethyl acetate, toluene, etc.) and mechanically digested at the same time. The fine suspension is decanted off from the glass beads, the solid is filtered off with suction and dried in vacuo. The crude chloro dimer of the formula $[Pt(L)Cl]_2$ obtained in this way is suspended in a mixture of 60 ml of 2-ethoxyethanol and 20 ml of water, and 20 mmol of co-ligand CL or co-ligand compound CL and 20 mmol of sodium carbonate are added. After 20 h under reflux, a further 100 ml of water are added dropwise, after cooling the solid is filtered off with suction, washed three times with 50 ml of water each time and three times with 50 ml of methanol each time and dried in vacuo. The solid obtained in this way is placed on a Celite bed with a depth of 3-5 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range from about 200-300° C. in a high vacuum (p about $10^{-6}$ mbar). The sublimation is carried out in the temperature range from about 250-350° C. in a high vacuum (p about $10^{-6}$ mbar), where the sublimation is preferably carried out in the form of a fractional sublimation.

| Ex. | Ligand L | Co-ligand CL | Pt complex | Yield |
|---|---|---|---|---|
| Pt(L3)(CL1) | L3 | CL1 | 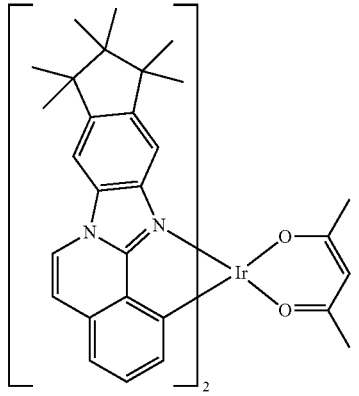 270° C./60 h/acetone Xylene | 20% |
| Pt(L126)(CL2) | L126 | CL2 | 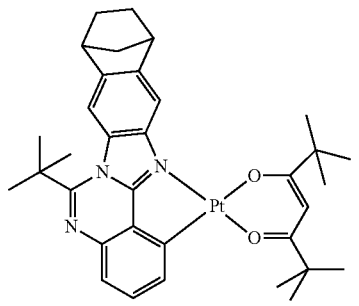 280° C./50 h/acetone Xylene | 23% |

4) Platinum Complexes of Tetradentate Ligands:
Variant A:

A mixture of 10 mmol of bis(benzonitrile)platinum(II) dichloride and 10 mmol of ligand L in 100 ml of benzonitrile is heated under reflux for 24 h. After dropwise addition of 100 ml of methanol to the cooled reaction mixture, the solid is filtered off with suction, washed five times with 25 ml of methanol each time and dried in vacuo. The solid obtained in this way is placed on a Celite bed (aluminium oxide, basic activity grade 1) with a depth of 3 cm in a hot extractor and then extracted with the extraction medium indicated (initially introduced amount about 300 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated; if a purity of 99.5-99.9% has been reached, the Pt complex is sublimed. The sublimation is carried out in the temperature range from about 350 to about 390° C. in a high vacuum (p about $10^{-6}$ mbar), where the sublimation is preferably carried out in the form of a fractional sublimation.

Pt(L283):

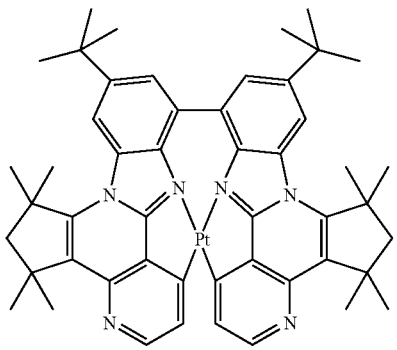

Use of 4.74 g (10 mmol) of bis(benzonitrile)platinum(II) dichloride and 7.55 g (10 mmol) of L283. Extractant: mesitylene. Yield: 3.22 g (3.4 mmol), 34%; purity: about 99.8% according to NMR.

E: Derivatisation of the Metal Complexes:

1) Halogenation of the Iridium Complexes:

A×11 mmol of N-halosuccinimide (halogen: Cl, Br, I) are added to a solution or suspension of 10 mmol of a complex carrying A×C—H groups (where A=1, 2 or 3) in the para-position to the iridium in 3000 ml of dichloromethane at 30° C. with exclusion of light and air, and the mixture is stirred for 20 h. Complexes which have low solubility in DCM can also be reacted in other solvents (TCE, THF, DMF, etc.) and at elevated temperature. The solvent is subsequently substantially removed in vacuo. The residue is boiled with 100 ml of MeOH, the solid is filtered off with suction, washed three times with 30 ml of methanol and then dried in vacuo.

Synthesis of Ir(L1-Br)$_3$:

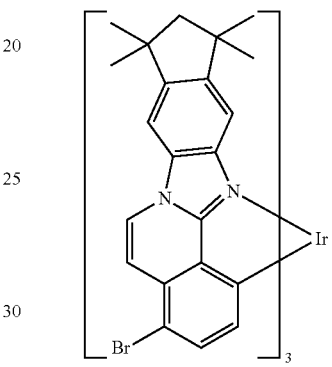

5.9 g (33 mmol) of N-bromosuccinimide are added in one portion to a suspension, stirred at 30° C., of 11.3 g (10 mmol) of Ir(L1)$_3$ in 3000 ml of DCM, and the mixture is then stirred for a further 20 h. After removal of about 2900 ml of the DCM in vacuo, 100 ml of methanol are added to the lemon-yellow suspension, the solid is filtered off with suction, washed three times with about 30 ml of methanol and then dried in vacuo. Yield: 13.8 g (9.7 mmol), 97%; purity: about 99.5% according to NMR.

The following compounds can be prepared analogously:

| Ex. | Complex | Brominated complex | Yield |
|---|---|---|---|
| Ir(L3-Br)$_3$ | Ir(L3)$_3$ | Ir(L3-Br)$_3$ | 95% |

| Ex. | Complex | Brominated complex | Yield |
|---|---|---|---|
| Ir(L8-Br)₃ | 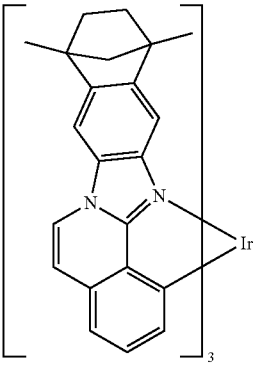<br>Ir(L8)₃<br>Λ,Δ-C3 | 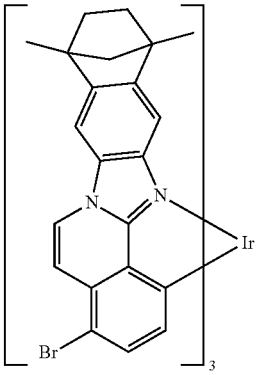<br>Ir(L8-Br)₃<br>Λ,Δ-C3 | 96% |
| Ir(L10-Br)₃ | 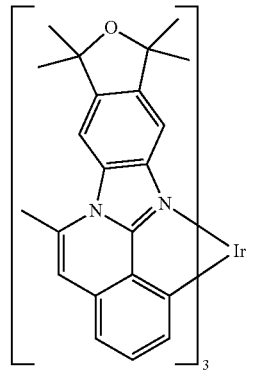<br>Ir(L10)₃ | 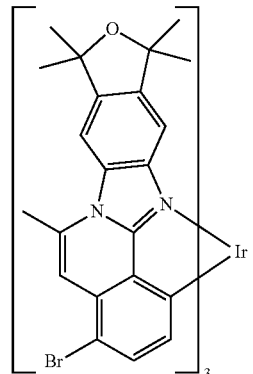<br>Ir(L10-Br)₃ | 95% |
| Ir(L55-Br)₃ | 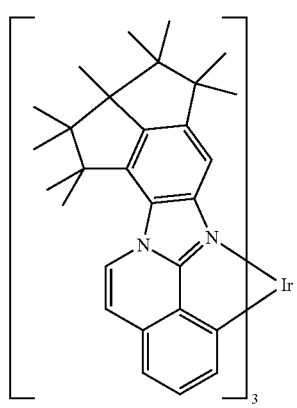<br>Ir(L55)₃<br>Diastereomer mixture | 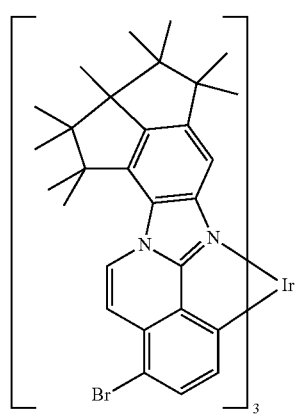<br>Ir(L55-Br)₃<br>Diastereomer mixture | 91% |

-continued

| Ex. | Complex | Brominated complex | Yield |
|---|---|---|---|
| Ir(L96-Br)₃ | Ir(L96)₃ | Ir(L96-Br)₃ | 98% |
| Ir(L120-Br)₃ | Ir(L120)₃ | Ir(L120-Br)₃ | 96% |
| Ir(L126-Br)₃ | Λ,Δ-C3-Ir(L126)₃ | Λ,Δ-C3-Ir(L126-Br)₃ | 97% |

| Ex. | Complex | Brominated complex | Yield |
|---|---|---|---|
| Ir(L113)₂(L109-Br) | Ir(L113)₂(L109)<br>1.1 eq. of NBS | Ir(L113)₂(L109-Br) | 95% |

2) Suzuki Coupling on the Iridium Complexes:
Variant A, Two-Phase Reaction Mixture:

0.6 mmol of tri-o-tolylphosphine and then 0.1 mmol of palladium(II) acetate are added to a suspension of 10 mmol of a brominated complex, 40-80 mmol of the boronic acid or boronic acid ester and 80 mmol of tripotassium phosphate in a mixture of 300 ml of toluene, 100 ml of dioxane and 300 ml of water, and the mixture is heated under reflux for 16 h. After cooling, 500 ml of water and 200 ml of toluene are added, the aqueous phase is separated off, the org. phase is washed three times with 200 ml of water, once with 200 ml of sat. sodium chloride solution and dried over magnesium sulfate. The solid material is filtered off through a Celite bed and rinsed with toluene, the toluene is removed virtually completely in vacuo, 300 ml of ethanol are added, the precipitated crude product is filtered off with suction, washed three times with 100 ml of EtOH each time and dried in vacuo. The crude product is passed through a silica-gel column with toluene twice. The metal complex is finally heated or sublimed. The heating is carried out in a high vacuum (p about $10^{-6}$ mbar) in the temperature range from about 200-300° C. The sublimation is carried out in a high vacuum (p about $10^{-6}$ mbar) in the temperature range from about 300-400° C., with the sublimation preferably being carried out in the form of a fractional sublimation.

Variant B, One-Phase Reaction Mixture:

0.6 mmol of tri-o-tolylphosphine and then 0.1 mmol of palladium(II) acetate are added to a suspension of 10 mmol of a brominated complex, 40-80 mmol of the boronic acid or boronic acid ester and 60-100 mmol of the base (potassium fluoride, tripotassium phosphate, potassium carbonate, caesium carbonate, etc., in each case anhydrous) and 100 g of glass beads (diameter 3 mm) in 100 ml-500 ml of an aprotic solvent (THF, dioxane, xylene, mesitylene, dimethylacetamide, NMP, DMSO, etc.), and the mixture is heated under reflux for 1-24 h. Alternatively, other phosphines, such as tri-tert-butylphosphine, di-tert-butylphosphine, S-Phos, xantphos, etc., can be employed, where the preferred phosphine:palladium ratio in the case of these phosphines is 2:1 to 1.2:1. The solvent is removed in vacuo, the product is taken up in a suitable solvent (toluene, dichloromethane, ethyl acetate, etc.) and purified as described under A.

Synthesis of Ir(L276)₃:

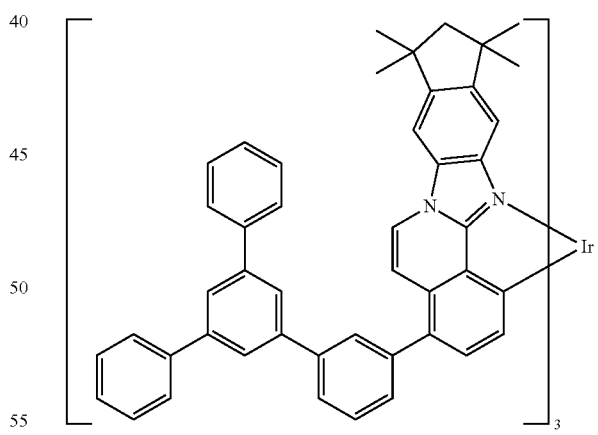

Variant B:

Use of 14.5 g (10 mmol) of Ir(L1-Br)₃ and 14.0 g (40 mmol) of quaterphenyl-boronic acid [1233200-59-3], caesium carbonate, tri-ortho-tolylphosphine, NMP, 180° C., 1 h. Yield: 12.1 g (5.9 mmol), 59%; purity: about 99.8% according to HPLC.

The following compounds can be prepared analogously:
| Ex. | Product Variant | Yield |
|---|---|---|
| Ir(L277)₃ | 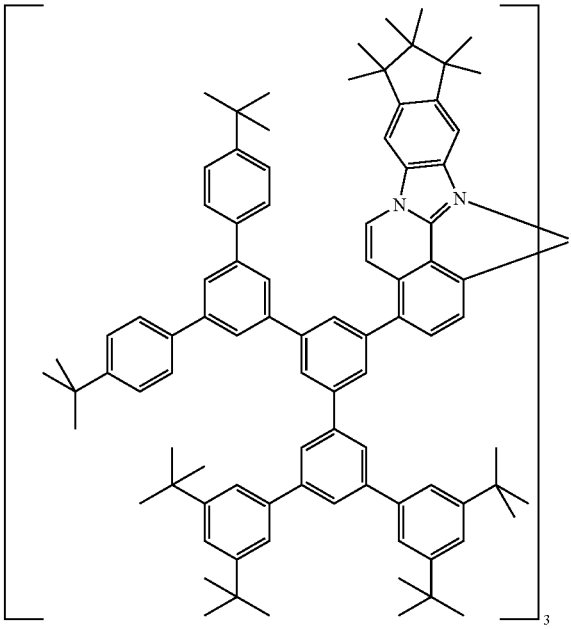 Ir(L3-Br)₃ + [952583-08-3] > Ir(277)₃<br>B, as IR(L276)₃ | 47% |
| Ir(L278)₃ | 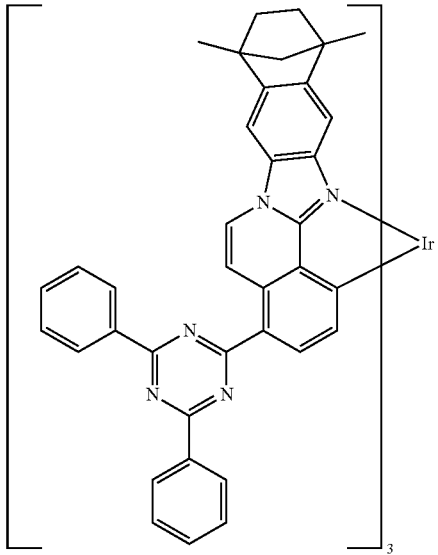 Ir(L8-Br)₃ + [1251825-65-6] > Ir(278)₃<br>A | 55% |

| Ex. | Product Variant | Yield |
|---|---|---|
| Ir(L279)₃ | 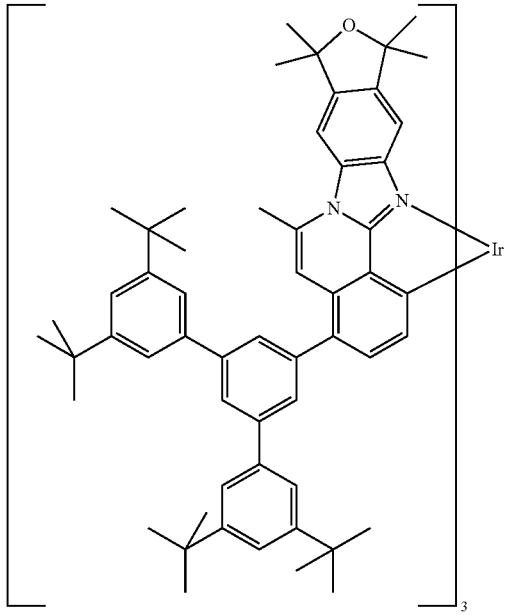<br>Ir(10-Br)₃ + [1071924-15-6] > Ir(278)₃<br>B, as Ir(L276)₃ | 46% |
| Ir(L280)₃ | 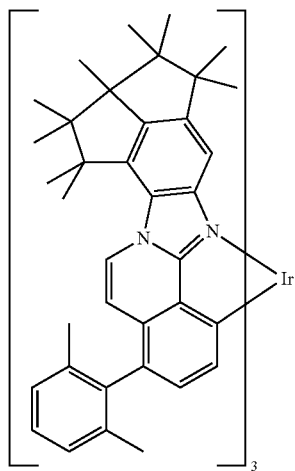<br>Ir(L55-Br)₃ + [100379-00-8] > Ir(L280)₃<br>Diastereomer mixture<br>B, as Ir(L276)₃, dioxane instead of NMP | 52% |

| Ex. | Product Variant | Yield |
|---|---|---|
| Ir(L281)₃ | 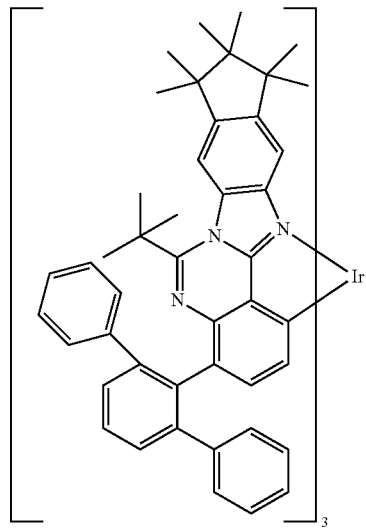<br>Ir(L96-Br)₃ + [1065663-52-6] > Ir(L281)₃<br>B, as Ir(L276)₃ | 23% |
| Ir(L282)₃ | 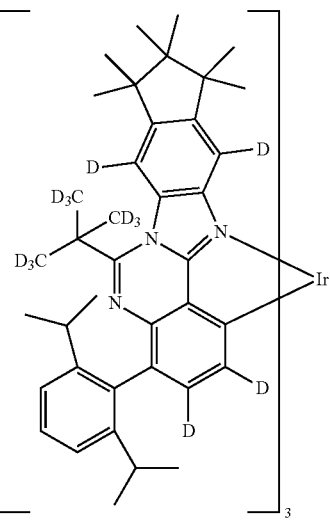<br>Ir(L120-Br)₃ + [363166-79-4] > Ir(L282)₃<br>B, Cs(CO₃)₂, NMP, S-Phos | 19% |

-continued

| Ex. | Product Variant | Yield |
|---|---|---|
| Ir(L283)₃ | Ir(L96-Br)₃ + [2156-04-9] > Ir(L283)₃<br>B, as Ir(L276)₃, DMAC instead of NMP | 25% |
| Ir(L284)₃ | Λ,Δ-C3-Ir(L126-Br)₃ +<br>[15016-43-0] > Λ,Δ-C3-Ir(L284)₃<br>B, as Ir(L276)₃, DMAC instead of NMP | 27% |
| Ir(L285)₃ | Ir(L113)₂(L109-Br) + [1233200-59-3] > Ir(L285)₃<br>A | 67% |

3) Buchwald Coupling on the Iridium Complexes:

0.4 mmol of tri-tert-butylphosphine and then 0.3 mmol of palladium(II) acetate are added to a mixture of 10 mmol of the brominated complex, 40 mmol of the diarylamine or carbazole, 45 mmol of sodium tert-butoxide in the case of the amines or 80 mmol of tripotassium phosphate, anhydrous, in the case of carbazoles, 100 g of glass beads (diameter 3 mm) and 300-500 ml of o-xylene or mesitylene, and the mixture is heated under reflux for 16 h with vigorous stirring. After cooling, the aqueous phase is separated off, washed twice with 200 ml of water, once with 200 ml of sat. sodium chloride solution and dried over magnesium sulfate. The solid material is filtered off through a Celite bed and rinsed with o-xylene or mesitylene, the solvent is removed virtually completely in vacuo, 300 ml of ethanol are added, the precipitated crude product is filtered off with suction, washed three times with 100 ml of EtOH each time and dried in vacuo. The crude product is passed through a silica-gel column with toluene twice. The metal complex is finally heated or sublimed. The heating is carried out in a high vacuum (p about $10^{-6}$ mbar) in the temperature range from about 200-300° C. The sublimation is carried out in a high vacuum (p about $10^{-6}$ mbar) in the temperature range from about 300-400° C., with the sublimation preferably being carried out in the form of a fractional sublimation.

Synthesis of Ir(L286)₃:

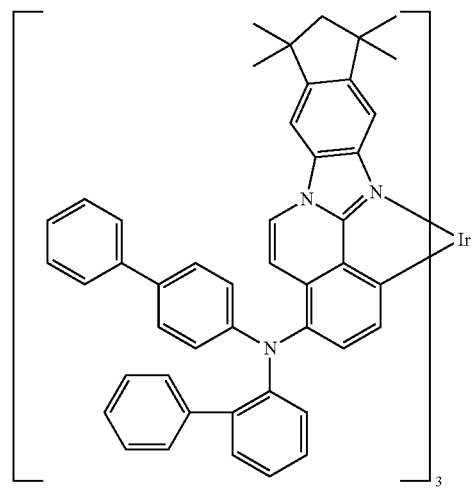

Use of 14.5 g (10 mmol) of Ir(L1-Br)₃ and 12.9 g (40 mmol) of p-biphenyl-o-biphenylamine [1372775-52-4], mesitylene. Yield: 9.8 g (4.7 mmol), 47%; purity: about 99.8% according to HPLC.

The following compounds can be prepared analogously:

| Ex. | Product | Yield |
|---|---|---|
| Ir(L287)₃ | Ir(L3-Br)₃ + [1257220-47-5] > Ir(287)₃ | 49% |
| Ir(L288)₃ | Ir(L96-Br)₃ + [244-78-0] > Ir(288)₃ | 53% |

4) Cyanation of the Iridium Complexes:

A mixture of 10 mmol of the brominated complex, 1.3 mmol of copper(I) cyanide per bromine function and 300 ml of NMP is stirred at 200° C. for 20 h. After cooling, the solvent is removed in vacuo, the residue is taken up in 500 ml of dichloromethane, the copper salts are filtered off over Celite, the dichloromethane is evaporated virtually to dryness in vacuo, 100 ml of ethanol are added, the precipitated solid is filtered off with suction, washed twice with 50 ml of ethanol each time and dried in vacuo. Hot extraction and sublimation as in 1) variant A. The crude product can alternatively be chromatographed on silica gel with dichloromethane, optionally with addition of ethyl acetate, and then sublimed.

Synthesis of Ir(L289)₃:

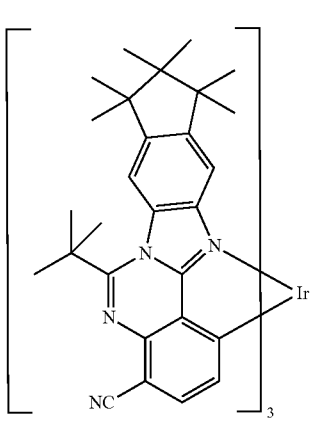

Use of 16.2 g (10 mmol) of Ir(L96-Br)₃ and 3.5 g (39 mmol) of copper(I) cyanide. Yield: 7.7 g (5.2 mmol), 52%; purity: about 99.8% according to HPLC.

The following compound can be prepared analogously:

| Ex. | Product | Yield |
|---|---|---|
| Ir(L290)₃ | 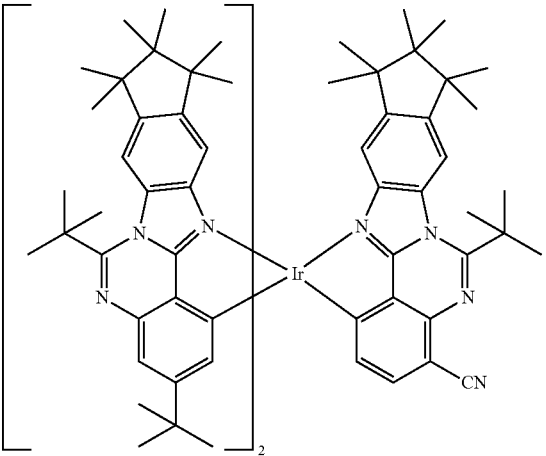<br>Ir(L113)₂(L109-Br) +CuCN > Ir(L290)₃ | 69% |

5) Borylation of the Iridium Complexes:

A mixture of 10 mmol of the brominated complex, 12 mmol of bis(pinacolato)diborane [73183-34-3] per bromine function, 30 mmol of potassium acetate, anhydrous, per bromine function, 0.2 mmol of tricyclohexylphosphine and 0.1 mmol of palladium(II) acetate and 300 ml of solvent (dioxane, DMSO, NMP, etc.) is stirred at 80°-160° C. for 4-16 h. After removal of the solvent in vacuo, the residue is taken up in 300 ml of dichloromethane, THF or ethyl acetate, filtered through a Celite bed, the filtrate is evaporated in vacuo until crystallisation commences, and finally about 100 ml of methanol are added dropwise in order to complete the crystallisation. The compounds can be recrystallised from dichloromethane, ethyl acetate or THF with addition of methanol or alternatively cyclohexane.

Synthesis of Ir(L1-B)₃:

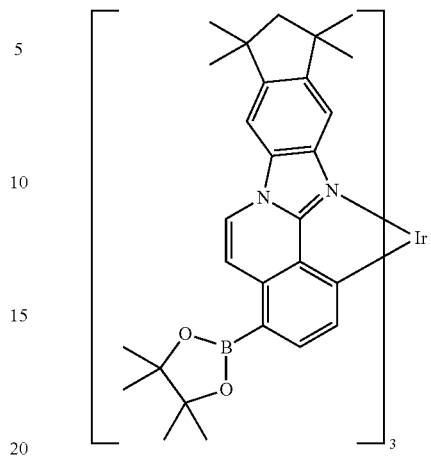

Use of 14.5 g (10 mmol) of Ir(L1-Br)₃ and 9.1 g (36 mmol) of bis(pinacolato)diborane [73183-34-3], DMSO, 140° C., 6 h, THF, recrystallisation from THF: methanol. Yield: 7.1 g (4.7 mmol), 47%; purity: about 99.7% according to HPLC.

E: Polymers Containing the Metal Complexes:

1) General Polymerisation Procedure for the Styryl Group as Polymerisable Group

The monomers in the composition indicated are dissolved in toluene at 80° C. in a total concentration of about 1 mol/l. 60 mg of AIBN are subsequently added, and the mixture is stirred at 80° C. for a further 2 h. After cooling to room temperature, the polymer is obtained by precipitation (dropwise addition) in 100 ml of methanol. The precipitate is filtered off with suction and subsequently again dissolved in a little toluene and re-precipitated in methanol, filtered off with suction and dried in vacuo. The reprecipitation process is carried out a further three times.

Monomers:

M1

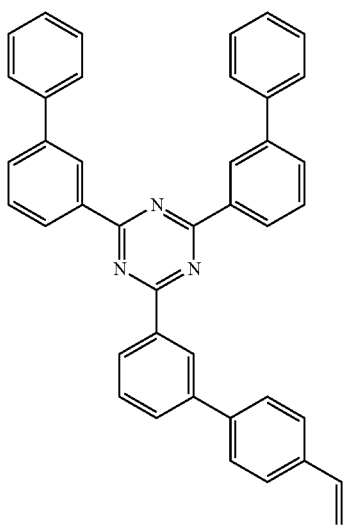

1354469-30-9

M2

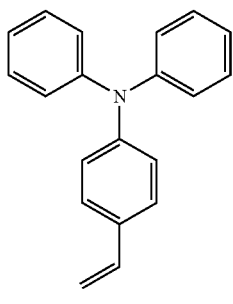

25069-74-3

M3

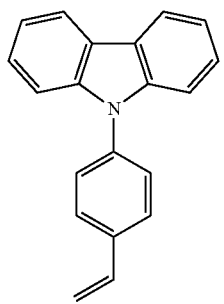

52913-19-6

M4

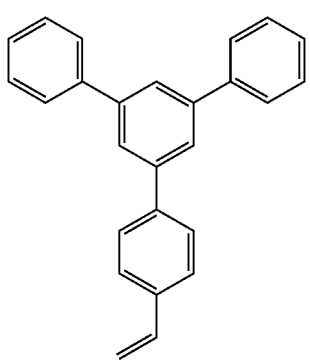

1354469-27-4

Polymers:

Composition of the polymers, mol %:

| Polymer | M1 [%] | M2 [%] | M3 [%] | M4 [%] | Ir complex/[%] |
|---|---|---|---|---|---|
| P1 | 80 | — | — | — | Ir(L283)$_3$/20 |
| P2 | 60 | — | 30 | — | Ir(L283)$_3$/10 |
| P3 | 50 | 10 | 30 | — | Ir(L283)$_3$/10 |
| P4 | 50 | 10 | 20 | 10 | Ir(L283)$_3$/10 |
| P5 | 60 | — | 30 | — | Ir(L284)$_3$/10 |

Molecular Weights and Yield of the Polymers According to the Invention

| Polymer | Mn [gmol$^{-1}$] | Mw [gmol$^{-1}$] | Yield |
|---|---|---|---|
| P1 | 77,000 | 17,100 | 53% |
| P2 | 133,000 | 50,600 | 64% |
| P3 | 127,000 | 72,000 | 60% |
| P4 | 121,000 | 51,400 | 57% |
| P5 | 76,800 | 23,260 | 49% |

2) General Polymerisation Procedure for the Bromides or Boronic Acid Derivatives as Polymerisable Group, Suzuki Polymerisation Variant A—Two-Phase Reaction Mixture:

The monomers (bromides and boronic acids or boronic acid esters, purity according to HPLC >99.8%) in the composition indicated in the table are dissolved or suspended in a mixture of 2 parts by volume of toluene:6 parts by volume of dioxane:1 part by volume of water in a total concentration of about 100 mmol/l. 2 mol equivalents of tripotassium phosphate per Br functionality employed are then added, the mixture is stirred for a further 5 min., 0.03 to 0.003 mol equivalent of tri-ortho-tolylphosphine and then 0.005 to 0.0005 mol equivalent of palladium(II) acetate (phosphine to Pd ratio preferably 6:1) per Br functionality employed are then added, and the mixture is then heated under reflux for 2-3 h with very vigorous stirring. If the viscosity of the mixture increases excessively, it can be diluted with a mixture of 2 parts by volume of toluene:3 parts by volume of dioxane. After a total reaction time of 4-6 h, 0.05 mol equivalent per boronic acid functionality employed of a monobromoaromatic compound are added for end capping, and then, 30 min. later, 0.05 mol equivalent per Br functionality employed of a monoboronic acid or a monoboronic acid ester is added, and the mixture is boiled for a further 1 h. After cooling, the mixture is diluted with 300 ml of toluene. The aqueous phase is separated off, the organic phase is washed twice with 300 ml of water each time, dried over magnesium sulfate, filtered through a Celite bed in order to remove palladium and then evaporated to dryness. The crude polymer is dissolved in THF (concentration about 10-30 g/l), and the solution is allowed to run slowly, with very vigorous stirring, into twice the volume of methanol. The polymer is filtered off with suction and washed three times with methanol. The reprecipitation process is repeated three times, the polymer is then dried to constant weight at 30-50° C. in vacuo.

Variant B—One-Phase Reaction Mixture:

The monomers (bromides and boronic acids or boronic acid esters, purity according to HPLC >99.8%) in the composition indicated in the table are dissolved or suspended in a solvent (THF, dioxane, xylene, mesitylene, dimethylacetamide, NMP, DMSO, etc.) in a total concentration of about 100 mmol/l. 3 mol equivalents of base (potassium fluoride, tripotassium phosphate, potassium carbonate, caesium carbonate, etc., in each case anhydrous) per Br functionality are then added, and the weight equivalent of glass beads (diameter 3 mm) is added, the mixture is stirred for a further 5 min., 0.03 to 0.003 mol equivalent of tri-ortho-tolylphosphine and then 0.005 to 0.0005 mol equivalent of palladium(II) acetate (phosphine to Pd ratio preferably 6:1) per Br functionality are then added, and the mixture is then heated under reflux for 2-3 h with very vigorous stirring. Alternatively, other phosphines, such as tri-tert-butylphosphine, di-tert-butylphosphine, S-Phos, xantphos, etc., can be employed, where the preferred phosphine:palladium ratio in the case of these phosphines is 2:1 to 1.3:1. After a total reaction time of 4-12 h, 0.05 mol equivalent of a monobromoaromatic compound and then, 30 min. later, 0.05 mol equivalent of a monoboronic acid or a monoboronic acid ester is added for end capping, and the mixture is boiled for a further 1 h. The solvent is substantially removed in vacuo, the residue is taken up in toluene, and the polymer is purified as described under variant A.

Monomers/End Cappers:

M1

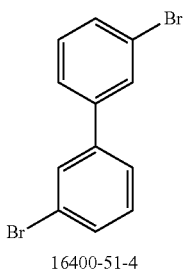

16400-51-4

M2

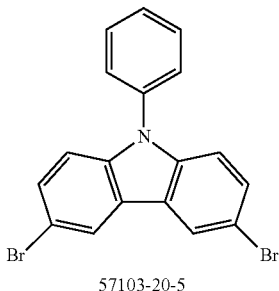

57103-20-5

M3

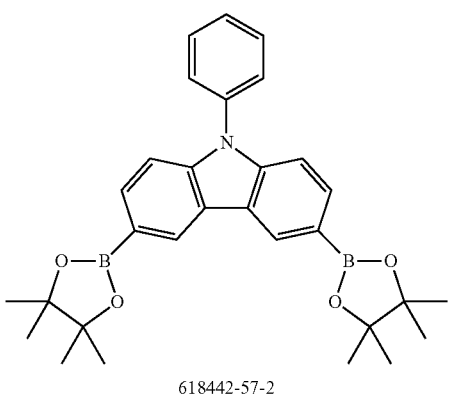

618442-57-2

M4

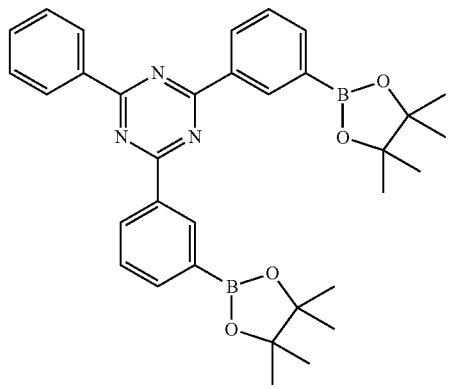

1238752-26-5

E1

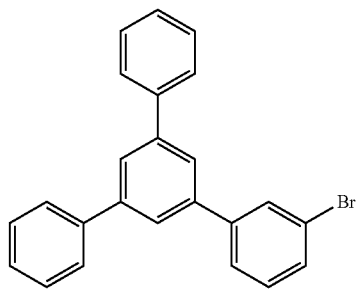

1233200-57-1

E2

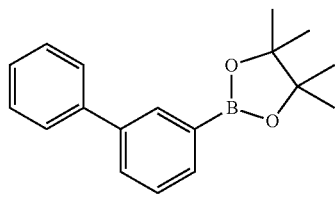

912844-88-3

Polymers:
Composition of the Polymers, Mol %:

| Polymer | M1 [%] | M2 [%] | M3 [%] | M4 [%] | Ir complex/[%] |
|---|---|---|---|---|---|
| P6 | — | 30 | — | 45 | Ir(L1-Br)$_3$/20 |
| P7 | 10 | 10 | — | 35 | Ir(L96-Br)$_3$/10 |
| P8 | 50 | — | 20 | 45 | Ir(L96-Br)$_3$/10 |
| P9 | 30 | 30 | — | 67.5 | Ir(L126-Br)$_3$/10 |

Molecular Weights and Yield of the Polymers According to the Invention

| Polymer | Mn [gmol$^{-1}$] | Polydispersity | Yield |
|---|---|---|---|
| P6 | 167,000 | 4.6 | 60% |
| P7 | 153,000 | 5.1 | 57% |
| P8 | 177,000 | 6.0 | 63% |
| P9 | 224,000 | 3.7 | 67% |

Production of OLEDs
1) Vacuum-Processed Devices:
OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples. Glass plates with structured ITO (indium tin oxide) form the substrates to which the OLEDs are applied. The OLEDs have in principle the following layer structure: substrate/hole-transport layer 1 (HTL1) consisting of HTM doped with 3% of NDP-9 (commercially available from Novaled), 20 nm/hole-transport layer 2 (HTL2)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as M3:M2:Ir(L1)$_3$ (55%:35%:10%) here means that material M3 is present in the layer in a proportion by volume of 55%, M2 is present in the layer in a proportion of 35% and Ir(L1)$_3$ is present in the layer in a proportion of 10%. Analogously, the electron-transport layer may also consist of a mixture of two materials. The precise structure of the OLEDs is shown in Table 1. The materials used for the production of the OLEDs are shown in Table 6.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT50 means that the lifetime given is the time at which the luminous density has dropped to 50% of the initial luminous density, i.e. from, for example, 1000 cd/m$^2$ to 500 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

Use of Compounds According to the Invention as Emitter Materials in Phosphorescent OLEDs The compounds according to the invention can be employed, inter alia, as phosphorescent emitter materials in the emission layer in OLEDs. The compounds Ir(Ref)$_3$ are used as comparison in accordance with the prior art. The results for the OLEDs are summarised in Table 2.

TABLE 1

Structure of the OLEDs

| Ex. | HTL2 Thickness | EBL Thickness | EML Thickness | HBL Thickness | ETL Thickness |
|---|---|---|---|---|---|
| D-Ir(Ref1)$_3$ | HTM 180 nm | EBM 20 nm | M1:M4:Ir(Ref1)$_3$ (65%:30%:5%) 25 nm | HBM 10 nm | ETM1:ETM2 (50%:50%) 20 nm |
| D-Ir(Ref2)$_3$ | HTM 180 nm | EBM 20 nm | M1:M3:Ir(Ref2)$_3$ (65%:30%:5%) 25 nm | HBM 10 nm | ETM1:ETM2 (50%:50%) 20 nm |
| D-Ir(Ref3)$_3$ | HTM 180 nm | EBM 20 nm | M1:M4:Ir(Ref3)$_3$ (65%:30%:5%) 25 nm | HBM 10 nm | ETM1:ETM2 (50%:50%) 20 nm |
| D-Ir(Ref4)$_3$ | HTM 180 nm | EBM 20 nm | M1:M4:Ir(Ref4)$_3$ (65%:30%:5%) 25 nm | HBM 10 nm | ETM1:ETM2 (50%:50%) 20 nm |
| D-Ir(Ref5)$_3$ | HTM 180 nm | EBM 20 nm | M1:M4:Ir(Ref5)$_3$ (65%:30%:5%) 25 nm | HBM 10 nm | ETM1:ETM2 (50%:50%) 20 nm |
| D-Ir(Ref6)$_3$ | HTM 180 nm | EBM 20 nm | M1:M4:Ir(Ref6)$_3$ (65%:30%:5%) 25 nm | HBM 10 nm | ETM1:ETM2 (50%:50%) 20 nm |
| D-Ir(Ref7)$_3$ | HTM 180 nm | EBM 20 nm | M1:M4:Ir(Ref7)$_3$ (65%:30%:5%) 25 nm | HBM 10 nm | ETM1:ETM2 (50%:50%) 20 nm |
| D-Ir(Ref8)$_3$ | HTM 180 nm | EBM 20 nm | M1:M4:Ir(Ref8)$_3$ (65%:30%:5%) 25 nm | HBM 10 nm | ETM1:ETM2 (50%:50%) 20 nm |
| D-Ir(Ref9)$_3$ | HTM 180 nm | EBM 20 nm | M1:M4:Ir(Ref9)$_3$ (65%:30%:5%) 25 nm | HBM 10 nm | ETM1:ETM2 (50%:50%) 20 nm |
| D-Ir(Ref10)$_3$ | HTM 180 nm | EBM 20 nm | M1:M4:Ir(Ref10)$_3$ (65%:30%:5%) 25 nm | HBM 10 nm | ETM1:ETM2 (50%/50%) 20 nm |
| D-Ir(L1)$_3$ | HTM 180 nm | EBM 20 nm | M1:M4:Ir(L1)$_3$ (65%:30%:5%) 25 nm | HBM 10 nm | ETM1:ETM2 (50%:50%) 20 nm |
| D-Ir(L96)$_3$ | HTM 180 nm | EBM 20 nm | M1:M4:Ir(L96)$_3$ (65%:30%:5%) 25 nm | HBM 10 nm | ETM1:ETM2 (50%:50%) 20 nm |
| D-Ir(L96)$_3$-2 | HTM 180 nm | EBM 20 nm | M2:M3:Ir(L96)$_3$ (65%:30%:5%) 25 nm | HBM 10 nm | ETM1:ETM2 (50%:50%) 20 nm |
| D-Ir(L167)$_3$ | HTM 180 nm | EBM 20 nm | M1:M4:Ir(L96)$_3$ (65%:30%:5%) 25 nm | HBM 10 nm | ETM1:ETM2 (50%/50%) 20 nm |

TABLE 1-continued

Structure of the OLEDs

| Ex. | HTL2 Thickness | EBL Thickness | EML Thickness | HBL Thickness | ETL Thickness |
|---|---|---|---|---|---|
| D-Ir(L192)$_3$ | HTM 180 nm | EBM 20 nm | M1:M4:Ir(L192)$_3$ (65%:30%:5%) 25 nm | HBM 10 nm | ETM1:ETM2 (50%:50%) 20 nm |
| D-Ir(L215)$_3$ | HTM 180 nm | EBM 20 nm | M1:M4:Ir(215)$_3$ (65%:30%:5%) 25 nm | HBM 10 nm | ETM1:ETM2 (50%:50%) 20 nm |
| D-Ir(L226)$_3$ | HTM 180 nm | EBM 20 nm | M1:M4:Ir(L226)$_3$ (65%:30%:5%) 25 nm | HBM 10 nm | ETM1:ETM2 (50%:50%) 20 nm |
| D-Ir(L227)$_3$ | HTM 180 nm | EBM 20 nm | M1:M4:Ir(L227)$_3$ (65%:30%:5%) 25 nm | HBM 10 nm | ETM1:ETM2 (50%:50%) 20 nm |
| D-Ir(L230)$_3$ | HTM 180 nm | EBM 20 nm | M1:M4:Ir(L230)$_3$ (65%:30%:5%) 25 nm | HBM 10 nm | ETM1:ETM2 (50%:50%) 20 nm |
| D-Ir(L231)$_3$ | HTM 180 nm | EBM 20 nm | M1:M4:Ir(L231)$_3$ (65%:30%:5%) 25 nm | HBM 10 nm | ETM1:ETM2 (50%:50%) 20 nm |
| D-Ir(L234)$_3$ | HTM 180 nm | EBM 20 nm | M1:M4:Ir(L234)$_3$ (65%:30%:5%) 25 nm | HBM 10 nm | ETM1:ETM2 (50%:50%) 20 nm |
| D-Ir(L243)$_3$ | HTM 180 nm | EBM 20 nm | M1:M4:Ir(L243)$_3$ (65%:30%:5%) 25 nm | HBM 10 nm | ETM1:ETM2 (50%:50%) 20 nm |
| D-Ir(L248)$_3$ | HTM 180 nm | EBM 20 nm | M1:M4:Ir(L248)$_3$ (65%:30%:5%) 25 nm | HBM 10 nm | ETM1:ETM2 (50%:50%) 20 nm |
| D-Ir(L252)$_3$ | HTM 180 nm | EBM 20 nm | M1:M4:Ir(L252)$_3$ (65%:30%:5%) 25 nm | HBM 10 nm | ETM1:ETM2 (50%:50%) 20 nm |
| D-Ir(L259)$_3$ | HTM 180 nm | EBM 20 nm | M1:M4:Ir(L259)$_3$ (65%:30%:5%) 25 nm | HBM 10 nm | ETM1:ETM2 (50%:50%) 20 nm |
| D-Ir(L260)$_3$ | HTM 180 nm | EBM 20 nm | M1:M4:Ir(L260)$_3$ (65%:30%:5%) 25 nm | HBM 10 nm | ETM1:ETM2 (50%:50%) 20 nm |
| D-Ir(L263)$_3$ | HTM 180 nm | EBM 20 nm | M1:M4:Ir(L263)$_3$ (65%:30%:5%) 25 nm | HBM 10 nm | ETM1:ETM2 (50%:50%) 20 nm |
| D-Ir(L264)$_3$ | HTM 180 nm | EBM 20 nm | M1:M4:Ir(L264)$_3$ (65%:30%:5%) 25 nm | HBM 10 nm | ETM1:ETM2 (50%:50%) 20 nm |
| D-Ir(L267)$_3$ | HTM 180 nm | EBM 20 nm | M1:M4:Ir(L267)$_3$ (65%:30%:5%) 25 nm | HBM 10 nm | ETM1:ETM2 (50%:50%) 20 nm |
| D-Ir(L268)$_3$ | HTM 180 nm | EBM 20 nm | M1:M4:Ir(L268)$_3$ (65%:30%:5%) 25 nm | HBM 10 nm | ETM1:ETM2 (50%:50%) 20 nm |
| D-Ir(L271)$_3$ | HTM 180 nm | EBM 20 nm | M1:M4:Ir(L271)$_3$ (65%:30%:5%) 25 nm | HBM 10 nm | ETM1:ETM2 (50%:50%) 20 nm |
| D-Ir(L279)$_3$ | HTM 180 nm | EBM 20 nm | M1:M4:Ir(L279)$_3$ (65%:30%:5%) 25 nm | HBM 10 nm | ETM1:ETM2 (50%:50%) 20 nm |
| D-Ir(L284) | HTM 180 nm | EBM 20 nm | M1:M4:Ir(L284) (65%:30%:5%) 25 nm | HBM 10 nm | ETM1:ETM2 (50%:50%) 20 nm |
| D-Ir(L3)$_2$(CL1) | HTM 180 nm | EBM 20 nm | M1:M4:Ir(L3)$_2$(CL1) (65%:30%:5%) 25 nm | HBM 10 nm | ETM1:ETM2 (50%:50%) 20 nm |
| D-Ir(L158)$_2$(CL8) | HTM 180 nm | EBM 20 nm | M1:M4:Ir(L158)$_2$(CL8) (65%:30%:5%) 25 nm | HBM 10 nm | ETM1:ETM2 (50%:50%) 20 nm |
| D-Ir(L113)$_2$(L109) | HTM 180 nm | EBM 20 nm | M1:M4:Ir(L113)$_2$(L109) (65%:30%:5%) 25 nm | HBM 10 nm | ETM1:ETM2 (50%:50%) 20 nm |
| Pt(L3)(CL1) | HTM 180 nm | EBM 20 nm | M1:M4:Pt(L3)(CL1) (55%:40%:5%) 25 nm | HBM 10 nm | ETM1:ETM2 (50%:50%) 20 nm |
| Pt(L283) | HTM 230 nm | EBM 20 nm | M1:M4:Pt(L283) (60%:35%:5%) 25 nm | HBM 10 nm | ETM1:ETM2 (50%:50%) 20 nm |

TABLE 2

Results of the vacuum-processed OLEDs

| Ex. | EQE (%) 1000 cd/m² | Voltage (V) 1000 cd/m² | CIE x/y 1000 cd/m² | LT50 (h) 1000 cd/m² |
|---|---|---|---|---|
| D-Ir(Ref1)₃ | 10.0 | 4.1 | 0.16/0.48 | 1700 |
| D-Ir(Ref2)₃ | 13.2 | 4.7 | 0.15/0.31 | 600 |
| D-Ir(Ref3)₃ | 11.8 | 4.2 | 0.16/0.33 | 1100 |
| D-Ir(Ref4)₃ | 10.3 | 4.4 | 0.15/0.24 | 600 |
| D-Ir(Ref5)₃ | 4.6 | 4.3 | 0.16/0.29 | — |
| D-Ir(Ref6)₃ | 4.7 | 4.5 | 0.15/0.26 | — |
| D-Ir(Ref7)₃ | 9.0 | 4.7 | 0.15/0.22 | 200 |
| D-Ir(Ref8)₃ | 6.3 | 4.7 | 0.15/0.17 | — |
| D-Ir(Ref9)₃ | 10.8 | 4.5 | 0.18/0.34 | 150 |
| D-Ir(Ref10)₃ | 7.9 | 4.3 | 0.25/0.61 | — |
| D-Ir(L1)₃ | 22.8 | 4.0 | 0.15/0.39 | 1400 |
| D-Ir(L96)₃ | 23.0 | 4.0 | 0.14/0.34 | 1200 |
| D-Ir(L96)₃ | 21.7 | 4.8 | 0.14/0.34 | 1000 |
| D-Ir(L167)₃ | 21.3 | 4.1 | 0.15/0.35 | 1600 |
| D-Ir(L192)₃ | 20.8 | 4.5 | 0.15/0.25 | 900 |
| D-Ir(L215)₃ | 23.7 | 4.1 | 0.22/0.71 | — |
| D-Ir(L226)₃ | 21.5 | 4.2 | 0.25/0.69 | 36000 |
| D-Ir(L227)₃ | 21.9 | 3.9 | 0.29/0.67 | — |
| D-Ir(L230)₃ | 9.7 | 4.3 | 0.14/0.30 | — |
| D-Ir(L231)₃ | 13.8 | 4.5 | 0.15/0.40 | — |
| D-Ir(L234)₃ | 19.9 | 4.5 | 0.14/0.28 | 600 |
| D-Ir(L243)₃ | 18.7 | 4.6 | 0.14/0.24 | 350 |
| D-Ir(L248)₃ | 19.2 | 4.6 | 0.14/0.21 | 300 |
| D-Ir(L252)₃ | 25.2 | 4.3 | 0.23/0.70 | — |
| D-Ir(L259)₃ | 22.9 | 4.2 | 0.23/0.69 | — |
| D-Ir(L260)₃ | 23.2 | 4.2 | 0.23/0.70 | — |
| D-Ir(L263)₃ | 18.7 | 4.3 | 0.15/0.26 | 600 |
| D-Ir(L264)₃ | 18.4 | 4.3 | 0.14/0.34 | 1400 |
| D-Ir(L267)₃ | 17.3 | 4.6 | 0.15/0.33 | — |
| D-Ir(L268)₃ | 17.7 | 4.6 | 0.15/0.26 | — |
| D-Ir(L271)₃ | 19.8 | 4.8 | 0.14/0.22 | — |
| D-Ir(L279)₃ | 16.7 | 4.3 | 0.15/0.22 | — |
| D-Ir(L284) | 17.0 | 4.4 | 0.15/0.24 | — |
| D-Ir(L3)₂(CL1) | 21.8 | 4.0 | 0.15/0.38 | — |
| D-Ir(L158)₂(CL8) | 23.1 | 4.3 | 0.15/0.25 | 1200 |
| D-Ir(L113)₂(L109) | 23.9 | 4.0 | 0.14/0.33 | 1300 |
| D-Ir(I500)₃ | 20.1 | 4.4 | 0.16/0.36 | 500 |
| D-Ir(I511)₃ | 22.7 | 4.1 | 0.24/0.65 | 41000 |
| Pt(L3)(CL1) | 17.4 | 4.6 | 0.16/0.38 | — |
| Pt(L283) | 21.4 | 4.5 | 0.26/0.63 | — |

1) Solution-Processed Devices:

A: From Soluble Functional Materials

The iridium complexes according to the invention can also be processed from solution, where they result in OLEDs which are significantly simpler as far as the process is concerned, compared with the vacuum-processed OLEDs, with nevertheless good properties. The production of components of this type is based on the production of polymeric light-emitting diodes (PLEDs), which has already been described many times in the literature (for example in WO 2004/037887).

The structure is composed of substrate/ITO/PEDOT (80 nm)/interlayer (80 nm)/emission layer (80 nm)/cathode. To this end, use is made of substrates from Technoprint (soda-lime glass), to which the ITO structure (indium tin oxide, a transparent, conductive anode) is applied. The substrates are cleaned with DI water and a detergent (Deconex 15 PF) in a clean room and then activated by a UV/ozone plasma treatment. An 80 nm layer of PEDOT (PEDOT is a polythiophene derivative (Baytron P VAI 4083sp.) from H. C. Starck, Goslar, which is supplied as an aqueous dispersion) is then applied as buffer layer by spin coating, likewise in the clean room. The spin rate required depends on the degree of dilution and the specific spin coater geometry (typically for 80 nm: 4500 rpm). In order to remove residual water from the layer, the substrates are dried by heating on a hotplate at 180° C. for 10 minutes. The interlayer used serves for hole injection, in this case HIL-012 from Merck is used. The interlayer may alternatively also be replaced by one or more layers, which merely have to satisfy the condition of not being detached again by the subsequent processing step of EML deposition from solution. In order to produce the emission layer, the emitters according to the invention are dissolved in toluene together with the matrix materials. The typical solids content of such solutions is between 16 and 25 g/l if, as here, the typical layer thickness of 80 nm for a device is to be achieved by means of spin coating. The solution-processed devices comprise an emission layer comprising (polystyrene): M5:M6:Ir(L)₃ (25%:25%:40%:10%). The emission layer is applied by spin coating in an inert-gas atmosphere, in the present case argon, and dried by heating at 130° C. for 30 min. Finally, a cathode is applied by vapour deposition from barium (5 nm) and then aluminium (100 nm) (high-purity metals from Aldrich, particularly barium 99.99% (Order No. 474711); vapour-deposition equipment from Lesker, inter alia, typical vapour-deposition pressure $5\times10^{-6}$ mbar). Optionally, firstly a hole-blocking layer and then an electron-transport layer and only then the cathode (for example Al or LiF/Al) can be applied by vacuum vapour deposition. In order to protect the device against air and atmospheric moisture, the device is finally encapsulated and then characterised. The OLED examples given have not yet been optimised, Table 3 summarises the data obtained.

B: From Polymeric Ir Complexes

The production of a polymeric organic light-emitting diode (PLED) has already been described many times in the literature (for example WO 2004/037887).

The substrates are prepared—as described under A: From soluble functional materials—then firstly 20 nm of an interlayer (typically a hole-dominated polymer, here HIL-012 from Merck) and then 65 nm of the polymer layers are applied from toluene solution (concentration of interlayer 5 g/l) under an inert-gas atmosphere (nitrogen or argon). The two layers are dried by heating at 180° C. for at least 10 minutes. The cathode is then applied by vapour deposition from barium (5 nm) and then aluminium (100 nm). In order to protect the device against air and atmospheric moisture, the device is finally encapsulated and then characterised. The OLED examples given have not yet been optimised, Table 3 summarises the data obtained.

TABLE 3

Results with solution-processed materials

| Ex. | Ir(L)₃ or Ir polymer | EQE (%) 1000 cd/m² | Voltage (V) 1000 cd/m² | CIE x/y 1000 cd/m² |
|---|---|---|---|---|
| D-Ir(L276)₃ | Ir(L276)₃ | 22.6 | 4.4 | 0.16/0.40 |
| D-Ir(L281)₃ | Ir(L281)₃ | 23.2 | 4.5 | 0.15/0.36 |
| D-Ir(L285)₃ | Ir(L285)₃ | 23.0 | 4.4 | 0.15/0.35 |
| D-Ir(L287)₃ | Ir(L287)₃ | 20.5 | 4.3 | 0.22/0.67 |
| D-P1 | P1 | 22.8 | 4.8 | 0.15/0.37 |
| D-P5 | P5 | 22.5 | 4.5 | 0.15/0.36 |
| D-P6 | P6 | 22.4 | 4.5 | 0.16/0.40 |
| D-P7 | P7 | 22.8 | 4.4 | 0.15/0.36 |
| D-P9 | P9 | 21.2 | 4.6 | 0.15/0.36 |

2) White-Emitting OLEDs

A white-emitting OLED having the following layer structure is produced in accordance with the general processes from 1):

TABLE 4

Structure of the white OLEDs

| Ex. | HTL2 Thickness | EML Red Thickness | EML Blue Thickness | EML Green Thickness | HBL Thickness | ETL Thickness |
|---|---|---|---|---|---|---|
| D-W1 | HTM 230 nm | EBM:Ir-R (97%:3%) 9 nm | M1:M3:Ir(L109)$_3$ (45%:50%:5%) 8 nm | M3:Ir-G (90%:10%) 7 nm | M3 10 nm | ETM1:ETM2 (50%:50%) 30 nm |

TABLE 5

Device results

| Ex. | EQE (%) 1000 cd/m$^2$ | Voltage (V) 1000 cd/m$^2$ | CIE x/y 1000 cd/m$^2$ CRI | LT50 (h) 1000 cd/m$^2$ |
|---|---|---|---|---|
| D-W1 | 23.0 | 6.3 | 0.45/0.44 80 | 3000 |

TABLE 6

Structural formulae of the materials used

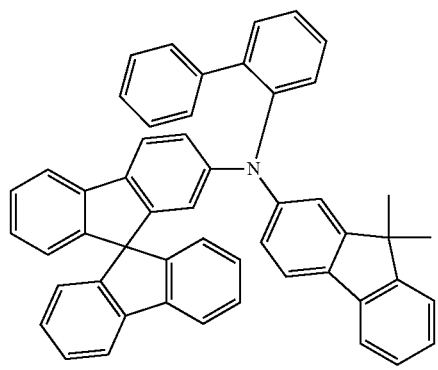 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HTM

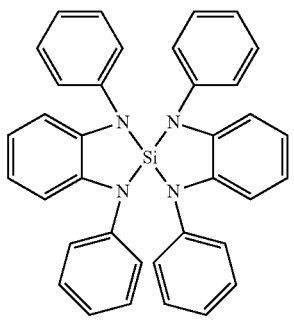 [SMILES: c1ccc(N2c3ccccc3N(c3ccccc3)[Si]23N(c2ccccc2)c2ccccc2N3c2ccccc2)cc1]

EBM

TABLE 6-continued

Structural formulae of the materials used

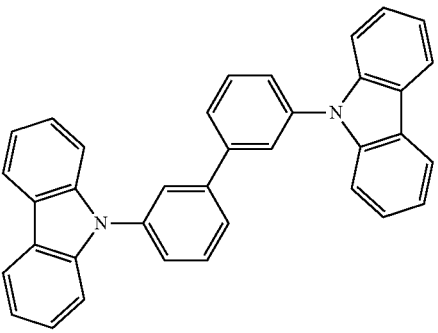 [SMILES: c1cc(-c2cccc(-n3c4ccccc4c4ccccc43)c2)cc(-n2c3ccccc3c3ccccc32)c1]

M1

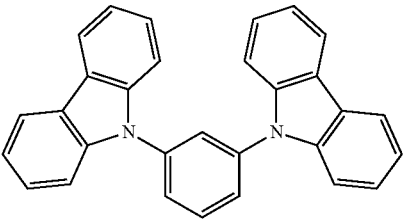 [SMILES: c1cc(-n2c3ccccc3c3ccccc32)cc(-n2c3ccccc3c3ccccc32)c1]

M2

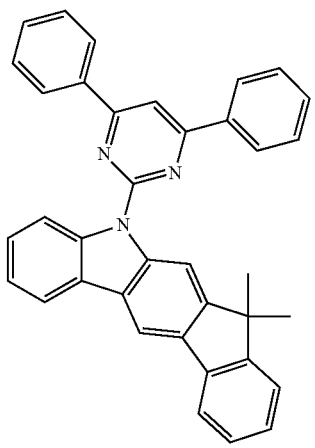 [SMILES: CC1(C)c2ccccc2-c2cc3c4ccccc4n(-c4nc(-c5ccccc5)cc(-c5ccccc5)n4)c3cc21]

M3

TABLE 6-continued
Structural formulae of the materials used
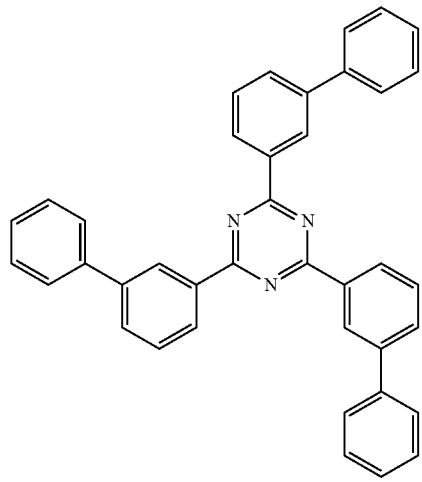 [SMILES: c1ccc(-c2cccc(-c3nc(-c4cccc(-c5ccccc5)c4)nc(-c4cccc(-c5ccccc5)c4)n3)c2)cc1]
M4 = HBM
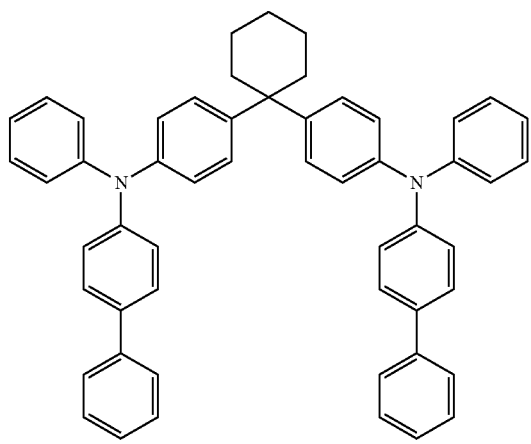 [SMILES: c1ccc(-c2ccc(N(c3ccccc3)c3ccc(C4(c5ccc(N(c6ccccc6)c6ccc(-c7ccccc7)cc6)cc5)CCCCC4)cc3)cc2)cc1]
M5
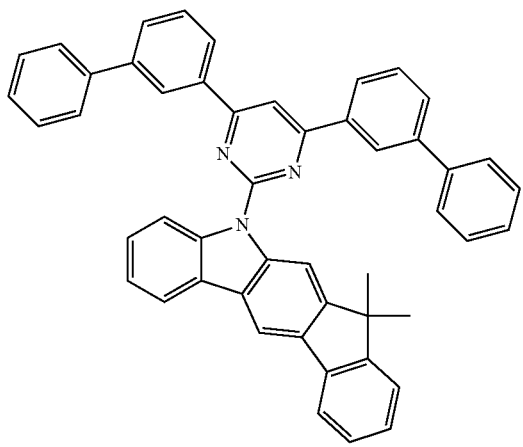 [SMILES: CC1(C)c2ccccc2-c2cc3c4ccccc4n(-c4nc(-c5cccc(-c6ccccc6)c5)cc(-c5cccc(-c6ccccc6)c5)n4)c3cc21]
M6
TABLE 6-continued
Structural formulae of the materials used
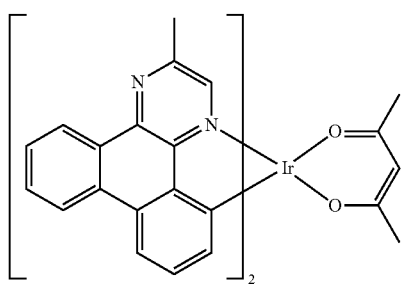
Ir-R
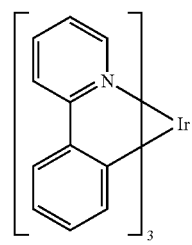
Ir-G
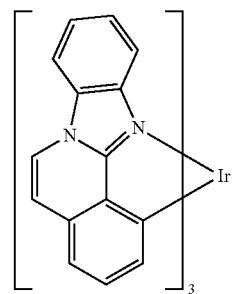
WO2010086089
Ir(Ref-1)$_3$
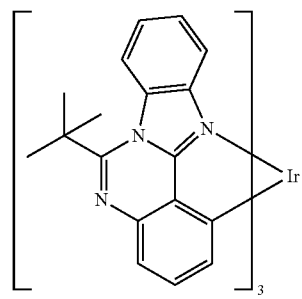
WO2011157339
Ir(Ref-2)$_3$ TABLE 6-continued Structural formulae of the materials used WO2011157339
Ir(Ref-3)₃

WO2011157339
Ir(Ref-4)₃

WO2011157339
Ir(Ref-5)₃

WO2011157339
Ir(Ref-6)₃

WO2011157339
Ir(Ref-7)₃

WO2011157339
Ir(Ref-8)₃

WO2008/156879
Ir(Ref-9)₃

TABLE 6-continued

Structural formulae of the materials used

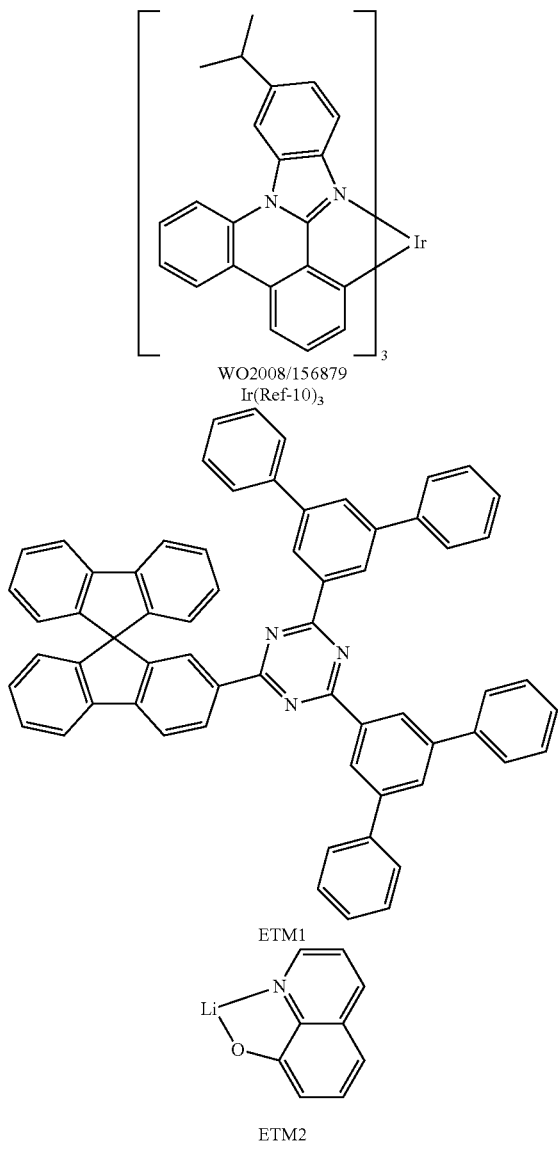

ETM1

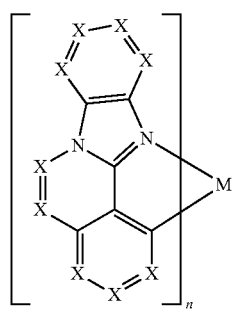

ETM2

The invention claimed is:
1. A compound of formula (1)

$$M(L)_n(L')_m \quad (1)$$

comprising a moiety $M(L)_n$ of formulae (2), (3), or (4):

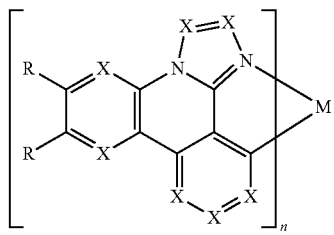

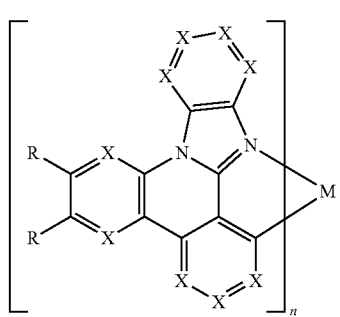

wherein:
M is a transition metal;
X is selected, on each occurrence, identically or differently, from the group consisting of CR and N;
R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy, or thioalkoxy group having 1 to 20 C atoms or an alkenyl or alkynyl group having 2 to 20 C atoms or a branched or cyclic alkyl, alkoxy, or thioalkoxy group having 3 to 20 C atoms, each of which are optionally substituted by one or more radicals $R^1$, and wherein one or more non-adjacent $CH_2$ groups are optionally replaced by $R^1C=CR^1$, $C\equiv C$, $Si(R^1)_2$, $C=O$, $NR^1$, O, S, or $CONR^1$, and wherein one or more H atoms are optionally replaced by D, F, Cl, Br, I, or CN, or an aromatic or heteroaromatic ring system having 5 to 60 aromatic ring atoms optionally substituted by one or more radicals $R^1$, or an aryloxy or heteroaryloxy group having 5 to 40 aromatic ring atoms optionally substituted by one or more radicals $R^1$, or an aralkyl or heteroaralkyl group having 5 to 40 aromatic ring atoms optionally substituted by one or more radicals $R^1$, or a diarylamino group, diheteroarylamino group, or aryl-heteroarylamino group having 10 to 40 aromatic ring atoms optionally substituted by one or more radicals $R^1$; and wherein two adjacent radicals R optionally define a mono- or polycyclic, aliphatic, aromatic, or heteroaromatic ring system with one another;
$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 20 C atoms or an alkenyl or alkynyl group having 2 to 20 C atoms or a branched or cyclic alkyl, alkoxy, or thioalkoxy group having 3 to 20 C atoms, each of which are optionally substituted by one or more radicals $R^2$, and wherein one or more non-adjacent $CH_2$ groups are optionally replaced by $R^2C=CR^2$, $C\equiv C$, $Si(R^2)_2$, $C=O$, $NR^2$, O, S, or $CONR^2$, and wherein one or more H atoms are optionally replaced by D, F, Cl, Br, I, CN, or $NO_2$, or an aromatic or heteroaromatic ring system having 5 to 60 aromatic ring atoms optionally substituted by one or more radicals $R^2$, or an aryloxy or heteroaryloxy group having 5 to 40 aromatic ring atoms optionally substituted by one or more radicals $R^2$, or an aralkyl or heteroaralkyl group having 5 to 40 aromatic ring atoms optionally substituted by one or more radicals $R^2$, or a diarylamino group, diheteroarylamino group, or arylheteroarylamino group having 10 to 40 aromatic ring atoms optionally substituted by one or more radicals $R^2$; and wherein two or more adjacent radicals $R^1$ with one another or $R^1$ with R optionally define a mono- or polycyclic, aliphatic, aromatic or heteroaromatic ring system;

$R^2$ is on each occurrence, identically or differently, H, D, F or an aliphatic, aromatic, and/or heteroaromatic hydrocarbon radical having 1 to 20 C atoms, wherein one or more H atoms are optionally replaced by F; and wherein two or more substituents $R^2$ optionally define a mono- or polycyclic, aliphatic ring system with one another;

L' is, identically or differently on each occurrence, any desired co-ligand;

n is 1, 2, or 3;

m is 0, 1, 2, 3, or 4;

wherein a plurality of ligands L are optionally linked to one another or L is optionally linked to L' via a single bond or a divalent or trivalent bridge and thus form a tridentate, tetradentate, pentadentate, or hexadentate ligand system;

a substituent R optionally additionally coordinates to the metal; and two adjacent groups X are CR and the respective radicals R, together with the C atoms, form a ring of formula (5) or (6);

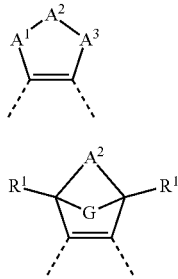

(5)

(6)

wherein $R^1$ and $R^2$ are as defined above;

the dashed bonds indicate the linking of the two carbon atoms in the ligand;

$A^1$ and $A^3$ are, identically or differently, on each occurrence, $C(R^3)_2$, O, S, $NR^3$, or C(=O);

$A^2$ is $C(R^1)_2$, O, S, $NR^3$, or C(=O);

G is an alkylene group having 1, 2, or 3 C atoms optionally substituted by one or more radicals $R^2$, or is —$CR^2$=$CR^2$— or an ortho-linked arylene or heteroarylene group having 5 to 14 aromatic ring atoms optionally substituted by one or more radicals $R^2$; and $R^3$ is, identically or differently on each occurrence, F, a straight-chain alkyl or alkoxy group having 1 to 20 C atoms, a branched or cyclic alkyl or alkoxy group having 3 to 20 C atoms optionally substituted by one or more radicals $R^2$, wherein one or more non-adjacent $CH_2$ groups are optionally replaced by $R^2C$=$CR^2$, C≡C, $Si(R^2)_2$, C=O, $NR^2$, O, S, or $CONR^2$ and wherein one or more H atoms are optionally replaced by D or F, or an aromatic or heteroaromatic ring system having 5 to 24 aromatic ring atoms optionally substituted by one or more radicals $R^2$, or an aryloxy or heteroaryloxy group having 5 to 24 aromatic ring atoms optionally substituted by one or more radicals $R^2$, or an aralkyl or heteroaralkyl group having 5 to 24 aromatic ring atoms optionally substituted by one or more radicals $R^2$; and wherein two radicals $R^3$ bonded to the same carbon atom optionally define an aliphatic or aromatic ring system with one another and thus form a spiro system; and wherein $R^3$ optionally defines an aliphatic ring system with an adjacent radical R or $R^1$; and with the proviso that two heteroatoms are not bonded directly to one another in $A^1$-$A^2$-$A^3$.

2. The compound of claim 1, wherein M is selected from the group consisting of chromium, molybdenum, tungsten, rhenium, ruthenium, osmium, rhodium, iridium, nickel, palladium, platinum, copper, silver, and gold.

3. The compound of claim 1, wherein M is selected from the group consisting of molybdenum, tungsten, rhenium, ruthenium, osmium, iridium, copper, platinum, and gold.

4. The compound of claim 1, wherein the moiety of formula (2) is selected from the group consisting of formulae (2-A) to (2-Q), the moiety of formula (3) is selected from the group consisting of formulae (3-A) to (3-F), the moiety of formula (4) is selected from the group consisting of formulae (4-A) to (4-F):

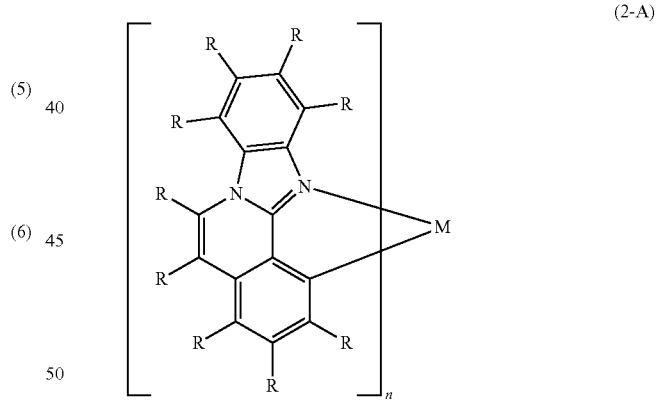

(2-A)

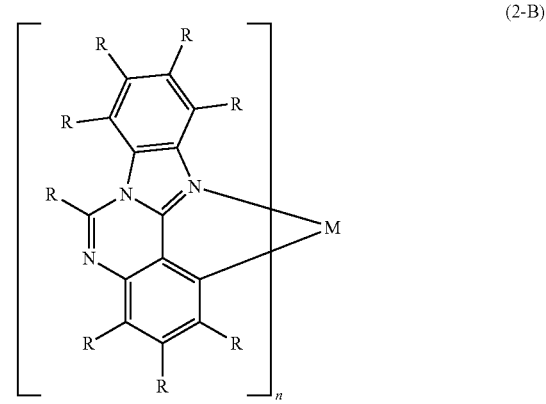

(2-B)

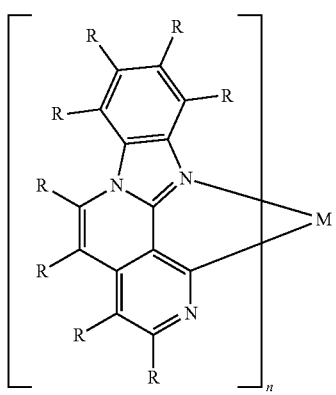 (2-C)
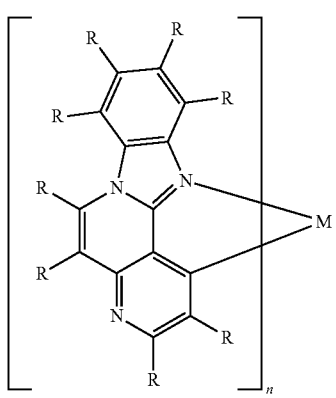 (2-D)
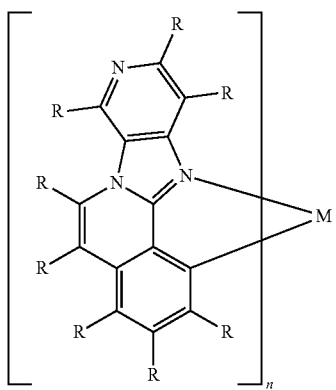 (2-E)
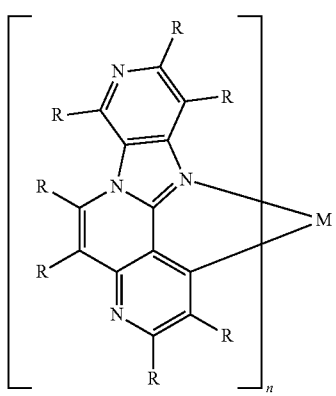 (2-F)
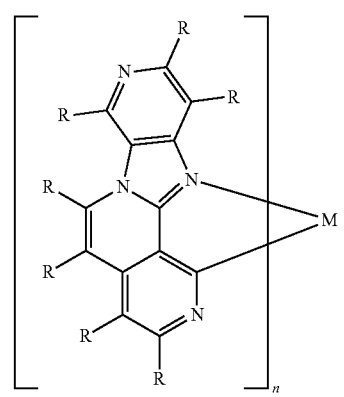 (2-G)
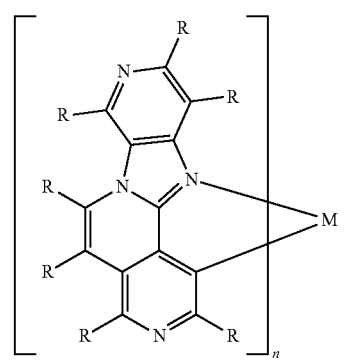 (2-H)
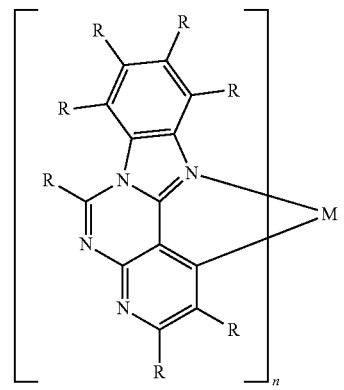 (2-I)
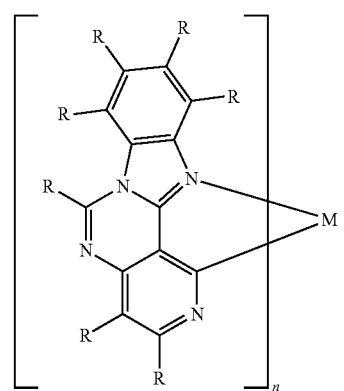 (2-J)

(2-K) 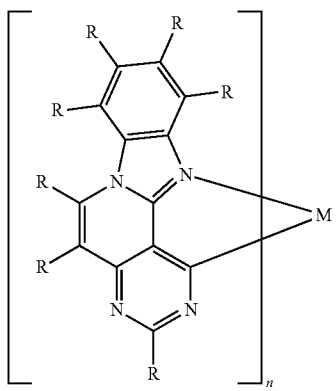
(2-L) 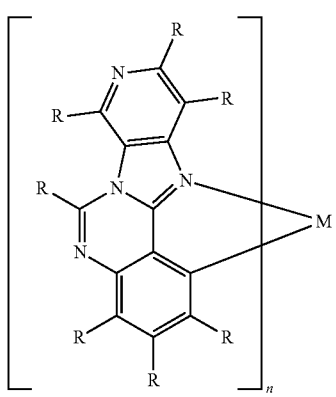
(2-M) 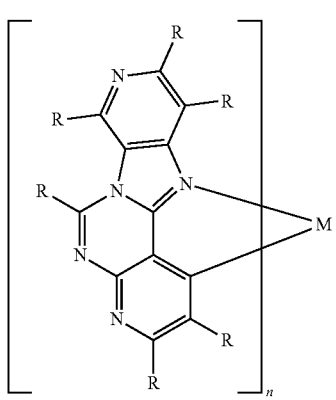
(2-N) 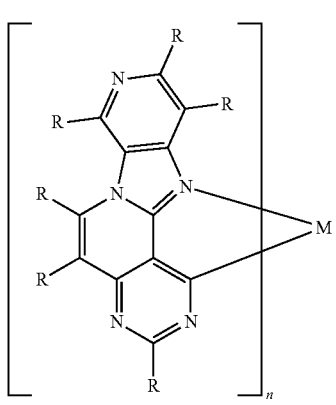
(2-O) 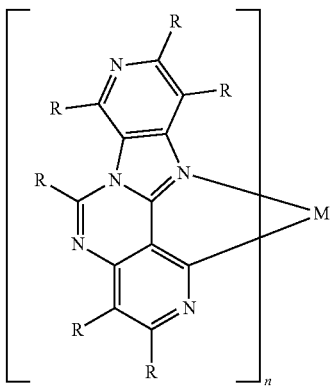
(2-P) 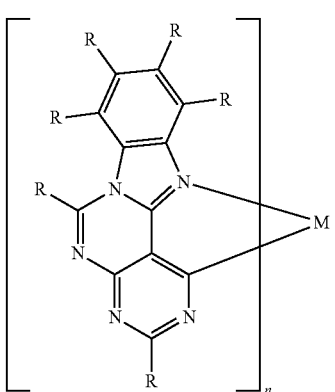
(2-Q) 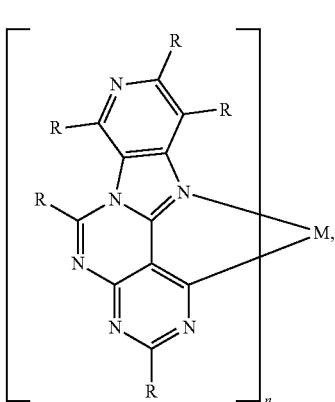
(3-A) 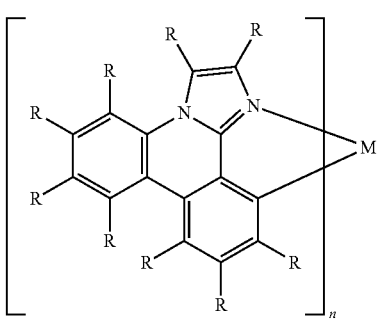

(3-B) 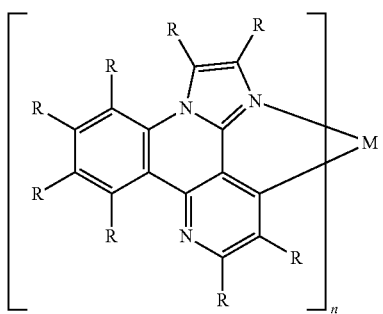
(3-C) 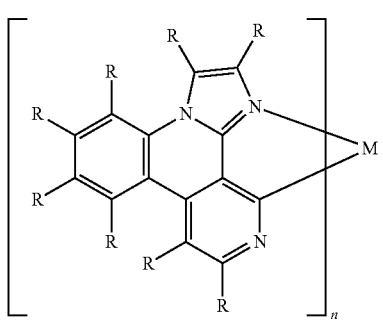
(3-D) 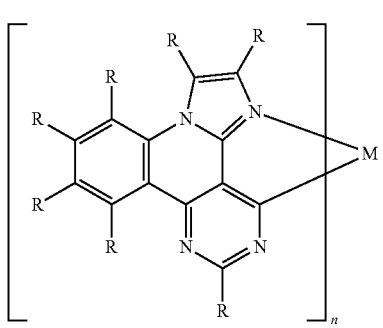
(3-E) 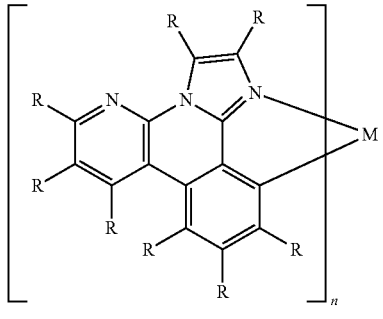
(3-F) 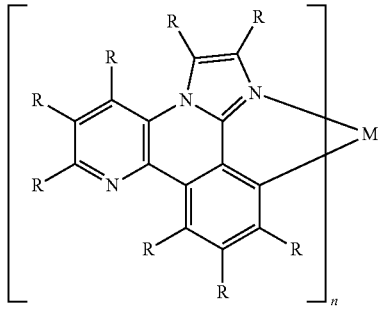
(4-A) 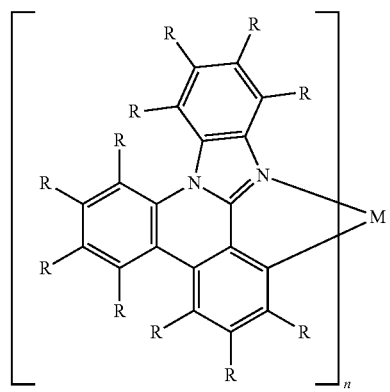
(4-B) 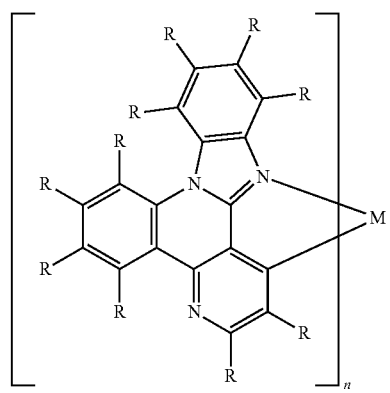
(4-C) 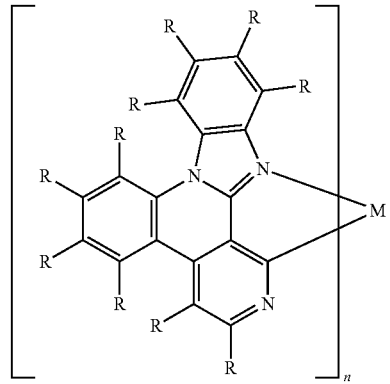
(4-D) 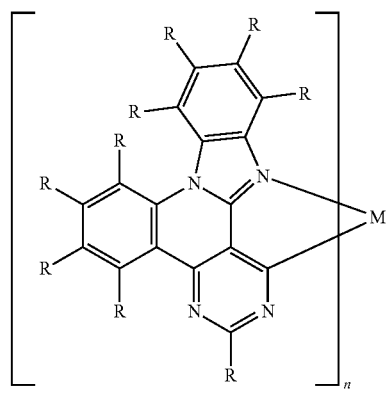

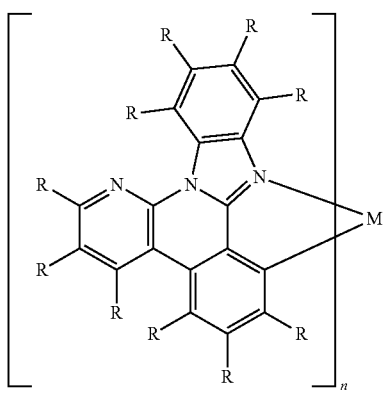
(4-E)
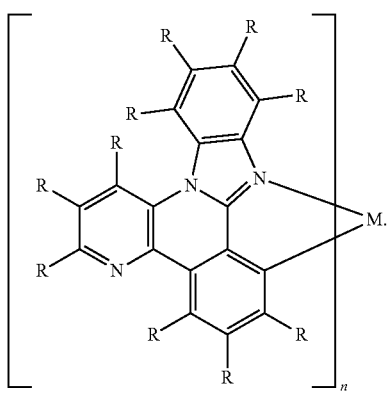
(4-F)
5. The compound of claim 1, wherein the moiety of formula (2) is selected from the group consisting of formulae (2-1) to (2-5), the moiety of formula (3) is selected from the group consisting of formulae (3-1) to (3-3), and the moiety of formula (4) is selected from the group consisting of formulae (4-1) to (4-4):
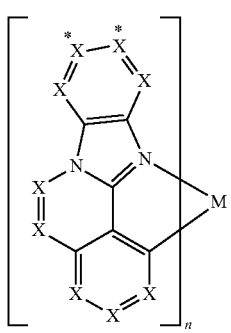
(2-1)
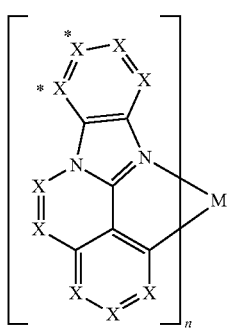
(2-2)
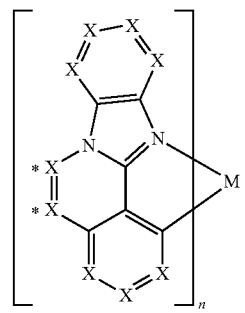
(2-3)
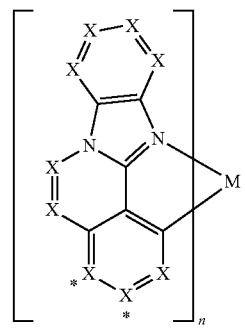
(2-4)
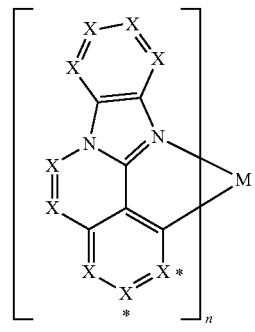
(2-5)
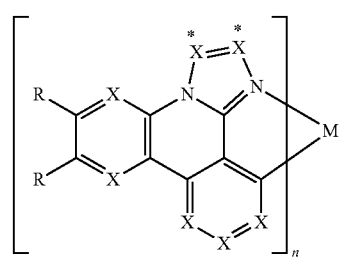
(3-1)
(3-2)

-continued (3-3)
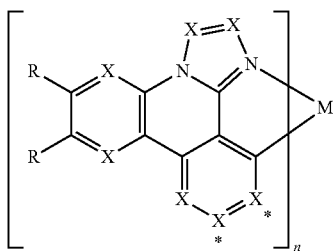

(4-1)
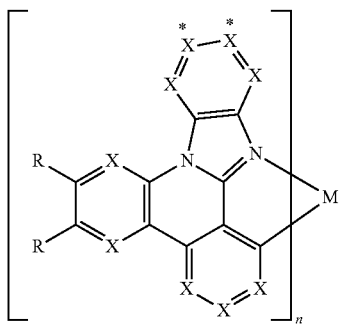

(4-2)
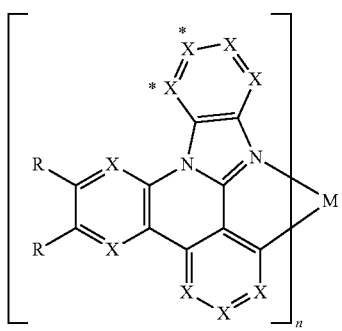

(4-3)
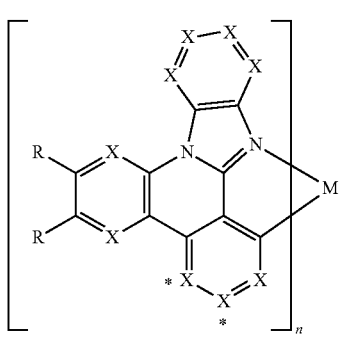

(4-4)
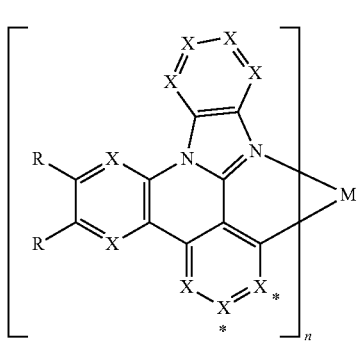

wherein
* in each case denotes the positions which are CR, wherein the respective radicals R, together with the C atoms to which they are bonded, define a ring of formula (5) or (6).

6. The compound of claim 1, wherein the structure of formula (5) is selected from the group consisting of formulae (5-A), (5-B), (5-C), and (5-D) and the structure of formula (6) is selected from the group consisting of formulae (6-A), (6-B), and (6-C):

(5-A)
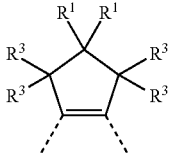

(5-B)
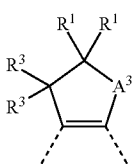

(5-C)
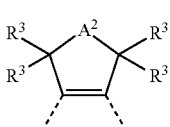

(5-D)
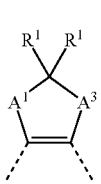

(6-A)
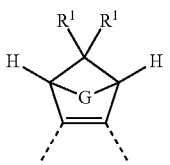

(6-B)
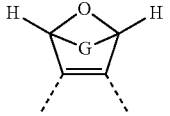

(6-C)
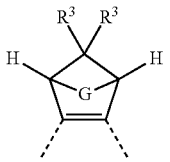

wherein
$A^1$, $A^2$, and $A^3$ are, identically or differently on each occurrence, O or $NR^3$.

7. The compound of claim 1, wherein G is an ethylene group optionally substituted by one or more radicals $R^2$.

8. The compound of claim 7, wherein $R^2$ is, identically or differently on each occurrence, an alkyl group having 1 to 4 C atoms or an ortho-arylene group having 6 to 10 C atoms optionally substituted by one or more radicals $R^2$.

9. The compound of claim 1, wherein, if one or more groups X is nitrogen, a group R selected from the group consisting of CF$_3$, OCF$_3$, an alkyl or alkoxy group having 1 to 10 C atoms, an aromatic ring system, a heteroaromatic ring system, an aralkyl group, and a heteroalkyl group, is bonded as a substituent adjacent to said nitrogen, or R defines a ring of formulae (5) or (6) with an adjacent group R.

10. The compound of claim 1, wherein R, which is bonded in the ortho-position to the metal coordination, is a group selected from the group consisting of aryl groups heteroaryl groups, aryl cyanides, alkyl cyanides, aryl isocyanides, alkyl isocyanides, amines, amides, alcohols, alcoholates, thioalcohols, thioalcoholates, phosphines, phosphites, carbonyl functions, carboxylates, carbamides, or arylacetylides, and alkylacetylides, which are likewise coordinated to the metal M.

11. The compound of claim 1, wherein said compound is selected from the structures of formulae (13) to (18):

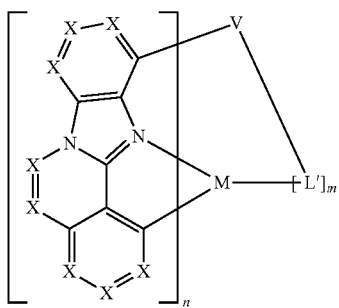
(13)

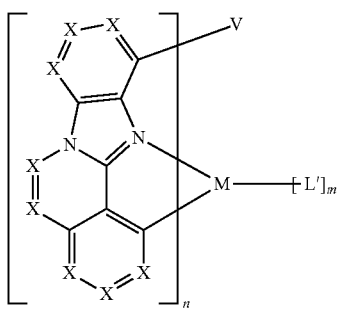
(14)

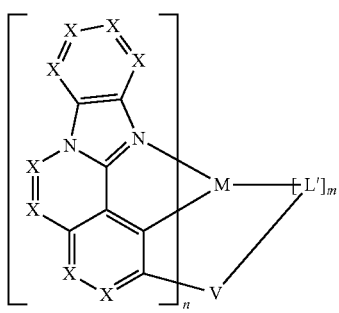
(15)

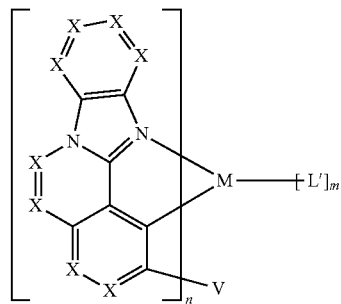
(16)

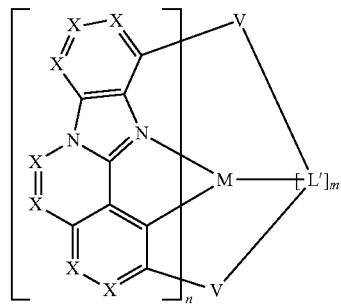
(17)

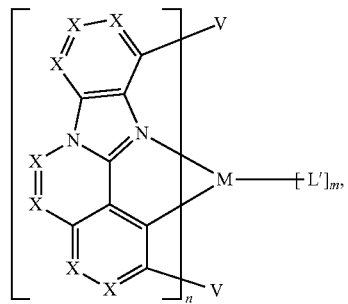
(18)

wherein
V is a single bond, a bridging unit containing 1 to 80 atoms from the third, fourth, fifth, and/or sixth main group (i.e., group 13, 14, 15, or 16 in accordance with IUPAC), or a 3- to 6-membered homo- or heterocycle and the part-ligands L are covalently bonded to one another or L is covalently bonded to L'.

12. The compound of claim 1, wherein L' is selected from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, F$^-$, Cl$^-$, Br$^-$, I$^-$, alkylacetylides, arylacetylides, cyanide, cyanate, isocyanate, thiocyanate, isothiocyanate, aliphatic alcoholates, aromatic alcoholates, aliphatic thioalcoholates, aromatic thioalcoholates, amides, carboxylates, aryl groups, O$^{2-}$, S$^{2-}$, carbides which result in coordination in the form R—C≡M, nitrenes which result in coordination in the form R—N=M, where R generally stands for a substituent, N$^{3-}$, diamines, imines, diimines, heterocycles containing two nitrogen atoms, diphosphines, 1,3-diketonates derived from 1,3-diketones, 3-ketonates derived from 3-ketoesters, carboxylates derived from aminocarboxylic acids, salicyliminates derived from salicylimines, dialcoholates, dithiolates, 3-(2-pyridyl)diazoles, 3-(2-pyridyl)triazoles, borates of nitrogen-containing heterocycles and bidentate monoanionic ligands L', bidentate neutral ligands L' and bidentate dianionic ligands L' which, with the metal, define a cyclometallated five-membered ring or six-membered ring having at least one metal-carbon bond.

13. A process for preparing a compound of claim 1 comprising reacting a corresponding free ligand with a metal alkoxide of formula (71), a metal ketoketonate of formula (72), a metal halide of formula (73), a dimeric metal complex of formula (74), or a metal complex of formula (75):

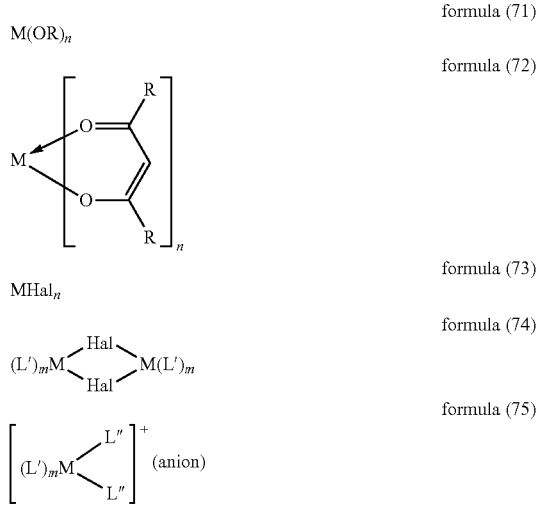

$$M(OR)_n \quad \text{formula (71)}$$

$$\text{formula (72)}$$

$$MHal_n \quad \text{formula (73)}$$

$$(L')_mM\underset{Hal}{\overset{Hal}{<}}M(L')_m \quad \text{formula (74)}$$

$$\left[(L')_mM\underset{L''}{\overset{L''}{<}}\right]^+ (\text{anion}) \quad \text{formula (75)}$$

wherein
Hal is F, Cl, Br or I,
L" is an alcohol or a nitrile, and
(anion) is a non-coordinating anion,
and wherein metal compounds which carry both alcoholate and/or halide and/or hydroxyl and also ketoketonate radicals are optionally employed.

14. An oligomer, polymer, or dendrimer comprising one or more compounds of claim 1, wherein one or more bonds are present from said one or more compounds to said polymer, oligomer, or dendrimer.

15. A formulation comprising an oligomer, polymer, or dendrimer of claim 14 and at least one further compound.

16. An electronic device comprising one or more oligomers, polymers, or dendrimers of claim 14.

17. The electronic device of claim 16, wherein said electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

18. The electronic device of claim 17, comprising an emitting layer comprising a matrix material selected from the group consisting of ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives, zinc complexes, dibenzofuran derivatives, bridged carbazole derivatives, and mixtures thereof.

19. A formulation comprising at least one compound of claim 1 and at least one further compound.

20. An electronic device comprising one or more compounds of claim 1.

21. The electronic device of claim 20, wherein said electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

22. The electronic device of claim 21, comprising an emitting layer comprising a matrix material selected from the group consisting of ketones, phosphine oxides, sulfoxides, sulfones, triarylamines, carbazole derivatives, indolocarbazole derivatives, indenocarbazole derivatives, azacarbazoles, bipolar matrix materials, silanes, azaboroles, boronic esters, diazasilole derivatives, diazaphosphole derivatives, triazine derivatives, zinc complexes, dibenzofuran derivatives, bridged carbazole derivatives, and mixtures thereof.

23. An organic electroluminescent device comprising a compound of claim 1 employed as an emitting compound in one or more emitting layers.

* * * * *